US011466083B2

(12) United States Patent
Nathwani et al.

(10) Patent No.: US 11,466,083 B2
(45) Date of Patent: *Oct. 11, 2022

(54) ROR1 ANTIBODIES

(71) Applicant: UCL Business LTD, London (GB)

(72) Inventors: Amit Nathwani, London (GB); Satyen Gohil, London (GB); Marco Della Peruta, London (GB)

(73) Assignee: UCL Business LTD, London (GB)

( * ) Notice: Subject to any disclaimer, the term of this patent is extended or adjusted under 35 U.S.C. 154(b) by 220 days.

This patent is subject to a terminal disclaimer.

(21) Appl. No.: 16/628,512

(22) PCT Filed: Jul. 5, 2018

(86) PCT No.: PCT/GB2018/051914
§ 371 (c)(1),
(2) Date: Jan. 3, 2020

(87) PCT Pub. No.: WO2019/008377
PCT Pub. Date: Jan. 10, 2019

(65) Prior Publication Data
US 2020/0354448 A1 Nov. 12, 2020

(30) Foreign Application Priority Data

Jul. 5, 2017 (GB) .................................... 1710835

(51) Int. Cl.
| | | |
|---|---|---|
| *A61K 39/00* | (2006.01) | |
| *A61K 39/395* | (2006.01) | |
| *C12Q 1/68* | (2018.01) | |
| *C12P 21/06* | (2006.01) | |
| *C12N 5/20* | (2006.01) | |
| *C07K 16/00* | (2006.01) | |
| *C07K 16/46* | (2006.01) | |
| *C07K 16/28* | (2006.01) | |

(52) U.S. Cl.
CPC .... *C07K 16/2803* (2013.01); *A61K 2039/505* (2013.01); *C07K 2317/24* (2013.01); *C07K 2317/34* (2013.01); *C07K 2317/622* (2013.01); *C07K 2317/734* (2013.01); *C07K 2317/77* (2013.01)

(58) Field of Classification Search
None
See application file for complete search history.

(56) References Cited

U.S. PATENT DOCUMENTS

| | | |
|---|---|---|
| 8,076,459 B2 | 12/2011 | Hofmeister et al. |
| 9,102,736 B2 | 8/2015 | Hofmeister et al. |
| 2013/0273073 A1 | 10/2013 | Kipps et al. |
| 2013/0281922 A1 | 10/2013 | Teige |
| 2015/0306141 A1 | 10/2015 | Jensen et al. |
| 2020/0030454 A1 | 1/2020 | Lannutti et al. |

FOREIGN PATENT DOCUMENTS

| | | |
|---|---|---|
| EP | 2789630 A1 | 10/2014 |
| WO | WO-2005/040220 A1 | 5/2005 |
| WO | WO-2007/146957 A2 | 12/2007 |
| WO | WO-2010/124188 A1 | 10/2010 |
| WO | WO-2011/054007 A1 | 5/2011 |
| WO | WO-2011/079902 A2 | 7/2011 |
| WO | WO-2012/045085 A1 | 4/2012 |
| WO | WO-2012/075158 A1 | 6/2012 |
| WO | WO-2012/076066 A1 | 6/2012 |
| WO | WO-2012/076727 A1 | 6/2012 |
| WO | WO-2014/031174 A1 | 2/2014 |
| WO | WO-2014/167022 A1 | 10/2014 |
| WO | WO-2015/184203 A1 | 12/2015 |
| WO | WO-2015/184207 A1 | 12/2015 |
| WO | WO-2016/016343 A1 | 2/2016 |
| WO | WO-2016/016344 A1 | 2/2016 |
| WO | WO-2016/039321 A1 | 3/2016 |
| WO | WO-2016/055592 A1 | 4/2016 |
| WO | WO-2016/055593 A1 | 4/2016 |
| WO | WO-2016/094873 A2 | 6/2016 |
| WO | WO-2016/115559 A1 | 7/2016 |
| WO | WO-2016/124553 A1 | 8/2016 |
| WO | WO-2016/187216 A1 | 11/2016 |
| WO | WO-2016/187220 A2 | 11/2016 |
| WO | WO-2017/072361 A1 | 5/2017 |
| WO | WO-2017/127499 A1 | 7/2017 |
| WO | WO-2017/127664 A1 | 7/2017 |
| WO | WO-2017/142928 A1 | 8/2017 |
| WO | WO-2017/156479 A1 | 9/2017 |
| WO | WO-2018/011138 A1 | 1/2018 |
| WO | WO-2018/119314 A1 | 6/2018 |

(Continued)

OTHER PUBLICATIONS

Gohil et al. Novel Humanised ROR1 Chimeric Antigen Receptors for the Treatment of Haematological Malignancies. Blood, (Dec. 2, 2016) vol. 128, No. 22. Abstract No. 3361. (Year: 2016).*
Gohil, S. et al., Pre-clinical development of novel ROR1 chimeric antigen receptor T cells and bispecific T cell engagers, 212 pages (Mar. 1, 2019).
Barat, B. et al., Development of a Humanized ROR1 x CD3 Bispecific DART Molecule for the Treatment of Solid and Liquid Tumors, presented at the 2016 American Association for Cancer Research Annual Meeting, one page, Apr. 16-20, 2016.
Baskar, S. et al., Targeting malignant B cells with an immunotoxin against ROR1, mAbs, 4:3, 349-361 (2012).
Daneshmanesh, A. et al., Monoclonal antibodies against ROR1 induce apoptosis of chronic lymphocytic leukemia (CLL) cells, Leukemia, 26:1348-1355 (2012).
Deniger, D. et al., Sleeping Beauty Transposition of Chimeric Antigen Receptors Targeting Receptor Tyrosine Kinase-Like Orphan Receptor-1 (ROR1) into Diverse Memory T-Cell Populations, PLOS One, 10(6): 19 pages (2015).

(Continued)

*Primary Examiner* — Maher M Haddad
(74) *Attorney, Agent, or Firm* — Choate, Hall & Stewart LLP; Brenda Herschbach Jarrell; Melissa M. Adams

(57) ABSTRACT

There is described Receptor Tyrosine Kinase Like Orphan Receptor 1 (ROR1) antibodies that specifically bind a ROR1 polypeptide, and their use. In particular, isolated monoclonal antibodies are described and their use in a number of applications, including in the detection, prevention and treatment of cancer.

19 Claims, 28 Drawing Sheets

Figure 1:
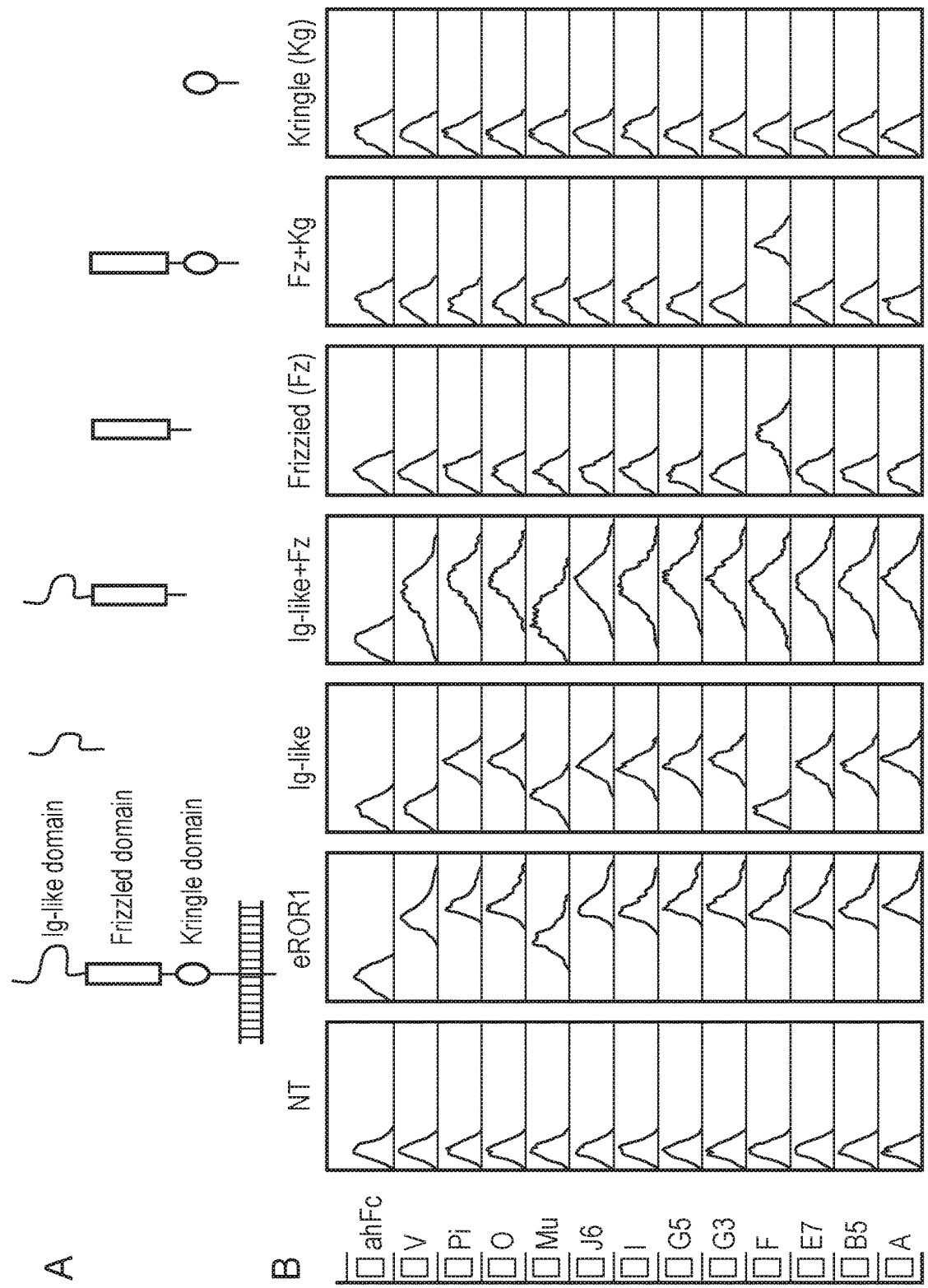
Figure 1:
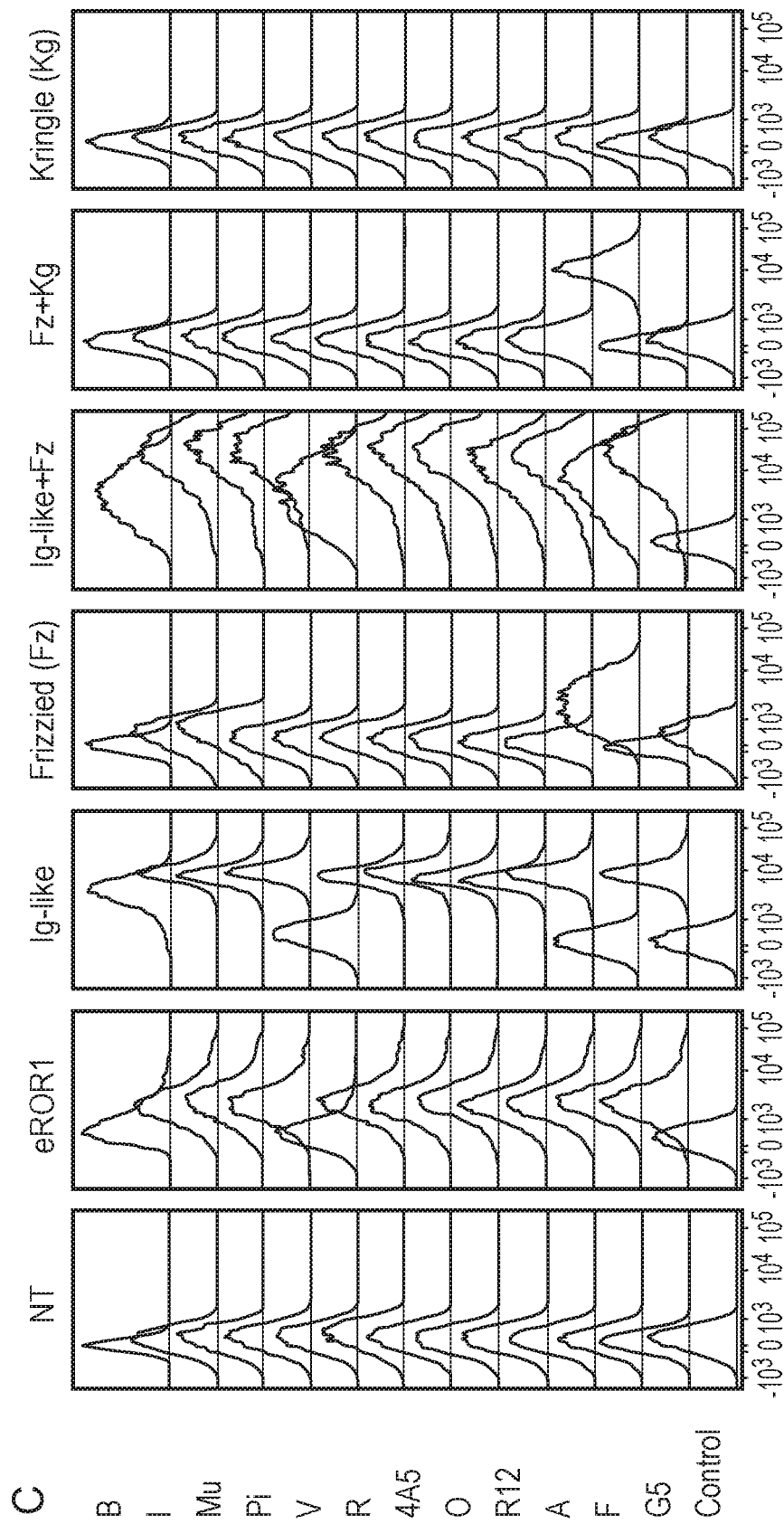

Specification includes a Sequence Listing.

(56) References Cited

FOREIGN PATENT DOCUMENTS

| WO | WO-2018/217799 A1 | 11/2018 |
|---|---|---|
| WO | WO-2018/237335 A1 | 12/2018 |
| WO | WO-2019/005636 A2 | 1/2019 |
| WO | WO-2019/005638 A2 | 1/2019 |
| WO | WO-2019/016381 A1 | 1/2019 |
| WO | WO-2019/030223 A1 | 2/2019 |
| WO | WO-2019/030240 A1 | 2/2019 |
| WO | WO-2019/090110 A1 | 5/2019 |
| WO | WO-2019/122445 A1 | 6/2019 |
| WO | WO-2019/122447 A1 | 6/2019 |
| WO | WO-2019/225992 A1 | 11/2019 |

OTHER PUBLICATIONS

Gohil, S. et al., An ROR1 bi-specific T-cell engager provides effective targeting and cytotoxicity against a range of solid tumors, Oncoimmunology, 6(7):e1326437, 11 pages (2017).

Gohil, S. et al., Preclinical development of novel humanised ROR1 targeting chimeric antigen receptor T cells and bispecific T-cell engagers, Poster Abstracts, one page (2017).

Hudecek, M. et al., Receptor Affinity and Extracellular Domain Modifications Affect Tumor Recognition by ROR1-Specific Chimeric Antigen Receptor T Cells, Clinical Cancer Research, 19(12):3153-3164 (2013).

Kershaw, M. et al., A Phase I Study on Adoptive Immunotherapy Using Gene-Modified T Cells for Ovarian Cancer, Clinical Cancer Research, 12:6106-6115 (2006).

Lamers, C. et al., Process validation and clinical evaluation of a protocol to generate gene-modified T lymphocytes for umunogene therapy for metastatic renal cell carcinoma: GMP-controlled transduction and expansion of patient's T lymphocytes using a carboxy anhydrase IX-specific scFvtransgene, Cytotherapy, 8(6):542-553 (2006).

Maus, M. et al., T Cells Expressing Chimeric ANtigen Receptors Can Cause Anaphylaxis in Humans, Cancer Immunology Research, 1(1):26-31 (2013).

Paredes-Moscosso, S. et al., Novel ROR1 Antibody is Able to Trigger Specific and Superior Complemente-Dependent Cytotoxicity (CDC) on Primary CLL Cells, Blood, 128(22):2052, 4 pages (2016).

Paredes-Moscosso, Solange Rosa, ROR1 as a Target for Cancer Immunotherapy, A thesis sumbitted to University College London (UCL) for the degree of Doctor of Philosophy, 305 pages (2017).

Gohil et al., A Novel Humanised ROR1 Bi-Specific T-Cell Engager Molecule for the Treatment of Chronic Lymphocytic Leukaemia, Blood (Dec. 2, 2016), 128(22):3244, 642. CLL: Therapy, Excluding Transplantation: Poster II (<https://doi.org/10.1182/blood.V128.22.3244.3244>).

Gohil et al., A ROR1 Bispecific T Cell Engager for the Treatment of Chronic Lymphocytic Leukaemia Demonstrates Enhanced Function Following Ibrutinib Treatment, Blood (Dec. 7, 2017), 130(Supplement 1):4316, 642. CLL: Therapy, Excluding Transplantation: Poster III (<https://doi.org/10.1182/blood.V130.Suppl_1.4316.4316>).

* cited by examiner

ROR1 ANTIBODIES

The invention relates to Receptor Tyrosine Kinase Like Orphan Receptor 1 (ROR1) antibodies that specifically bind a ROR1 polypeptide, and their use.

SEQUENCE LISTING

The instant application contains a Sequence Listing which has been submitted electronically as a .txt file named "2013607_0003_SL.txt". The .txt file was created on Jul. 5, 2017, and is 108,528 bytes in size. The entire contents of the Sequence Listing are herein incorporated by reference.

BACKGROUND OF THE INVENTION

Receptor Tyrosine Kinase Like Orphan Receptor 1 (ROR1) (also known as Neurotrophic Tyrosine Kinase, Receptor-Related 1, NTRKR1) is an onco-foetal antigen expressed during embryogenesis but with limited expression on normal adult tissue. It is however expressed on a number of haematological and solid malignancies: Chronic Lymphocytic Leukaemia (CLL), Acute Lymphoblastic Leukaemia (ALL), Mantle Cell Leukaemia, Hairy Cell Leukaemia, Pancreatic cancer, Prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

As such, ROR1 is an attractive therapeutic target. Furthermore, a need remains for agents that can be used to treat and/or diagnose the aforementioned cancers.

SUMMARY OF THE INVENTION

A first aspect of the invention relates to an isolated monoclonal antibody comprising a light chain variable domain and a heavy chain variable domain wherein the light chain variable domain comprises a light chain complementarity determining region (LCDR)1, an LCDR2 and an LCDR3, wherein LCDR1 comprises an amino acid sequence set forth in SEQ ID NO: 30, SEQ ID NO: 24, SEQ ID NO: 9, SEQ ID NO: 37, SEQ ID NO: 44, SEQ ID NO: 50, SEQ ID NO: 56, SEQ ID NO: 67, SEQ ID NO: 71, SEQ ID NO: 2, SEQ ID NO: 16, or SEQ ID NO: 22; LCDR2 comprises an amino acid sequence set forth in SEQ ID NO: 32, SEQ ID NO: 26, SEQ ID NO: 11, SEQ ID NO: 39, SEQ ID NO: 46, SEQ ID NO: 52, SEQ ID NO: 58, SEQ ID NO: 4 or SEQ ID NO: 18; and LCDR3 comprises an amino acid sequence set forth in SEQ ID NO: 34, SEQ ID NO: 28, SEQ ID NO: 13, SEQ ID NO: 41, SEQ ID NO: 48, SEQ ID NO: 54, SEQ ID NO: 60, SEQ ID NO: 65, SEQ ID NO: 68, SEQ ID NO: 74, SEQ ID NO: 6, or SEQ ID NO: 20; and wherein the heavy chain variable domain comprises a heavy chain complementarity determining region (HCDR)1, an HCDR2 and an HCDR3, wherein HCDR1 comprises an amino acid sequence set forth in SEQ ID NO: 121, SEQ ID NO: 115, SEQ ID NO: 96, SEQ ID NO: 127, SEQ ID NO: 134, SEQ ID NO: 140, SEQ ID NO: 146, SEQ ID NO: 152, SEQ ID NO: 158, SEQ ID NO: 163, SEQ ID NO: 89, SEQ ID NO: 103 or SEQ ID NO: 110; HCDR2 comprises an amino acid sequence set forth in SEQ ID NO: 123, SEQ ID NO: 117, SEQ ID NO: 98, SEQ ID NO: 129, SEQ ID NO: 136, SEQ ID NO: 142, SEQ ID NO: 148, SEQ ID NO: 154, SEQ ID NO: 160, SEQ ID NO: 165, SEQ ID NO: 91 or SEQ ID NO: 105; and HCDR3 comprises an amino acid sequences set forth in SEQ ID NO: 248, SEQ ID NO: 252, SEQ ID NO: 100, SEQ ID NO: 131, SEQ ID NO: 138, SEQ ID NO: 144, SEQ ID NO: 150, SEQ ID NO: 156, SEQ ID NO: 162, SEQ ID NO: 167, SEQ ID NO: 93, SEQ ID NO: 107 or SEQ ID NO: 113, wherein the sequence of each complementarity determining region may differ from the given sequence at up to two amino acid positions, and wherein the monoclonal antibody specifically binds to a ROR1 polypeptide.

Preferably the isolated monoclonal antibody comprises a light chain variable domain, wherein the light chain variable domain comprises a light chain complementarity determining region (LCDR)1, an LCDR2 and an LCDR3, wherein (a) the LCDR1 comprises the amino acid sequence set forth as SEQ ID NO: 30, the LCDR2 comprises the amino acid sequence set forth as SEQ ID NO: 32, and the LCDR3 comprises the amino acid sequence set forth as SEQ ID NO: 34;

(b) the LCDR1 comprises the amino acid sequence set forth as SEQ ID NO: 24, the LCDR2 comprises the amino acid sequence set forth as SEQ ID NO: 26, and the LCDR3 comprises the amino acid sequence set forth as SEQ ID NO: 28;

(c) the LCDR1 comprises the amino acid sequence set forth as SEQ ID NO: 9, the LCDR2 comprises the amino acid sequence set forth as SEQ ID NO: 11, and the LCDR3 comprises the amino acid sequence set forth as SEQ ID NO: 13;

(d) the LCDR1 comprises the amino acid sequence set forth as SEQ ID NO: 37, the LCDR2 comprises the amino acid sequence set forth as SEQ ID NO: 39, and the LCDR3 comprises the amino acid sequence set forth as SEQ ID NO: 41;

(e) the LCDR1 comprises the amino acid sequence set forth as SEQ ID NO: 44, the LCDR2 comprises the amino acid sequence set forth as SEQ ID NO: 46, and the LCDR3 comprises the amino acid sequence set forth as SEQ ID NO: 48;

(f) the LCDR1 comprises the amino acid sequence set forth as SEQ ID NO: 50, the LCDR2 comprises the amino acid sequence set forth as SEQ ID NO: 52, and the LCDR3 comprises the amino acid sequence set forth as SEQ ID NO: 54;

(g) the LCDR1 comprises the amino acid sequence set forth as SEQ ID NO: 56, the LCDR2 comprises the amino acid sequence set forth as SEQ ID NO: 58, and the LCDR3 comprises the amino acid sequence set forth as SEQ ID NO: 60;

(h) the LCDR1 comprises the amino acid sequence set forth as SEQ ID NO: 44, the LCDR2 comprises the amino acid sequence set forth as SEQ ID NO: 46, and the LCDR3 comprises the amino acid sequence set forth as SEQ ID NO: 65;

(i) the LCDR1 comprises the amino acid sequence set forth as SEQ ID NO: 67, the LCDR2 comprises the amino acid sequence set forth as SEQ ID NO: 58, and the LCDR3 comprises the amino acid sequence set forth as SEQ ID NO: 68;

(j) the LCDR1 comprises the amino acid sequence set forth as SEQ ID NO: 71, the LCDR2 comprises the amino acid sequence set forth as SEQ ID NO: 26, and the LCDR3 comprises the amino acid sequence set forth as SEQ ID NO: 74;

(k) the LCDR1 comprises the amino acid sequence set forth as SEQ ID NO: 2, the LCDR2 comprises the amino acid sequence set forth as SEQ ID NO: 4, and the LCDR3 comprises the amino acid sequence set forth as SEQ ID NO: 6;

(l) the LCDR1 comprises the amino acid sequence set forth as SEQ ID NO: 16, the LCDR2 comprises the amino acid sequence set forth as SEQ ID NO: 18, and the LCDR3 comprises the amino acid sequence set forth as SEQ ID NO: 20; or (m) the LCDR1 comprises the amino acid sequence set forth as SEQ ID NO: 22, the LCDR2 comprises the amino acid sequence set forth as SEQ ID NO: 18, and the LCDR3 comprises the amino acid sequence set forth as SEQ ID NO: 20;

wherein the sequence of each complementarity determining region may differ from the given sequence at up to two amino acid positions, and wherein the monoclonal antibody specifically binds to a ROR1 polypeptide.

Preferably the isolated monoclonal antibody comprises a heavy chain variable domain, wherein the heavy chain variable domain comprises a heavy chain complementarity determining region (HCDR)1, an HCDR2 and an HCDR3, wherein (a) the HCDR1 comprises the amino acid sequence set forth as SEQ ID NO: 121, the HCDR2 comprises the amino acid sequence set forth as SEQ ID NO: 123, and the HCDR3 comprises the amino acid sequence set forth as SEQ ID NO: 248;

(b) the HCDR1 comprises the amino acid sequence set forth as SEQ ID NO: 115, the HCDR2 comprises the amino acid sequence set forth as SEQ ID NO: 117, and the HCDR3 comprises the amino acid sequence set forth as SEQ ID NO: 252;

(c) the HCDR1 comprises the amino acid sequence set forth as SEQ ID NO: 96, the HCDR2 comprises the amino acid sequence set forth as SEQ ID NO: 98, and the HCDR3 comprises the amino acid sequence set forth as SEQ ID NO: 100;

(d) the HCDR1 comprises the amino acid sequence set forth as SEQ ID NO: 127, the HCDR2 comprises the amino acid sequence set forth as SEQ ID NO: 129, and the HCDR3 comprises the amino acid sequence set forth as SEQ ID NO: 131;

(e) the HCDR1 comprises the amino acid sequence set forth as SEQ ID NO: 134, the HCDR2 comprises the amino acid sequence set forth as SEQ ID NO: 136, and the HCDR3 comprises the amino acid sequence set forth as SEQ ID NO: 138;

(f) the HCDR1 comprises the amino acid sequence set forth as SEQ ID NO: 140, the HCDR2 comprises the amino acid sequence set forth as SEQ ID NO: 142, and the HCDR3 comprises the amino acid sequence set forth as SEQ ID NO: 144;

(g) the HCDR1 comprises the amino acid sequence set forth as SEQ ID NO: 146, the HCDR2 comprises the amino acid sequence set forth as SEQ ID NO: 148, and the HCDR3 comprises the amino acid sequence set forth as SEQ ID NO: 150;

(h) the HCDR1 comprises the amino acid sequence set forth as SEQ ID NO: 152, the HCDR2 comprises the amino acid sequence set forth as SEQ ID NO: 154, and the HCDR3 comprises the amino acid sequence set forth as SEQ ID NO: 156;

(i) the HCDR1 comprises the amino acid sequence set forth as SEQ ID NO: 158, the HCDR2 comprises the amino acid sequence set forth as SEQ ID NO: 160, and the HCDR3 comprises the amino acid sequence set forth as SEQ ID NO: 162;

(j) the HCDR1 comprises the amino acid sequence set forth as SEQ ID NO: 163, the HCDR2 comprises the amino acid sequence set forth as SEQ ID NO: 165, and the HCDR3 comprises the amino acid sequence set forth as SEQ ID NO: 167;

(k) the HCDR1 comprises the amino acid sequence set forth as SEQ ID NO: 89, the HCDR2 comprises the amino acid sequence set forth as SEQ ID NO: 91, and the HCDR3 comprises the amino acid sequence set forth as SEQ ID NO: 93;

(l) the HCDR1 comprises the amino acid sequence set forth as SEQ ID NO: 103, the HCDR2 comprises the amino acid sequence set forth as SEQ ID NO: 105, and the HCDR3 comprises the amino acid sequence set forth as SEQ ID NO: 107; or (m) the HCDR1 comprises the amino acid sequence set forth as SEQ ID NO: 110, the HCDR2 comprises the amino acid sequence set forth as SEQ ID NO: 105, and the HCDR3 comprises the amino acid sequence set forth as SEQ ID NO: 113;

wherein the sequence of each complementarity determining region may differ from the given sequence at up to two amino acid positions, and wherein the monoclonal antibody specifically binds to a ROR1 polypeptide.

More preferably, the isolated monoclonal antibody comprises a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein (a) the LCDR1 comprises the amino acid sequence set forth as SEQ ID NO: 30, the LCDR2 comprises the amino acid sequence set forth as SEQ ID NO: 32, the LCDR3 comprises the amino acid sequence set forth as SEQ ID NO: 34, the HCDR1 comprises the amino acid sequence set forth as SEQ ID NO: 121, the HCDR2 comprises the amino acid sequence set forth as SEQ ID NO: 123, and the HCDR3 comprises the amino acid sequence set forth as SEQ ID NO: 248;

(b) the LCDR1 comprises the amino acid sequence set forth as SEQ ID NO: 24, the LCDR2 comprises the amino acid sequence set forth as SEQ ID NO: 26, the LCDR3 comprises the amino acid sequence set forth as SEQ ID NO: 28, the HCDR1 comprises the amino acid sequence set forth as SEQ ID NO: 115, the HCDR2 comprises the amino acid sequence set forth as SEQ ID NO: 117, and the HCDR3 comprises the amino acid sequence set forth as SEQ ID NO: 252;

(c) the LCDR1 comprises the amino acid sequence set forth as SEQ ID NO: 9, the LCDR2 comprises the amino acid sequence set forth as SEQ ID NO: 11, the LCDR3 comprises the amino acid sequence set forth as SEQ ID NO: 13, the HCDR1 comprises the amino acid sequence set forth as SEQ ID NO: 96, the HCDR2 comprises the amino acid sequence set forth as SEQ ID NO: 98, and the HCDR3 comprises the amino acid sequence set forth as SEQ ID NO: 100;

(d) the LCDR1 comprises the amino acid sequence set forth as SEQ ID NO: 37, the LCDR2 comprises the amino acid sequence set forth as SEQ ID NO: 39, the LCDR3 comprises the amino acid sequence set forth as SEQ ID NO: 41, the HCDR1 comprises the amino acid sequence set forth as SEQ ID NO: 127, the HCDR2 comprises the amino acid sequence set forth as SEQ ID NO: 129, and the HCDR3 comprises the amino acid sequence set forth as SEQ ID NO: 131;

(e) the LCDR1 comprises the amino acid sequence set forth as SEQ ID NO: 44, the LCDR2 comprises the amino acid sequence set forth as SEQ ID NO: 46, the LCDR3 comprises the amino acid sequence set forth as SEQ ID NO: 48, the HCDR1 comprises the amino acid sequence set forth as SEQ ID NO: 134, the HCDR2 comprises the amino acid sequence set forth as SEQ ID NO: 136, and the HCDR3 comprises the amino acid sequence set forth as SEQ ID NO: 138;

(f) the LCDR1 comprises the amino acid sequence set forth as SEQ ID NO: 50, the LCDR2 comprises the amino acid sequence set forth as SEQ ID NO: 52, the LCDR3 comprises the amino acid sequence set forth as SEQ ID NO: 54, the HCDR1 comprises the amino acid sequence set forth as SEQ ID NO: 140, the HCDR2 comprises the amino acid sequence set forth as SEQ ID NO: 142, and the HCDR3 comprises the amino acid sequence set forth as SEQ ID NO: 144;

(g) the LCDR1 comprises the amino acid sequence set forth as SEQ ID NO: 56, the LCDR2 comprises the amino acid sequence set forth as SEQ ID NO: 58, the LCDR3 comprises the amino acid sequence set forth as SEQ ID NO: 60, the HCDR1 comprises the amino acid sequence set forth as SEQ ID NO: 146, the HCDR2 comprises the amino acid sequence set forth as SEQ ID NO: 148, and the HCDR3 comprises the amino acid sequence set forth as SEQ ID NO: 150;

(h) the LCDR1 comprises the amino acid sequence set forth as SEQ ID NO: 44, the LCDR2 comprises the amino acid sequence set forth as SEQ ID NO: 46, the LCDR3 comprises the amino acid sequence set forth as SEQ ID NO: 65, the HCDR1 comprises the amino acid sequence set forth as SEQ ID NO: 152, the HCDR2 comprises the amino acid sequence set forth as SEQ ID NO: 154, and the HCDR3 comprises the amino acid sequence set forth as SEQ ID NO: 156;

(i) the LCDR1 comprises the amino acid sequence set forth as SEQ ID NO: 67, the LCDR2 comprises the amino acid sequence set forth as SEQ ID NO: 58, the LCDR3 comprises the amino acid sequence set forth as SEQ ID NO: 68, the HCDR1 comprises the amino acid sequence set forth as SEQ ID NO: 158, the HCDR2 comprises the amino acid sequence set forth as SEQ ID NO: 160, and the HCDR3 comprises the amino acid sequence set forth as SEQ ID NO: 162;

(j) the LCDR1 comprises the amino acid sequence set forth as SEQ ID NO: 71, the LCDR2 comprises the amino acid sequence set forth as SEQ ID NO: 26, the LCDR3 comprises the amino acid sequence set forth as SEQ ID NO: 74, the HCDR1 comprises the amino acid sequence set forth as SEQ ID NO: 163, the HCDR2 comprises the amino acid sequence set forth as SEQ ID NO: 165, and the HCDR3 comprises the amino acid sequence set forth as SEQ ID NO: 167;

(k) the LCDR1 comprises the amino acid sequence set forth as SEQ ID NO: 2, the LCDR2 comprises the amino acid sequence set forth as SEQ ID NO: 4, the LCDR3 comprises the amino acid sequence set forth as SEQ ID NO: 6, the HCDR1 comprises the amino acid sequence set forth as SEQ ID NO: 89, the HCDR2 comprises the amino acid sequence set forth as SEQ ID NO: 91, and the HCDR3 comprises the amino acid sequence set forth as SEQ ID NO: 93;

(l) the LCDR1 comprises the amino acid sequence set forth as SEQ ID NO: 16, the LCDR2 comprises the amino acid sequence set forth as SEQ ID NO: 18, the LCDR3 comprises the amino acid sequence set forth as SEQ ID NO: 20, the HCDR1 comprises the amino acid sequence set forth as SEQ ID NO: 103, the HCDR2 comprises the amino acid sequence set forth as SEQ ID NO:105, and the HCDR3 comprises the amino acid sequence set forth as SEQ ID NO: 107; or (m) the LCDR1 comprises the amino acid sequence set forth as SEQ ID NO: 22, the LCDR2 comprises the amino acid sequence set forth as SEQ ID NO: 18, the LCDR3 comprises the amino acid sequence set forth as SEQ ID NO: 20, the HCDR1 comprises the amino acid sequence set forth as SEQ ID NO: 110, the HCDR2 comprises the amino acid sequence set forth as SEQ ID NO: 105, and the HCDR3 comprises the amino acid sequence set forth as SEQ ID NO: 113;

wherein the sequence of each complementarity determining region may differ from the given sequence at up to two amino acid positions, and wherein the monoclonal antibody specifically binds to a ROR1 polypeptide.

A second aspect of the invention relates to an isolated monoclonal antibody comprising a light chain variable domain wherein the light chain variable domain comprises a light chain complementarity determining region (LCDR)1, an LCDR2 and an LCDR3, wherein LCDR1 comprises an amino acid sequence set forth in SEQ ID NO: 30, SEQ ID NO: 24, SEQ ID NO: 9, SEQ ID NO: 37, SEQ ID NO: 44, SEQ ID NO: 50, SEQ ID NO: 56, SEQ ID NO: 67, SEQ ID NO: 71, SEQ ID NO: 2, SEQ ID NO: 16, or SEQ ID NO: 22; LCDR2 comprises an amino acid sequence set forth in SEQ ID NO: 32, SEQ ID NO: 26, SEQ ID NO: 11, SEQ ID NO: 39, SEQ ID NO: 46, SEQ ID NO: 52, SEQ ID NO: 58, SEQ ID NO: 4 or SEQ ID NO: 18; and LCDR3 comprises an amino acid sequence set forth in SEQ ID NO: 34, SEQ ID NO: 28, SEQ ID NO: 13, SEQ ID NO: 41, SEQ ID NO: 48, SEQ ID NO: 54, SEQ ID NO: 60, SEQ ID NO: 65, SEQ ID NO: 68, SEQ ID NO: 74, SEQ ID NO: 6, or SEQ ID NO: 20; wherein the sequence of each complementarity determining region may differ from the given sequence at up to two amino acid positions, and wherein the monoclonal antibody specifically binds to a ROR1 polypeptide.

A third aspect of the invention relates to an isolated monoclonal antibody comprising a heavy chain variable domain wherein the heavy chain variable domain comprises a heavy chain complementarity determining region (HCDR) 1, an HCDR2 and an HCDR3, wherein HCDR1 comprises an amino acid sequence set forth in SEQ ID NO: 121, SEQ ID NO: 115, SEQ ID NO: 96, SEQ ID NO: 127, SEQ ID NO: 134, SEQ ID NO: 140, SEQ ID NO: 146, SEQ ID NO: 152, SEQ ID NO: 158, SEQ ID NO: 163, SEQ ID NO: 89, SEQ ID NO: 103 or SEQ ID NO: 110; HCDR2 comprises an amino acid sequence set forth in SEQ ID NO: 123, SEQ ID NO: 117, SEQ ID NO: 98, SEQ ID NO: 129, SEQ ID NO: 136, SEQ ID NO: 142, SEQ ID NO: 148, SEQ ID NO: 154, SEQ ID NO: 160, SEQ ID NO: 165, SEQ ID NO: 91 or SEQ ID NO: 105; and HCDR3 comprises an amino acid sequences set forth in SEQ ID NO: 248, SEQ ID NO: 252, SEQ ID NO: 100, SEQ ID NO: 131, SEQ ID NO: 138, SEQ ID NO: 144, SEQ ID NO: 150, SEQ ID NO: 156, SEQ ID NO: 162, SEQ ID NO: 167, SEQ ID NO: 93, SEQ ID NO: 107 or SEQ ID NO: 113, wherein the sequence of each complementarity determining region may differ from the given sequence at up to two amino acid positions, and wherein the monoclonal antibody specifically binds to a ROR1 polypeptide.

The present invention also relates to an isolated antigen binding fragment of the disclosed antibodies; a composition comprising an effective amount of the disclosed antibodies or antigen binding fragments in combination with a pharmaceutically acceptable carrier; and an isolated nucleic acid molecule encoding the disclosed monoclonal antibodies or antigen binding fragments.

The invention further relates to a method of detecting cancer in a subject comprising contacting a biological sample from the subject with at least one of the disclosed isolated monoclonal antibodies or antigen binding fragments thereof; and detecting antibody bound to the sample, wherein the presence of antibody bound to the sample indicates that the subject has cancer.

Additionally, the present invention relates to a method for preventing or treating cancer in a subject, comprising administering to the subject a therapeutically effective amount of at least one of the disclosed antibodies or an antigen binding fragment thereof, a nucleic acid encoding the antibody, and/or a nucleic acid encoding the antigen binding fragment, thereby preventing or treating cancer, as well as the disclosed monoclonal antibodies or an antigen binding fragment thereof for use in the treatment or prevention of cancer.

The disclosed monoclonal antibodies specifically bind to a ROR1 polypeptide. In additional embodiments, the monoclonal antibodies specifically bind a ROR1 polypeptide with an equilibrium constant ($K_D$) of about $6 \times 10^{-9}$ M or less. In some embodiments, the monoclonal antibodies specifically bind a ROR1 polypeptide with a $K_D$ of about $1.6 \times 10^{-9}$ M or less, about $2 \times 10^{-9}$ M or less, about $3 \times 10^{-9}$ M or less, about $4 \times 10^{-9}$ M or less or about $5 \times 10^{-9}$ M or less.

The disclosed monoclonal antibodies provide a number of advantages over known ROR1 antibodies, in particular, those based on clones A and F (more details below). Compared to ROR1 antibodies described in the prior art, the antibodies described herein may have one or more of the following advantages, amongst others: a relatively high binding affinity for ROR1 (e.g. a low $K_D$), bind to a unique ROR1 epitope, can bind in scFv format, show toxicity on cells expressing ROR1 (e.g. cancer cells such as CLL), can be internalised, invoke different cytokine release, show enhanced persistence, and have decreased immunogenicity.

DETAILED DESCRIPTION

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs.

Administration: The introduction of a composition into a subject by a chosen route. Administration can be local or systemic. For example, if the chosen route is intravenous, the composition is administered by introducing the composition into a vein of the subject. In some examples a disclosed antibody specific for a ROR1 polypeptide, is administered to a subject.

Agent: Any substance or any combination of substances that is useful for achieving an end or result; for example, a substance or combination of substances useful for preventing or treating cancer. Agents include, and are not limited to, proteins, nucleic acid molecules, compounds, small molecules, organic compounds, inorganic compounds, or other molecules of interest. An agent can include a therapeutic agent (such as an anti-viral agent), a diagnostic agent or a pharmaceutical agent. In some embodiments, the agent is a polypeptide agent (such as a neutralizing antibody). The skilled artisan will understand that particular agents may be useful to achieve more than one result.

Amino acid substitution: The replacement of one amino acid in a peptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as a ROR1 polypeptide, or an immunogenic fragment thereof. Immunoglobulin genes include the kappa, lambda, alpha, gamma, delta, epsilon and mu constant region genes, as well as the myriad immunoglobulin variable region genes.

Antibodies exist, for example, as intact immunoglobulins and as a number of well characterised fragments produced by digestion with various peptidases. For instance, Fabs, Fvs, scFvs that specifically bind to a ROR1 polypeptide, or fragments of this polypeptide, are specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, *Pierce Catalog and Handbook*, 1994-1995 (Pierce Chemical Co., Rockford, Ill.); Kuby, *Immunology*, 3$^{rd}$ Ed., W.H. Freeman & Co., New York, 1997.

Antibody fragments include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Antigen binding fragments of an antibody can be produced by the modification of whole antibodies or those synthesized de novo using recombinant DNA methodologies. In some examples, the term antibody includes the amino acid sequences of one or more of the CDRs from the antibody grafted onto a scaffold.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. The disclosed antibodies can be class switched.

Each heavy and light chain contains a constant region and a variable region, (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest,* U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for antigen binding. The sequences of the framework regions of different light or heavy chains are relatively conserved within a species. The framework region of an antibody, that is the combined framework regions of the constituent light and heavy chains, serves to position and align the CDRs in three-dimensional space.

The CDRs of each chain are typically referred to as CDR1, CDR2, and CDR3 (from the N-terminus to C-terminus), and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs can also be referred to as CDR L1, CDR L2 and CDR L3, or LCDR1, LCDR2 and LCDR3. Heavy chain CDRs can be referred to as CDR H1, CDR H2 and CDR H3, or HCDR1, HCDR2 and HCDR3.

References to "$V_H$" or "VH" refer to the variable region of an immunoglobulin heavy chain, including that of an antibody fragment, such as Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas". In some embodiments, monoclonal antibodies can be humanized monoclonal antibodies. In some embodiments, monoclonal antibodies can be chimeric antibodies. In some examples monoclonal antibodies are isolated from a subject. The amino acid sequences of such isolated monoclonal antibodies can be determined.

A "humanised" antibody is an antibody including a human framework region and one or more CDRs from a non-human (such as a chimpanzee, mouse, rat, or synthetic) immunoglobulin. The non-human antibody providing the CDRs is termed a "donor", and the human antibody providing the framework is termed an "acceptor". In one embodiment, all the CDRs are from the donor antibody in a humanised antibody. Constant regions need not be present, but if they are, they must be substantially identical to human antibody constant regions, such as at least about 85-90%, such as about 95% or more identical. Hence, all parts of a humanised antibody, except possibly the CDRs, are substantially identical to corresponding parts of natural human antibody sequences. A "humanised antibody" can include a humanised light chain and a humanised heavy chain. A humanised antibody binds to the same antigen as the donor antibody that provides the CDRs. The acceptor framework of a humanised antibody may have a limited number of substitutions by amino acids taken from the donor framework. Humanised or other monoclonal antibodies can have additional conservative amino acid substitutions which have substantially no effect on antigen binding or other immunoglobulin functions. Humanised immunoglobulins can be constructed by means of genetic engineering (for example, see U.S. Pat. No. 5,585,089). Preferably, the antibodies of the present invention are humanised.

A "chimeric" antibody is an antibody which includes sequences from two different antibodies, which typically are of different species. For example, a chimeric antibody may comprise heavy and light chain variable regions derived from a first species and heavy and light chain constant regions derived from a second species. The variable and constant regions of the light chain may be derived from a first species while the variable region of the heavy chain may be derived from the first species and the constant region of the heavy chain is derived from a second species.

A "neutralizing antibody" is an antibody which reduces effect of a virus, bacteria or tumour for example, by binding to a specific antigen on the virus, bacteria or tumour. In some examples, an antibody that is specific for a ROR1 neutralises the effect of the tumour.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. Antigens can include peptides derived from a pathogen of interest or from a cancerous cell. Exemplary pathogens include bacteria, fungi, viruses and parasites. In some embodiments, an antigen is derived from a cancerous cell such as a haematological cancerous cell (chronic lymphocytic leukaemia—CLL, acute lymphoblastic leukaemia, mantle cell lymphoma) or a solid malignancy (breast, pancreatic, melanoma). In some embodiments, the antigen is a ROR1 polypeptide or antigenic fragment thereof.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody.

Binding affinity: Affinity of an antibody or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, at least about $5.0 \times 10^{-8}$ M, or at least about $1 \times 10^{-8}$ M.

Clonal variant: Any sequence, which differs by one or more nucleotides or amino acids, in presence of V region with identical mutations compared to the germline, identical VDJ or VJ gene usage, and identical D and J length. The "germline" sequence is intended to be the sequence coding for the antibody/immunoglobulin (or of any fragment thereof) deprived of mutations, for example somatic mutations. The percentage of homology represents an indication of the mutational events which any type of heavy chain portion undergoes after contact with an antigen.

Conjugate: A complex of two molecules linked together, for example, linked together by a covalent bond. In one embodiment, an antibody is linked to an effector molecule; for example, an antibody that specifically binds to a ROR1 polypeptide, covalently linked to an effector molecule or to a toxin. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules." In one embodiment, an antibody linked to an effector molecule is further joined to a lipid or other molecule to a protein or peptide to increase its half-life in the body.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a sample obtained from a healthy patient. In other embodiments, the control is a tissue sample obtained from a patient diagnosed with cancer that serves as a positive control. In still other embodiments, the control is a historical control or standard reference value or range of values (such as a previously tested control sample, such as a group of infected patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In particular embodiments of the invention, the antibody or fragment thereof can be labelled with a detectable marker.

Detecting: To identify the existence, presence, or fact of something. General methods of detecting are known to the skilled artisan (see, for example, U.S. Pat. No. 7,635,476) and may be supplemented with the protocols and reagents disclosed herein. For example, included herein are methods of detecting a cell that expresses a ROR1 polypeptide in a subject.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on the surface of ROR1.

Framework Region: Amino acid sequences interposed between CDRs. The term includes variable light and variable heavy framework regions. The framework regions serve to hold the CDRs in an appropriate orientation for antigen binding.

Fc polypeptide: The polypeptide comprising the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index. For IgA, the Fc region comprises immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in size of the tumour/cancer, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B-cell, a nucleic acid, peptide, protein, heavy chain domain or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids. In some examples an antibody, such as an antibody specific for a ROR1 polypeptide can be isolated, for example isolated from a subject with a tumour expressing ROR1.

$K_d$: The dissociation constant for a given interaction, such as a polypeptide ligand interaction or an antibody antigen interaction. For example, for the bimolecular interaction of an antibody (such as any of the antibodies disclosed herein) and an antigen (such as a ROR1 polypeptide) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed antibody is labeled.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

ClustalW is a program that aligns three or more sequences in a computationally efficient manner. Aligning multiple sequences highlights areas of similarity which may be associated with specific features that have been more highly conserved than other regions. Thus, this program can classify sequences for phylogenetic analysis, which aims to model the substitutions that have occurred over evolution and derive the evolutionary relationships between sequences. The ClustalW multiple sequence alignment web form is available on the internet from EMBL-EBI (ebi.ac.uk/Tools/msa/clustalw2/), see also Larkin et al., *Bioinformatics* 2007 23(21): 2947-2948.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids, which include, but are not limited to, water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples a pharmaceutical agent includes one or more of the disclosed antibodies.

Polypeptide: Any chain of amino acids, regardless of length or post-translational modification (e.g., glycosylation or phosphorylation). In one embodiment, the polypeptide is a ROR1 polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms may be used as described above. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet (along with a description of how to determine sequence identity using this program).

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Nucleic acids that "selectively hybridise" or "selectively bind" do so under moderately or highly stringent conditions that excludes non-related nucleotide sequences. In nucleic acid hybridisation reactions, the conditions used to achieve a particular level of stringency will vary, depending on the nature of the nucleic acids being hybridised. For example, the length, degree of complementarity, nucleotide sequence composition (for example, GC v. AT content), and nucleic acid type (for example, RNA versus DNA) of the hybridising regions of the nucleic acids can be considered in selecting hybridisation conditions. An additional consideration is whether one of the nucleic acids is immobilised, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a tumour, for example ROR1) and do not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar, such as less than about $10^{-7}$ Molar, $10^{-8}$ Molar, $10^{-9}$, or even less than about $10^{-10}$ Molar.

Therapeutic agent: Used in a generic sense, it includes treating agents, prophylactic agents, and replacement agents.

Therapeutically effective amount or effective amount: A quantity of a specific substance, such as a disclosed antibody, sufficient to achieve a desired effect in a subject being treated. For instance, this can be the amount necessary to inhibit tumour growth. In several embodiments, a therapeutically effective amount is the amount necessary to reduce a symptom of the disease. When administered to a subject, a dosage will generally be used that will achieve target tissue concentrations that has been shown to achieve a desired in vitro effect.

Vector: A nucleic acid molecule may be introduced into a host cell by a vector, thereby producing a transformed host cell. A vector may include nucleic acid sequences that permit it to replicate in a host cell, such as an origin of replication. A vector may also include one or more selectable marker genes and other genetic elements known in the art.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Specifically Bind to ROR1

Clinically and diagnostically useful rat-derived monoclonal antibodies (MAb) that specifically bind ROR1 are disclosed herein.

In some embodiments the monoclonal antibodies specifically bind a ROR1 polypeptide with an equilibrium constant ($K_d$) of about $6\times10^{-9}$ M or less. In some embodiments, the monoclonal antibodies specifically bind a ROR1 polypeptide with a $K_d$ of about $1.6\times10^{-9}$ M or less, about $2\times10^{-9}$ M or less, about $3\times10^{-9}$ M or less, about $4\times10^{-9}$ M or less or about $5\times10^{-9}$ M or less.

The MAb can be of any isotype. The MAb can be, for example, an IgM or an IgG antibody, such as $IgG_1$ or an $IgG_2$. The class of an antibody that specifically binds ROR1 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds ROR1 that was originally IgM may be class switched to an IgG. Class switching can be used to convert one IgG subclass to another, such as from $IgG_1$ to $IgG_2$.

The monoclonal antibodies disclosed herein can be rat antibodies, and can include a rat framework region. In some preferred embodiments, the antibodies are humanised, and thus include one or more human framework regions. In some embodiments, the MAbs disclosed herein are chimeric antibodies. In some embodiments, the MAbs include rat and human regions.

The monoclonal antibody can specifically bind a ROR1 polypeptide. Preferably, the monoclonal antibody can specifically bind a human ROR1 polypeptide. The antibody preferably comprises a heavy chain and a light chain and preferably each VH and VL is composed of three CDRs and four FWRs, arranged from amino-terminus to carboxy-terminus in the following order: FWR1, CDR1, FWR2, CDR2, FWR3, CDR3, FWR4 as described above.

In a first embodiment, the isolated monoclonal antibody comprises a light chain variable domain and a heavy chain variable domain wherein the light chain variable domain comprises a light chain complementarity determining region (LCDR)1, an LCDR2 and an LCDR3, wherein LCDR1 comprises an amino acid sequence set forth in SEQ ID NO: 30, SEQ ID NO: 24, SEQ ID NO: 9, SEQ ID NO: 37, SEQ ID NO: 44, SEQ ID NO: 50, SEQ ID NO: 56, SEQ ID NO: 67, SEQ ID NO: 71, SEQ ID NO: 2, SEQ ID NO: 16, or SEQ ID NO: 22; LCDR2 comprises an amino acid sequence set forth in SEQ ID NO: 32, SEQ ID NO: 26, SEQ ID NO: 11, SEQ ID NO: 39, SEQ ID NO: 46, SEQ ID NO: 52, SEQ ID NO: 58, SEQ ID NO: 4 or SEQ ID NO: 18; and LCDR3 comprises an amino acid sequence set forth in SEQ ID NO: 34, SEQ ID NO: 28, SEQ ID NO: 13, SEQ ID NO: 41, SEQ ID NO: 48, SEQ ID NO: 54, SEQ ID NO: 60, SEQ ID NO: 65, SEQ ID NO: 68, SEQ ID NO: 74, SEQ ID NO: 6, or SEQ ID NO: 20; and wherein the heavy chain variable domain comprises a heavy chain complementarity determining region (HCDR)1, an HCDR2 and an HCDR3, wherein HCDR1 comprises an amino acid sequence set forth in SEQ ID NO: 121, SEQ ID NO: 115, SEQ ID NO: 96, SEQ ID NO: 127, SEQ ID NO: 134, SEQ ID NO: 140, SEQ ID NO: 146, SEQ ID NO: 152, SEQ ID NO: 158, SEQ ID NO: 163, SEQ ID NO: 89, SEQ ID NO: 103 or SEQ ID NO: 110; HCDR2 comprises an amino acid sequence set forth in SEQ ID NO: 123, SEQ ID NO: 117, SEQ ID NO: 98, SEQ ID NO: 129, SEQ ID NO: 136, SEQ ID NO: 142, SEQ ID NO: 148, SEQ ID NO: 154, SEQ ID NO: 160, SEQ ID NO: 165, SEQ ID NO: 91 or SEQ ID NO: 105; and HCDR3 comprises an amino acid sequences set forth in SEQ ID NO: 248, SEQ ID NO: 252, SEQ ID NO: 100, SEQ ID NO: 131, SEQ ID NO: 138, SEQ ID NO: 144, SEQ ID NO: 150, SEQ ID NO: 156, SEQ ID NO: 162, SEQ ID NO: 167, SEQ ID NO: 93, SEQ ID NO: 107 or SEQ ID NO: 113, wherein the sequence of each complementarity determining region may differ from the given sequence at up to two amino acid positions, and wherein the monoclonal antibody specifically binds to a ROR1 polypeptide.

The isolated monoclonal antibody may comprises a light chain variable domain and a heavy chain variable domain wherein the light chain variable domain comprises a light chain complementarity determining region (LCDR)1, an LCDR2 and an LCDR3, wherein LCDR1 comprises an amino acid sequence set forth in SEQ ID NO: 30, SEQ ID NO: 24, SEQ ID NO: 9, SEQ ID NO: 37, SEQ ID NO: 44, SEQ ID NO: 50, SEQ ID NO: 56, SEQ ID NO: 67 or SEQ ID NO: 71; LCDR2 comprises an amino acid sequence set forth in SEQ ID NO: 32, SEQ ID NO: 26, SEQ ID NO: 11, SEQ ID NO: 39, SEQ ID NO: 46, SEQ ID NO: 52 or SEQ ID NO: 58; and LCDR3 comprises an amino acid sequence set forth in SEQ ID NO: 34, SEQ ID NO: 28, SEQ ID NO: 13, SEQ ID NO: 41, SEQ ID NO: 48, SEQ ID NO: 54, SEQ ID NO: 60, SEQ ID NO: 65, SEQ ID NO: 68 or SEQ ID NO: 74; and wherein the heavy chain variable domain comprises a heavy chain complementarity determining region (HCDR) 1, an HCDR2 and an HCDR3, wherein HCDR1 comprises an amino acid sequence set forth in SEQ ID NO: 121, SEQ ID NO: 115, SEQ ID NO: 96, SEQ ID NO: 127, SEQ ID NO: 134, SEQ ID NO: 140, SEQ ID NO: 146, SEQ ID NO: 152, SEQ ID NO: 158 or SEQ ID NO: 163; HCDR2 comprises an amino acid sequence set forth in SEQ ID NO: 123, SEQ ID NO: 117, SEQ ID NO: 98, SEQ ID NO: 129, SEQ ID NO: 136, SEQ ID NO: 142, SEQ ID NO: 148, SEQ ID NO: 154, SEQ ID NO: 160 or SEQ ID NO: 165; and HCDR3 comprises an amino acid sequences set forth in SEQ ID NO: 248, SEQ ID NO: 252, SEQ ID NO: 100, SEQ ID NO: 131, SEQ ID NO: 138, SEQ ID NO: 144, SEQ ID NO: 150, SEQ ID NO: 156, SEQ ID NO: 162 or SEQ ID NO: 167, wherein the sequence of each complementarity determining region may differ from the given sequence at up to two amino acid positions, and wherein the monoclonal antibody specifically binds to a ROR1 polypeptide.

Preferably the isolated monoclonal antibody comprises a light chain variable domain, wherein the light chain variable domain comprises a light chain complementarity determining region (LCDR)1, an LCDR2 and an LCDR3, wherein (a) the LCDR1 comprises the amino acid sequence set forth as SEQ ID NO: 30, the LCDR2 comprises the amino acid sequence set forth as SEQ ID NO: 32, and the LCDR3 comprises the amino acid sequence set forth as SEQ ID NO: 34;

(b) the LCDR1 comprises the amino acid sequence set forth as SEQ ID NO: 24, the LCDR2 comprises the amino acid sequence set forth as SEQ ID NO: 26, and the LCDR3 comprises the amino acid sequence set forth as SEQ ID NO: 28;

(c) the LCDR1 comprises the amino acid sequence set forth as SEQ ID NO: 9, the LCDR2 comprises the amino acid sequence set forth as SEQ ID NO: 11, and the LCDR3 comprises the amino acid sequence set forth as SEQ ID NO: 13;

(d) the LCDR1 comprises the amino acid sequence set forth as SEQ ID NO: 37, the LCDR2 comprises the amino acid sequence set forth as SEQ ID NO: 39, and the LCDR3 comprises the amino acid sequence set forth as SEQ ID NO: 41;

(e) the LCDR1 comprises the amino acid sequence set forth as SEQ ID NO: 44, the LCDR2 comprises the amino acid sequence set forth as SEQ ID NO: 46, and the LCDR3 comprises the amino acid sequence set forth as SEQ ID NO: 48;

(f) the LCDR1 comprises the amino acid sequence set forth as SEQ ID NO: 50, the LCDR2 comprises the amino acid sequence set forth as SEQ ID NO: 52, and the LCDR3 comprises the amino acid sequence set forth as SEQ ID NO: 54;

(g) the LCDR1 comprises the amino acid sequence set forth as SEQ ID NO: 56, the LCDR2 comprises the amino acid sequence set forth as SEQ ID NO: 58, and the LCDR3 comprises the amino acid sequence set forth as SEQ ID NO: 60;

(h) the LCDR1 comprises the amino acid sequence set forth as SEQ ID NO: 44, the LCDR2 comprises the amino acid sequence set forth as SEQ ID NO: 46, and the LCDR3 comprises the amino acid sequence set forth as SEQ ID NO: 65;

(i) the LCDR1 comprises the amino acid sequence set forth as SEQ ID NO: 67, the LCDR2 comprises the amino acid sequence set forth as SEQ ID NO: 58, and the LCDR3 comprises the amino acid sequence set forth as SEQ ID NO: 68;

(j) the LCDR1 comprises the amino acid sequence set forth as SEQ ID NO: 71, the LCDR2 comprises the amino acid sequence set forth as SEQ ID NO: 26, and the LCDR3 comprises the amino acid sequence set forth as SEQ ID NO: 74;

(k) the LCDR1 comprises the amino acid sequence set forth as SEQ ID NO: 2, the LCDR2 comprises the amino acid sequence set forth as SEQ ID NO: 4, and the LCDR3 comprises the amino acid sequence set forth as SEQ ID NO: 6;

(l) the LCDR1 comprises the amino acid sequence set forth as SEQ ID NO: 16, the LCDR2 comprises the amino acid sequence set forth as SEQ ID NO: 18, and the LCDR3 comprises the amino acid sequence set forth as SEQ ID NO: 20; or (m) the LCDR1 comprises the amino acid sequence set forth as SEQ ID NO: 22, the LCDR2 comprises the amino acid sequence set forth as SEQ ID NO: 18, and the LCDR3 comprises the amino acid sequence set forth as SEQ ID NO: 20;

wherein the sequence of each complementarity determining region may differ from the given sequence at up to two amino acid positions, and wherein the monoclonal antibody specifically binds to a ROR1 polypeptide.

Preferably the isolated monoclonal antibody comprises a heavy chain variable domain, wherein the heavy chain variable domain comprises a heavy chain complementarity determining region (HCDR)1, an HCDR2 and an HCDR3, wherein (a) the HCDR1 comprises the amino acid sequence set forth as SEQ ID NO: 121, the HCDR2 comprises the amino acid sequence set forth as SEQ ID NO: 123, and the HCDR3 comprises the amino acid sequence set forth as SEQ ID NO: 248;

(b) the HCDR1 comprises the amino acid sequence set forth as SEQ ID NO: 115, the HCDR2 comprises the amino acid sequence set forth as SEQ ID NO: 117, and the HCDR3 comprises the amino acid sequence set forth as SEQ ID NO: 252;

(c) the HCDR1 comprises the amino acid sequence set forth as SEQ ID NO: 96, the HCDR2 comprises the amino acid sequence set forth as SEQ ID NO: 98, and the HCDR3 comprises the amino acid sequence set forth as SEQ ID NO: 100;

(d) the HCDR1 comprises the amino acid sequence set forth as SEQ ID NO: 127, the HCDR2 comprises the amino acid sequence set forth as SEQ ID NO: 129, and the HCDR3 comprises the amino acid sequence set forth as SEQ ID NO: 131;

(e) the HCDR1 comprises the amino acid sequence set forth as SEQ ID NO: 134, the HCDR2 comprises the amino acid sequence set forth as SEQ ID NO: 136, and the HCDR3 comprises the amino acid sequence set forth as SEQ ID NO: 138;

(f) the HCDR1 comprises the amino acid sequence set forth as SEQ ID NO: 140, the HCDR2 comprises the amino acid sequence set forth as SEQ ID NO: 142, and the HCDR3 comprises the amino acid sequence set forth as SEQ ID NO: 144;

(g) the HCDR1 comprises the amino acid sequence set forth as SEQ ID NO: 146, the HCDR2 comprises the amino acid sequence set forth as SEQ ID NO: 148, and the HCDR3 comprises the amino acid sequence set forth as SEQ ID NO: 150;

(h) the HCDR1 comprises the amino acid sequence set forth as SEQ ID NO: 152, the HCDR2 comprises the amino acid sequence set forth as SEQ ID NO: 154, and the HCDR3 comprises the amino acid sequence set forth as SEQ ID NO: 156;

(i) the HCDR1 comprises the amino acid sequence set forth as SEQ ID NO: 158, the HCDR2 comprises the amino acid sequence set forth as SEQ ID NO: 160, and the HCDR3 comprises the amino acid sequence set forth as SEQ ID NO: 162;

(j) the HCDR1 comprises the amino acid sequence set forth as SEQ ID NO: 163, the HCDR2 comprises the amino acid sequence set forth as SEQ ID NO: 165, and the HCDR3 comprises the amino acid sequence set forth as SEQ ID NO: 167;

(k) the HCDR1 comprises the amino acid sequence set forth as SEQ ID NO: 89, the HCDR2 comprises the amino acid sequence set forth as SEQ ID NO: 91, and the HCDR3 comprises the amino acid sequence set forth as SEQ ID NO: 93;

(l) the HCDR1 comprises the amino acid sequence set forth as SEQ ID NO: 103, the HCDR2 comprises the amino acid sequence set forth as SEQ ID NO: 105, and the HCDR3 comprises the amino acid sequence set forth as SEQ ID NO: 107; or (m) the HCDR1 comprises the amino acid sequence set forth as SEQ ID NO: 110, the HCDR2 comprises the amino acid sequence set forth as SEQ ID NO: 105, and the HCDR3 comprises the amino acid sequence set forth as SEQ ID NO: 113;

wherein the sequence of each complementarity determining region may differ from the given sequence at up to two amino acid positions, and wherein the monoclonal antibody specifically binds to a ROR1 polypeptide.

In a particularly preferred embodiment, the isolated monoclonal antibody comprises a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein (a) the LCDR1 comprises the amino acid sequence set forth as SEQ ID NO: 30, the LCDR2 comprises the amino acid sequence set forth as SEQ ID NO: 32, the LCDR3 comprises the amino acid sequence set forth as SEQ ID NO: 34, the HCDR1 comprises the amino acid sequence set forth as SEQ ID NO: 121, the HCDR2 comprises the amino acid sequence set forth as SEQ ID NO: 123, and the HCDR3 comprises the amino acid sequence set forth as SEQ ID NO: 248;

(b) the LCDR1 comprises the amino acid sequence set forth as SEQ ID NO: 24, the LCDR2 comprises the amino acid sequence set forth as SEQ ID NO: 26, the LCDR3 comprises the amino acid sequence set forth as SEQ ID NO: 28, the HCDR1 comprises the amino acid sequence set forth as SEQ ID NO: 115, the HCDR2 comprises the amino acid sequence set forth as SEQ ID NO: 117, and the HCDR3 comprises the amino acid sequence set forth as SEQ ID NO: 252;

(c) the LCDR1 comprises the amino acid sequence set forth as SEQ ID NO: 9, the LCDR2 comprises the amino acid sequence set forth as SEQ ID NO: 11, the LCDR3 comprises the amino acid sequence set forth as SEQ ID NO: 13, the HCDR1 comprises the amino acid sequence set forth as SEQ ID NO: 96, the HCDR2 comprises the amino acid sequence set forth as SEQ ID NO: 98, and the HCDR3 comprises the amino acid sequence set forth as SEQ ID NO: 100;

(d) the LCDR1 comprises the amino acid sequence set forth as SEQ ID NO: 37, the LCDR2 comprises the amino acid sequence set forth as SEQ ID NO: 39, the LCDR3 comprises the amino acid sequence set forth as SEQ ID NO: 41, the HCDR1 comprises the amino acid sequence set forth as SEQ ID NO: 127, the HCDR2 comprises the amino acid sequence set forth as SEQ ID NO: 129, and the HCDR3 comprises the amino acid sequence set forth as SEQ ID NO: 131;

(e) the LCDR1 comprises the amino acid sequence set forth as SEQ ID NO: 44, the LCDR2 comprises the amino acid sequence set forth as SEQ ID NO: 46, the LCDR3 comprises the amino acid sequence set forth as SEQ ID NO: 48, the HCDR1 comprises the amino acid sequence set forth as SEQ ID NO: 134, the HCDR2 comprises the amino acid sequence set forth as SEQ ID NO: 136, and the HCDR3 comprises the amino acid sequence set forth as SEQ ID NO: 138;

(f) the LCDR1 comprises the amino acid sequence set forth as SEQ ID NO: 50, the LCDR2 comprises the amino acid sequence set forth as SEQ ID NO: 52, the LCDR3 comprises the amino acid sequence set forth as SEQ ID NO: 54, the HCDR1 comprises the amino acid sequence set forth as SEQ ID NO: 140, the HCDR2 comprises the amino acid sequence set forth as SEQ ID NO: 142, and the HCDR3 comprises the amino acid sequence set forth as SEQ ID NO: 144;

(g) the LCDR1 comprises the amino acid sequence set forth as SEQ ID NO: 56, the LCDR2 comprises the amino acid sequence set forth as SEQ ID NO: 58, the LCDR3 comprises the amino acid sequence set forth as SEQ ID NO: 60, the HCDR1 comprises the amino acid sequence set forth as SEQ ID NO: 146, the HCDR2 comprises the amino acid sequence set forth as SEQ ID NO: 148, and the HCDR3 comprises the amino acid sequence set forth as SEQ ID NO: 150;

(h) the LCDR1 comprises the amino acid sequence set forth as SEQ ID NO: 44, the LCDR2 comprises the amino acid sequence set forth as SEQ ID NO: 46, the LCDR3 comprises the amino acid sequence set forth as SEQ ID NO: 65, the HCDR1 comprises the amino acid sequence set forth as SEQ ID NO: 152, the HCDR2 comprises the amino acid sequence set forth as SEQ ID NO: 154, and the HCDR3 comprises the amino acid sequence set forth as SEQ ID NO: 156;

(i) the LCDR1 comprises the amino acid sequence set forth as SEQ ID NO: 67, the LCDR2 comprises the amino acid sequence set forth as SEQ ID NO: 58, the LCDR3 comprises the amino acid sequence set forth as SEQ ID NO: 68, the HCDR1 comprises the amino acid sequence set forth as SEQ ID NO: 158, the HCDR2 comprises the amino acid sequence set forth as SEQ ID NO: 160, and the HCDR3 comprises the amino acid sequence set forth as SEQ ID NO: 162;

(j) the LCDR1 comprises the amino acid sequence set forth as SEQ ID NO: 71, the LCDR2 comprises the amino acid sequence set forth as SEQ ID NO: 26, the LCDR3 comprises the amino acid sequence set forth as SEQ ID NO: 74, the HCDR1 comprises the amino acid sequence set forth as SEQ ID NO: 163, the HCDR2 comprises the amino acid sequence set forth as SEQ ID NO: 165, and the HCDR3 comprises the amino acid sequence set forth as SEQ ID NO: 167;

(k) the LCDR1 comprises the amino acid sequence set forth as SEQ ID NO: 2, the LCDR2 comprises the amino acid sequence set forth as SEQ ID NO: 4, the LCDR3 comprises the amino acid sequence set forth as SEQ ID NO: 6, the HCDR1 comprises the amino acid sequence set forth as SEQ ID NO: 89, the HCDR2 comprises the amino acid sequence set forth as SEQ ID NO: 91, and the HCDR3 comprises the amino acid sequence set forth as SEQ ID NO: 93;

(l) the LCDR1 comprises the amino acid sequence set forth as SEQ ID NO: 16, the LCDR2 comprises the amino acid sequence set forth as SEQ ID NO: 18, the LCDR3 comprises the amino acid sequence set forth as SEQ ID NO: 20, the HCDR1 comprises the amino acid sequence set forth as SEQ ID NO: 103, the HCDR2 comprises the amino acid sequence set forth as SEQ ID NO:105, and the HCDR3 comprises the amino acid sequence set forth as SEQ ID NO: 107; or (m) the LCDR1 comprises the amino acid sequence set forth as SEQ ID NO: 22, the LCDR2 comprises the amino acid sequence set forth as SEQ ID NO: 18, the LCDR3 comprises the amino acid sequence set forth as SEQ ID NO: 20, the HCDR1 comprises the amino acid sequence set forth as SEQ ID NO: 110, the HCDR2 comprises the amino acid sequence set forth as SEQ ID NO: 105, and the HCDR3 comprises the amino acid sequence set forth as SEQ ID NO: 113;

wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 30, the LCDR2 comprises the amino acid sequence set forth as SEQ ID NO: 32, the LCDR3 comprises the amino acid sequence set forth as SEQ ID NO: 34, the HCDR1 comprises the amino acid sequence set forth as SEQ ID NO: 121, the HCDR2 comprises the amino acid sequence set forth as SEQ ID NO: 123, and the HCDR3 comprises the amino acid sequence set forth as SEQ ID NO: 248; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 24, the LCDR2 comprises the amino acid sequence set forth as SEQ ID NO: 26, the LCDR3 comprises the amino acid sequence set forth as SEQ ID NO: 28, the HCDR1 comprises the amino acid sequence set forth as SEQ ID NO: 115, the HCDR2 comprises the amino acid sequence set forth as SEQ ID NO: 117, and the HCDR3 comprises the amino acid sequence set forth as SEQ ID NO: 252; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 9, the LCDR2 comprises the amino acid sequence set forth as SEQ ID NO: 11, the LCDR3 comprises the amino acid sequence set forth as SEQ ID NO: 13, the HCDR1 comprises the amino acid sequence set forth as SEQ ID NO: 96, the HCDR2 comprises the amino acid sequence set forth as SEQ ID NO: 98, and the HCDR3 comprises the amino acid sequence set forth as SEQ ID NO: 100; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 37, the LCDR2 comprises the amino acid sequence set forth as SEQ ID NO: 39, the LCDR3 comprises the amino acid sequence set forth as SEQ ID NO: 41, the HCDR1 comprises the amino acid sequence set forth as SEQ ID NO: 127, the HCDR2 comprises the amino acid sequence set forth as SEQ ID NO: 129, and the HCDR3 comprises the amino acid sequence set forth as SEQ ID NO: 131; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 44, the LCDR2 comprises the amino acid sequence set forth as SEQ ID NO: 46, the LCDR3 comprises the amino acid sequence set forth as SEQ ID NO: 48, the HCDR1 comprises the amino acid sequence set forth as SEQ ID NO: 134, the HCDR2 comprises the amino acid sequence set forth as SEQ ID NO: 136, and the HCDR3 comprises the amino acid sequence set forth as SEQ ID NO: 138; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 50, the LCDR2 comprises the amino acid sequence set forth as SEQ ID NO: 52, the LCDR3 comprises the amino acid sequence set forth as SEQ ID NO: 54, the HCDR1 comprises the amino acid sequence set forth as SEQ ID NO: 140, the HCDR2 comprises the amino acid sequence set forth as SEQ ID NO: 142, and the HCDR3 comprises the amino acid sequence set forth as SEQ ID NO: 144; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 56, the LCDR2 comprises the amino acid sequence set forth as SEQ ID NO: 58, the LCDR3 comprises the amino acid sequence set forth as SEQ ID NO: 60, the HCDR1 comprises the amino acid sequence set forth as SEQ ID NO: 146, the HCDR2 comprises the amino acid sequence set forth as SEQ ID NO: 148, and the HCDR3 comprises the amino acid sequence set forth as SEQ ID NO: 150; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 44, the LCDR2 comprises the amino acid sequence set forth as SEQ ID NO: 46, the LCDR3 comprises the amino acid sequence set forth as SEQ ID NO: 65, the HCDR1 comprises the amino acid sequence set forth as SEQ ID NO: 152, the HCDR2 comprises the amino acid sequence set forth as SEQ ID NO: 154, and the HCDR3 comprises the amino acid sequence set forth as SEQ ID NO: 156; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 67, the LCDR2 comprises the amino acid sequence set forth as SEQ ID NO: 58, the LCDR3 comprises the amino acid sequence set forth as SEQ ID NO: 68, the HCDR1 comprises the amino acid sequence set forth as SEQ ID NO: 158, the HCDR2 comprises the amino acid sequence set forth as SEQ ID NO: 160, and the HCDR3 comprises the amino acid sequence set forth as SEQ ID NO: 162; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 71, the LCDR2 comprises the amino acid sequence set forth as SEQ ID NO: 26, the LCDR3 comprises the amino acid sequence set forth as SEQ ID NO: 74, the HCDR1 comprises the amino acid sequence set forth as SEQ ID NO: 163, the HCDR2 comprises the amino acid sequence set forth as SEQ ID NO: 165, and the HCDR3 comprises the amino acid sequence set forth as SEQ ID NO: 167; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 2, the LCDR2 comprises the amino acid sequence set forth as SEQ ID NO: 4, the LCDR3 comprises the amino acid sequence set forth as SEQ ID NO: 6, the HCDR1 comprises the amino acid sequence set forth as SEQ ID NO: 89, the HCDR2 comprises the amino acid sequence set forth as SEQ ID NO: 91, and the HCDR3 comprises the amino acid sequence set forth as SEQ ID NO: 93; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 16, the LCDR2 comprises the amino acid sequence set forth as SEQ ID NO: 18, the LCDR3 comprises the amino acid sequence set forth as SEQ ID NO: 20, the HCDR1 comprises the amino acid sequence set forth as SEQ ID NO: 103, the HCDR2 comprises the amino acid sequence set forth as SEQ ID NO:105, and the HCDR3 comprises the amino acid sequence set forth as SEQ ID NO: 107; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 22, the LCDR2 comprises the amino acid sequence set forth as SEQ ID NO: 18, the LCDR3 comprises the amino acid sequence set forth as SEQ ID NO: 20, the HCDR1 comprises the amino acid sequence set forth as SEQ ID NO: 110, the HCDR2 comprises the amino acid sequence set forth as SEQ ID NO: 105, and the HCDR3 comprises the amino acid sequence set forth as SEQ ID NO: 113; wherein the sequence of each complementarity determining region may differ from the given sequence at up to two amino acid positions, and wherein the monoclonal antibody specifically binds to a ROR1 polypeptide.

The isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 30, the LCDR2 comprises the amino acid sequence set forth as SEQ ID NO: 32, the LCDR3 comprises the amino acid sequence set forth as SEQ ID NO: 34, the HCDR1 comprises the amino acid sequence set forth as SEQ ID NO: 121, the HCDR2 comprises the amino acid sequence set forth as SEQ ID NO: 123, and the HCDR3 comprises the amino acid sequence set forth as SEQ ID NO: 248; wherein the sequence of each complementarity determining region may differ from the given sequence at up to two amino acid positions, and wherein the monoclonal antibody specifically binds to a ROR1 polypeptide; or the isolated monoclonal antibody may comprise a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein the LCDR1 comprises the amino acid sequence set forth as SEQ ID NO: 24, the LCDR2 comprises the amino acid sequence set forth as SEQ ID NO: 26, the LCDR3 comprises the amino acid sequence set forth as SEQ ID NO: 28, the HCDR1 comprises the amino acid sequence set forth as SEQ ID NO: 115, the HCDR2 comprises the amino acid sequence set forth as SEQ ID NO: 117, and the HCDR3 comprises the amino acid sequence set forth as SEQ ID NO: 252; wherein the sequence of each complementarity determining region may differ from the given sequence at up to two amino acid positions, and wherein the monoclonal antibody specifically binds to a ROR1 polypeptide.

As indicated in various embodiments above, the sequence of each CDR may differ from the given sequence at up to two amino acid positions. This means that the CDR may contain one or two amino acid substitutions compared to the given sequence. However, if one or more of the CDRs does contain amino acid substitutions, the antibody can still selectively bind to ROR1. Preferably, the amino acid substitutions are conservative substitutions.

Preferably, the sequence of each CDR may differ from the given sequence at one amino acid position. This means that the CDR may contain one amino acid substitution compared to the given sequence. Preferably, the amino acid substitution is a conservative substitution. In some embodiment, the CDRs do not contain any amino acid substitutions.

In some embodiments above, heavy chain complementarity determining region 3 (HCDR3) comprises an amino acid sequence having the sequence set forth as SEQ ID NO: 248. In such embodiments, HCDR3 preferably comprises an amino acid sequence as set forth in SEQ ID NO: 125, 246 or 247.

In some embodiments above, heavy chain complementarity determining region 3 (HCDR3) comprises an amino acid sequence having the sequence set forth as SEQ ID NO:

252. In such embodiments, HCDR3 preferably comprises an amino acid sequence as set forth in SEQ ID NO: 119, 249, 250 or 251.

The isolated monoclonal antibody according to the preferred and particularly preferred embodiments part (a) may have a light chain variable domain which comprises a Light Chain Framework Region (LCFR)1 comprising the amino acid sequence as set forth as one of SEQ ID NO: 29, SEQ ID NO: 197, SEQ ID NO: 201 or SEQ ID NO: 208; an LCFR2 comprising the amino acid sequence as set forth as one of SEQ ID NO: 31, SEQ ID NO: 198, SEQ ID NO: 202, SEQ ID NO: 204 or SEQ ID NO: 206; an LCFR3 comprising the amino acid sequence as set forth as one of SEQ ID NO: 33, SEQ ID NO: 199, SEQ ID NO: 203 or SEQ ID NO: 207; and an LCFR4 comprising the amino acid sequence as set forth as one of SEQ ID NO: 35, SEQ ID NO: 200, SEQ ID NO: 205 or SEQ ID NO: 209.

The isolated monoclonal antibody according to the preferred and particularly preferred embodiments part (a) may have a heavy chain variable domain which comprises a Heavy Chain Framework Region (HCFR)1 comprising the amino acid sequence as set forth as one of SEQ ID NO: 120, SEQ ID NO: 181, SEQ ID NO: 188 or SEQ ID NO: 190; an HCFR2 comprising the amino acid sequence as set forth as one of SEQ ID NO: 122, SEQ ID NO: 182 or SEQ ID NO: 184; an HCFR3 comprising the amino acid sequence as set forth as one of SEQ ID NO: 124, SEQ ID NO: 183, SEQ ID NO: 185, SEQ ID NO: 187, SEQ ID NO: 189 or SEQ ID NO: 191; and an HCFR4 comprising the amino acid sequence as set forth as one of SEQ ID NO: 94, SEQ ID NO: 108 or SEQ ID NO: 186.

Preferably the light chain variable domain comprises the amino acid sequence as set forth as one of SEQ ID NO: 80, SEQ ID NO: 210, SEQ ID NO: 211, SEQ ID NO: 212, SEQ ID NO; 213 or SEQ ID NO: 214.

Preferably the heavy chain variable domain comprises the amino acid sequence as set forth as one of SEQ ID NO: 173, SEQ ID NO: 192, SEQ ID NO: 193, SEQ ID NO: 194, SEQ ID NO: 195 or SEQ ID NO: 196.

More preferably,
(a) the light chain variable domain comprises the amino acid sequence as set forth as SEQ ID NO: 80 and the heavy chain variable domain comprises the amino acid sequence as set forth as SEQ ID NO: 173;
(b) the light chain variable domain comprises the amino acid sequence as set forth as SEQ ID NO: 210 and the heavy chain variable domain comprises the amino acid sequence as set forth as SEQ ID NO: 192;
(c) the light chain variable domain comprises the amino acid sequence as set forth as SEQ ID NO: 211 and the heavy chain variable domain comprises the amino acid sequence as set forth as SEQ ID NO: 193;
(d) the light chain variable domain comprises the amino acid sequence as set forth as SEQ ID NO: 212 and the heavy chain variable domain comprises the amino acid sequence as set forth as SEQ ID NO: 194;
(e) the light chain variable domain comprises the amino acid sequence as set forth as SEQ ID NO: 213 and the heavy chain variable domain comprises the amino acid sequence as set forth as SEQ ID NO: 195; or
(f) the light chain variable domain comprises the amino acid sequence as set forth as SEQ ID NO: 214 and the heavy chain variable domain comprises the amino acid sequence as set forth as SEQ ID NO: 196.

The isolated monoclonal antibody according to the preferred and particularly preferred embodiments part (b) may have a light chain variable domain which comprises a Light Chain Framework Region (LCFR)1 comprising the amino acid sequence as set forth as one of SEQ ID NO: 23, SEQ ID NO: 230, SEQ ID NO: 238 or SEQ ID NO: 239; an LCFR2 comprising the amino acid sequence as set forth as one of SEQ ID NO: 25, SEQ ID NO: 231, SEQ ID NO: 233 or SEQ ID NO: 236; an LCFR3 comprising the amino acid sequence as set forth as one of SEQ ID NO: 27, SEQ ID NO: 232, SEQ ID NO: 234, SEQ ID NO: 237 or SEQ ID NO: 240; and an LCFR4 comprising the amino acid sequence as set forth as one of SEQ ID NO: 14, SEQ ID NO: 205 or SEQ ID NO: 234.

The isolated monoclonal antibody according to the preferred and particularly preferred embodiments part (b) may have a heavy chain variable domain which comprises a Heavy Chain Framework Region (HCFR)1 comprising the amino acid sequence as set forth as one of SEQ ID NO: 114, SEQ ID NO: 215, SEQ ID NO: 218 or SEQ ID NO: 223; an HCFR2 comprising the amino acid sequence as set forth as one of SEQ ID NO: 116, SEQ ID NO: 216, SEQ ID NO: 219 or SEQ ID NO: 221; an HCFR3 comprising the amino acid sequence as set forth as one of SEQ ID NO: 118, SEQ ID NO: 217, SEQ ID NO: 220, SEQ ID NO: 222 or SEQ ID NO: 224; and an HCFR4 comprising the amino acid sequence as set forth as one of SEQ ID NO: 94, SEQ ID NO: 186 or SEQ ID NO: 108.

Preferably, the light chain variable domain comprises the amino acid sequence as set forth as one of SEQ ID NO: 79, SEQ ID NO: 241, SEQ ID NO: 242, SEQ ID NO: 243, SEQ ID NO: 244 or SEQ ID NO: 245.

Preferably, the heavy chain variable domain comprises the amino acid sequence as set forth as one of SEQ ID NO: 172, SEQ ID NO: 225, SEQ ID NO: 226, SEQ ID NO: 227, SEQ ID NO: 228 or SEQ ID NO: 229.

More preferably,
(a) the light chain variable domain comprises the amino acid sequence as set forth as SEQ ID NO: 79 and the heavy chain variable domain comprises the amino acid sequence as set forth as SEQ ID NO: 172;
(b) the light chain variable domain comprises the amino acid sequence as set forth as SEQ ID NO: 241 and the heavy chain variable domain comprises the amino acid sequence as set forth as SEQ ID NO: 225;
(c) the light chain variable domain comprises the amino acid sequence as set forth as SEQ ID NO: 242 and the heavy chain variable domain comprises the amino acid sequence as set forth as SEQ ID NO: 226;
(d) the light chain variable domain comprises the amino acid sequence as set forth as SEQ ID NO: 243 and the heavy chain variable domain comprises the amino acid sequence as set forth as SEQ ID NO: 227;
(e) the light chain variable domain comprises the amino acid sequence as set forth as SEQ ID NO: 244 and the heavy chain variable domain comprises the amino acid sequence as set forth as SEQ ID NO: 228; or
(f) the light chain variable domain comprises the amino acid sequence as set forth as SEQ ID NO: 245 and the heavy chain variable domain comprises the amino acid sequence as set forth as SEQ ID NO: 229.

The isolated monoclonal antibody according to the preferred and particularly preferred embodiments part (c) may have a light chain variable domain which comprises a Light Chain Framework Region (LCFR)1 comprising the amino acid sequence as set forth as SEQ ID NO: 8; an LCFR2 comprising the amino acid sequence as set forth as SEQ ID NO: 10; an LCFR3 comprising the amino acid sequence as set forth as SEQ ID NO: 12; and an LCFR4 comprising the amino acid sequence as set forth as SEQ ID NO: 14.

The isolated monoclonal antibody according to the preferred and particularly preferred embodiments part (c) may have a heavy chain variable domain which comprises a Heavy Chain Framework Region (HCFR)1 comprising the amino acid sequence as set forth as SEQ ID NO: 95; an HCFR2 comprising the amino acid sequence as set forth as SEQ ID NO: 97; an HCFR3 comprising the amino acid sequence as set forth as SEQ ID NO: 99; and an HCFR4 comprising the amino acid sequence as set forth as SEQ ID NO: 101.

Preferably, the light chain variable domain comprises the amino acid sequence as set forth as SEQ ID NO: 76.

Preferably, the heavy chain variable domain comprises the amino acid sequence as set forth as SEQ ID NO: 169.

More preferably, the light chain variable domain comprises the amino acid sequence as set forth as SEQ ID NO: 76 and the heavy chain variable domain comprises the amino acid sequence as set forth as SEQ ID NO: 169.

The isolated monoclonal antibody according to the preferred and particularly preferred embodiments part (d) may have a light chain variable domain which comprises a Light Chain Framework Region (LCFR)1 comprising the amino acid sequence as set forth as SEQ ID NO: 36; an LCFR2 comprising the amino acid sequence as set forth as SEQ ID NO: 38; an LCFR3 comprising the amino acid sequence as set forth as SEQ ID NO: 40; and an LCFR4 comprising the amino acid sequence as set forth as SEQ ID NO: 42.

The isolated monoclonal antibody according to the preferred and particularly preferred embodiments part (d) may have a heavy chain variable domain comprises a Heavy Chain Framework Region (HCFR)1 comprising the amino acid sequence as set forth as SEQ ID NO: 126; an HCFR2 comprising the amino acid sequence as set forth as SEQ ID NO: 128; an HCFR3 comprising the amino acid sequence as set forth as SEQ ID NO: 130; and an HCFR4 comprising the amino acid sequence as set forth as SEQ ID NO: 132.

Preferably, the light chain variable domain comprises the amino acid sequence as set forth as SEQ ID NO: 81.

Preferably, the heavy chain variable domain comprises the amino acid sequence as set forth as SEQ ID NO: 174.

More preferably, the light chain variable domain comprises the amino acid sequence as set forth as SEQ ID NO: 81 and the heavy chain variable domain comprises the amino acid sequence as set forth as SEQ ID NO: 174.

The isolated monoclonal antibody according to the preferred and particularly preferred embodiments part (e) may have a light chain variable domain which comprises a Light Chain Framework Region (LCFR)1 comprising the amino acid sequence as set forth as SEQ ID NO: 43; an LCFR2 comprising the amino acid sequence as set forth as SEQ ID NO: 45; an LCFR3 comprising the amino acid sequence as set forth as SEQ ID NO: 47; and an LCFR4 comprising the amino acid sequence as set forth as SEQ ID NO: 21.

The isolated monoclonal antibody according to the preferred and particularly preferred embodiments part (e) may have heavy chain variable domain comprises a Heavy Chain Framework Region (HCFR)1 comprising the amino acid sequence as set forth as SEQ ID NO: 133; an HCFR2 comprising the amino acid sequence as set forth as SEQ ID NO: 135; an HCFR3 comprising the amino acid sequence as set forth as SEQ ID NO: 137; and an HCFR4 comprising the amino acid sequence as set forth as SEQ ID NO: 108.

Preferably, the light chain variable domain comprises the amino acid sequence as set forth as SEQ ID NO: 82.

Preferably, wherein the heavy chain variable domain comprises the amino acid sequence as set forth as SEQ ID NO: 175.

More preferably, the light chain variable domain comprises the amino acid sequence as set forth as SEQ ID NO: 82 and the heavy chain variable domain comprises the amino acid sequence as set forth as SEQ ID NO: 175.

The isolated monoclonal antibody according to the preferred and particularly preferred embodiments part (f) may have light chain variable domain which comprises a Light Chain Framework Region (LCFR)1 comprising the amino acid sequence as set forth as SEQ ID NO: 49; an LCFR2 comprising the amino acid sequence as set forth as SEQ ID NO: 51; an LCFR3 comprising the amino acid sequence as set forth as SEQ ID NO: 53; and an LCFR4 comprising the amino acid sequence as set forth as SEQ ID NO: 21.

The isolated monoclonal antibody according to the preferred and particularly preferred embodiments part (f) may have heavy chain variable domain comprises a Heavy Chain Framework Region (HCFR)1 comprising the amino acid sequence as set forth as SEQ ID NO: 139; an HCFR2 comprising the amino acid sequence as set forth as SEQ ID NO: 141; an HCFR3 comprising the amino acid sequence as set forth as SEQ ID NO: 143; and an HCFR4 comprising the amino acid sequence as set forth as SEQ ID NO: 108.

Preferably, the light chain variable domain comprises the amino acid sequence as set forth as SEQ ID NO: 83.

Preferably, the heavy chain variable domain comprises the amino acid sequence as set forth as SEQ ID NO: 176.

More preferably, the light chain variable domain comprises the amino acid sequence as set forth as SEQ ID NO: 83 and the heavy chain variable domain comprises the amino acid sequence as set forth as SEQ ID NO: 176.

The isolated monoclonal antibody according to the preferred and particularly preferred embodiments part (g) may have a light chain variable domain which comprises a Light Chain Framework Region (LCFR)1 comprising the amino acid sequence as set forth as SEQ ID NO: 55; an LCFR2 comprising the amino acid sequence as set forth as SEQ ID NO: 57; an LCFR3 comprising the amino acid sequence as set forth as SEQ ID NO: 59; and an LCFR4 comprising the amino acid sequence as set forth as SEQ ID NO: 61.

The isolated monoclonal antibody according to the preferred and particularly preferred embodiments part (g) may have heavy chain variable domain which comprises a Heavy Chain Framework Region (HCFR)1 comprising the amino acid sequence as set forth as SEQ ID NO: 145; an HCFR2 comprising the amino acid sequence as set forth as SEQ ID NO: 147; an HCFR3 comprising the amino acid sequence as set forth as SEQ ID NO: 149; and an HCFR4 comprising the amino acid sequence as set forth as SEQ ID NO: 108.

Preferably, wherein the light chain variable domain comprises the amino acid sequence as set forth as SEQ ID NO: 84.

Preferably, the heavy chain variable domain comprises the amino acid sequence as set forth as SEQ ID NO: 177.

More preferably, the light chain variable domain comprises the amino acid sequence as set forth as SEQ ID NO: 84 and the heavy chain variable domain comprises the amino acid sequence as set forth as SEQ ID NO: 177.

The isolated monoclonal antibody according to the preferred and particularly preferred embodiments part (h) may have light chain variable domain which comprises a Light Chain Framework Region (LCFR)1 comprising the amino acid sequence as set forth as SEQ ID NO: 62; an LCFR2 comprising the amino acid sequence as set forth as SEQ ID NO: 63; an LCFR3 comprising the amino acid sequence as set forth as SEQ ID NO: 64; and an LCFR4 comprising the amino acid sequence as set forth as SEQ ID NO: 66.

The isolated monoclonal antibody according to the preferred and particularly preferred embodiments part (h) may have a heavy chain variable domain which comprises a Heavy Chain Framework Region (HCFR)1 comprising the amino acid sequence as set forth as SEQ ID NO: 151; an HCFR2 comprising the amino acid sequence as set forth as SEQ ID NO: 153; an HCFR3 comprising the amino acid sequence as set forth as SEQ ID NO: 155; and an HCFR4 comprising the amino acid sequence as set forth as SEQ ID NO: 108.

Preferably, the light chain variable domain comprises the amino acid sequence as set forth as SEQ ID NO: 85.

Preferably, the heavy chain variable domain comprises the amino acid sequence as set forth as SEQ ID NO: 178.

More preferably, the light chain variable domain comprises the amino acid sequence as set forth as SEQ ID NO: 85 and the heavy chain variable domain comprises the amino acid sequence as set forth as SEQ ID NO: 178.

The isolated monoclonal antibody according to the preferred and particularly preferred embodiments part (i) may have a light chain variable domain which comprises a Light Chain Framework Region (LCFR)1 comprising the amino acid sequence as set forth as SEQ ID NO: 55; an LCFR2 comprising the amino acid sequence as set forth as SEQ ID NO: 57; an LCFR3 comprising the amino acid sequence as set forth as SEQ ID NO: 59; and an LCFR4 comprising the amino acid sequence as set forth as SEQ ID NO: 69.

The isolated monoclonal antibody according to the preferred and particularly preferred embodiments part (i) may have a heavy chain variable domain which comprises a Heavy Chain Framework Region (HCFR)1 comprising the amino acid sequence as set forth as SEQ ID NO: 157; an HCFR2 comprising the amino acid sequence as set forth as SEQ ID NO: 159; an HCFR3 comprising the amino acid sequence as set forth as SEQ ID NO: 161; and an HCFR4 comprising the amino acid sequence as set forth as SEQ ID NO: 108.

Preferably, the light chain variable domain comprises the amino acid sequence as set forth as SEQ ID NO: 86.

Preferably, the heavy chain variable domain comprises the amino acid sequence as set forth as SEQ ID NO: 179.

More preferably, the light chain variable domain comprises the amino acid sequence as set forth as SEQ ID NO: 86 and the heavy chain variable domain comprises the amino acid sequence as set forth as SEQ ID NO: 179.

The isolated monoclonal antibody according to the preferred and particularly preferred embodiments part (j) may have a light chain variable domain which comprises a Light Chain Framework Region (LCFR)1 comprising the amino acid sequence as set forth as SEQ ID NO: 70; an LCFR2 comprising the amino acid sequence as set forth as SEQ ID NO: 72; an LCFR3 comprising the amino acid sequence as set forth as SEQ ID NO: 73; and an LCFR4 comprising the amino acid sequence as set forth as SEQ ID NO: 21.

The isolated monoclonal antibody according to the preferred and particularly preferred embodiments part (j) may have heavy chain variable domain which comprises a Heavy Chain Framework Region (HCFR)1 comprising the amino acid sequence as set forth as SEQ ID NO: 114; an HCFR2 comprising the amino acid sequence as set forth as SEQ ID NO: 164; an HCFR3 comprising the amino acid sequence as set forth as SEQ ID NO: 166; and an HCFR4 comprising the amino acid sequence as set forth as SEQ ID NO: 108.

Preferably, the light chain variable domain comprises the amino acid sequence as set forth as SEQ ID NO: 87.

Preferably, the heavy chain variable domain comprises the amino acid sequence as set forth as SEQ ID NO: 180.

More preferably, the light chain variable domain comprises the amino acid sequence as set forth as SEQ ID NO: 87 and the heavy chain variable domain comprises the amino acid sequence as set forth as SEQ ID NO: 180.

The isolated monoclonal antibody according to the preferred and particularly preferred embodiments part (k) may have a light chain variable domain which comprises a Light Chain Framework Region (LCFR)1 comprising the amino acid sequence as set forth as SEQ ID NO: 1; an LCFR2 comprising the amino acid sequence as set forth as SEQ ID NO: 3; an LCFR3 comprising the amino acid sequence as set forth as SEQ ID NO: 5; and an LCFR4 comprising the amino acid sequence as set forth as SEQ ID NO: 7.

The isolated monoclonal antibody according to the preferred and particularly preferred embodiments part (k) may have heavy chain variable domain which comprises a Heavy Chain Framework Region (HCFR)1 comprising the amino acid sequence as set forth as SEQ ID NO: 88; an HCFR2 comprising the amino acid sequence as set forth as SEQ ID NO: 90; an HCFR3 comprising the amino acid sequence as set forth as SEQ ID NO: 92; and an HCFR4 comprising the amino acid sequence as set forth as SEQ ID NO: 94.

Preferably, the light chain variable domain comprises the amino acid sequence as set forth as SEQ ID NO: 75.

Preferably, the heavy chain variable domain comprises the amino acid sequence as set forth as SEQ ID NO: 168.

More preferably, the light chain variable domain comprises the amino acid sequence as set forth as SEQ ID NO: 75 and the heavy chain variable domain comprises the amino acid sequence as set forth as SEQ ID NO: 168.

The isolated monoclonal antibody according to the preferred and particularly preferred embodiments part (l) may have a light chain variable domain which comprises a Light Chain Framework Region (LCFR)1 comprising the amino acid sequence as set forth as SEQ ID NO: 15; an LCFR2 comprising the amino acid sequence as set forth as SEQ ID NO: 17; an LCFR3 comprising the amino acid sequence as set forth as SEQ ID NO: 19; and an LCFR4 comprising the amino acid sequence as set forth as SEQ ID NO: 21.

The isolated monoclonal antibody according to the preferred and particularly preferred embodiments part (l) may have heavy chain variable domain which comprises a Heavy Chain Framework Region (HCFR)1 comprising the amino acid sequence as set forth as SEQ ID NO: 102; an HCFR2 comprising the amino acid sequence as set forth as SEQ ID NO: 104; an HCFR3 comprising the amino acid sequence as set forth as SEQ ID NO: 106; and an HCFR4 comprising the amino acid sequence as set forth as SEQ ID NO: 108.

Preferably, the light chain variable domain comprises the amino acid sequence as set forth as SEQ ID NO: 77.

Preferably, the heavy chain variable domain comprises the amino acid sequence as set forth as SEQ ID NO: 170.

More preferably, the light chain variable domain comprises the amino acid sequence as set forth as SEQ ID NO: 77 and the heavy chain variable domain comprises the amino acid sequence as set forth as SEQ ID NO: 170.

The isolated monoclonal antibody according to the preferred and particularly preferred embodiments part (m) may have a light chain variable domain which comprises a Light Chain Framework Region (LCFR)1 comprising the amino acid sequence as set forth as SEQ ID NO: 15; an LCFR2 comprising the amino acid sequence as set forth as SEQ ID NO: 17; an LCFR3 comprising the amino acid sequence as set forth as SEQ ID NO: 19; and an LCFR4 comprising the amino acid sequence as set forth as SEQ ID NO: 21.

The isolated monoclonal antibody according to the preferred and particularly preferred embodiments part (m) may have heavy chain variable domain which comprises a Heavy Chain Framework Region (HCFR)1 comprising the amino acid sequence as set forth as SEQ ID NO: 109; an HCFR2 comprising the amino acid sequence as set forth as SEQ ID NO: 111; an HCFR3 comprising the amino acid sequence as set forth as SEQ ID NO: 112; and an HCFR4 comprising the amino acid sequence as set forth as SEQ ID NO: 108.

Preferably, the light chain variable domain comprises the amino acid sequence as set forth as SEQ ID NO: 78.

Preferably, the heavy chain variable domain comprises the amino acid sequence as set forth as SEQ ID NO: 171.

More preferably, the light chain variable domain comprises the amino acid sequence as set forth as SEQ ID NO: 78 and the heavy chain variable domain comprises the amino acid sequence as set forth as SEQ ID NO: 171.

In particular embodiments, the light chain variable domain comprises the amino acid sequence as set forth as one of SEQ ID NOs: 80, 210, 211, 212, 213 and 214. More preferably, the light chain variable domain comprises the amino acid sequence as set forth as one of SEQ ID NOs: 210, 211, 212, 213 and 214.

Preferably, the heavy chain variable domain comprises the amino acid sequence as set forth as one of SEQ ID NOs: 173, 192, 193, 194, 195 and 196. More preferably, the heavy chain variable domain comprises the amino acid sequence as set forth as one of SEQ ID NOs: 192, 193, 194, 195 and 196.

SEQ ID NOs: 210, 211, 212, 213 and 214 are humanised light chain variable regions produced from clone A. SEQ ID NOs: 192, 193, 194, 195 and 196 are humanised heavy chain variable regions produced from clone A. The combination of these light and heavy chain regions results in 25 different constructs.

Therefore, in some embodiments, the light chain variable domain comprises the amino acid sequence as set forth as SEQ ID NO: 210 and the heavy chain variable domain comprises the amino acid sequence as set forth as one of SEQ ID NOs: 192, 193, 194, 195 and 196.

In other embodiments, the light chain variable domain comprises the amino acid sequence as set forth as SEQ ID NO: 211 and the heavy chain variable domain comprises the amino acid sequence as set forth as one of SEQ ID NOs: 192, 193, 194, 195 and 196.

In further embodiments, the light chain variable domain comprises the amino acid sequence as set forth as SEQ ID NO: 212 and the heavy chain variable domain comprises the amino acid sequence as set forth as one of SEQ ID NOs: 192, 193, 194, 195 and 196.

In alternative embodiments, the light chain variable domain comprises the amino acid sequence as set forth as SEQ ID NO: 213 and the heavy chain variable domain comprises the amino acid sequence as set forth as one of SEQ ID NOs: 192, 193, 194, 195 and 196.

In various embodiments, the light chain variable domain comprises the amino acid sequence as set forth as SEQ ID NO: 214 and the heavy chain variable domain comprises the amino acid sequence as set forth as one of SEQ ID NOs: 192, 193, 194, 195 and 196.

Similarly, in some embodiments, the heavy chain variable domain comprises the amino acid sequence as set forth as SEQ ID NO: 192 and the light chain variable domain comprises the amino acid sequence as set forth as one of SEQ ID NOs: 210, 211, 212, 213 and 214.

In other embodiments, the heavy chain variable domain comprises the amino acid sequence as set forth as SEQ ID NO: 193 and the light chain variable domain comprises the amino acid sequence as set forth as one of SEQ ID NOs: 210, 211, 212, 213 and 214.

In further embodiments, the heavy chain variable domain comprises the amino acid sequence as set forth as SEQ ID NO: 194 and the light chain variable domain comprises the amino acid sequence as set forth as one of SEQ ID NOs: 210, 211, 212, 213 and 214.

In alternative embodiments, the heavy chain variable domain comprises the amino acid sequence as set forth as SEQ ID NO: 195 and the light chain variable domain comprises the amino acid sequence as set forth as one of SEQ ID NOs: 210, 211, 212, 213 and 214.

In various embodiments, the heavy chain variable domain comprises the amino acid sequence as set forth as SEQ ID NO: 196 and the light chain variable domain comprises the amino acid sequence as set forth as one of SEQ ID NOs: 210, 211, 212, 213 and 214.

In certain embodiments, the light chain variable domain comprises the amino acid sequence as set forth as one of SEQ ID NOs: 79, 241, 242, 243, 244 and 245. More preferably, the light chain variable domain comprises the amino acid sequence as set forth as one of SEQ ID NOs: 241, 242, 243, 244 and 245.

Preferably, the heavy chain variable domain comprises the amino acid sequence as set forth as one of SEQ ID NOs: 172, 225, 226, 227, 228 and 229. More preferably, the heavy chain variable domain comprises the amino acid sequence as set forth as one of SEQ ID NOs: 225, 226, 227, 228 and 229.

SEQ ID NOs: 241, 242, 243, 244 and 245 are humanised light chain variable regions produced from clone F. SEQ ID NOs: 225, 226, 227, 228 and 229 are humanised heavy chain variable regions produced from clone F. The combination of these light and heavy chain regions results in 25 different constructs.

Therefore, in some embodiments, the light chain variable domain comprises the amino acid sequence as set forth as SEQ ID NO: 241 and the heavy chain variable domain comprises the amino acid sequence as set forth as one of SEQ ID NOs: 225, 226, 227, 228 and 229.

In other embodiments, the light chain variable domain comprises the amino acid sequence as set forth as SEQ ID NO: 242 and the heavy chain variable domain comprises the amino acid sequence as set forth as one of SEQ ID NOs: 225, 226, 227, 228 and 229.

In further embodiments, the light chain variable domain comprises the amino acid sequence as set forth as SEQ ID NO: 243 and the heavy chain variable domain comprises the amino acid sequence as set forth as one of SEQ ID NOs: 225, 226, 227, 228 and 229.

In alternative embodiments, the light chain variable domain comprises the amino acid sequence as set forth as SEQ ID NO: 244 and the heavy chain variable domain comprises the amino acid sequence as set forth as one of SEQ ID NOs: 225, 226, 227, 228 and 229.

In various embodiments, the light chain variable domain comprises the amino acid sequence as set forth as SEQ ID NO: 245 and the heavy chain variable domain comprises the amino acid sequence as set forth as one of SEQ ID NOs: 225, 226, 227, 228 and 229.

Similarly, in some embodiments, the heavy chain variable domain comprises the amino acid sequence as set forth as SEQ ID NO: 225 and the light chain variable domain comprises the amino acid sequence as set forth as one of SEQ ID NOs: 241, 242, 243, 244 and 245.

In other embodiments, the heavy chain variable domain comprises the amino acid sequence as set forth as SEQ ID NO: 226 and the light chain variable domain comprises the amino acid sequence as set forth as one of SEQ ID NOs: 241, 242, 243, 244 and 245.

In further embodiments, the heavy chain variable domain comprises the amino acid sequence as set forth as SEQ ID NO: 227 and the light chain variable domain comprises the amino acid sequence as set forth as one of SEQ ID NOs: 241, 242, 243, 244 and 245.

In alternative embodiments, the heavy chain variable domain comprises the amino acid sequence as set forth as SEQ ID NO: 228 and the light chain variable domain comprises the amino acid sequence as set forth as one of SEQ ID NOs: 241, 242, 243, 244 and 245.

In various embodiments, the heavy chain variable domain comprises the amino acid sequence as set forth as SEQ ID NO: 229 and the light chain variable domain comprises the amino acid sequence as set forth as one of SEQ ID NOs: 241, 242, 243, 244 and 245.

As indicated below, the sequence of each light chain variable domain and heavy chain variable domain referred to above may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions.

In the embodiments referred to above, the Light Chain Framework Regions, the Heavy Chain Framework Regions, the Light Chain Variable Domains and the Heavy Chain Variable Domains may comprise an amino acid sequence at least 90%, 91%, 92%, 93%, 94%, 95%, 96%, 97%, 98% or 99% identical to the amino acid sequences as set forth above. For example, the Light Chain Framework Regions, the Heavy Chain Framework Regions, the Light Chain Variable Domains and the Heavy Chain Variable Domains may include at most 10, at most 9, at most 8, at most 7, at most 6, at most 5, at most 4, at most 3, at most two or at most one amino acid substitutions in the amino acid sequences as set forth above. Where there is variation in the sequences of the Light Chain Variable Domain and the Heavy Chain Variable Domain, any amino acid substitutions are preferably not in the CDRs. In particular, the Light Chain Framework Regions and/or the Heavy Chain Framework Regions of the antibodies described above may comprise an amino acid sequence at least 90%, 91%, 92%, 93%, 94%, 95%, 96%, 97%, 98% or 99% identical to the amino acid sequences as set forth above. Further, the Light Chain Framework Regions and/or the Heavy Chain Framework Regions may include at most 10, at most 9, at most 8, at most 7, at most 6, at most 5, at most 4, at most 3, at most two or at most one amino acid substitutions in the amino acid sequences as set forth above. Preferably the amino acid substitutions are conservative substitutions as described above. For example, the framework regions may comprise such substitutions in order to humanise the sequence. Preferably, the framework regions are humanised.

In a second embodiment, the isolated monoclonal antibody comprises a light chain variable domain and a heavy chain variable domain, wherein the light chain variable domain comprises a light chain complementarity determining region (LCDR)1, an LCDR2 and an LCDR3 and the heavy chain variable domain comprises a heavy chain complementarity determining region (HCDR)1, an HCDR2 and an HCDR3, wherein (a) the LCDR1 comprises the amino acid sequence set forth as SEQ ID NO: 277, the LCDR2 comprises the amino acid sequence set forth as SEQ ID NO: 278, the LCDR3 comprises the amino acid sequence set forth as SEQ ID NO: 34, the HCDR1 comprises the amino acid sequence set forth as SEQ ID NO: 279, the HCDR2 comprises the amino acid sequence set forth as SEQ ID NO: 280, and the HCDR3 comprises the amino acid sequence set forth as SEQ ID NO: 281;

(b) the LCDR1 comprises the amino acid sequence set forth as SEQ ID NO: 272, the LCDR2 comprises the amino acid sequence set forth as SEQ ID NO: 273, the LCDR3 comprises the amino acid sequence set forth as SEQ ID NO: 28, the HCDR1 comprises the amino acid sequence set forth as SEQ ID NO: 274, the HCDR2 comprises the amino acid sequence set forth as SEQ ID NO: 275, and the HCDR3 comprises the amino acid sequence set forth as SEQ ID NO: 276;

(c) the LCDR1 comprises the amino acid sequence set forth as SEQ ID NO: 260, the LCDR2 comprises the amino acid sequence set forth as SEQ ID NO: 261, the LCDR3 comprises the amino acid sequence set forth as SEQ ID NO: 13, the HCDR1 comprises the amino acid sequence set forth as SEQ ID NO: 262, the HCDR2 comprises the amino acid sequence set forth as SEQ ID NO: 263, and the HCDR3 comprises the amino acid sequence set forth as SEQ ID NO: 264;

(d) the LCDR1 comprises the amino acid sequence set forth as SEQ ID NO: 282, the LCDR2 comprises the amino acid sequence set forth as SEQ ID NO: 283, the LCDR3 comprises the amino acid sequence set forth as SEQ ID NO: 41, the HCDR1 comprises the amino acid sequence set forth as SEQ ID NO: 284, the HCDR2 comprises the amino acid sequence set forth as SEQ ID NO: 285, and the HCDR3 comprises the amino acid sequence set forth as SEQ ID NO: 286;

(e) the LCDR1 comprises the amino acid sequence set forth as SEQ ID NO: 287, the LCDR2 comprises the amino acid sequence set forth as SEQ ID NO: 288, the LCDR3 comprises the amino acid sequence set forth as SEQ ID NO: 48, the HCDR1 comprises the amino acid sequence set forth as SEQ ID NO: 289, the HCDR2 comprises the amino acid sequence set forth as SEQ ID NO: 290, and the HCDR3 comprises the amino acid sequence set forth as SEQ ID NO: 291;

(f) the LCDR1 comprises the amino acid sequence set forth as SEQ ID NO: 292, the LCDR2 comprises the amino acid sequence set forth as SEQ ID NO: 293, the LCDR3 comprises the amino acid sequence set forth as SEQ ID NO: 54, the HCDR1 comprises the amino acid sequence set forth as SEQ ID NO: 294, the HCDR2 comprises the amino acid sequence set forth as SEQ ID NO: 295, and the HCDR3 comprises the amino acid sequence set forth as SEQ ID NO: 296;

(g) the LCDR1 comprises the amino acid sequence set forth as SEQ ID NO: 297, the LCDR2 comprises the amino acid sequence set forth as SEQ ID NO: 298, the LCDR3 comprises the amino acid sequence set forth as SEQ ID NO: 60, the HCDR1 comprises the amino acid sequence set forth as SEQ ID NO: 299, the HCDR2 comprises the amino acid sequence set forth as SEQ ID NO: 300, and the HCDR3 comprises the amino acid sequence set forth as SEQ ID NO: 301;

(h) the LCDR1 comprises the amino acid sequence set forth as SEQ ID NO: 287, the LCDR2 comprises the amino acid sequence set forth as SEQ ID NO: 302, the LCDR3 comprises the amino acid sequence set forth as SEQ ID NO: 65, the HCDR1 comprises the amino acid sequence set forth as SEQ ID NO: 289, the HCDR2 comprises the amino acid sequence set forth as SEQ ID NO: 303, and the HCDR3 comprises the amino acid sequence set forth as SEQ ID NO: 304;
(i) the LCDR1 comprises the amino acid sequence set forth as SEQ ID NO: 305, the LCDR2 comprises the amino acid sequence set forth as SEQ ID NO: 298, the LCDR3 comprises the amino acid sequence set forth as SEQ ID NO: 68, the HCDR1 comprises the amino acid sequence set forth as SEQ ID NO: 306, the HCDR2 comprises the amino acid sequence set forth as SEQ ID NO: 307, and the HCDR3 comprises the amino acid sequence set forth as SEQ ID NO: 308;
(j) the LCDR1 comprises the amino acid sequence set forth as SEQ ID NO: 309, the LCDR2 comprises the amino acid sequence set forth as SEQ ID NO: 310, the LCDR3 comprises the amino acid sequence set forth as SEQ ID NO: 74, the HCDR1 comprises the amino acid sequence set forth as SEQ ID NO: 311, the HCDR2 comprises the amino acid sequence set forth as SEQ ID NO: 312, and the HCDR3 comprises the amino acid sequence set forth as SEQ ID NO: 313;
(k) the LCDR1 comprises the amino acid sequence set forth as SEQ ID NO: 255, the LCDR2 comprises the amino acid sequence set forth as SEQ ID NO: 256, the LCDR3 comprises the amino acid sequence set forth as SEQ ID NO: 6, the HCDR1 comprises the amino acid sequence set forth as SEQ ID NO: 257, the HCDR2 comprises the amino acid sequence set forth as SEQ ID NO: 258, and the HCDR3 comprises the amino acid sequence set forth as SEQ ID NO: 259;
(l) the LCDR1 comprises the amino acid sequence set forth as SEQ ID NO: 265, the LCDR2 comprises the amino acid sequence set forth as SEQ ID NO: 266, the LCDR3 comprises the amino acid sequence set forth as SEQ ID NO: 20, the HCDR1 comprises the amino acid sequence set forth as SEQ ID NO: 267, the HCDR2 comprises the amino acid sequence set forth as SEQ ID NO: 268, and the HCDR3 comprises the amino acid sequence set forth as SEQ ID NO: 269; or
(m) the LCDR1 comprises the amino acid sequence set forth as SEQ ID NO: 270, the LCDR2 comprises the amino acid sequence set forth as SEQ ID NO: 266, the LCDR3 comprises the amino acid sequence set forth as SEQ ID NO: 20, the HCDR1 comprises the amino acid sequence set forth as SEQ ID NO: 267, the HCDR2 comprises the amino acid sequence set forth as SEQ ID NO: 268, and the HCDR3 comprises the amino acid sequence set forth as SEQ ID NO: 271;
wherein the sequence of each complementarity determining region may differ from the given sequence at up to two amino acid positions, and
wherein the monoclonal antibody specifically binds to a ROR1 polypeptide.

As indicated in the embodiment above, the sequence of each CDR may differ from the given sequence at up to two amino acid positions. This means that the CDR may contain one or two amino acid substitutions compared to the given sequence. However, if one or more of the CDRs does contain amino acid substitutions, the antibody can still selectively bind to ROR1. Preferably, the amino acid substitutions are conservative substitutions.

Preferably, the sequence of each CDR may differ from the given sequence at one amino acid position. This means that the CDR may contain one amino acid substitution compared to the given sequence. Preferably, the amino acid substitution is a conservative substitution. In some embodiments, the CDRs do not contain any amino acid substitutions.

The isolated monoclonal antibody according to part (a) of the second embodiment may have a light chain variable domain which comprises the amino acid sequence as set forth as one of SEQ ID NO: 80, SEQ ID NO: 210, SEQ ID NO: 211, SEQ ID NO: 212, SEQ ID NO; 213 or SEQ ID NO: 214. The heavy chain variable domain may comprise the amino acid sequence as set forth as one of SEQ ID NO: 173, SEQ ID NO: 192, SEQ ID NO: 193, SEQ ID NO: 194, SEQ ID NO: 195 or SEQ ID NO: 196.

More preferably,
(a) the light chain variable domain comprises the amino acid sequence as set forth as SEQ ID NO: 80 and the heavy chain variable domain comprises the amino acid sequence as set forth as SEQ ID NO: 173;
(b) the light chain variable domain comprises the amino acid sequence as set forth as SEQ ID NO: 210 and the heavy chain variable domain comprises the amino acid sequence as set forth as SEQ ID NO: 192;
(c) the light chain variable domain comprises the amino acid sequence as set forth as SEQ ID NO: 211 and the heavy chain variable domain comprises the amino acid sequence as set forth as SEQ ID NO: 193;
(d) the light chain variable domain comprises the amino acid sequence as set forth as SEQ ID NO: 212 and the heavy chain variable domain comprises the amino acid sequence as set forth as SEQ ID NO: 194;
(e) the light chain variable domain comprises the amino acid sequence as set forth as SEQ ID NO: 213 and the heavy chain variable domain comprises the amino acid sequence as set forth as SEQ ID NO: 195; or
(f) the light chain variable domain comprises the amino acid sequence as set forth as SEQ ID NO: 214 and the heavy chain variable domain comprises the amino acid sequence as set forth as SEQ ID NO: 196.

The isolated monoclonal antibody according to the part (b) of the second embodiment may have a light chain variable domain which comprises the amino acid sequence as set forth as one of SEQ ID NO: 79, SEQ ID NO: 241, SEQ ID NO: 242, SEQ ID NO: 243, SEQ ID NO: 244 or SEQ ID NO: 245. The heavy chain variable domain may comprise the amino acid sequence as set forth as one of SEQ ID NO: 172, SEQ ID NO: 225, SEQ ID NO: 226, SEQ ID NO: 227, SEQ ID NO: 228 or SEQ ID NO: 229.

More preferably,
(a) the light chain variable domain comprises the amino acid sequence as set forth as SEQ ID NO: 79 and the heavy chain variable domain comprises the amino acid sequence as set forth as SEQ ID NO: 172;
(b) the light chain variable domain comprises the amino acid sequence as set forth as SEQ ID NO: 241 and the heavy chain variable domain comprises the amino acid sequence as set forth as SEQ ID NO: 225;
(c) the light chain variable domain comprises the amino acid sequence as set forth as SEQ ID NO: 242 and the heavy chain variable domain comprises the amino acid sequence as set forth as SEQ ID NO: 226;
(d) the light chain variable domain comprises the amino acid sequence as set forth as SEQ ID NO: 243 and the heavy chain variable domain comprises the amino acid sequence as set forth as SEQ ID NO: 227;
(e) the light chain variable domain comprises the amino acid sequence as set forth as SEQ ID NO: 244 and the heavy chain variable domain comprises the amino acid sequence as set forth as SEQ ID NO: 228; or
(f) the light chain variable domain comprises the amino acid sequence as set forth as SEQ ID NO: 245 and the heavy chain variable domain comprises the amino acid sequence as set forth as SEQ ID NO: 229.

The isolated monoclonal antibody according to the part (c) of the second embodiment may have a light chain variable domain which comprises the amino acid sequence as set forth as SEQ ID NO: 76. The heavy chain variable domain may comprise the amino acid sequence as set forth as SEQ ID NO: 169.

The isolated monoclonal antibody according to the part (d) of the second embodiment may have a light chain variable domain which comprises the amino acid sequence as set forth as SEQ ID NO: 81. The heavy chain variable domain comprises the amino acid sequence as set forth as SEQ ID NO: 174.

The isolated monoclonal antibody according to the part (e) of the second embodiment may have a light chain variable domain which comprises the amino acid sequence as set forth as SEQ ID NO: 82. The heavy chain variable domain may comprise the amino acid sequence as set forth as SEQ ID NO: 175.

The isolated monoclonal antibody according to the part (f) of the second embodiment may have a light chain variable domain which comprises the amino acid sequence as set forth as SEQ ID NO: 83. The heavy chain variable domain may comprise the amino acid sequence as set forth as SEQ ID NO: 176.

The isolated monoclonal antibody according to the part (g) of the second embodiment may have a light chain variable domain which comprises the amino acid sequence as set forth as SEQ ID NO: 84. The heavy chain variable domain may comprise the amino acid sequence as set forth as SEQ ID NO: 177.

The isolated monoclonal antibody according to the part (h) of the second embodiment may have a light chain variable domain which comprises the amino acid sequence as set forth as SEQ ID NO: 85. The heavy chain variable domain may comprise the amino acid sequence as set forth as SEQ ID NO: 178.

The isolated monoclonal antibody according to the part (i) of the second embodiment may have a light chain variable domain which comprises the amino acid sequence as set forth as SEQ ID NO: 86. The heavy chain variable domain may comprise the amino acid sequence as set forth as SEQ ID NO: 179.

The isolated monoclonal antibody according to the part (j) of the second embodiment may have a light chain variable domain which comprises the amino acid sequence as set forth as SEQ ID NO: 87. The heavy chain variable domain may comprise the amino acid sequence as set forth as SEQ ID NO: 180.

The isolated monoclonal antibody according to the part (k) of the second embodiment may have a light chain variable domain which comprises the amino acid sequence as set forth as SEQ ID NO: 75. The heavy chain variable domain may comprise the amino acid sequence as set forth as SEQ ID NO: 168.

The isolated monoclonal antibody according to the part (1) of the second embodiment may have a light chain variable domain which comprises the amino acid sequence as set forth as SEQ ID NO: 77. The heavy chain variable domain may comprise the amino acid sequence as set forth as SEQ ID NO: 170.

The isolated monoclonal antibody according to the part (m) of the second embodiment may have a light chain variable domain which comprises the amino acid sequence as set forth as SEQ ID NO: 78. The heavy chain variable domain may comprise the amino acid sequence as set forth as SEQ ID NO: 171.

The sequence of each light chain variable domain and heavy chain variable domain referred to above for the second embodiment may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions.

With reference to all the embodiments described above, one skilled in the art will be aware that any substitutions will retain critical amino acid residues necessary for correct folding and stabilizing between the $V_H$ and the $V_L$ regions, and will retain the charge characteristics of the residues in order to preserve the low pI and low toxicity of the molecules. Thus, one of skill in the art can readily review the sequences shown above, identify a conservative substitution, and produce the conservative variant using well-known molecular techniques.

Epitope mapping has been carried out for some of the antibodies discussed above. In one embodiment, it has been found that residues Asn-47 and Ile-48 of human ROR1 are essential for antibody binding. Therefore, there is provided a monoclonal antibody that binds to an epitope of ROR1, wherein the epitope comprises amino acids Asn-47 and/or Ile-48. Preferably, the epitope comprises amino acids Asn-47 and Ile-48. In some embodiments, the epitope may comprise amino acids Asn-47, Ile-48, Ser-49, Ser-50 and Glu-51 (NISSE-SEQ ID NO: 253).

In another embodiment, it has been found that residue Gln-261 of human ROR1 is essential for antibody binding. Therefore, there is also provided a monoclonal antibody that binds to an epitope of ROR1, wherein the epitope comprises amino acid Gln-261.

Antibody fragments are encompassed by the present disclosure, such as Fab, F(ab')2, and Fv which include a heavy chain and light chain variable region and are capable of binding the epitopic determinant on ROR1. These antibody fragments retain the ability to selectively bind with the antigen and are described above. The fragments can be included in a bispecific antibody. Methods of making these fragments are known in the art (see for example, Harlow and Lane, *Antibodies: A Laboratory Manual*, Cold Spring Harbor Laboratory, New York, 1988).

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

The antibodies or antibody fragments disclosed herein can be derivatized or linked to another molecule (such as another peptide or protein). In general, the antibody or portion thereof is derivatized such that the binding to the ROR1 polypeptide is not affected adversely by the derivatization or labeling. For example, the antibody can be functionally linked, for example, by chemical coupling, genetic fusion, noncovalent association or otherwise to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody that specifically binds a ROR1 polypeptide can be labeled with a detectable moiety or marker as described above.

An antibody can also be labeled with a radiolabeled amino acid. Examples of radiolabels include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I. The radiolabel may be used for both diagnostic and therapeutic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Polynucleotides and Expression

Nucleotide sequences encoding an antibody that specifically binds a ROR1 polypeptide are also provided. The antibody can specifically bind ROR1. Expression vectors are also provided for their efficient expression in cells (for example, mammalian cells).

Recombinant expression of an antibody generally requires construction of an expression vector containing a polynucleotide that encodes the antibody or antibody fragment. Replicable vectors are provided including a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of an antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Nucleic acid molecules (also referred to as polynucleotides) encoding the polypeptides provided herein (including, but not limited to antibodies) can readily be produced by one of skill in the art. For example, these nucleic acids can be produced using the amino acid sequences provided herein (such as the CDR sequences, heavy chain and light chain sequences), sequences available in the art (such as framework sequences), and the genetic code.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the antibodies that specifically bind a ROR1 poypeptide, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3 SR). A wide variety of cloning methods, host cells, and in vitro amplification methodologies are well known to persons of skill.

Any of the nucleic acids encoding any of the antibodies, $V_H$ and/or $V_L$, disclosed herein (or fragment thereof) can be expressed in a recombinantly engineered cell such as bacteria, plant, yeast, insect and mammalian cells. These antibodies can be expressed as individual $V_H$ and/or $V_L$ chain, or can be expressed as a fusion protein. An immunoadhesin can also be expressed. Thus, in some examples, nucleic acids encoding a $V_H$ and $V_L$, and immunoadhesin are provided. The nucleic acid sequences can optionally encode a leader sequence.

To create a single chain antibody, (scFv) the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

The nucleic acid encoding the $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to a ROR1 polypeptide and another antigen. The encoded $V_H$ and $V_L$ optionally can include a furin cleavage site between the $V_H$ and $V_L$ domains.

It is expected that those of skill in the art are knowledgeable in the numerous expression systems available for expression of proteins including E. coli, other bacterial hosts, yeast, and various higher eukaryotic cells such as the COS, CHO, HeLa and myeloma cell lines. Once the expression vector is transferred to a host cell by conventional techniques, the transfected cells are then cultured by conventional techniques, such as to produce an antibody. Thus, host cells are provided containing a polynucleotide encoding an antibody or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines are of use. In one embodiment, the human cell line PER.C6. (Crucell, Netherlands) can be used. Additional cell lines which may be used as hosts for expression of recombinant antibodies include, but are not limited to, insect cells (e.g. Sf21/Sf9, Trichoplusia ni Bti-Tn5b1-4) or yeast cells (e.g. S. cerevisiae, Pichia, U.S. Pat. No. 7,326,681), plant cells (US Published Patent Application No. 20080066200); and chicken cells (PCT Publication No. WO2008142124).

The host cell can be a gram positive bacteria including, but not limited to, Bacillus, Streptococcus, Streptomyces, Staphylococcus, Enterococcus, Lactobacillus, Lactococcus, Clostridium, Geobacillus, and Oceanobacillus. Methods for expressing protein in gram positive bacteria, such as Lactobaccillus are well known in the art, see for example, U.S. Published Patent Application No. 20100/080774. Expression vectors for lactobacillus are described, for example in U.S. Pat. Nos. 6,100,388, and 5,728,571. Leader sequences can be included for expression in Lactobacillus. Gram negative bacteria include, but not limited to, E. coli, Pseudomonas, Salmonella, Campylobacter, Helicobacter, Flavobacterium, Fusobacterium, Ilyobacter, Neisseria, and Ureaplasma.

One or more DNA sequences encoding the antibody or fragment thereof can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the isolated proteins described herein can be achieved by operably linking the DNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthe-* sis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art. Once an antibody molecule has been produced, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies or fragments thereof may be fused to heterologous polypeptide sequences (referred to herein as "tags") described above or otherwise known in the art to facilitate purification.

Compositions and Therapeutic Methods

A method for preventing or treating cancer in a subject is also disclosed, the method comprising administering to the subject a therapeutically effective amount of at least one of the disclosed antibodies, an antigen binding fragment thereof, a nucleic acid encoding the antibody, and/or a nucleic acid encoding the antigen binding fragment, thereby preventing or treating cancer.

The disclosed antibodies can be cytotoxic to cancer cells.

Preferably, the cancer is leukaemia (such as Chronic Lymphocytic Leukaemia (CLL), Acute Lymphoblastic Leukaemia (ALL), Mantle Cell Leukaemia or Hairy Cell Leukaemia), pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

The present invention also relates to the disclosed isolated monoclonal antibodies and antigen binding fragments thereof for use in the treatment or prevention of cancer. Further, the present invention also relates to use of the disclosed isolated monoclonal antibodies and antigen binding fragments thereof in the manufacture of a medicament for the treatment or prevention of cancer.

Preferably, the cancer is leukaemia (such as Chronic Lymphocytic Leukaemia (CLL), Acute Lymphoblastic Leukaemia (ALL), Mantle Cell Leukaemia or Hairy Cell Leukaemia), pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

The cancer or tumour does not need to be completely eliminated for the composition to be effective. For example, a composition can reduce the tumour by a desired amount, for example by at least 10%, at least 20%, at least 50%, at least 60%, at least 70%, at least 80%, at least 90%, at least 95%, at least 98%, or 100%, as compared to the absence of the composition.

In another example, the subject can also be administered an effective amount of an additional agent, such as a chemotherapy agent. The methods can include administration of one on more additional agents known in the art.

A therapeutically effective amount of a ROR1-specific antibody or antigen binding fragment (or the nucleic acid encoding the antibody or antigen binding fragment), or nucleic acid, will depend upon the severity of the disease and the general state of the patient's health. A therapeutically effective amount of the antibody can provide either subjective relief of a symptom(s) or an objectively identifiable improvement as noted by the clinician or other qualified observer. As noted above, these compositions can be administered in conjunction with another therapeutic agent, either simultaneously or sequentially. For any application, the antibody, antigen binding fragment, or nucleic acid encoding the antibody or antigen binding fragment can be combined with chemotherapy.

Single or multiple administrations of the compositions including the antibody, antigen binding fragment, or nucleic acid encoding the antibody or antigen binding fragment, that are disclosed herein, are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Compositions are further disclosed that include one or more of the antibodies that specifically bind a ROR1 polypeptide, or antigen binding fragments of any of these antibodies, and nucleic acids encoding these antibodies (and antigen binding fragments) that are disclosed herein in a carrier. The compositions can be prepared in unit dosage forms for administration to a subject. The amount and timing of administration are at the discretion of the treating physician to achieve the desired purposes. The antibody and/or nucleic acid can be formulated for systemic or local administration. In one example, the antibody and/or nucleic acid is formulated for parenteral administration, such as intravenous administration. In some embodiments, administration is intramuscular.

Active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the immunogens or antibodies can be prepared by such methods as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. The everse-phase evaporation method can be used with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described, for example, in Martin et al., J. Biol. Chem., 257:286-288 (1982) via a disulfide interchange reaction.

The compositions for administration can include a solution of the antibody that specifically binds a ROR1 polypeptide, dissolved in a pharmaceutically acceptable carrier, such as an aqueous carrier. A variety of aqueous carriers can be used, for example, buffered saline and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs. In some embodiments, administration is intravenous.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)).

A typical pharmaceutical composition for intravenous administration includes about 0.1 to 10 mg/kg of antibody per day, or 0.5 to 15 mg/kg of antibody per day. Dosages from 0.1 up to about 100 mg/kg per subject per day may be used, particularly if the agent is administered to a secluded site and not into the circulatory or lymph system, such as into a body cavity or into a lumen of an organ. Exemplary doses include 1 to 10 mg/kg, such as 2 to 8 mg/kg, such as 3 to 6 mg/kg. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.1 to 10 mg/kg or 0.5 to 15 mg/kg of body weight. Exemplary doses include 1 to 10 mg/kg, such as 2 to 8 mg/kg, such as 3 to 6 mg/kg. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding the antibody or an antigen binding fragment thereof can be administered to a subject in need thereof. One approach to administration of nucleic acids is direct immunization with plasmid DNA, such as with a mammalian expression plasmid. The nucleotide sequence encoding the antibody or fragment thereof can be placed under the control of a promoter to increase expression of the molecule. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids to an organism. The methods include liposomal delivery of the nucleic acids.

In another approach to using nucleic acids, an antibody or antigen binding fragment thereof can also be expressed by attenuated viral hosts or vectors or bacterial vectors, which can be administered to a subject. Recombinant vaccinia virus, adeno-associated virus (AAV), herpes virus, retrovirus, cytomegalovirus, poxvirus or other viral vectors can be used to express the antibody. For example, vaccinia vectors are described in U.S. Pat. No. 4,722,848. BCG (Bacillus Calmette Guerin) provides another vector for expression of the disclosed antibodies (see Stover, *Nature* 351:456-460, 1991).

In one embodiment, a nucleic acid encoding the antibody or an antigen binding fragment thereof is introduced directly into cells. For example, the nucleic acid can be loaded onto gold microspheres by standard methods and introduced into the skin by a device such as Bio-Rad's Heliosä Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In some examples, a subject is administered the DNA encoding the antibody or antibody binding fragments thereof to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

Diagnostic Methods and Kits

A method of detecting cancer in a subject is disclosed, the method comprising:
contacting a biological sample from the subject with at least one disclosed isolated monoclonal antibody or an antigen binding fragment thereof; and
detecting antibody bound to the sample,
wherein the presence of antibody bound to the sample indicates that the subject has cancer.

Preferably the antibody specifically binds a ROR1 polypeptide, and the presence of antibody bound to the sample indicates that the subject has leukaemia (such as Chronic Lymphocytic Leukaemia (CLL), Acute Lymphoblastic Leukaemia (ALL), Mantle Cell Leukaemia or Hairy Cell Leukaemia), pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

Preferably, the isolated monoclonal antibody is directly labeled.

The method may further comprise contacting the sample with a second antibody that specifically binds the isolated monoclonal antibody; and detecting the binding of the second antibody, wherein an increase in binding of the second antibody to the sample as compared to binding of the second antibody to a control sample detects the presence of cancer in the subject.

The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid, nasopharyngeal secretions or urine.

Also disclosed is a method of detecting ROR1 comprising:
contacting a biological sample from a subject with at least one disclosed isolated monoclonal antibody or an antigen binding fragment thereof; and
detecting antibody bound to the sample.

The detection of ROR1 can be achieved, for example, by contacting a sample to be tested, optionally along with a control sample, with the antibody under conditions that allow for formation of a complex between the antibody and the polypeptide. Complex formation is then detected (e.g., using an ELISA). When using a control sample along with the test sample, complex is detected in both samples and any statistically significant difference in the formation of complexes between the samples is indicative of the presence of ROR1 in the test sample.

In some embodiments, an antibody is directly labeled with a detectable label. In another embodiment, the antibody that binds the ROR1 (the first antibody) is unlabeled and a second antibody or other molecule that can bind the antibody that binds the ROR1 polypeptide is utilized. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above.

The immunoassays and method disclosed herein can be used for a number of purposes. Kits for detecting a ROR1 polypeptide will typically comprise an antibody that binds a ROR1 polypeptide, for example, any of the antibodies disclosed herein. In some embodiments, an antibody fragment, such as an Fv fragment or a Fab is included in the kit. In a further embodiment, the antibody is labeled (for example, with a fluorescent, radioactive, or an enzymatic label).

In one embodiment, a kit includes instructional materials disclosing means of use. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting the ROR1 polypeptide in a biological sample generally includes the steps of contacting the biological sample with an antibody which specifically reacts, under immunologically reactive conditions, to the viral polypeptide. The antibody is allowed to specifically bind under immunologically reactive conditions to form an immune complex, and the presence of the immune complex (bound antibody) is detected directly or indirectly.

The following examples are provided to illustrate certain particular features and/or embodiments. These examples should not be construed to limit the disclosure to the particular features or embodiments described. The examples should be read in combination with the figures which are as follows:

FIG. 1: Identification of ROR1 binding domain: (A) SUP-T1 cells were transduced with retroviral vectors containing either the full extracellular portion of ROR1 or only one or two extracellular domains. Non-transduced SUP-T1 (SUP-T1 NT) cells served as negative control. (B) All 12 chimeric antibodies and (C) all 10 positive clones in scFv format were incubated with SUP-T1 NT and the new stable cell lines at 4° C. for 30 min. Cells were washed and stained with a secondary antibody (anti-human Fc-Dylight647), which was used as negative control. eROR1=extracellular ROR1, Ig-like=Immunoglobulin-like domain, Fz=Frizzled domain, Kg=Kringle domain.

Figure 2:
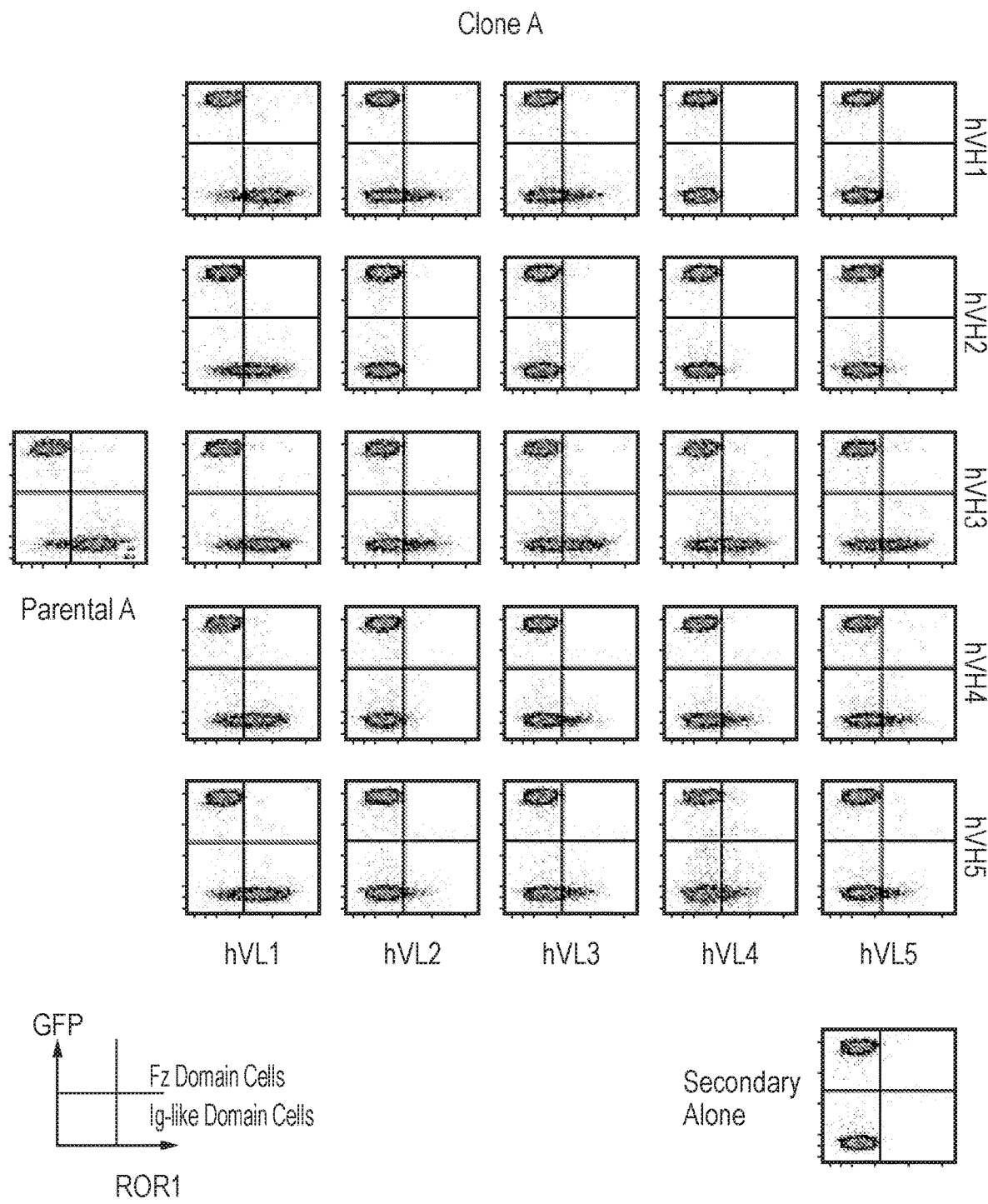
Figure 2:
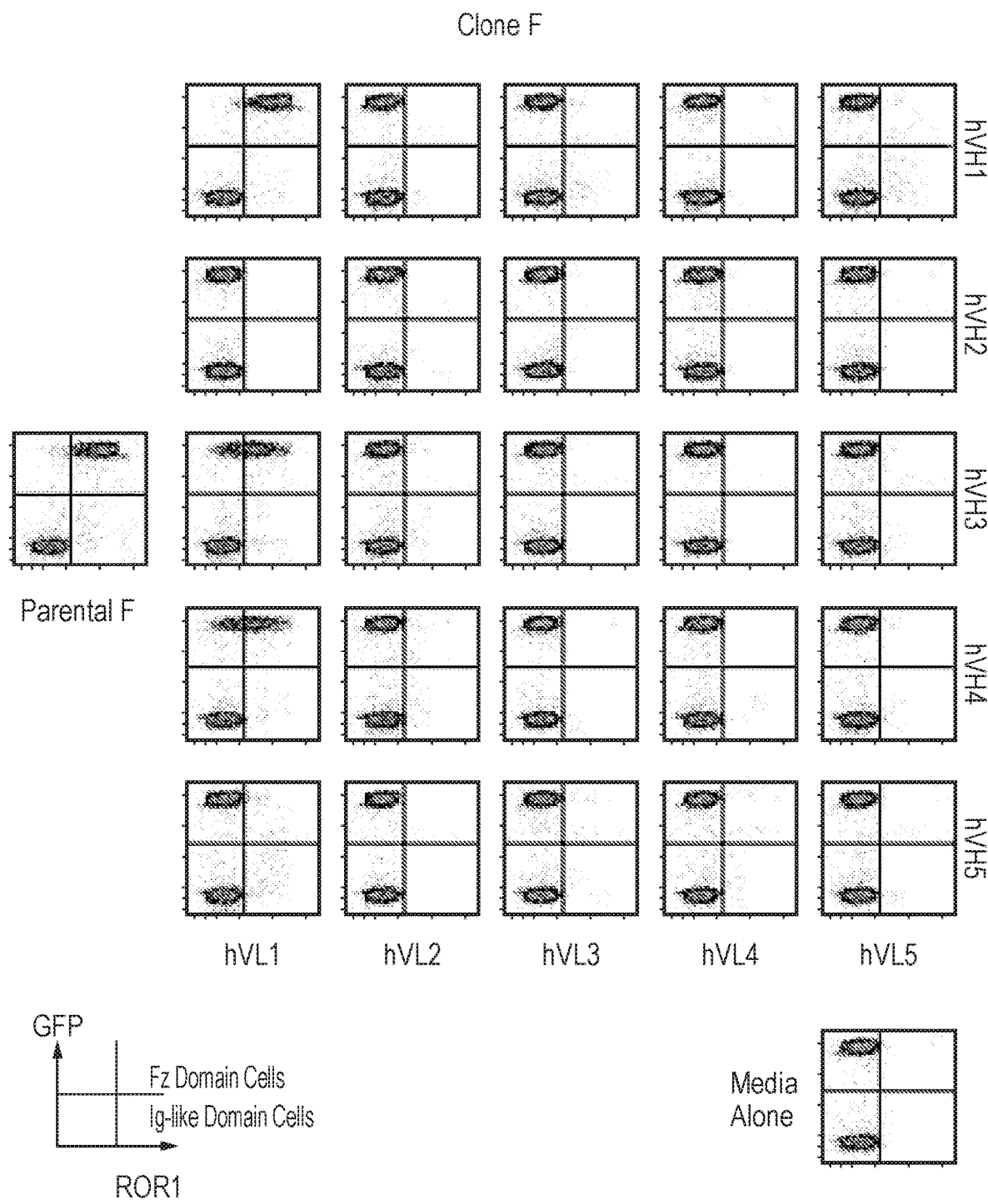

FIG. 2: Humanization of rat scFvs: A total of 25 constructs per clone were generated by combining five VH and five VL. All 25 scFv constructs were tested on ROR1$^+$ and ROR1$^-$ cell lines. Secondary antibody alone and media alone served as negative controls, whilst the parental versions of each clone acted as positive control.

Figure 3:
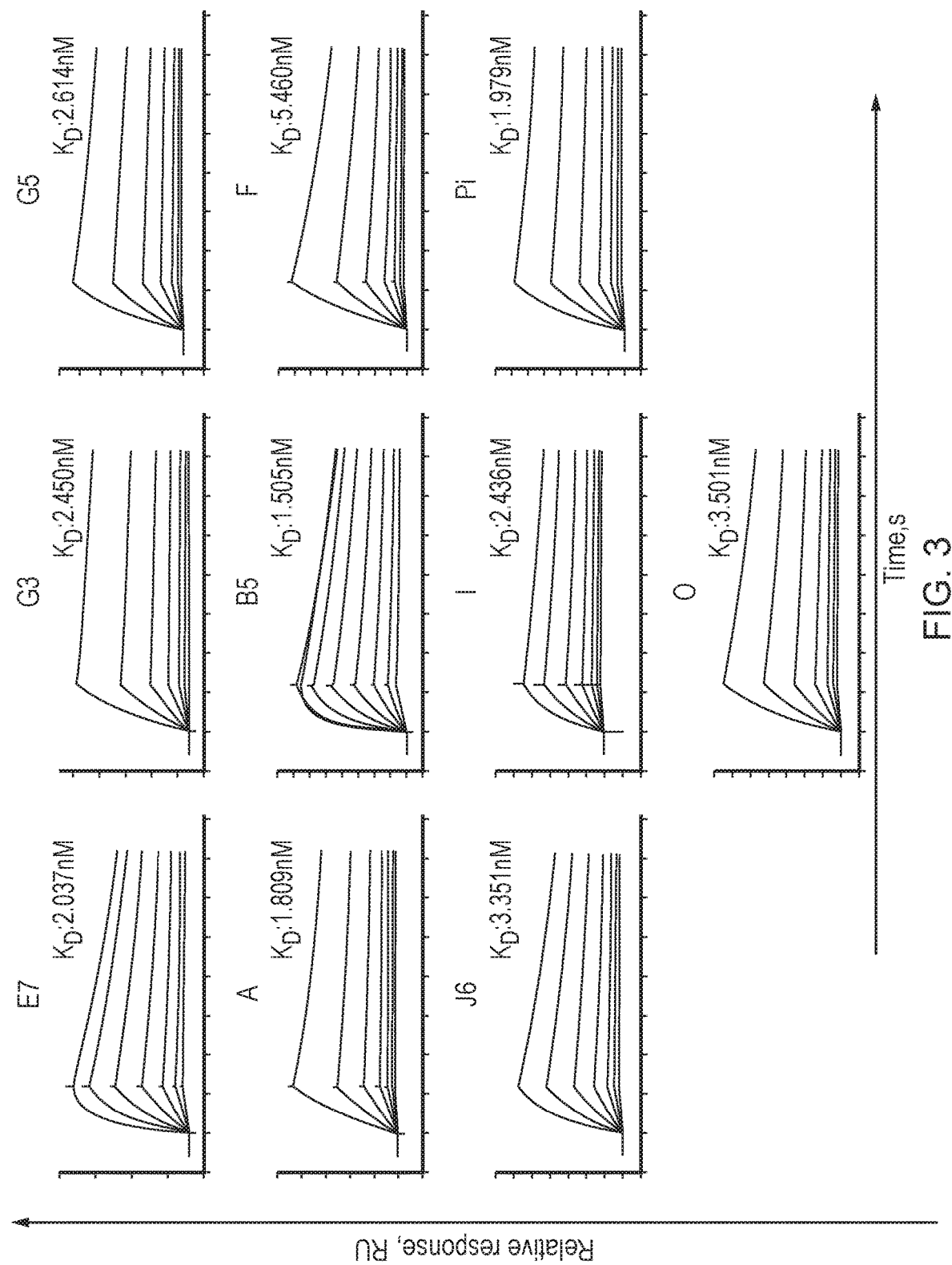

FIG. 3: $K_D$ determination by surface plasmon resonance. Sensorgrams obtained using a Biacore X100 instrument are shown. Briefly, ROR1 antibodies were immobilized using a CMS chip and seven different concentrations of the Histidine-tagged ROR1 protein (extracellular region) were injected. Concentrations ranged from 1.5 to 100 nm.

FIG. 4: Complement-dependent cytotoxicity of ROR1 MAbs on CLL cells (n=3). (A) Chimeric ROR1 MAbs supernatants were tested at 0.5 ug/ml on CLL cells and PBMCs. Only clone A showed a significant toxicity compared to the isotype (p<0.001). Rituximab (Rtx) was used as positive control at 0.5 ug/ml and 10 ug/ml, and achieved significant cytotoxicity on CLL1 and CLL2 samples (p<0.001). Cytotoxicity on CLL samples was normalized to PBMCs' data. (B) Cell surface staining for CD20 and ROR1 by flow cytometry. The red area represents the isotype control. Error bars in (A) represent SD. Experiments were done in triplicates.

FIG. 5: Epitope mapping of ROR1 clone A MAb. (A) Reactivity of clone A with ROR1-derived overlapping peptides was analyzed by ELISA. (B) Amino acid substitution within the epitope binding region was performed in ROR1-transduced cell lines. Also, the previously described clones R12, 4a5 and D10 were also included for comparison. Red circles indicate essential amino acids for antibody binding. One out of three experiments is shown. Experiments were done in triplicates. Error bars represent SD.

FIG. 6: Epitope mapping of ROR1 clone F MAb. (A) Reactivity of clone F with ROR1-derived overlapping peptides was analyzed by ELISA. Since no linear epitope was identified, (B) amino acid substitution of non-conserved regions within the Fz domain was performed in ROR1-Fz transduced cell lines. Circles indicate essential amino acids for antibody binding. One out of three experiments is shown. Experiments were done in triplicates. Error bars represent SD.

Figure 7:
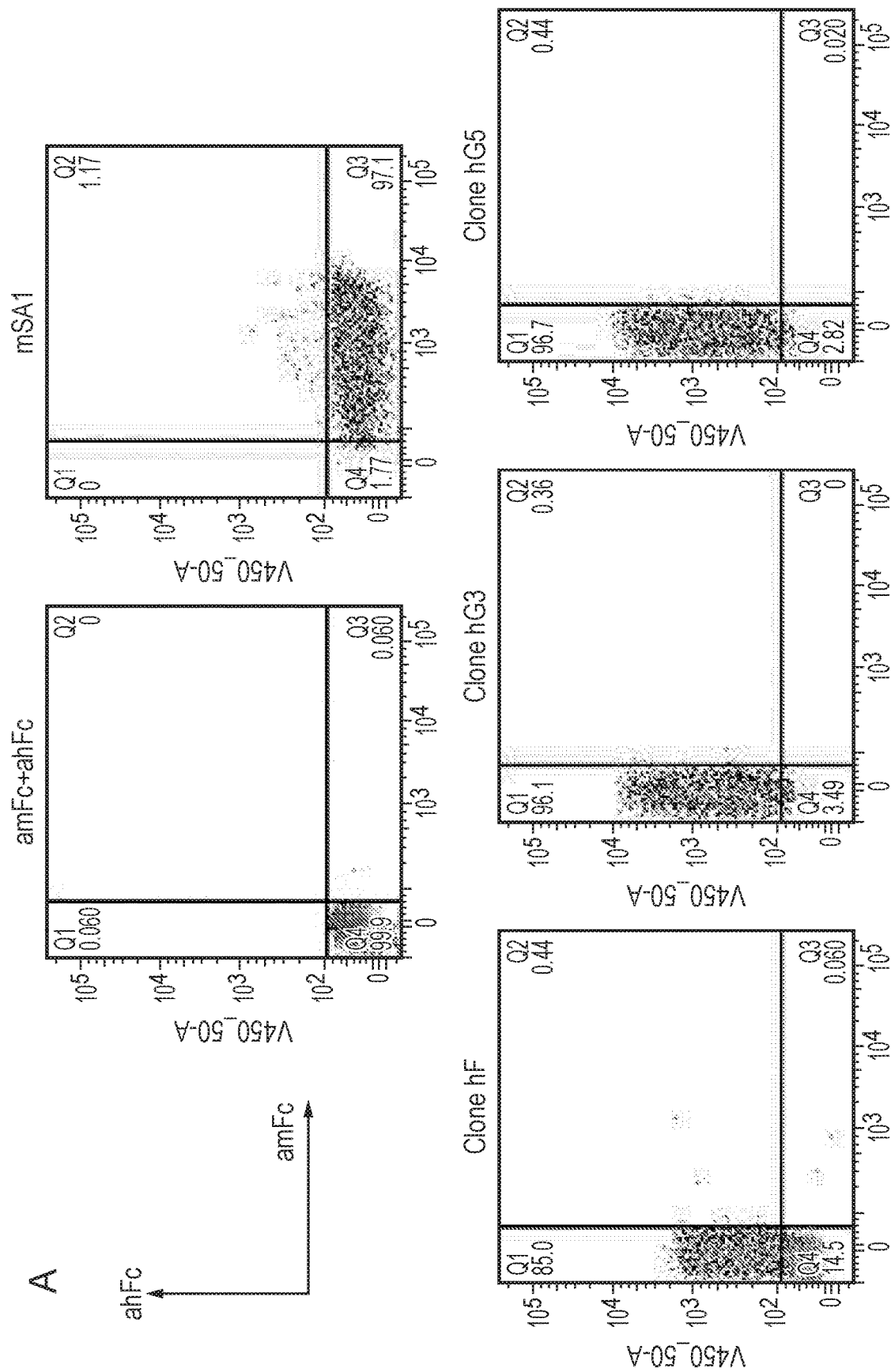
Figure 7:
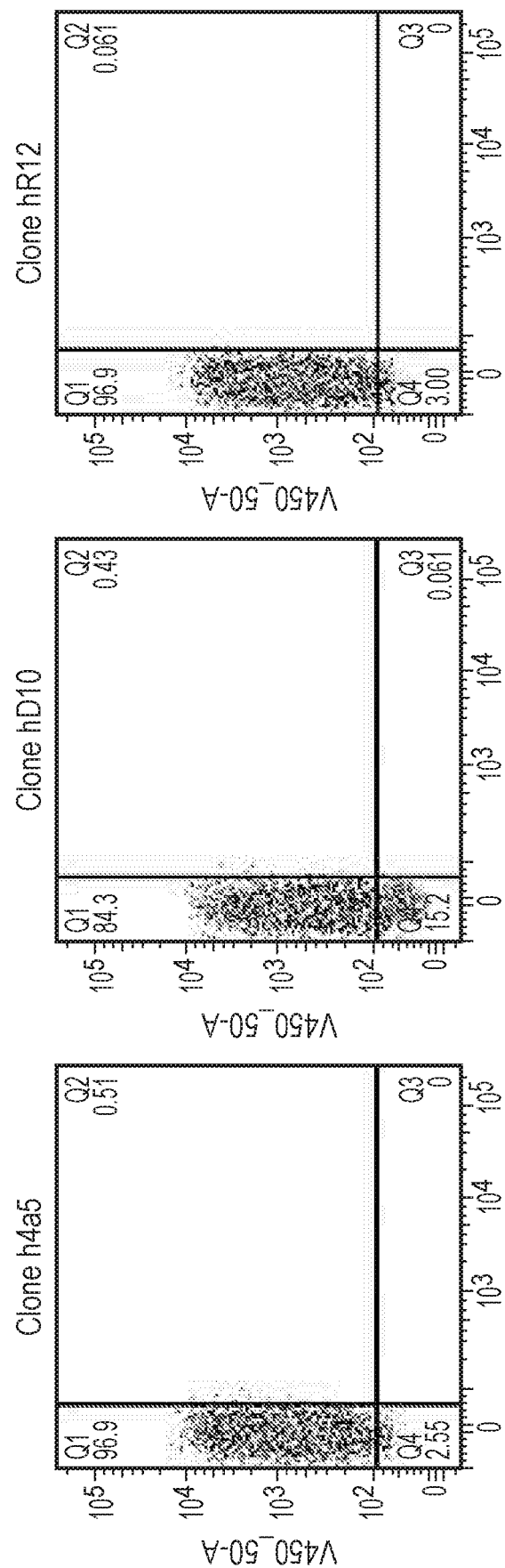
Figure 7:
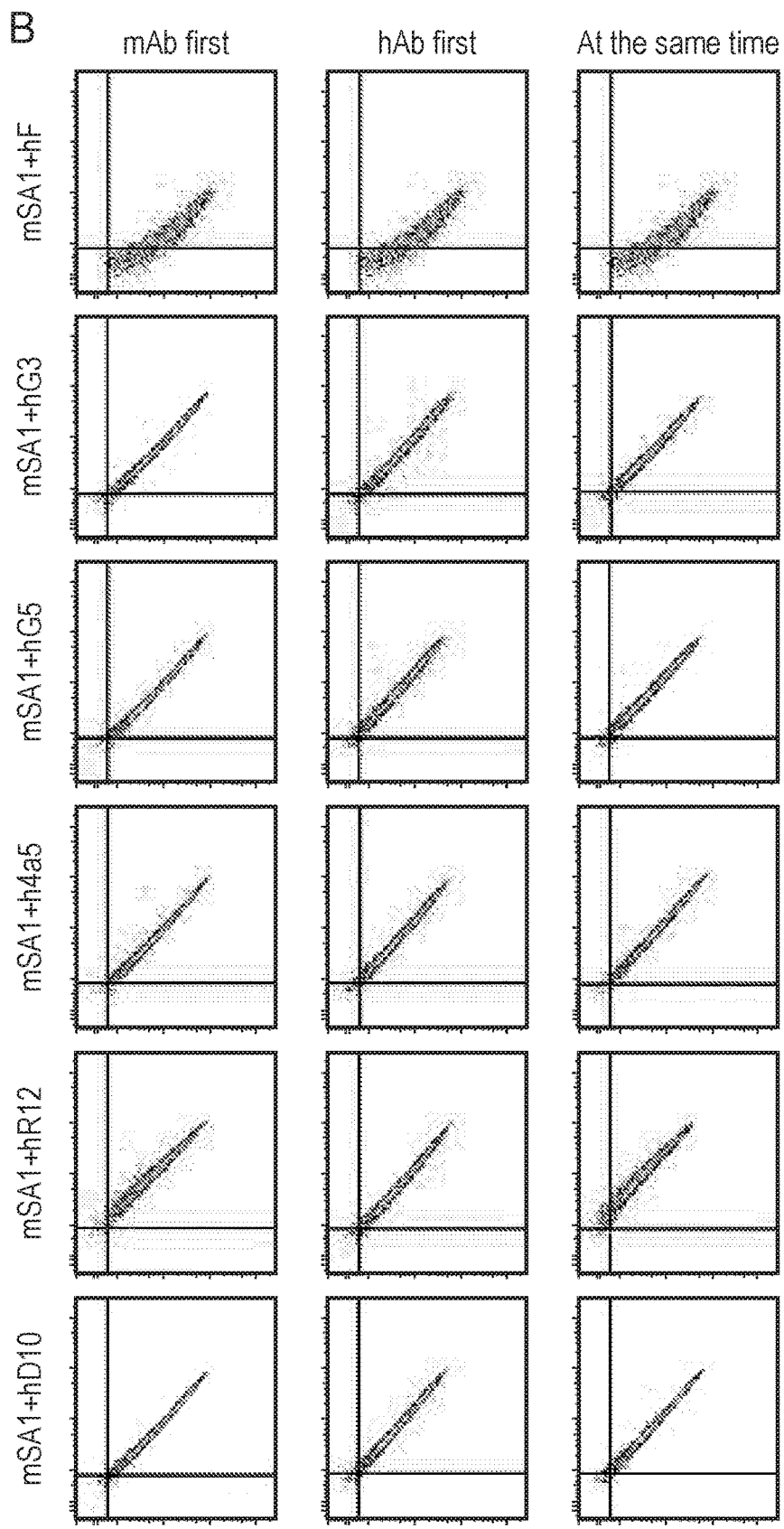

FIG. 7: Competition assay by flow cytometry. Clone A (SA1) in murine IgG2a, k (mSA1) along with other ROR1 MAbs in human IgG1, k—including previously published 4a5, D10 and R12 clones—were used for staining ROR1-transduced cells. MAb staining was done as (A) single agents or (B) in combination with clone A (mSA1). Anti-human IgG (450) and anti-mouse IgG (DyLight649) were used as secondary antibodies. Combined staining using clones F and mSA1 acted as negative control for overlapping epitopes.

Figure 8:
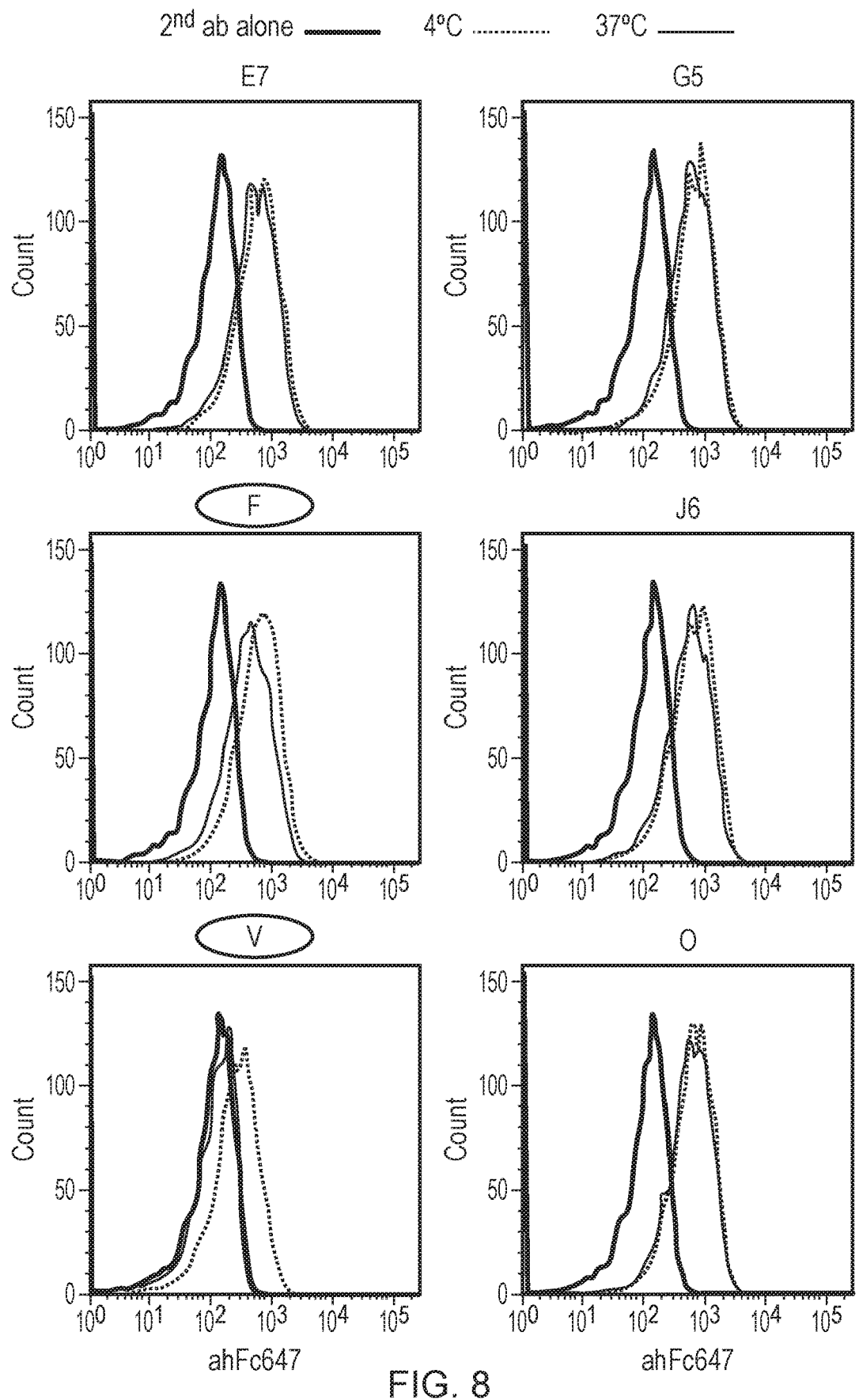
Figure 8:
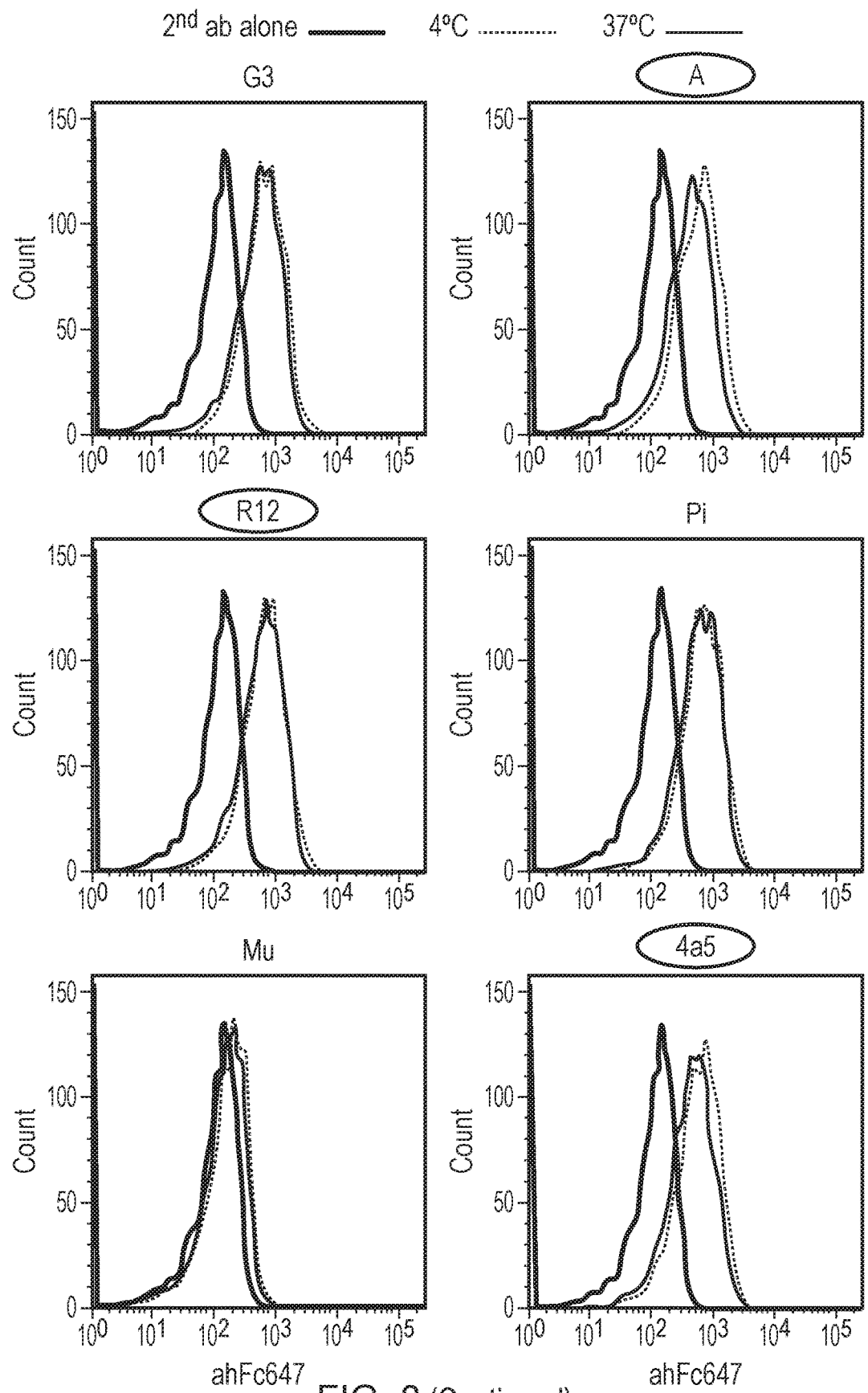
Figure 8:
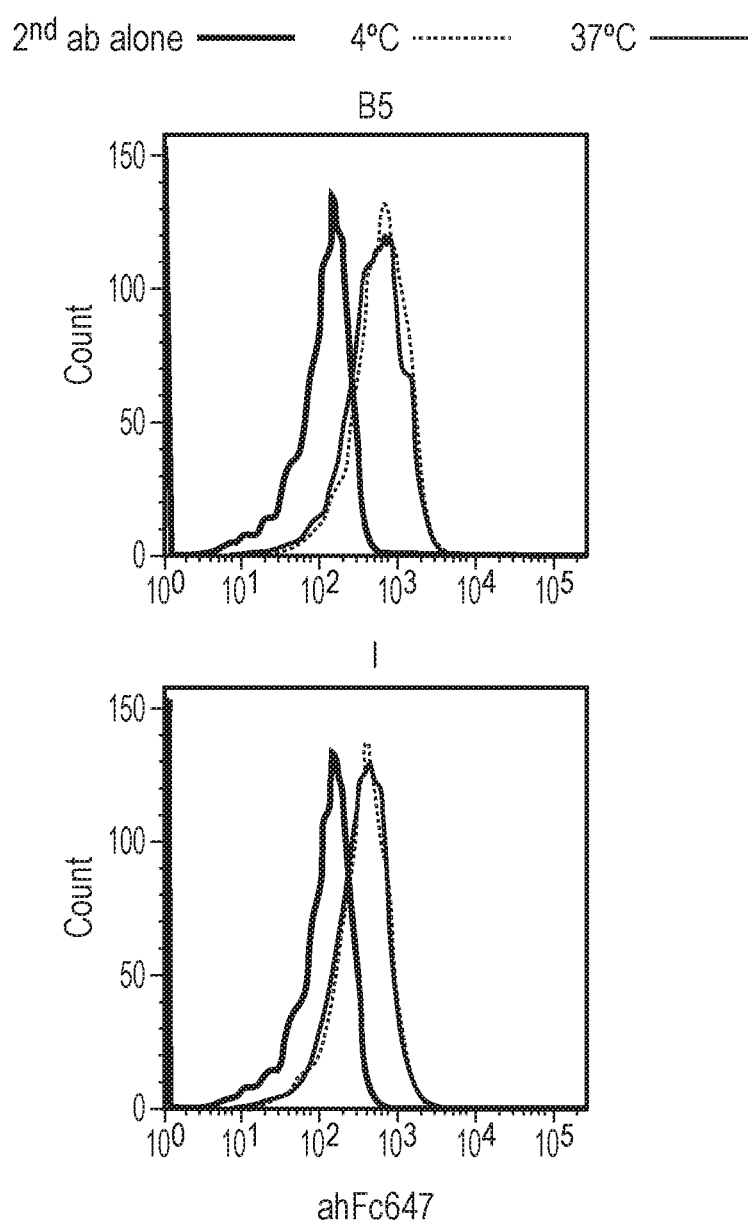

FIG. 8: Internalisation of ROR1 antibodies on SKW 6.4 GFP cells by flow cytometry. SKW 6.4 GFP cells were stained at 4° C. and either kept on ice (blue line) or incubated at 37° C. (yellow line) for 1 h. Of all tested MAbs, clone V showed a pronounced reduction in MFI (green circle). Clones A, F and Mu (purple circle) were selected for further investigation. Clones R12 and 4a5 (in black) served as negative and positive control, respectively. Anti-human Fc-Dylight 647 was used as secondary antibody and as staining control (red line). MFI=Median Fluorescence Intensity.

Figure 9:
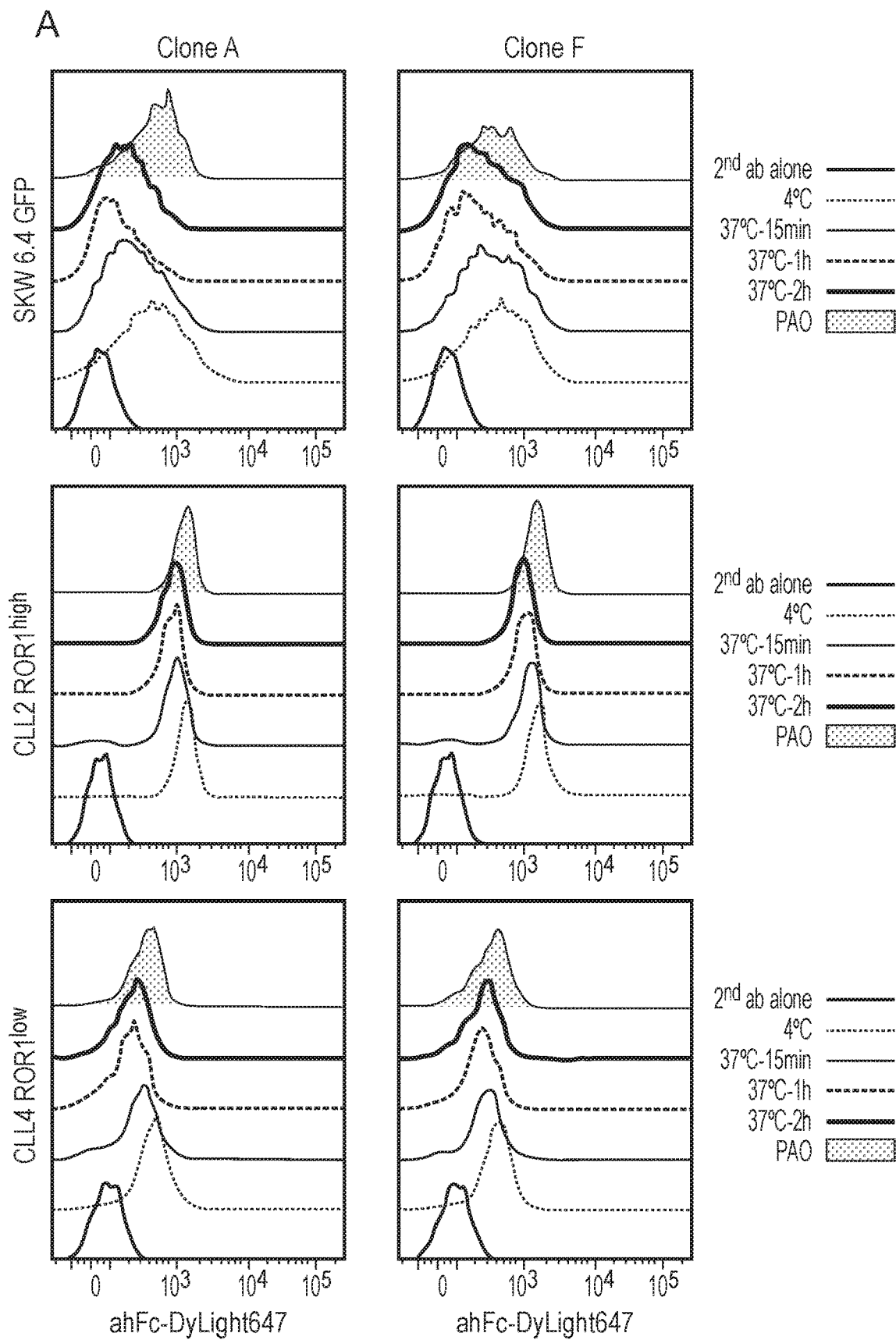
Figure 9:
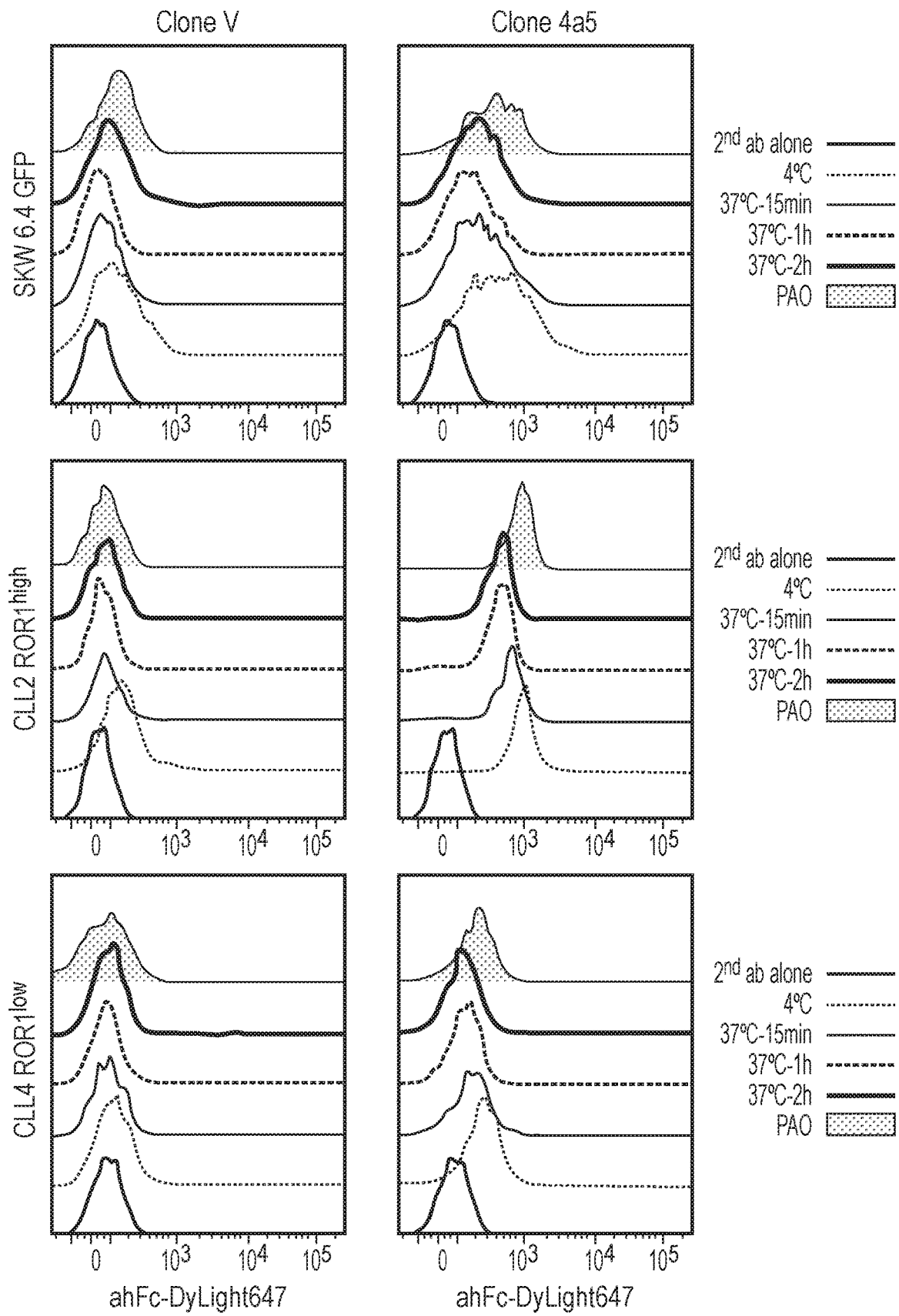
Figure 9:
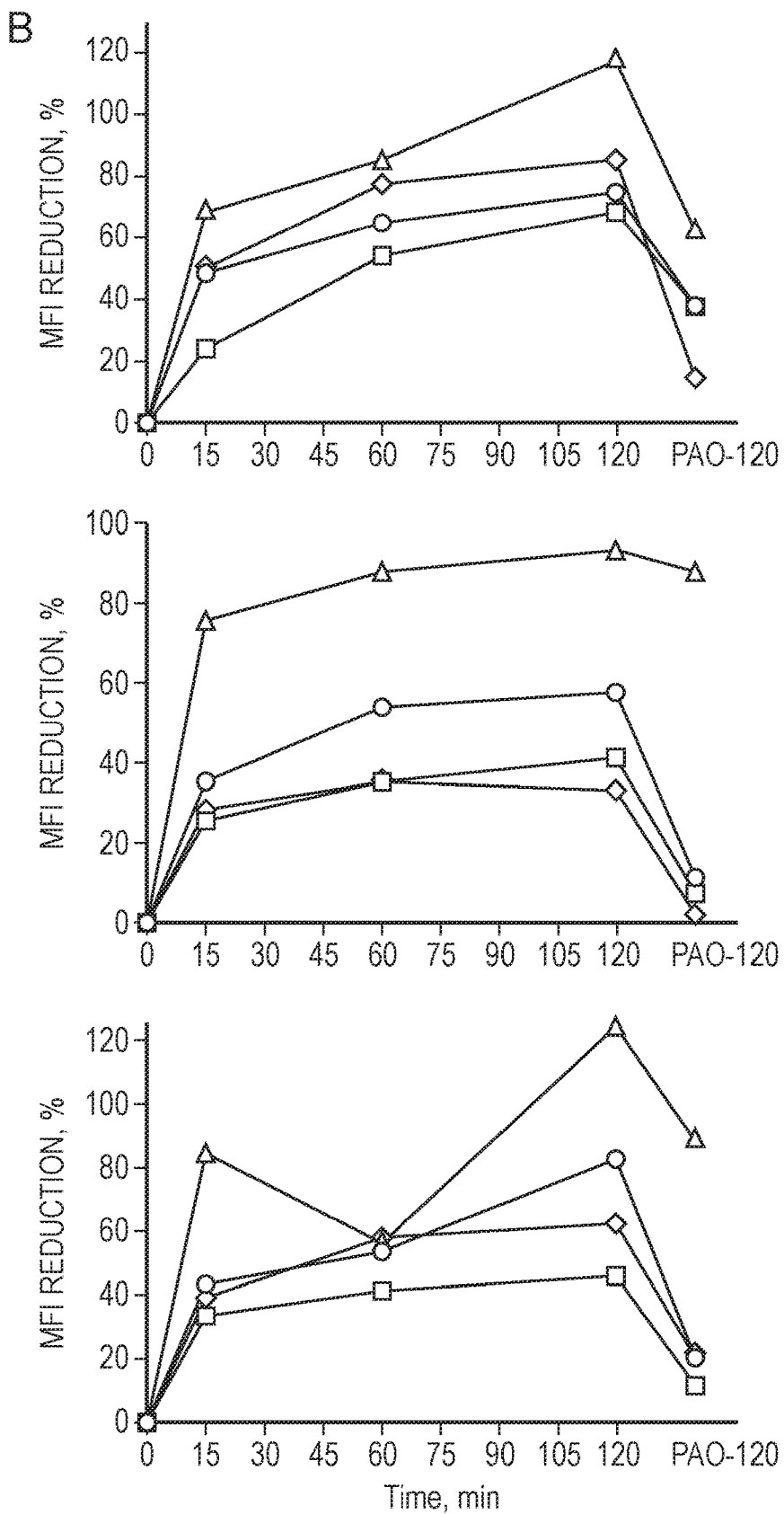

FIG. 9: Internalisation of ROR1 MAbs on SKW 6.4 GFP and CLL cells by flow cytometry. Cells were stained at 4° C. and either left on ice or incubated at 37° C. for 15 min, 1 h and 2 h. Cells were then analysed using an anti-human IgG as secondary antibody. (A) Histograms and (B) Trends over time showing the MFI reduction over time are presented. The % of MFI reduction was calculated as described in the Materials and Methods chapter. Phenylarsine oxide (PAO), an endocytosis inhibitor, acted as negative control (PAO-120).

EXAMPLES

Example 1

Immunization of Rats and Production of ROR1 Antibodies

A total of 3 Wistar rats were immunized using a DNA-based protocol. Briefly, human ROR1 coding sequence cloned into an immunization plasmid was introduced into the rats, the target protein was expressed and an immune response was generated. Four applications of DNA using a gene gun were initially performed. Rat serum was then analyzed, followed by 4 additional applications. After confirming that serum from all three challenged rats showed presence of anti-human ROR1 antibodies by flow cytometry, animals were sacrificed after 102 days of immunization. Lymph nodes were removed and pooled in order to produce oligoclonal hybridoma cell lines.

A total of 38 positive hybridomas were identified by testing their binding ability to cells transfected with either pB1-ROR1-hum or with an irrelevant construct. As before, this was assessed by flow cytometry.

Antibody sequences were obtained by 5' Rapid Amplification of cDNA ends. Oligoclonal hybridomas from Aldevron GmBH were separated into single cell clones either by dilution or single cell sorting into 96 well plates and colonies grown until confluent (approximately 2 weeks). Supernatant was screened against ROR1 positive and negative cell lines to ensure the presence of a specific anti-ROR1 antibody and also used for isotyping using rat immunoglobulin isotyping kits (eBioscience or BD Bioscience).

Clones were grown until confluence in 6 well plates or 10 cm plates and then pelleted into RNAlater (Life Technologies) before RNA was extracted using RNA MiniPlus Kit (Qiagen). RNA was reverse transcribed to cDNA using Quantitect Reverse Transcriptase (Qiagen). An aliquot of this cDNA was assessed with GAPDH primers which were able to differentiate genomic and cDNA to ensure quality of samples. cDNA had a polyC tail added with Terminal Transferase (New England Biolabs) and nested PCR reactions were performed (Phusion Taq; New England Biolabs or Platinum Taq High Fidelity: Life Technologies) to identify the variable regions of the heavy and light chains, using primers specific for light chain isotype and heavy chain isotype.

PCR products were run on a 1% TBE gel and post-stained with Gelstar (Lonza). Bands of the correct size were extracted and sent for direct sequencing or inserted into Topo subcloning vectors (Life Technologies) for subsequent sequencing.

Sequence data was compared to the IMGT V-QUEST database of Rat germline immunoglobulin sequences and consensus sequences obtained that were productive and had an in frame signal sequence (Brochet et al., 2008, Alamyar et al., 2012). Overlap extension primers were designed to amplify the heavy and light chains whilst introducing a linker sequence to generate ScFv constructs. A secreted version of the ScFv was produced by cloning the ScFv sequence in frame with murine IgG2a constant region using NcoI and BamHI sites (or if needed the compatible Bg1II or B1I sites).

Antibodies were generated by cloning the variable sequence in frame with human IgG1 or mouse heavy IgG2a chain constant regions, and light chain with the corresponding human or mouse kappa constant regions. NcoI and MluI sites (or if needed, the compatible BspHI or PciI sites) were used. For humanized antibodies, variable regions were cloned in frame with human heavy IgG1 and light kappa constant regions.

A total of 17 novel scFvs were generated. Out of these, 12 clones bound as antibodies and 10 bound in a single chain variable fragment (scFv) format (See Table 1). Additionally, to identify the binding domain of all positive clones, stable cell lines expressing either the full extracellular region of ROR1 (eROR1) or varying regions of its extracellular domains: Ig-like alone, Ig-like+Frizzled (Fz), Fz alone, Fz+Kringle (Kg) and Kg alone were generated by transducing SUP-T1 cells with retroviral supernatants (See FIG. 1A).

In FIGS. 1B and 1C, we present flow cytometry data showing the binding domains of all 12 antibodies and 10 scFvs, respectively.

TABLE 1

|  | Binding Domain | Binds as whole immunoglobulin | Binds in scFv format |
| --- | --- | --- | --- |
| Clone G3 | Ig | Yes | No |
| Clone G5 | Ig | Yes | Yes |
| Clone E7 | Ig | Yes | No |
| Clone J | Ig | Yes | No |
| Clone F | Fz | Yes | Yes |
| Clone B | Ig | Yes | Yes |
| Clone A | Ig | Yes | Yes |
| Clone I | Ig | Yes | Yes |
| Clone O | Ig | Yes | Yes |
| Clone Pi | Ig | Yes | Yes |
| Clone Mu | Ig | Yes | Yes |
| Clone R | Ig | Not tested | Yes |
| Clone V | Between Ig and Fz | Yes | Yes |

As can be seen in FIG. 1C, in addition to the 10 scFv clones, two known ROR1 antibodies (R12 and 4A5) were also tested.

With the exception of clone F, which binds the frizzled domain and clone V, which binds only the Ig-Fz protein, all other clones bound the immunoglobulin domain. Interestingly, and somewhat surprisingly, the prior art antibodies R12 and 4A5 show different and distinct binding characteristics to Clone F.

Example 2

Humanisation of Rat scFvs

Clones A and F were selected for humanisation. The variable domain sequences of rat scFvs were searched against the human IgG germline database. Five human framework sequences with high homology to each rat antibody were chosen as human acceptors for both light and heavy chains CDRs. The sequences of five humanized VLs and humanized VHs were obtained after directly grafting the CDRs of each rat antibody to the human acceptor frameworks.

For each clone, a total of 25 constructs were generated by combining all five VH and five VL. Cloning was performed as described above. Binding was then tested on ROR1+ and ROR1− cell lines. Parental versions of clone A and F scFvs served as positive control for antibody staining, whilst media alone and secondary antibody alone acted as negative controls (See FIG. 2).

Example 3

Binding Efficiencies

We undertook surface plasmon resonance evaluation using a Biacore X100 instrument. ROR1 chimeric antibodies were immobilised using an anti-human IgG1 antibody capture kit and a CM5 sensor chip. Seven different concentrations, ranging from 1.5-100 nM, of the extracellular portion of ROR1 bearing a Histidine tag were then injected.

Surface plasmon resonance analysis showed that clones B5, A and Pi possessed the strongest affinities (1.51, 1.81 and 1.98 nM, respectively), whilst clone F presented the weakest one (5.46 nM).

Table 2 below further illustrates the binding kinetics of our ROR1 chimeric antibodies.

Affinity Values ($K_D$) of Chimeric ROR1 Antibodies

| ROR1 Antibody | $K_{on}$, $(10^5)M^{-1}s^{-1}$ | $K_{off}$, $(10^{-4})s^{-1}$ | $K_D$, $10^{-9}M$ |
| --- | --- | --- | --- |
| E7 | 4.168 | 8.490 | 2.037 |
| G3 | 1.086 | 2.660 | 2.450 |
| G5 | 1.593 | 4.164 | 2.614 |
| A | 5.774 | 10.44 | 1.809 |
| B5 | 4.639 | 6.980 | 1.505 |
| F | 1.531 | 8.362 | 5.460 |
| J6 | 2.492 | 8.351 | 3.351 |
| I | 2.093 | 5.100 | 2.436 |
| Pi | 1.763 | 3.487 | 1.979 |
| O | 1.735 | 6.075 | 3.501 |

Example 4

Anti-Human ROR1 Antibody Cytotoxicity on Chronic Lymphoid Leukemia (CLL) Cells-Complement-Dependent Cytotoxicity (CDC) Assay A CDC assay of the antibodies described above was carried out. Two antibodies from other groups, namely R12 and 4A5, were also tested to see how the antibodies of the invention compared to previously published antibodies. Antibodies were generated with human IgG1 Fc domain. The antibodies were incubated for two hours with CLL cells, after which cytotoxicity on the cells was determined.

Antibodies were tested at a concentration of 0.5 ug/ml. The isotype and Rituximab (Rtx) controls were therefore used at this concentration. For Rituximab however we used an additional concentration of 10 ug/ml in order to have a true positive control for the assay.

Figure 4A:
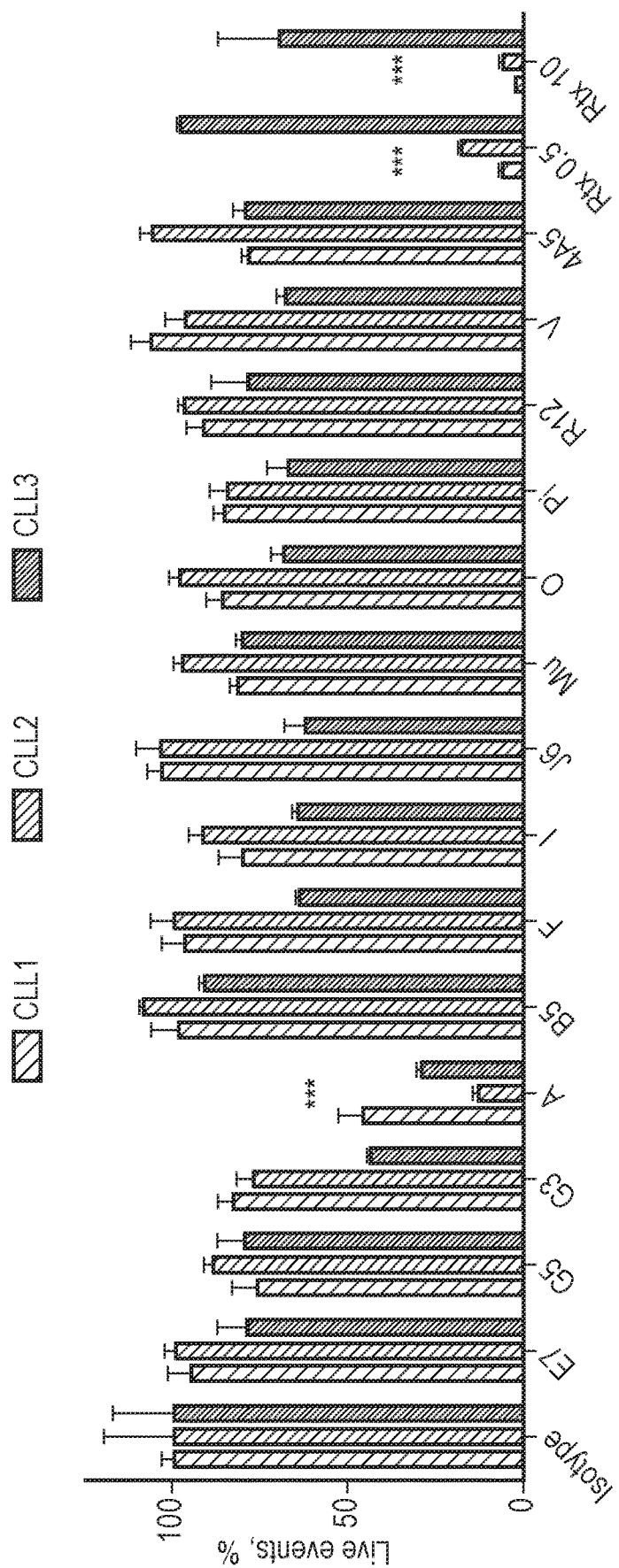

In FIG. 4A, CDC activity elicited by all 12 of our own ROR1 chimeric antibodies can be observed. Of all antibodies evaluated, clone A was the only one that showed significant cytotoxicity compared to the isotype ($p<0.001$). Remarkably, clone A was also better at killing CLL cells than the known ROR1 antibodies R12 and 4a5 but was still not as CDC active as Rituximab.

Figure 4B:
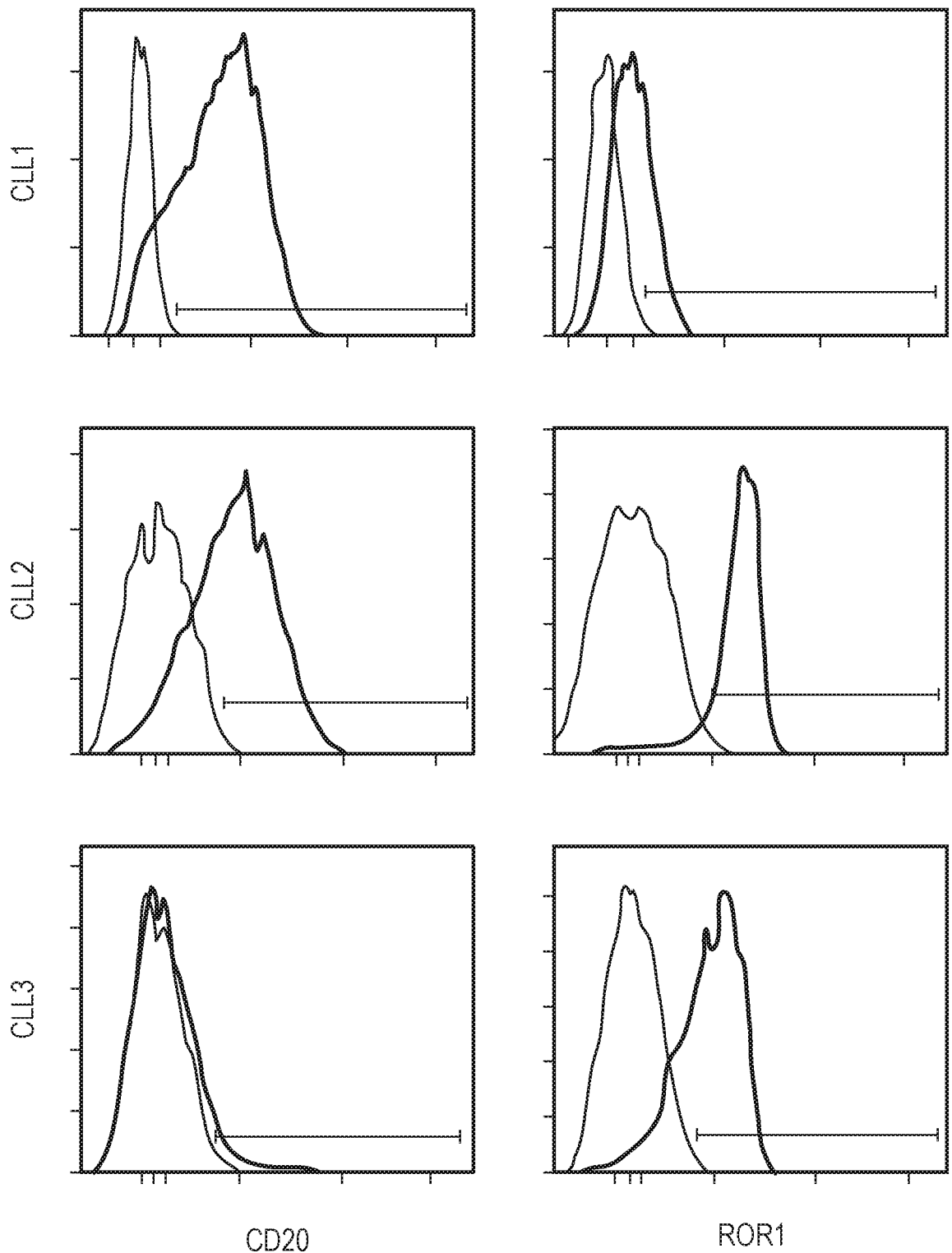

The expression levels of both CD20 and ROR1 antigens on the surface of CLL samples was also assessed. FIG. 4B explains why Rituximab is able to kill CD20 expressing cells very efficiently (CLL1 and 2), but not CLL3, as the latter was virtually negative for CD20 expression.

Example 5

Epitope Mapping

The epitopes of clones A and F described above were mapped by two approaches: peptide library ELISA and amino acid substitution.

Figure 5A:
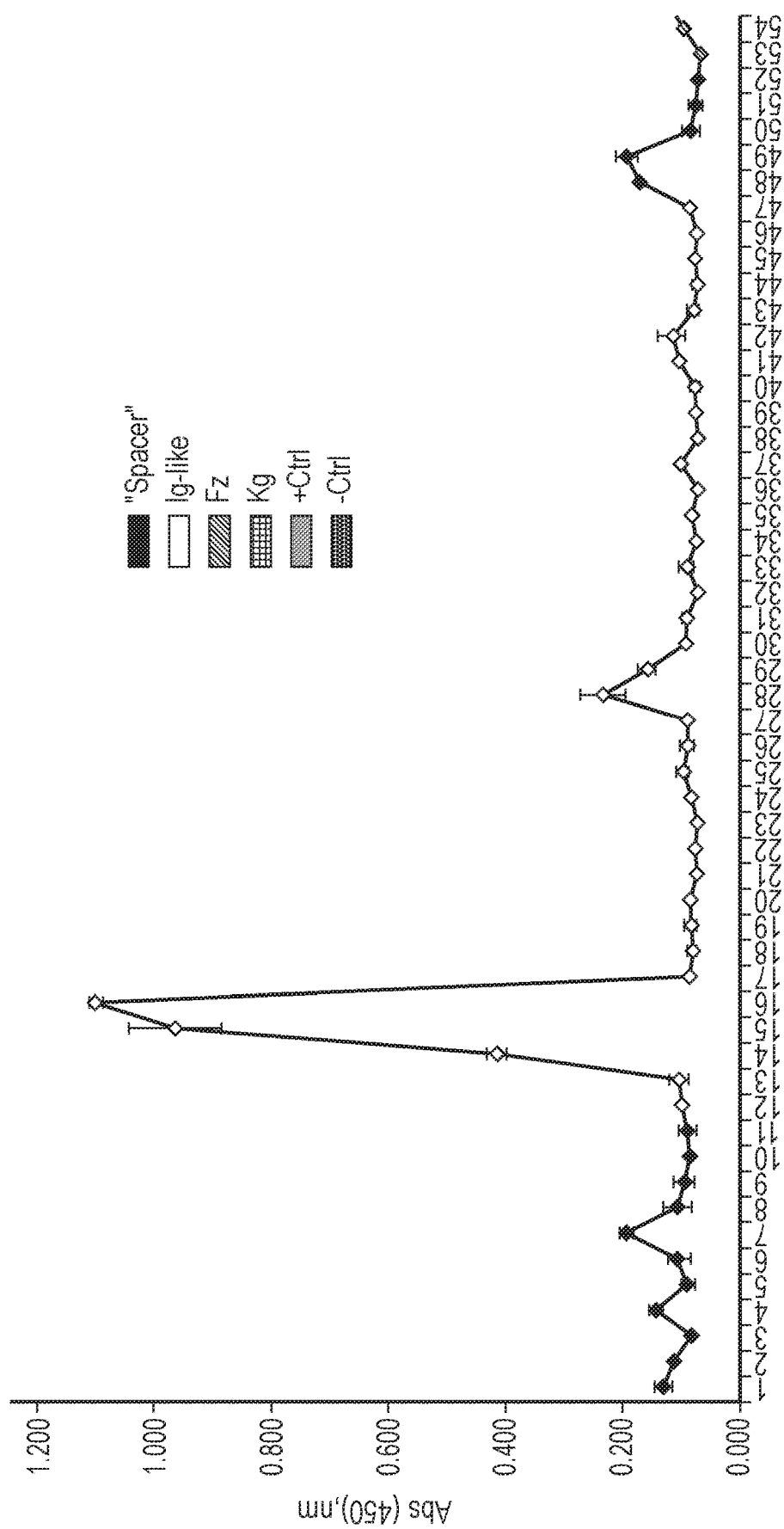
Figure 5A:
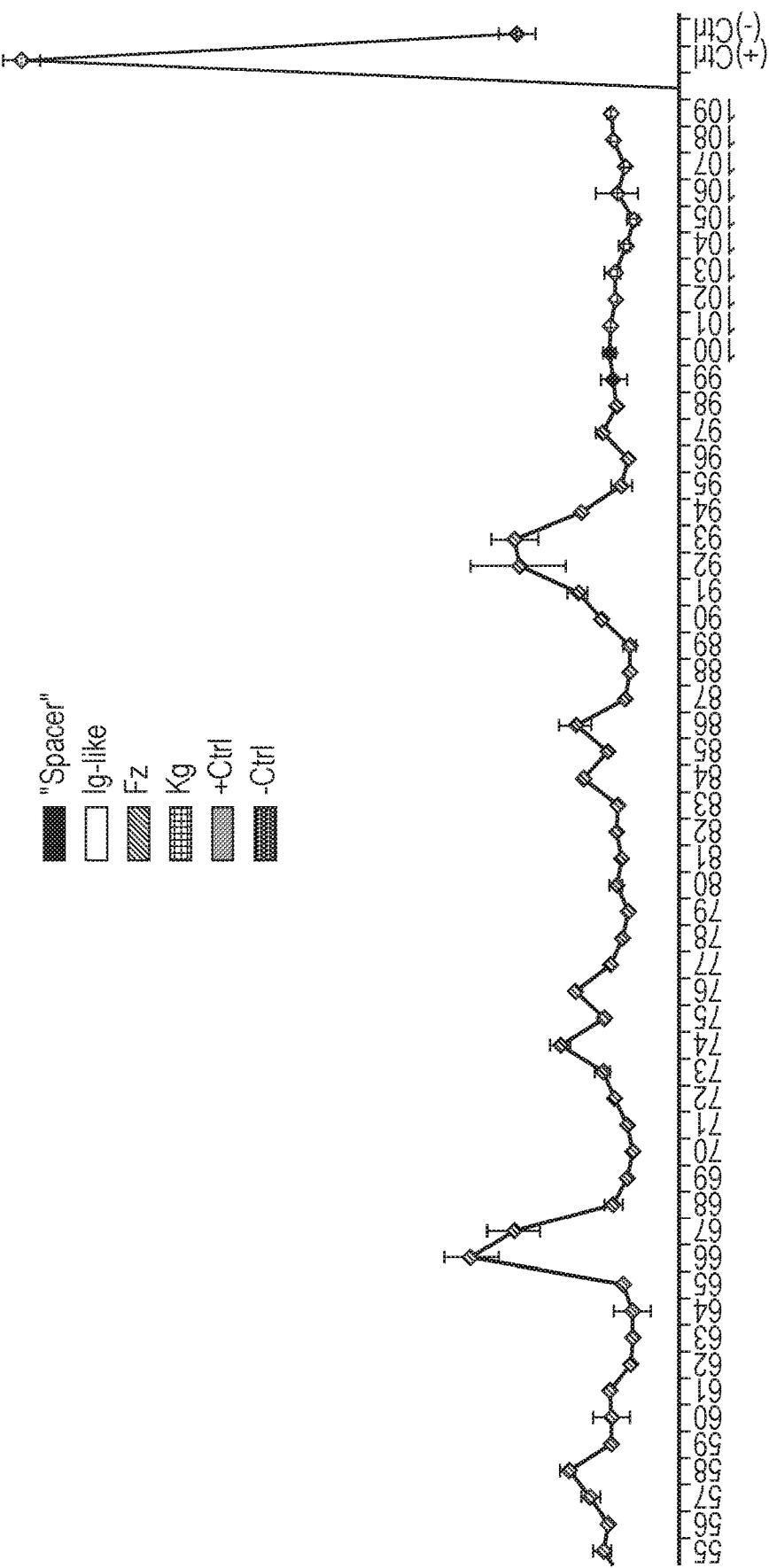
Figure 5B:
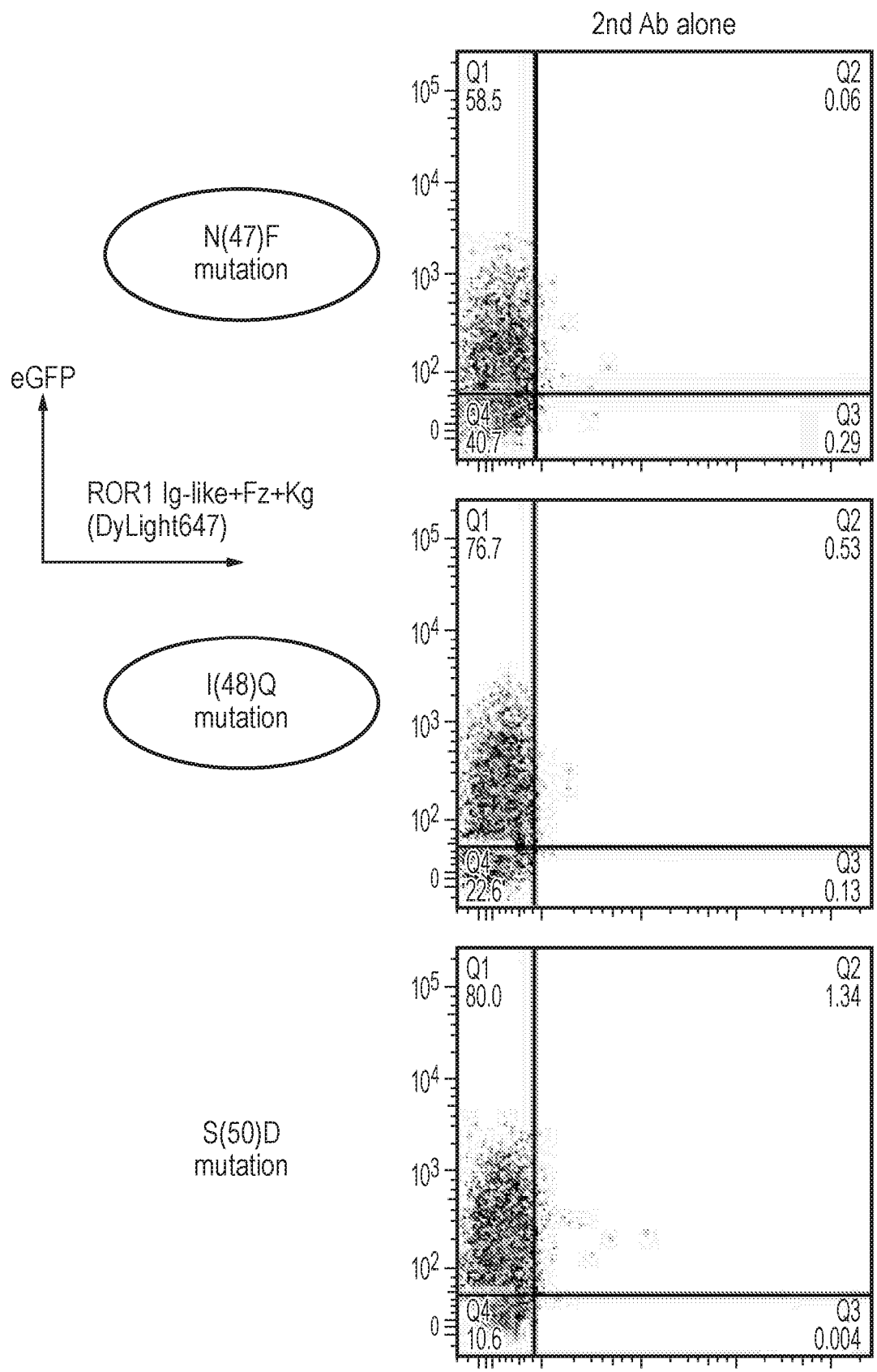
Figure 5B:
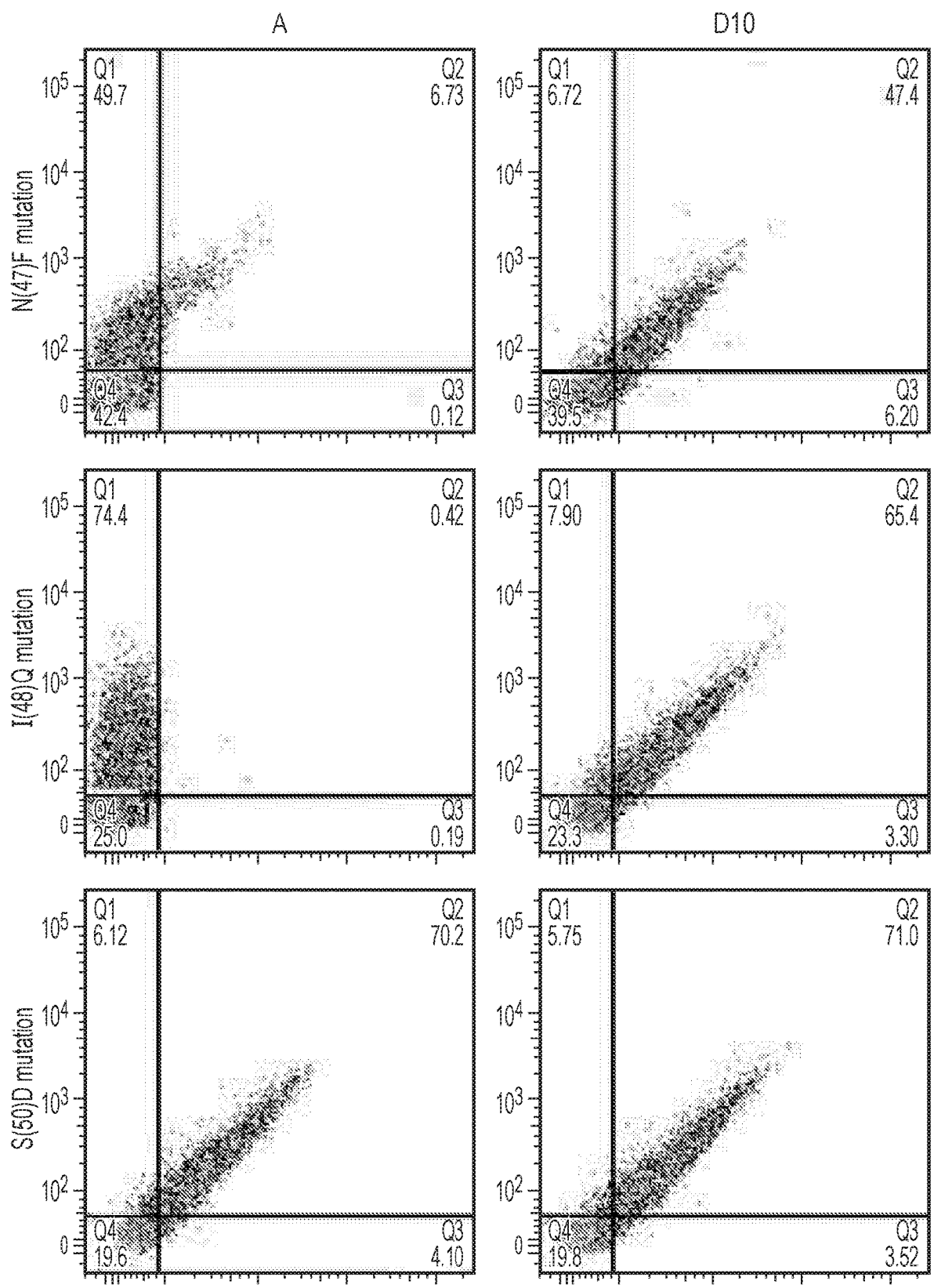
Figure 5B:
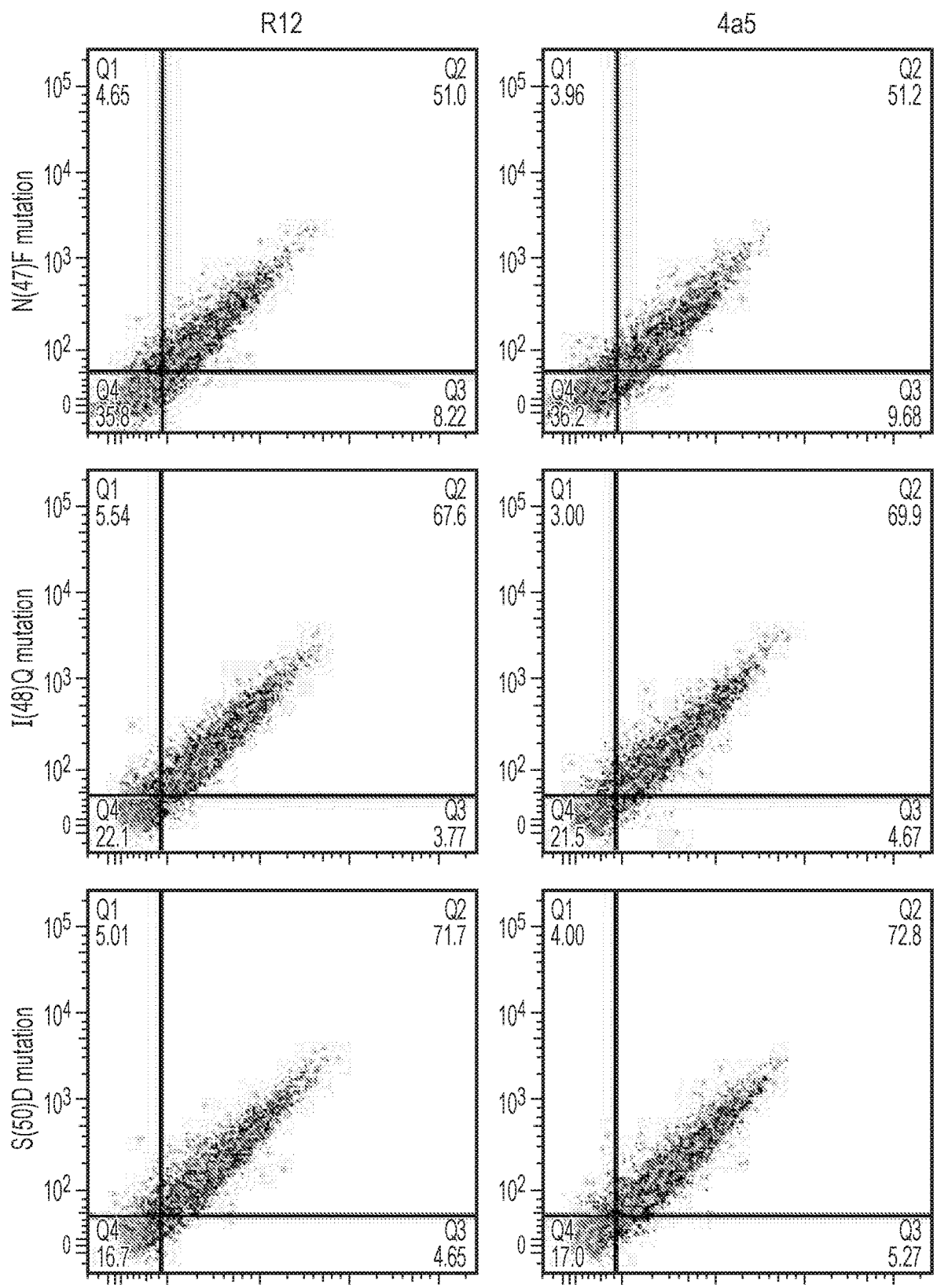
Figure 5B:
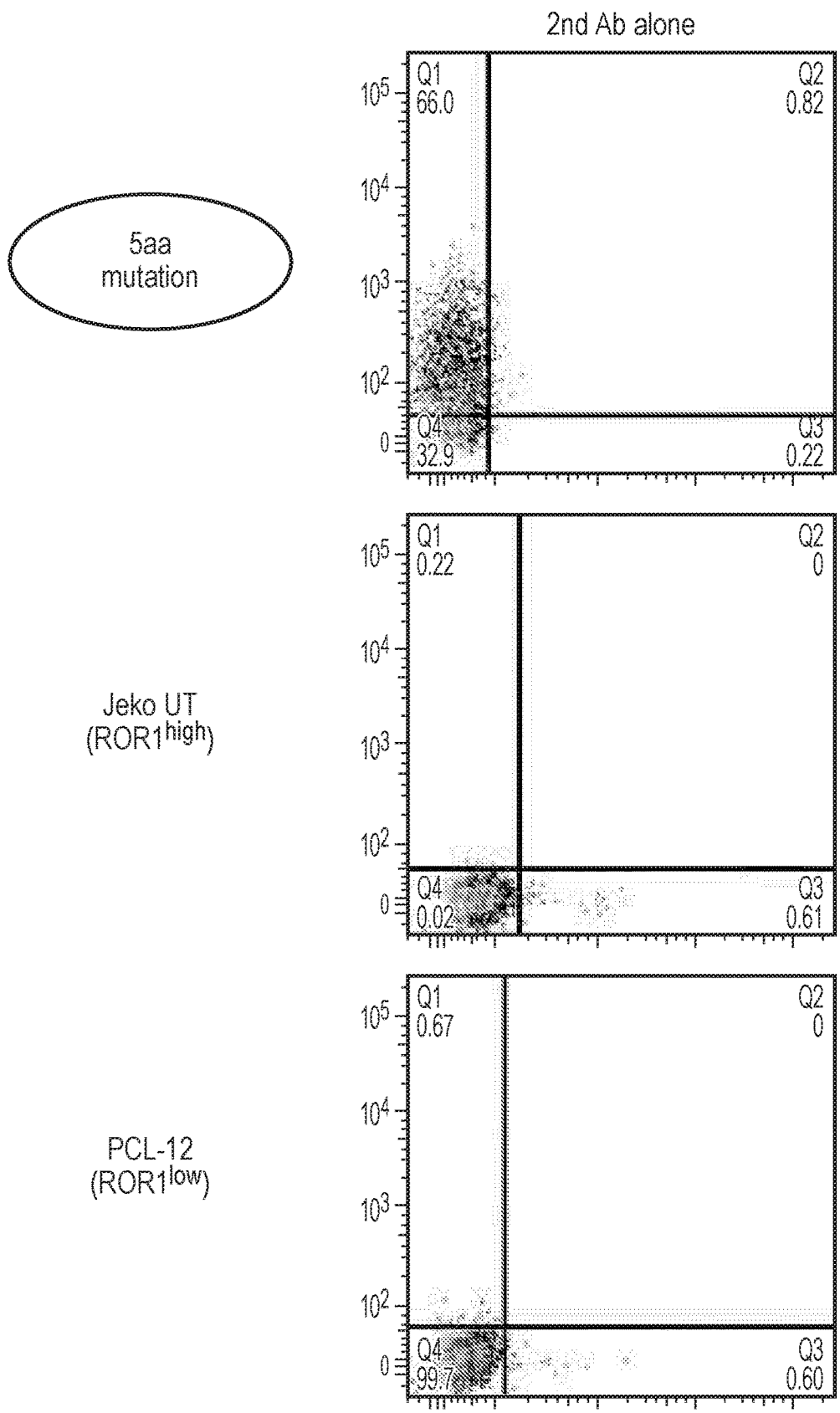
Figure 5B:
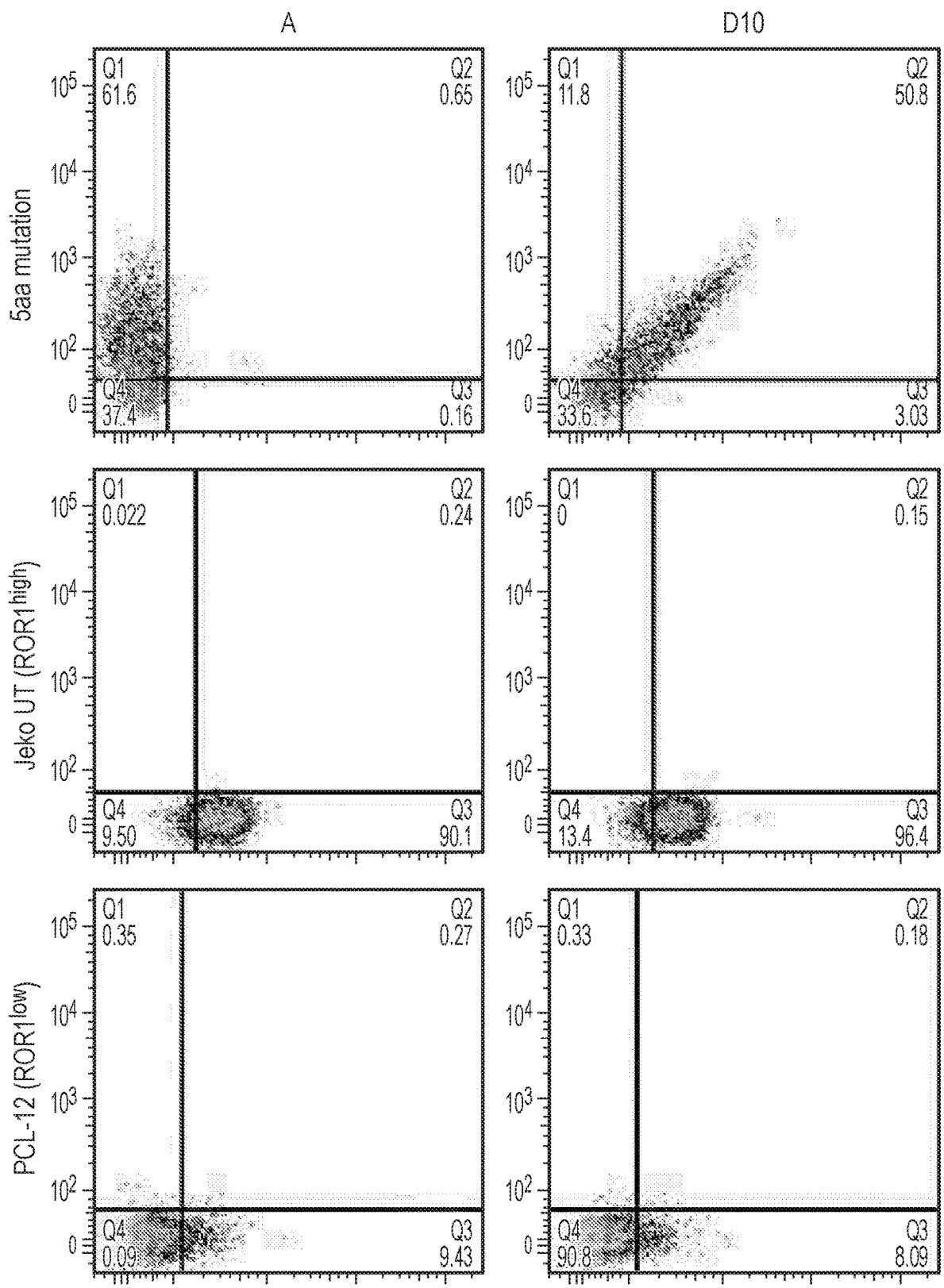
Figure 5B:
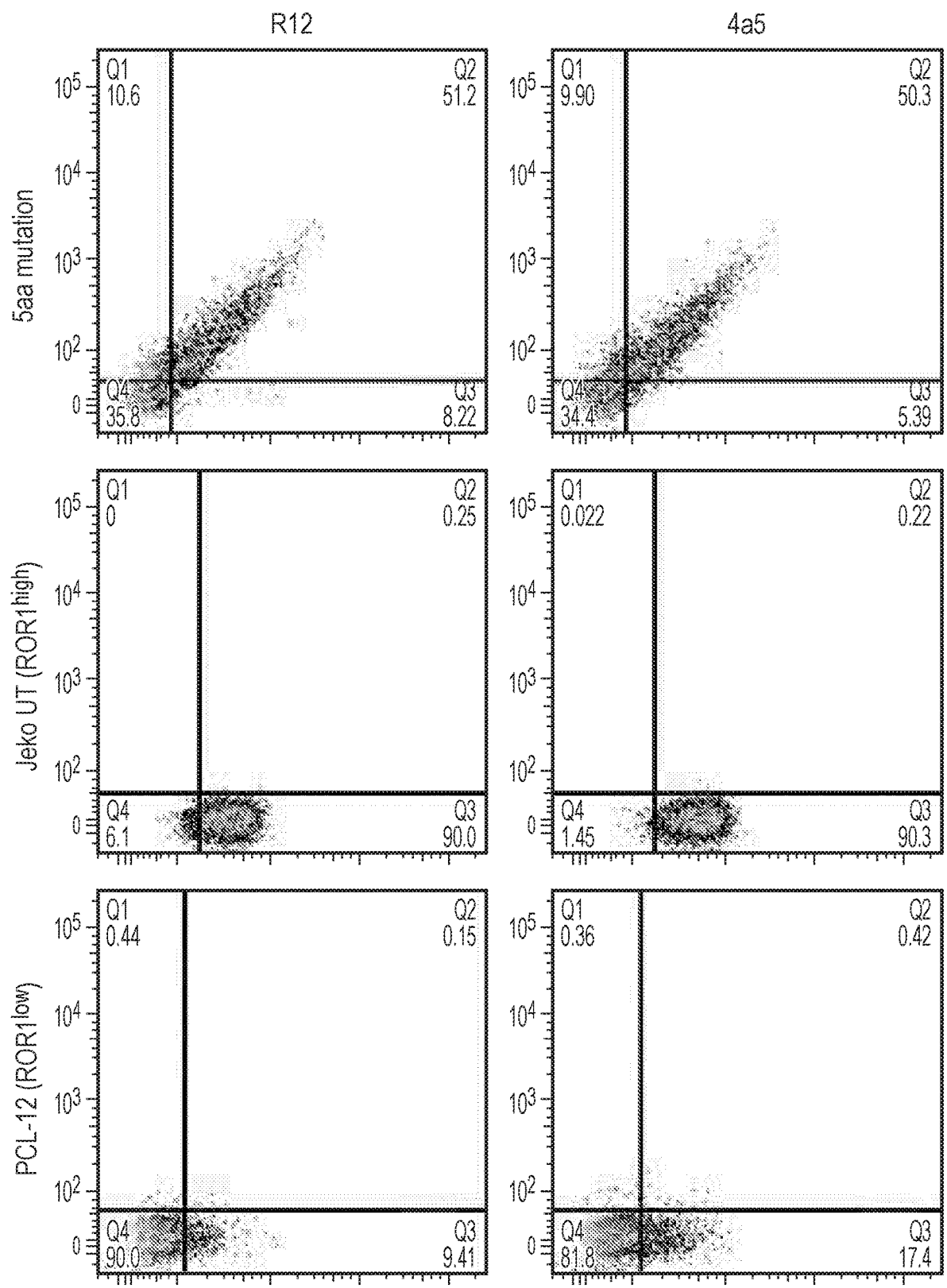
Figure 6A:
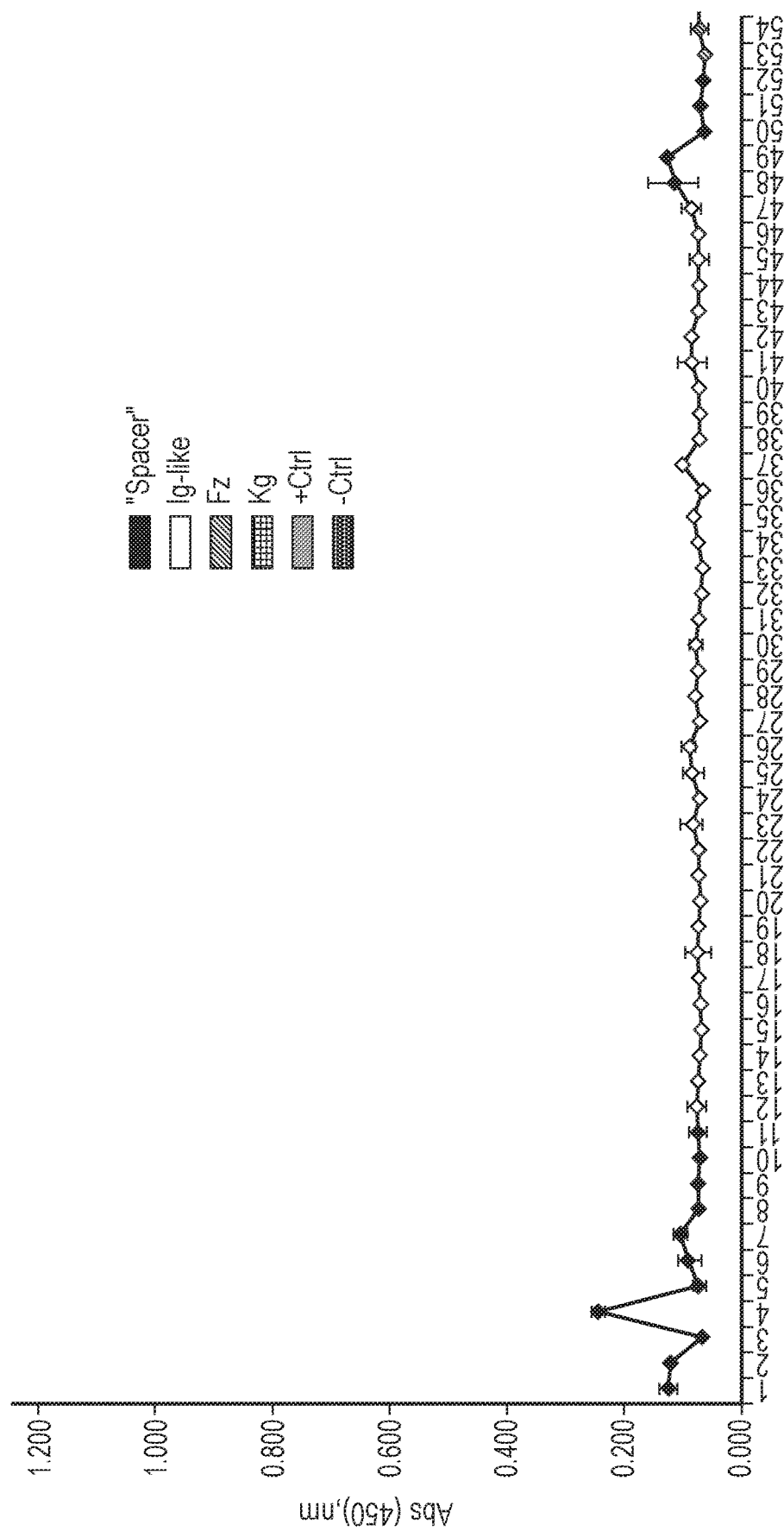
Figure 6A:
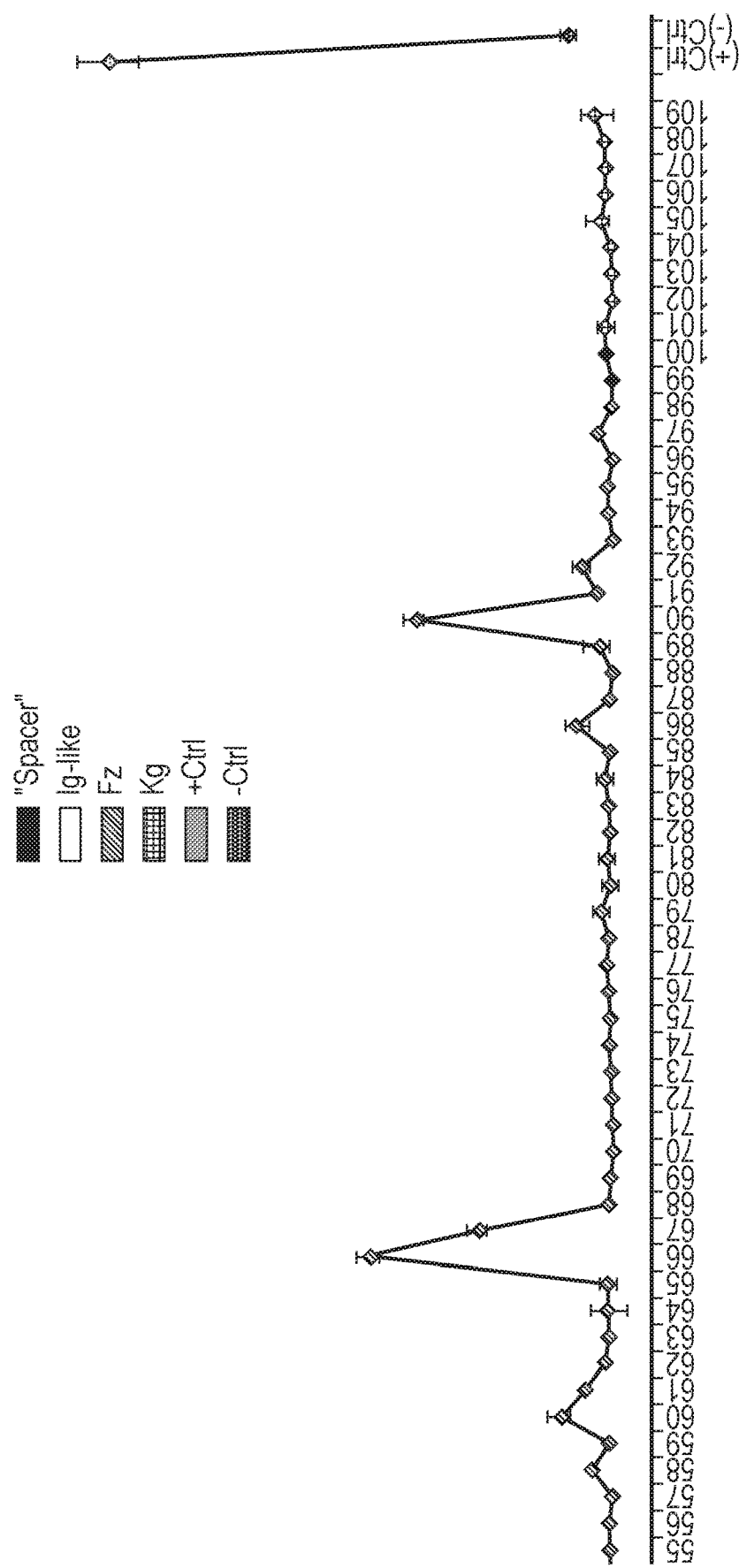
Figure 6B:
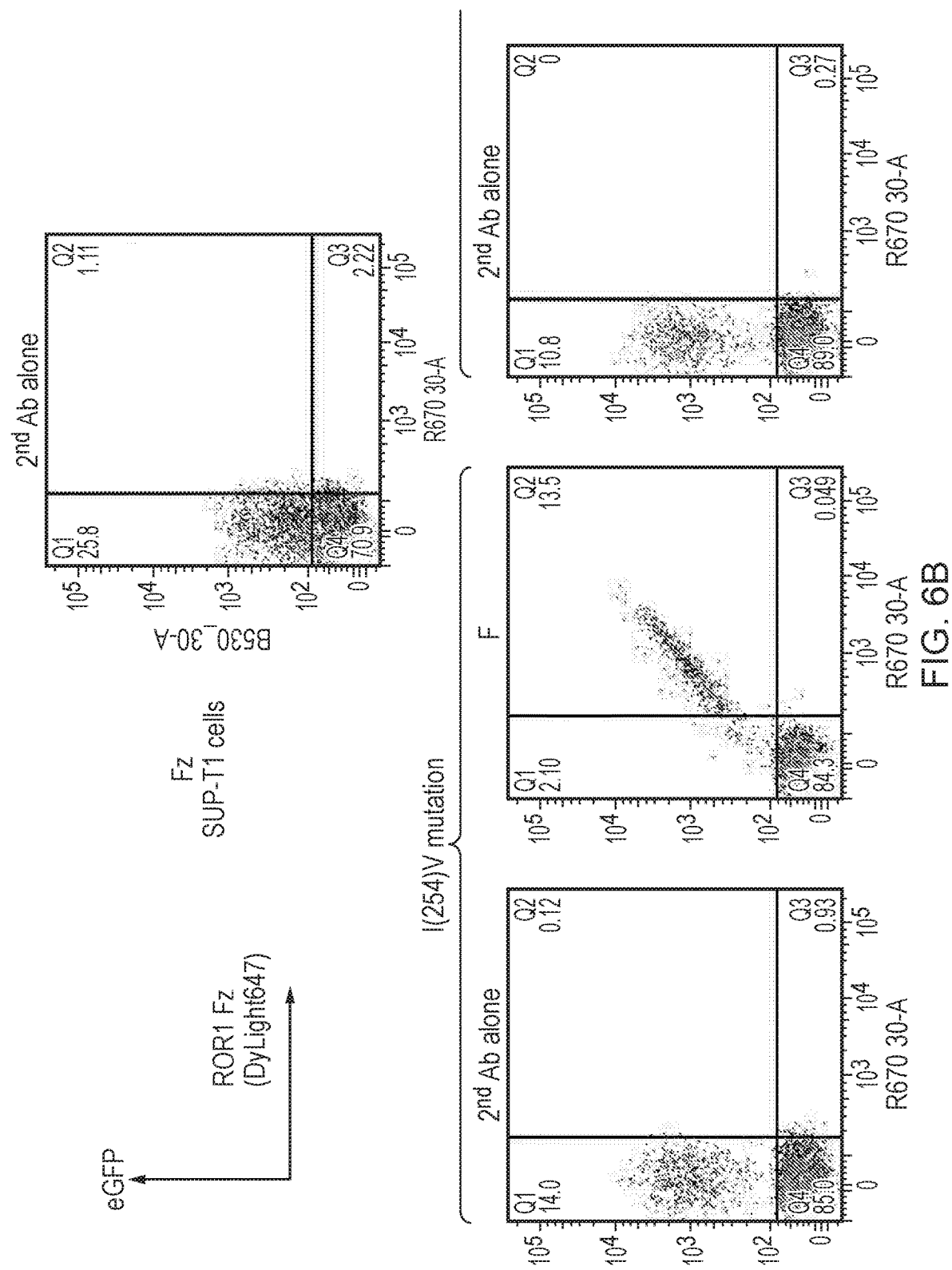
Figure 6B:
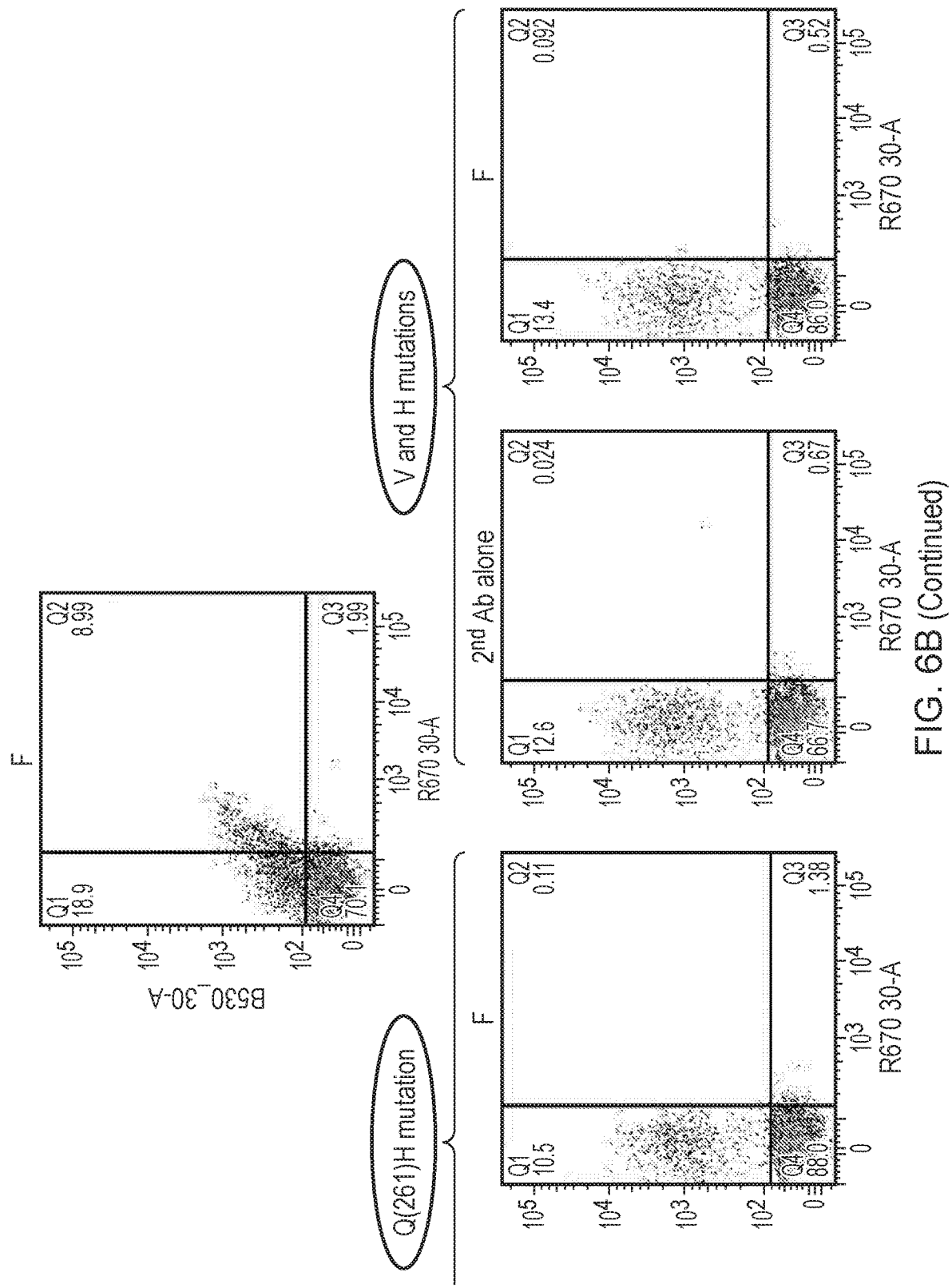

Binding of clones A and F on overlapping peptides, covering all three extracellular domains of ROR1, was tested by ELISA. This approach allowed us to narrow down the epitope of clone A to a five amino acid region within the Ig-like domain (FIG. 5A).

Point mutations were then generated for the Ig-like domain of human ROR1 at positions 47 to 51. The particular mutations used were N(47)F, I(48)Q, S(50)D and the substitution of the five amino acid sequence NISSE (SEQ ID NO: 253) at residues 47 to 51 with the sequence FQDDL (SEQ ID NO: 254).

Retroviral vectors were used for transducing SUP-T1 cells and transduction was tested by GFP expression using flow cytometry.

It was found that the N(47)F and the I(48)Q substitutions reduced or stopped the clone A antibody binding to ROR1-Ig like domain, whereas the S(50)D substitution did not seem to affect binding. Further, the five amino acid substitution also prevented antibody binding. Therefore, it seems that Asn-47 and Ile-48 are essential for antibody binding. It was found that this epitope is unique to clone A and there is no overlap with previously published ROR1 clones (R12, 4a5 and D10, the prototype of Cirmtuzumab). Results can be seen in FIG. 5B.

For clone F, peptide library ELISA data showed that it was not possible to detect any binding signal above background (FIG. 6A), suggesting that this antibody does not bind to a linear sequence, rather it might potentially recognize a conformational epitope. Point mutations were therefore generated for the Fz domain of human ROR1 at non-conserved regions (positions 254 and 261). The particular mutations used were I(254)V and Q(261)H.

Retroviral vectors were used for transducing SUP-T1 cells and transduction was tested by GFP expression using flow cytometry.

It was found that the Q(261)H substitution reduced or stopped the clone F antibody binding to ROR1-Fz domain, whereas the I(254)V substitution did not seem to affect binding. Further, the combination of Q(261)H and I(254)V also prevented antibody binding. Therefore, it seems that Gln-261 is essential for antibody binding. Results can be seen in FIG. 6B.

Example 6

Competition Assay by Flow Cytometry

To further challenge our previous observations—whereby clone A had a distinct epitope that was not shared with other anti-ROR1 antibodies—we decided to compare the binding of A to ROR1 with other relevant clones through a flow cytometry-based competition assay.

Based on previous studies, we hypothesised that consecutive- and/or simultaneous-staining of ROR1$^+$ cells, using clone A in combination with other anti-ROR1 antibodies, would allow us to identify overlapping epitopes by flow cytometry analysis.

To this end, we fused the variable region of clone A to a mouse IgG2a, kappa constants following the same protocols discussed in previous chapters. All other chimeric antibodies were kept in their existing rat-human format. We needed to generate A in a distinct constant region in order to allow simultaneous and specific detection of every pair of clones we were testing. In other words, since we were investigating unlabelled clones, a secondary antibody staining against clones possessing different isotypes was required. Also, for ease of analysis, ROR1$^+$ GFP$^+$ cells were used.

FIG. 7A shows strong ROR1 binding when antibodies were used as single agents, which confirmed their correct expression and detection of ROR1. Since A and F antibodies detect different extracellular domains, this combination was included in our studies as negative control for overlapping epitopes.

In FIG. 7B, three different columns are presented. Dot plots on the first column correspond to ROR1 binding assessed when SUP-T1 ROR1 cells were stained with clone A (SA1) (mIgG) in the first instance. After a washing step, cells were stained with a competitor antibody (hIgG), followed by another washing step. Both antibodies were then detected by a third staining step using the appropriate secondary antibodies. In the second column, a similar approach was taken when staining these cells, except that this time it was the antibody in hIgG1, k format the one used for the first staining step, followed by clone A (SA1) staining. On the third column, both antibodies were used at the same time.

In all cases, a clear and defined shift of all events was observed; indicating that, independent of the order in which cells were stained, antibodies used in the first staining step did not impede binding of the antibodies used in the second step. This was further confirmed when both antibodies were assessed at the same time. Hence, these results confirm that clone A binds to a unique epitope within the Ig-like domain, which is not shared (not even partially) with other reported clones.

Example 7

Assessment of Internalisation

Antibody internalisation can have important implications as it could provide us with the opportunity to develop armed antibodies that could be conjugated to toxic payloads, such as toxins, radioisotopes or chemotherapeutic agents. This class of therapeutic antibodies are called Antibody-Drug Conjugates (ADCs). Interestingly, ADCs could have a therapeutic advantage over naked antibodies (unconjugated), in terms of potency and efficacy, as their cytotoxicity relies on the payload they carry rather than the immune system of patients. Thus, we next investigated whether our antibodies were able to get internalised into ROR1$^+$ cells by flow cytometry and pH-Amine dye labelling.

By Flow Cytometry

SKW 6.4 cells, Epstein-Barr virus-transformed B cells endogenously expressing comparable levels of ROR1 as CLL patients, were incubated on ice with all 12 ROR1 chimeric antibodies. After 30 min, cells were washed with ice-cold PBS, and either left on ice or incubated at 37° C. for 1 h. Subsequent staining with an anti-human Fc-Dylight 647 was used to detect any primary antibody that had remained on the cell surface. Previously reported clones R12 and 4a5 were also included in this assay as negative and positive controls, respectively (FIG. 8).

From all tested antibodies, clone V (green circle) showed almost complete MFI reduction. A modest but detectable decrease in MFI levels was observed in clones A and F (purple circles), similar to the one detected for clone 4a5. As previously reported, clone R12 did not show significant MFI reduction after 1 h incubation at 37° C.

MFI reduction could be caused by dissociation or internalisation or a combination of both (15). In order to further investigate what was triggering this drop in MFI for clones V, A and F, we decided to use an endocytosis inhibitor in our next experiments.

Endocytosis Inhibition

Phenylarsine oxide (PAO), a trivalent arsenical compound, is the typical chemical chosen to block Clathryn-mediated endocytosis (CME), although it can also inhibit macropinocytosis and phagocytosis. CME is the best studied mechanism of endocytosis, and it has been established that receptor tyrosine kinases (RTKs), such as ROR1, predominantly use this form of internalisation when engulfed by the cell membrane and drawn inside the cell.

To distinguish between dissociation and internalisation, SKW 6.4 cells were incubated on ice in the presence of our selected antibodies for 30 min. Cells were then washed with ice-cold PBS and either left on ice or incubated at 37° C. for 15 min, 1 h or 2 h. For the 2 h time point, a duplicate sample was incubated with PAO (10 µM). Immediately after incubation, all samples were washed with ice-cold PBS and stained with an anti-human Fc-Dylight 647 for 30 min. Cells were analysed by flow cytometry and MFI reduction was calculated.

Flow cytometry analysis showed that although clone V had an important MFI reduction, it was mainly due to dissociation as PAO did not considerably block the drop in MFI after 2 h incubation at 37° C. A combination of internalisation and dissociation was more evident for the other 3 clones, being internalisation the dominating factor for clone 4a5. This was even more evident for clone A.

To verify these results, we repeated the experiment using SKW 6.4 cells and 2 samples of primary cells from CLL patients, expressing either high or low levels of ROR1 (FIG. 9). Samples were processed as mentioned above and analysed by flow cytometry. Interestingly, these data confirmed that whilst both dissociation and internalisation were involved in the MFI reduction, for clone V dissociation was the main reason for decrease in MFI. This was even clearer on CLL cells, where virtually no internalisation of clone V was detected.

The dissociation of clones F, 4a5 and A from the cell surface of CLL cells was very similar between samples and seemed to be independent of ROR1 levels. In this case, internalisation appeared to be the main contributing factor to MFI reduction. A similar observation was detected on SKW 6.4 cells; although on this cell model, clone A was the only antibody where MFI drop was almost completely blocked by PAO and only partially for clones F and 4a5, suggesting that although these last 3 antibodies might get partially internalised, clone A might be the most promising one.

Example 8

Clone F is Unique to Other Antibodies Generated (Murine and Rabbit) Because of Sequence Homology Human, murine, rabbit and rat ROR1 protein sequences were aligned using Uniprot web based software (http://www.uniprot.org/align/) and the variation between the different species highlighted. Uniprot accession numbers: Human (Q01973), Murine (Q9Z139) and Rabbit (G1U5L1). For rat ROR1, NCBI reference sequence NP 001102141.1 was used as the corresponding Uniprot sequence was only partially complete.

Clone F binds to Q261, which was possible due to differences between rat and human amino acids at this position (the human amino acid at position 261 is glutamine (Q) whereas the corresponding amino acid at this position in rat is histidine (H)). When rats are immunised with human ROR1, this amino acid difference is recognised as an immunogen relative to the rat ROR1 sequence, against which an antibody is produced.

The known antibody R12 (rabbit) and murine ROR1 binders show homology with human ROR1 at this site (i.e. they all have glutamine (Q) at this position). As a result, immunisation of rabbits or mice with human ROR1 does not result in antibody production directed to this position as it is not immunogenic. In view of this, clone F is unique in its ability to bind to this epitope.

Example 9

Humanisation Imparts Advantages Compared to Non-Humanised Comparator Constructs

One of the rationales for targeting ROR1 as opposed to CD19, is sparing of the normal ROR1 negative B cell population. However at the same time, continued presence of normal CD19+ B cells allows for immune responses directed against a rat derived scFv. This has been seen with murine scFvs and have led to clinically significant outcomes, including anaphylaxis with mRNA modified mesothelin CAR T cells (Maus et al., 2013) or antibody responses, with α-folate receptor or carbonic anhydrase IX specific CAR T cells (Lamers et al., 2006, Kershaw et al., 2006). T cell mediated immune responses are also possible due to cross presentation of components of the CAR on MHC. CD19 CART cells by comparison, inherently diminish the risk of antibody based immune responses by eradicating the normal B cell population, with B cell recurrence associated with a higher risk of relapse. By undertaking humanisation, we have decreased the likelihood of immune responses against the antibody leading to enhanced persistence and decreased immunogenicity.

Sequence Listing
The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| DVVMTQTPVSLPVSLGGQVSISCRSS | G3 | Rat Light Chain Framework Region 1 | 1 |
| QSLEHSNGDTF | G3 | Light Chain CDR1 | 2 |
| LHWYLQKPGQSPRLLIY | G3 | Rat Light Chain Framework Region 2 | 3 |
| RVS | G3 | Light Chain CDR2 | 4 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
| --- | --- | --- | --- |
| NRFSGVPDRFSGSGSGTDFTLKISRIEPEDLGDYYC | G3 | Rat Light Chain Framework Region 3 | 5 |
| LQSTHFPNT | G3 | Light Chain CDR3 | 6 |
| FGAGTKLELK | G3 | Rat Light Chain Framework Region 4 | 7 |
| DIQLTQSPSTLSASLGERVTISCRAS | G5 | Rat Light Chain Framework Region 1 | 8 |
| QSISNS | G5 | Light Chain CDR1 | 9 |
| LNWYQQKPDGTVKRLIY | G5 | Rat Light Chain Framework Region 2 | 10 |
| STS | G5 | Light Chain CDR2 | 11 |
| TLESGVPSRFSGSGSGTDFSLSISSLESEDFAMYYC | G5 | Rat Light Chain Framework Region 3 | 12 |
| LQFATYPQVT | G5 | Light Chain CDR3 | 13 |
| FGSGTKLEIK | G5 | Rat Light Chain Framework Region 4 | 14 |
| DIVLTQSPALAVSVGQRATISCRAS | E7 | Rat Light Chain Framework Region 1 | 15 |
| QSVSISRYNF | E7 | Light Chain CDR1 | 16 |
| MHWYQQKPGQQPKLLIY | E7 | Rat Light Chain Framework Region 2 | 17 |
| RAS | E7 | Light Chain CDR2 | 18 |
| NLASGIPARFSGSGSGTDFTLTINPVQADDIATYYC | E7 | Rat Light Chain Framework Region 3 | 19 |
| QQNRESPRT | E7 | Light Chain CDR3 | 20 |
| FGGGTKLELK | E7 | Rat Light Chain Framework Region 4 | 21 |
| DIVLTQSPALAVSVGQRATISCRAS | J | Rat Light Chain Framework Region 1 | 15 |
| QSVSISRYDF | J | Light Chain CDR1 | 22 |
| MHWYQQKPGQQPKLLIY | J | Rat Light Chain Framework Region 2 | 17 |
| RAS | J | Light Chain CDR2 | 18 |
| NLASGIPARFSGSGSGTDFTLTINPVQADDIATYYC | J | Rat Light Chain Framework Region 3 | 19 |
| QQNRESPRT | J | Light Chain CDR3 | 20 |
| FGGGTKLELK | J | Rat Light Chain Framework Region 4 | 21 |
| DIQMTQSPSFLSASVGDRVTINCKAS | F | Rat Light Chain Framework Region 1 | 23 |
| QNIDRY | F | Light Chain CDR1 | 24 |
| LNWYQQKLGEAPKRLLY | F | Rat Light Chain Framework Region 2 | 25 |
| NTN | F | Light Chain CDR2 | 26 |
| KLQTGIPSRFSGSGSATDFTLTISSLQPEDFATYFC | F | Rat Light Chain Framework Region 3 | 27 |
| LQYNSLPLT | F | Light Chain CDR3 | 28 |
| FGSGTKLEIK | F | Rat Light Chain Framework Region 4 | 14 |
| DIQMTQSPSSMSASLGDRVTFTCQAS | A | Rat Light Chain Framework Region 1 | 29 |

-continued

Sequence Listing
The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| QDIGNN | A | Light Chain CDR1 | 30 |
| LIWFQQKPGKSPRPLMY | A | Rat Light Chain Framework Region 2 | 31 |
| FAT | A | Light Chain CDR2 | 32 |
| SLANGVPSRFSGSRSGSDYSLTISSLESEDLADYHC | A | Rat Light Chain Framework Region 3 | 33 |
| LQYREYPLT | A | Light Chain CDR3 | 34 |
| FGSGTKLDLK | A | Rat Light Chain Framework Region 4 | 35 |
| DIRMTQSPASLSASLGETVTIECLTS | B | Rat Light Chain Framework Region 1 | 36 |
| EDIYSD | B | Light Chain CDR1 | 37 |
| LAWFQQKPGKSPQLLIY | B | Rat Light Chain Framework Region 2 | 38 |
| DAN | B | Light Chain CDR2 | 39 |
| SLQNGVPSRFGGCGSGTQYSLQISSLQSEDVATYFC | B | Rat Light Chain Framework Region 3 | 40 |
| QQYKNYPPT | B | Light Chain CDR3 | 41 |
| FGGGTKLVLK | B | Rat Light Chain Framework Region 4 | 42 |
| DIQLTQSPSSMSASLGDRVSLTCQSS | I | Rat Light Chain Framework Region 1 | 43 |
| QGIGKY | I | Light Chain CDR1 | 44 |
| LSWYQHKPGKPPKAMIY | I | Rat Light Chain Framework Region 2 | 45 |
| YAT | I | Light Chain CDR2 | 46 |
| KLADGVPSRFSGSRSGSDFSLTISSLESEDIAIYYC | I | Rat Light Chain Framework Region 3 | 47 |
| LQFDDYPWT | I | Light Chain CDR3 | 48 |
| FGGGTKLELK | I | Rat Light Chain Framework Region 4 | 21 |
| DIVLTQSPALAVSLEQRVTIACKTS | O | Rat Light Chain Framework Region 1 | 49 |
| QNVDNHGISY | O | Light Chain CDR1 | 50 |
| MHWYQQKSGQEPKLLIY | O | Rat Light Chain Framework Region 2 | 51 |
| EGS | O | Light Chain CDR2 | 52 |
| NLAVGIPARFSGSGSGTDFTLTIDPVEADDIETYYC | O | Rat Light Chain Framework Region 3 | 53 |
| QQSKDDPRT | O | Light Chain CDR3 | 54 |
| FGGGTKLELK | O | Rat Light Chain Framework Region 4 | 21 |
| QFTLTQPKSVSGSLRSTITIPCERS | R | Rat Light Chain Framework Region 1 | 55 |
| SGDIGDSY | R | Light Chain CDR1 | 56 |
| VSWYQQHLGRPPINVIY | R | Rat Light Chain Framework Region 2 | 57 |
| ADD | R | Light Chain CDR2 | 58 |
| QRPSEVSDRFSGSIDSSSNSASLTITNLQMDDEADYFC | R | Rat Light Chain Framework Region 3 | 59 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| QSYDRNVDFNTV | R | Light Chain CDR3 | 60 |
| FGGGTKVTVL | R | Rat Light Chain Framework Region 4 | 61 |
| DIQLTQSPSSLSASLGDRVSLTCQSS | Pi | Rat Light Chain Framework Region 1 | 62 |
| QGIGKY | Pi | Light Chain CDR1 | 44 |
| LSWFQHKPGKPPKPVIN | Pi | Rat Light Chain Framework Region 2 | 63 |
| YAT | Pi | Light Chain CDR2 | 46 |
| NLADGVPSRFSGRRSGSDFSLTISSLESEDTAIYYC | Pi | Rat Light Chain Framework Region 3 | 64 |
| LQFDDFRWT | Pi | Light Chain CDR3 | 65 |
| VGGGTKLELK | Pi | Rat Light Chain Framework Region 4 | 66 |
| QFTLTQPKSVSGSLRSTITIPCERS | Mu | Rat Light Chain Framework Region 1 | 55 |
| SGDIGDNY | Mu | Light Chain CDR1 | 67 |
| VSWYQQHLGRPPINVIY | Mu | Rat Light Chain Framework Region 2 | 57 |
| ADD | Mu | Light Chain CDR2 | 58 |
| QRPSEVSDRFSGSIDSSSNSASLTITNLQMDDEADYFC | Mu | Rat Light Chain Framework Region 3 | 59 |
| QSFDSNFDIPV | Mu | Light Chain CDR3 | 68 |
| FGGGTKLTVL | Mu | Rat Light Chain Framework Region 4 | 69 |
| DIKMTQSPSFLSASVGDRVTINCKAS | V | Rat Light Chain Framework Region 1 | 70 |
| QNITRF | V | Light Chain CDR1 | 71 |
| LNWYQQELGEAPTLLIY | V | Rat Light Chain Framework Region 2 | 72 |
| NTN | V | Light Chain CDR2 | 26 |
| NLQTGIPSRFSGSGSGTDFTLTISSLQPEDVATYFC | V | Rat Light Chain Framework Region 3 | 73 |
| LQHGSRPRT | V | Light Chain CDR3 | 74 |
| FGGGTKLELK | V | Rat Light Chain Framework Region 4 | 21 |
| DVVMTQTPVSLPVSLGGQVSISCRSSQSLEHSNGDTFLHWYLQKPGQSPRLLIYRVSNRFSGVPDRFSGSGSGTDFTLKISRIEPEDLGDYYCLQSTHFPNTFGAGTKLELK | G3 | Rat Light Chain Variable Region | 75 |
| DIQLTQSPSTLSASLGERVTISCRASQSISNSLNWYQQKPDGTVKRLIYSTSTLESGVPSRFSGSGSGTDFSLSISSLESEDFAMYYCLQFATYPQVTFGSGTKLEIK | G5 | Rat Light Chain Variable Region | 76 |
| DIVLTQSPALAVSVGQRATISCRASQSVSISRYNFMHWYQQKPGQQPKLLIYRASNLASGIPARFSGSGSGTDFTLTINPVQADDIATYYCQQNRESPRTFGGGTKLELK | E7 | Rat Light Chain Variable Region | 77 |
| DIVLTQSPALAVSVGQRATISCRASQSVSISRYDFMHWYQQKPGQQPKLLIYRASNLASGIPARFSGSGSGTDFTLTINPVQADDIATYYCQQNRESPRTFGGGTKLELK | J | Rat Light Chain Variable Region | 78 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| DIQMTQSPSFLSASVGDRVTINCKASQNIDR YLNWYQQKLGEAPKRLLYNTNKLQTGIPSRF SGSGSATDFTLTISSLQPEDFATYFCLQYNSLP LTFGSGTKLEIK | F | Rat Light Chain Variable Region | 79 |
| DIQMTQSPSSMSASLGDRVTFTCQASQDIG NNLIWFQQKPGKSPRPLMYFATSLANGVPS RFSGSRSGSDYSLTISSLESEDLADYHCLQYRE YPLTFGSGTKLDLK | A | Rat Light Chain Variable Region | 80 |
| DIRMTQSPASLSASLGETVTIECLTSEDIYSDL AWFQQKPGKSPQLLIYDANSLQNGVPSRFG GCGSGTQYSLQISSLQSEDVATYFCQQYKNY PPTFGGGTKLVLK | B | Rat Light Chain Variable Region | 81 |
| DIQLTQSPSSMSASLGDRVSLTCQSSQGIGK YLSWYQHKPGKPPKAMIYYATKLADGVPSRF SGSRSGSDFSLTISSLESEDIAIYYCLQFDDYP WTFGGGTKLELK | I | Rat Light Chain Variable Region | 82 |
| DIVLTQSPALAVSLEQRVTIACKTSQNVDNH GISYMHWYQQKSGQEPKLLIYEGSNLAVGIP ARFSGSGSGTDFTLTIDPVEADDIETYYCQQS KDDPRTFGGGTKLELK | O | Rat Light Chain Variable Region | 83 |
| QFTLTQPKSVSGSLRSTITIPCERSSGDIGDSY VSWYQQHLGRPPINVIYADDQRPSEVSDRFS GSIDSSSNSASLTITNLQMDDEADYFCQSYD RNVDFNTVFGGGTKVTVL | R | Rat Light Chain Variable Region | 84 |
| DIQLTQSPSSLSASLGDRVSLTCQSSQGIGKYL SWFQHKPGKPPKPVINYATNLADGVPSRFS GRRSGSDFSLTISSLESEDTAIYYCLQFDDFR WTVGGGTKLELK | Pi | Rat Light Chain Variable Region | 85 |
| QFTLTQPKSVSGSLRSTITIPCERSSGDIGDNY VSWYQQHLGRPPINVIYADDQRPSEVSDRFS GSIDSSSNSASLTITNLQMDDEADYFCQSFDS NFDIPVFGGGTKLTVL | Mu | Rat Light Chain Variable Region | 86 |
| DIKMTQSPSFLSASVGDRVTINCKASQNITRF LNWYQQELGEAPTLLIYNTNNLQTGIPSRFS GSGSGTDFTLTISSLQPEDVATYFCLQHGSRP RTFGGGTKLELK | V | Rat Light Chain Variable Region | 87 |
| EVQLQESGPGLVKPAQSLSLTCSVT | G3 | Rat Heavy Chain Framework Region 1 | 88 |
| GYSITNMYR | G3 | Heavy Chain CDR1 | 89 |
| WNWIRKFPGNKLEWMGY | G3 | Rat Heavy Chain Framework Region 2 | 90 |
| INTAGST | G3 | Heavy Chain CDR2 | 91 |
| DYSPSLRGRVSITGDTSKNQFFLHLTSVTTED TATYYC | G3 | Rat Heavy Chain Framework Region 3 | 92 |
| AGFITNPFDF | G3 | Heavy Chain CDR3 | 93 |
| WGQGVMVTVSS | G3 | Rat Heavy Chain Framework Region 4 | 94 |
| EVQVVESGGGLVQPGRSLKLSCVPS | G5 | Rat Heavy Chain Framework Region 1 | 95 |
| GFTFNNYW | G5 | Heavy Chain CDR1 | 96 |
| MTWIRQAPGKAPEWVAS | G5 | Rat Heavy Chain Framework Region 2 | 97 |
| ISNTGGST | G5 | Heavy Chain CDR2 | 98 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| FYPDSVRGRFSISRDNTKGTLYLHMTSLRSEDTATYYC | G5 | Rat Heavy Chain Framework Region 3 | 99 |
| IRNMDA | G5 | Heavy Chain CDR3 | 100 |
| WGQGTSVTVSS | G5 | Rat Heavy Chain Framework Region 4 | 101 |
| GKLVESGGGLLKPGGSLKLSCVAS | E7 | Rat Heavy Chain Framework Region 1 | 102 |
| GFTFDKYW | E7 | Heavy Chain CDR1 | 103 |
| MHWVRQAPGKGLEWIAE | E7 | Rat Heavy Chain Framework Region 2 | 104 |
| IEYDGTET | E7 | Heavy Chain CDR2 | 105 |
| NYAPSIKDRFTISRDNAKNTLYLQMSNVRSEDAATYFC | E7 | Rat Heavy Chain Framework Region 3 | 106 |
| TTEEMYTTDYYYGFAY | E7 | Heavy Chain CDR3 | 107 |
| WGQGTLVTVSS | E7 | Rat Heavy Chain Framework Region 4 | 108 |
| DVKLVESGGGLLKPGGSLKLSCVAS | J | Rat Heavy Chain Framework Region 1 | 109 |
| GFSFSKYW | J | Heavy Chain CDR1 | 110 |
| MHWVRQAPGQGLEWIAE | J | Rat Heavy Chain Framework Region 2 | 111 |
| IEYDGTET | J | Heavy Chain CDR2 | 105 |
| NYAPSIKDRFTISRDNAKNTLYLQMSNVRFEDAATYFC | J | Rat Heavy Chain Framework Region 3 | 112 |
| TTEEMHTTDYYYGFAY | J | Heavy Chain CDR3 | 113 |
| WGQGTLVTVSS | J | Rat Heavy Chain Framework Region 4 | 108 |
| EVQLVESGGGLVQPGRSLKLSCAAS | F | Rat Heavy Chain Framework Region 1 | 114 |
| GFIFSEHN | F | Heavy Chain CDR1 | 115 |
| MAWVRQAPKKGLEWVAT | F | Rat Heavy Chain Framework Region 2 | 116 |
| ISDDGRNT | F | Heavy Chain CDR2 | 117 |
| YYRDSMRGRFTISRENARSTLYLQLDSLRSEDTATYYC | F | Rat Heavy Chain Framework Region 3 | 118 |
| ASHRYNLFDS | F | Heavy Chain CDR3 | 119 |
| WGQGVMVTVSS | F | Rat Heavy Chain Framework Region 4 | 94 |
| QVQLQQSGTELVKPASSVRISCKAS | A | Rat Heavy Chain Framework Region 1 | 120 |
| GYTLTTNY | A | Heavy Chain CDR1 | 121 |
| MHWIRQQPGNGLEWIGW | A | Rat Heavy Chain Framework Region 2 | 122 |
| IYPGNGNT | A | Heavy Chain CDR2 | 123 |
| KFNHKFDGRTTLTADKSSSIVYMQLSSLTSEDSAVYFC | A | Rat Heavy Chain Framework Region 3 | 124 |
| ARSDFDY | A | Heavy Chain CDR3 | 125 |
| WGQGVMVTVSS | A | Rat Heavy Chain Framework Region 4 | 94 |
| DVQLEESGGGLVRPGRSLKLSCADS | B | Rat Heavy Chain Framework Region 1 | 126 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
| --- | --- | --- | --- |
| GVNFSNRG | B | Heavy Chain CDR1 | 127 |
| MAWVRQAPTKGLEWVAT | B | Rat Heavy Chain Framework Region 2 | 128 |
| ISYDGRII | B | Heavy Chain CDR2 | 129 |
| YYRDSVKGRFSISRENAKSTLYLQMDSLRSEDTATYYC | B | Rat Heavy Chain Framework Region 3 | 130 |
| ARHPIAADWYFDF | B | Heavy Chain CDR3 | 131 |
| WGPGTMVTVSS | B | Rat Heavy Chain Framework Region 4 | 132 |
| EVQLVESGGGSVQPGRSLKLSCAAS | I | Rat Heavy Chain Framework Region 1 | 133 |
| GFTFSDYN | I | Heavy Chain CDR1 | 134 |
| MAWVRQAPKKGPEWVAT | I | Rat Heavy Chain Framework Region 2 | 135 |
| ITYDVHNA | I | Heavy Chain CDR2 | 136 |
| YYRDSVKGRFTISRDDAKSTLYLQMDSLRSEDTATYFC | I | Rat Heavy Chain Framework Region 3 | 137 |
| ARPGAY | I | Heavy Chain CDR3 | 138 |
| WGQGTLVTVSS | I | Rat Heavy Chain Framework Region 4 | 108 |
| QVRLLQSGAALVKPGASVKMSCKAS | O | Rat Heavy Chain Framework Region 1 | 139 |
| GYTFTDYW | O | Heavy Chain CDR1 | 140 |
| MSWVKQSHGKSLEWIGE | O | Rat Heavy Chain Framework Region 2 | 141 |
| IYPNSGAT | O | Heavy Chain CDR2 | 142 |
| NFNEKFKDKATLTVDRSTSTAYMELSRLTSEDSAIYYC | O | Rat Heavy Chain Framework Region 3 | 143 |
| ARGFPNNYLSWFAY | O | Heavy Chain CDR3 | 144 |
| WGQGTLVTVSS | O | Rat Heavy Chain Framework Region 4 | 108 |
| QIQLVQSGPELKKPGESVKISCKAS | R | Rat Heavy Chain Framework Region 1 | 145 |
| GYTFTNYG | R | Heavy Chain CDR1 | 146 |
| MYWVKQAPGQGLQYMGW | R | Rat Heavy Chain Framework Region 2 | 147 |
| INTETGKP | R | Heavy Chain CDR2 | 148 |
| TYADDFKGRFVFFLETSASTAYLQINNLKNEDMATYFC | R | Rat Heavy Chain Framework Region 3 | 149 |
| AREVKHGLFHWFAY | R | Heavy Chain CDR3 | 150 |
| WGQGTLVTVSS | R | Rat Heavy Chain Framework Region 4 | 108 |
| EVQLVESGGGLVQPGRSLTLSCSAS | Pi | Rat Heavy Chain Framework Region 1 | 151 |
| GFTFRDYN | Pi | Heavy Chain CDR1 | 152 |
| MAWVRQAPRKGLEWVAT | Pi | Rat Heavy Chain Framework Region 2 | 153 |
| ISFDDYNT | Pi | Heavy Chain CDR2 | 154 |
| YYRDSVKGRFTISRDDAKSTLYLQMDSLRSEDTATYYC | Pi | Rat Heavy Chain Framework Region 3 | 155 |

Sequence Listing
The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| ARPGTY | Pi | Heavy Chain CDR3 | 156 |
| WGQGTLVTVSS | Pi | Rat Heavy Chain Framework Region 4 | 108 |
| QVQLQQSGAELVKPGSSVRISCKAS | Mu | Rat Heavy Chain Framework Region 1 | 157 |
| GYTITSYD | Mu | Heavy Chain CDR1 | 158 |
| MHWIKQQPGNGLEGIGW | Mu | Rat Heavy Chain Framework Region 2 | 159 |
| IHPGNGKI | Mu | Heavy Chain CDR2 | 160 |
| KYNQKFNGKATLTVDKSSSTAYMQLSSLTSEDSAVYFC | Mu | Rat Heavy Chain Framework Region 3 | 161 |
| ARGTTRVFPWFAY | Mu | Heavy Chain CDR3 | 162 |
| WGQGTLVTVSS | Mu | Rat Heavy Chain Framework Region 4 | 108 |
| EVQLVESGGGLVQPGRSLKLSCAAS | V | Rat Heavy Chain Framework Region 1 | 114 |
| GFSFSNYG | V | Heavy Chain CDR1 | 163 |
| MHWIRQAPTKGLEWVAS | V | Rat Heavy Chain Framework Region 2 | 164 |
| ISPTGGNT | V | Heavy Chain CDR2 | 165 |
| YYRDSVKGRFTISRDNTKSTLYLQMDSLRSEDTATYYC | V | Rat Heavy Chain Framework Region 3 | 166 |
| ATDDLYYSGPFAY | V | Heavy Chain CDR3 | 167 |
| WGQGTLVTVSS | V | Rat Heavy Chain Framework Region 4 | 108 |
| EVQLQESGPGLVKPAQSLSLTCSVTGYSITNMYRWNWIRKFPGNKLEWMGYINTAGSTDYSPSLRGRVSITGDTSKNQFFLHLTSVTTEDTATYYCAGFITNPFDFWGQGVMVTVSS | G3 | Rat Heavy Chain Variable Region | 168 |
| EVQVVESGGGLVQPGRSLKLSCVPSGFTFNNYWMTWIRQAPGKAPEWVASISNTGGSTFYPDSVRGRFSISRDNTKGTLYLHMTSLRSEDTATYYCIRNMDAWGQGTSVTVSS | G5 | Rat Heavy Chain Variable Region | 169 |
| GKLVESGGGLLKPGGSLKLSCVASGFTFDKYWMHWVRQAPGKGLEWIAEIEYDGTETNYAPSIKDRFTISRDNAKNTLYLQMSNVRSEDAATYFCTTEEMYTTDYYYGFAYWGQGTLVTVSS | E7 | Rat Heavy Chain Variable Region | 170 |
| DVKLVESGGGLLKPGGSLKLSCVASGFSFSKYWMHWVRQAPGQGLEWIAEIEYDGTETNYAPSIKDRFTISRDNAKNTLYLQMSNVRFEDAATYFCTTEEMHTTDYYYGFAYWGQGTLVTVSS | J | Rat Heavy Chain Variable Region | 171 |
| EVQLVESGGGLVQPGRSLKLSCAASGFIFSEHNMAWVRQAPKKGLEWVATISDDGRNTYYRDSMRGRFTISRENARSTLYLQLDSLRSEDTATYYCASHRYNLFDSWGQGVMVTVSS | F | Rat Heavy Chain Variable Region | 172 |
| QVQLQQSGTELVKPASSVRISCKASGYTLTTNYMHWIRQQPGNGLEWIGWIYPGNGNTKFNHKFDGRTTLTADKSSSIVYMQLSSLTSEDSAVYFCARSDFDYWGQGVMVTVSS | A | Rat Heavy Chain Variable Region | 173 |
| DVQLEESGGGLVRPGRSLKLSCADSGVNFSNRGMAWVRQAPTKGLEWVATISYDGRIIYRDSVKGRFSISRENAKSTLYLQMDSLRSEDTATYYCARHPIAADWYFDFWGPGTMVTVSS | B | Rat Heavy Chain Variable Region | 174 |

Sequence Listing
The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| EVQLVESGGGSVQPGRSLKLSCAASGFTFSD YNMAWVRQAPKKGPEWVATITYDVHNAYY RDSVKGRFTISRDDAKSTLYLQMDSLRSEDT ATYFCARPGAYWGQGTLVTVSS | I | Rat Heavy Chain Variable Region | 175 |
| QVRLLQSGAALVKPGASVKMSCKASGYTFT DYWMSWVKQSHGKSLEWIGEIYPNSGATN FNEKFKDKATLTVDRSTSTAYMELSRLTSEDS AIYYCARGFPNNYLSWFAYWGQGTLVTVSS | O | Rat Heavy Chain Variable Region | 176 |
| QIQLVQSGPELKKPGESVKISCKASGYTFTNY GMYWVKQAPGQGLQYMGWINTETGKPTY ADDFKGRFVFFLETSASTAYLQINNLKNEDM ATYFCAREVKHGLFHWFAYWGQGTLVTVSS | R | Rat Heavy Chain Variable Region | 177 |
| EVQLVESGGGLVQPGRSLTLSCSASGFTFRD YNMAWVRQAPRKGLEWVATISFDDYNTYY RDSVKGRFTISRDDAKSTLYLQMDSLRSEDT ATYYCARPGTYWGQGTLVTVSS | Pi | Rat Heavy Chain Variable Region | 178 |
| QVQLQQSGAELVKPGSSVRISCKASGYTITSY DMHWIKQQPGNGLEGIGWIHPGNGKIKYN QKFNGKATLTVDKSSSTAYMQLSSLTSEDSA VYFCARGTTRVFPWFAYWGQGTLVTVSS | Mu | Rat Heavy Chain Variable Region | 179 |
| EVQLVESGGGLVQPGRSLKLSCAASGFSFSN YGMHWIRQAPTKGLEWVASISPTGGNTYYR DSVKGRFTISRDNTKSTLYLQMDSLRSEDTAT YYCATDDLYYSGPFAYWGQGTLVTVSS | V | Rat Heavy Chain Variable Region | 180 |
| QVQLVQSGAEVKKPGASVKVSCKAS | A | Humanised 1 Heavy Chain FR 1 | 181 |
| MHWVRQAPGQRLEWMGW | A | Humanised 1 Heavy Chain FR 2 | 182 |
| KFNHKFDGRVTITRDTSASTAYMELSSLRSED TAVYYC | A | Humanised 1 Heavy Chain FR 3 | 183 |
| WGQGTLVTVSS | A | Humanised 1 Heavy Chain FR 4 | 108 |
| QVQLVQSGAEVKKPGASVKVSCKAS | A | Humanised 2 Heavy Chain FR 1 | 181 |
| MHWVRQAPGQGLEWMGW | A | Humanised 2 Heavy Chain FR 2 | 184 |
| KFNHKFDGRVTMTRDTSTSTVYMELSSLRSE DTAVYYC | A | Humanised 2 Heavy Chain FR 3 | 185 |
| WGQGTMVTVSS | A | Humanised 2 Heavy Chain FR 4 | 186 |
| QVQLVQSGAEVKKPGASVKVSCKAS | A | Humanised 3 Heavy Chain FR 1 | 181 |
| MHWVRQAPGQGLEWMGW | A | Humanised 3 Heavy Chain FR 2 | 184 |
| KFNHKFDGRVTMTRDTSISTAYMELSRLRSD DTAVYYC | A | Humanised 3 Heavy Chain FR 3 | 187 |
| WGQGTLVTVSS | A | Humanised 3 Heavy Chain FR 4 | 108 |
| QVQLVQSGAEVKKPGSSVKVSCKAS | A | Humanised 4 Heavy Chain FR 1 | 188 |
| MHWVRQAPGQGLEWMGW | A | Humanised 4 Heavy Chain FR 2 | 184 |
| KFNHKFDGRVTITADKSTSTAYMELSSLRSED TAVYYC | A | Humanised 4 Heavy Chain FR 3 | 189 |
| WGQGTLVTVSS | A | Humanised 4 Heavy Chain FR 4 | 108 |
| QVQLVQSGSELKKPGASVKVSCKAS | A | Humanised 5 Heavy Chain FR 1 | 190 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| MHWVRQAPGQGLEWMGW | A | Humanised 5 Heavy Chain FR 2 | 184 |
| KFNHKFDGRFVFSLDTSVSTAYLQISSLKAED TAVYYC | A | Humanised 5 Heavy Chain FR 3 | 191 |
| WGQGTLVTVSS | A | Humanised 5 Heavy Chain FR 4 | 108 |
| QVQLVQSGAEVKKPGASVKVSCKASGYTLTT NYMHWVRQAPGQRLEWMGWIYPGNGNT KFNHKFDGRVTITRDTSASTAYMELSSLRSED TAVYYCARSDFDYWGQGTLVTVSS | A | Humanised 1 Heavy Chain Variable Region | 192 |
| QVQLVQSGAEVKKPGASVKVSCKASGYTLTT NYMHWVRQAPGQGLEWMGWIYPGNGNT KFNHKFDGRVTMTRDTSTSTVYMELSSLRSE DTAVYYCAISDFDYWGQGTMVTVSS | A | Humanised 2 Heavy Chain Variable Region | 193 |
| QVQLVQSGAEVKKPGASVKVSCKASGYTLTT NYMHWVRQAPGQGLEWMGWIYPGNGNT KFNHKFDGRVTMTRDTSISTAYMELSRLRSD DTAVYYCARSDFDYWGQGTLVTVSS | A | Humanised 3 Heavy Chain Variable Region | 194 |
| QVQLVQSGAEVKKPGSSVKVSCKASGYTLTT NYMHWVRQAPGQGLEWMGWIYPGNGNT KFNHKFDGRVTITADKSTSTAYMELSSLRSED TAVYYCATSDFDYWGQGTLVTVSS | A | Humanised 4 Heavy Chain Variable Region | 195 |
| QVQLVQSGSELKKPGASVKVSCKASGYTLTT NYMHWVRQAPGQGLEWMGWIYPGNGNT KFNHKFDGRFVFSLDTSVSTAYLQISSLKAED TAVYYCARSDFDYWGQGTLVTVSS | A | Humanised 5 Heavy Chain Variable Region | 196 |
| DIQMTQSPSSLSASVGDRVTITCQAS | A | Humanised 1 Light Chain FR 1 | 197 |
| LIWFQQKPGKAPKSLIY | A | Humanised 1 Light Chain FR 2 | 198 |
| SLANGVPSRFSGSGSGTDFTLTISSLQPEDFA TYYC | A | Humanised 1 Light Chain FR 3 | 199 |
| FGPGTKVDIK | A | Humanised 1 Light Chain FR 4 | 200 |
| DIQMTQSPSAMSASVGDRVTITCQAS | A | Humanised 2 Light Chain FR 1 | 201 |
| LIWFQQKPGKVPKRLIY | A | Humanised 2 Light Chain FR 2 | 202 |
| SLANGVPSRFSGSGSGTEFTLTISSLQPEDFAT YYC | A | Humanised 2 Light Chain FR 3 | 203 |
| FGPGTKVDIK | A | Humanised 2 Light Chain FR 4 | 200 |
| DIQMTQSPSSLSASVGDRVTITCQAS | A | Humanised 3 Light Chain FR 1 | 197 |
| LIWYQQKPGKAPKRLIY | A | Humanised 3 Light Chain FR 2 | 204 |
| SLANGVPSRFSGSGSGTEFTLTISSLQPEDFAT YYC | A | Humanised 3 Light Chain FR 3 | 203 |
| FGQGTKLEIK | A | Humanised 3 Light Chain FR 4 | 205 |
| DIQMTQSPSSLSASVGDRVTITCQAS | A | Humanised 4 Light Chain FR 1 | 197 |
| LIWYQQKPGKAPKLLIY | A | Humanised 4 Light Chain FR 2 | 206 |
| SLANGVPSRFSGSGSGTDFTFTISSLQPEDIAT YYC | A | Humanised 4 Light Chain FR 3 | 207 |
| FGQGTKLEIK | A | Humanised 4 Light Chain FR 4 | 205 |
| DIQMTQSPSSVSASVGDRVTITCQAS | A | Humanised 5 Light Chain FR 1 | 208 |

-continued

Sequence Listing
The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| LIWYQQKPGKAPKLLIY | A | Humanised 5 Light Chain FR 2 | 206 |
| SLANGVPSRFSGSGSGTDFTLTISSLQPEDFATYYC | A | Humanised 5 Light Chain FR 3 | 199 |
| FGQGTKVEIK | A | Humanised 5 Light Chain FR 4 | 209 |
| DIQMTQSPSSLSASVGDRVTITCQASQDIGNNLIWFQQKPGKAPKSLIYFATSLANGVPSRFSGSGSGTDFTLTISSLQPEDFATYYCLQYREYPLTFGPGTKVDIK | A | Humanised 1 Light Chain Variable Region | 210 |
| DIQMTQSPSAMSASVGDRVTITCQASQDIGNNLIWFQQKPGKVPKRLIYFATSLANGVPSRFSGSGSGTEFTLTISSLQPEDFATYYCLQYREYPLTFGPGTKVDIK | A | Humanised 2 Light Chain Variable Region | 211 |
| DIQMTQSPSSLSASVGDRVTITCQASQDIGNNLIWYQQKPGKAPKRLIYFATSLANGVPSRFSGSGSGTEFTLTISSLQPEDFATYYCLQYREYPLTFGQGTKLEIK | A | Humanised 3 Light Chain Variable Region | 212 |
| DIQMTQSPSSLSASVGDRVTITCQASQDIGNNLIWYQQKPGKAPKLLIYFATSLANGVPSRFSGSGSGTDFTFTISSLQPEDIATYYCLQYREYPLTFGQGTKLEIK | A | Humanised 4 Light Chain Variable Region | 213 |
| DIQMTQSPSSVSASVGDRVTITCQASQDIGNNLIWYQQKPGKAPKLLIYFATSLANGVPSRFSGSGSGTDFTLTISSLQPEDFATYYCLQYREYPLTFGQGTKVEIK | A | Humanised 5 Light Chain Variable Region | 214 |
| QVQLVESGGGVVQPGRSLRLSCAAS | F | Humanised 1 Heavy Chain FR 1 | 215 |
| MAWVRQAPGKGLEWVAT | F | Humanised 1 Heavy Chain FR 2 | 216 |
| YYRDSMRGRFTISRDNSKNTLYLQMNSLRAEDTAVYYC | F | Humanised 1 Heavy Chain FR 3 | 217 |
| WGQGTMVTVSS | F | Humanised 1 Heavy Chain FR 4 | 186 |
| EVQLVESGGGLVQPGGSLRLSCAAS | F | Humanised 2 Heavy Chain FR 1 | 218 |
| MAWVRQAPGKGLEWVST | F | Humanised 2 Heavy Chain FR 2 | 219 |
| YYRDSMRGRFTISRDNSKNTLYLQMNSLRAEDTAVYYC | F | Humanised 2 Heavy Chain FR 3 | 217 |
| WGQGTLVTVSS | F | Humanised 2 Heavy Chain FR 4 | 108 |
| EVQLVESGGGLVQPGGSLRLSCAAS | F | Humanised 3 Heavy Chain FR 1 | 218 |
| MAWVRQAPGKGLEWVAT | F | Humanised 3 Heavy Chain FR 2 | 216 |
| YYRDSMRGRFTISRDNAKNSLYLQMNSLRAEDTAVYYC | F | Humanised 3 Heavy Chain FR 3 | 220 |
| WGQGTMVTVSS | F | Humanised 3 Heavy Chain FR 4 | 186 |
| EVQLVESGGGLVQPGGSLRLSCAAS | F | Humanised 4 Heavy Chain FR 1 | 218 |
| MAWVRQAPGKGLVWVST | F | Humanised 4 Heavy Chain FR 2 | 221 |
| YYRDSMRGRFTISRDNAKNTLYLQMNSLRAEDTAVYYC | F | Humanised 4 Heavy Chain FR 3 | 222 |
| WGQGTLVTVSS | F | Humanised 4 Heavy Chain FR 4 | 108 |

Sequence Listing

The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| EVQLVESGGGLVQPGRSLRLSCAAS | F | Humanised 5 Heavy Chain FR 1 | 223 |
| MAWVRQAPGKGLEWVST | F | Humanised 5 Heavy Chain FR 2 | 219 |
| YYRDSMRGRFTISRDNAKNSLYLQMNSLRAEDTALYYC | F | Humanised 5 Heavy Chain FR 3 | 224 |
| WGQGTLVTVSS | F | Humanised 5 Heavy Chain FR 4 | 108 |
| QVQLVESGGGVVQPGRSLRLSCAASGFIFSEHNMAWVRQAPGKGLEWVATISDDGRNTYYRDSMRGRFTISRDNSKNTLYLQMNSLRAEDTAVYYCTSHRYNLFDSWGQGTMVTVSS | F | Humanised 1 Heavy Chain Variable Region | 225 |
| EVQLVESGGGLVQPGGSLRLSCAASGFIFSEHNMAWVRQAPGKGLEWVSTISDDGRNTYYRDSMRGRFTISRDNSKNTLYLQMNSLRAEDTAVYYCAKHRYNLFDSWGQGTLVTVSS | F | Humanised 2 Heavy Chain Variable Region | 226 |
| EVQLVESGGGLVQPGGSLRLSCAASGFIFSEHNMAWVRQAPGKGLEWVATISDDGRNTYYRDSMRGRFTISRDNAKNSLYLQMNSLRAEDTAVYYCARHRYNLFDSWGQGTMVTVSS | F | Humanised 3 Heavy Chain Variable Region | 227 |
| EVQLVESGGGLVQPGGSLRLSCAASGFIFSEHNMAWVRQAPGKGLVWVSTISDDGRNTYYRDSMRGRFTISRDNAKNTLYLQMNSLRAEDTAVYYCARHRYNLFDSWGQGTLVTVSS | F | Humanised 4 Heavy Chain Variable Region | 228 |
| EVQLVESGGGLVQPGRSLRLSCAASGFIFSEHNMAWVRQAPGKGLEWVSTISDDGRNTYYRDSMRGRFTISRDNAKNSLYLQMNSLRAEDTALYYCAKHRYNLFDSWGQGTLVTVSS | F | Humanised 5 Heavy Chain Variable Region | 229 |
| DIQMTQSPSSLSASVGDRVTITCKAS | F | Humanised 1 Light Chain FR 1 | 230 |
| LNWYQQKPGKAPKRLIY | F | Humanised 1 Light Chain FR 2 | 231 |
| KLQTGVPSRFSGSGSGTEFTLTISSLQPEDFATYYC | F | Humanised 1 Light Chain FR 3 | 232 |
| FGQGTKLEIK | F | Humanised 1 Light Chain FR 4 | 205 |
| DIQMTQSPSSLSASVGDRVTITCKAS | F | Humanised 2 Light Chain FR 1 | 230 |
| LNWFQQKPGKAPKSLIY | F | Humanised 2 Light Chain FR 2 | 233 |
| KLQTGVPSKFSGSGSGTDFTLTISSLQPEDFATYYC | F | Humanised 2 Light Chain FR 3 | 234 |
| FGQGTRLEIK | F | Humanised 2 Light Chain FR 4 | 235 |
| DIQMTQSPSSLSASVGDRVTITCKAS | F | Humanised 3 Light Chain FR 1 | 230 |
| LNWYQQKPGKAPKLLIY | F | Humanised 3 Light Chain FR 2 | 236 |
| KLQTGVPSRFSGSGSGTDFTLTISSLQPEDFATYYC | F | Humanised 3 Light Chain FR 3 | 237 |
| FGQGTKLEIK | F | Humanised 3 Light Chain FR 4 | 205 |
| DIQLTQSPSFLSASVGDRVTITCKAS | F | Humanised 4 Light Chain FR 1 | 238 |
| LNWYQQKPGKAPKLLIY | F | Humanised 4 Light Chain FR 2 | 236 |
| KLQTGVPSRFSGSGSGTEFTLTISSLQPEDFATYYC | F | Humanised 4 Light Chain FR 3 | 232 |
| FGQGTKLEIK | F | Humanised 4 Light Chain FR 4 | 205 |

-continued

Sequence Listing
The amino acid sequences listed are shown in the application using standard one letter codes for amino acids. The sequences below relate to 13 clones (G3, G5, E7, J, F, B, A, I, O, Pi, Mu, R and V) that were developed. Also contained in the table below are sequences relating to the humanisation of clones A and F.

| Sequence | Clone | Description | SEQ ID NO: |
|---|---|---|---|
| DIQMTQSPSTLSASVGDRVTITCKAS | F | Humanised 5 Light Chain FR 1 | 239 |
| LNWYQQKPGKAPKLLIY | F | Humanised 5 Light Chain FR 2 | 236 |
| KLQTGVPSRFSGSGSGTEFTLTISSLQPDDFATYYC | F | Humanised 5 Light Chain FR 3 | 240 |
| FGQGTKLEIK | F | Humanised 5 Light Chain FR 4 | 205 |
| DIQMTQSPSSLSASVGDRVTITCKASQNIDRYLNWYQQKPGKAPKRLIYNTNKLQTGVPSRFSGSGSGTEFTLTISSLQPEDFATYYCLQYNSLPLTFGQGTKLEIK | F | Humanised 1 Light Chain Variable Region | 241 |
| DIQMTQSPSSLSASVGDRVTITCKASQNIDRYLNWFQQKPGKAPKSLIYNTNKLQTGVPSKFSGSGSGTDFTLTISSLQPEDFATYYCLQYNSLPLTFGQGTRLEIK | F | Humanised 2 Light Chain Variable Region | 242 |
| DIQMTQSPSSLSASVGDRVTITCKASQNIDRYLNWYQQKPGKAPKLLIYNTNKLQTGVPSRFSGSGSGTDFTLTISSLQPEDFATYYCLQYNSLPLTFGQGTKLEIK | F | Humanised 3 Light Chain Variable Region | 243 |
| DIQLTQSPSFLSASVGDRVTITCKASQNIDRYLNWYQQKPGKAPKLLIYNTNKLQTGVPSRFSGSGSGTEFTLTISSLQPEDFATYYCLQYNSLPLTFGQGTKLEIK | F | Humanised 4 Light Chain Variable Region | 244 |
| DIQMTQSPSTLSASVGDRVTITCKASQNIDRYLNWYQQKPGKAPKLLIYNTNKLQTGVPSRFSGSGSGTEFTLTISSLQPDDFATYYCLQYNSLPLTFGQGTKLEIK | F | Humanised 5 Light Chain Variable Region | 245 |
| ARSDFDY | A | Humanised 1 Heavy Chain CDR3 | 125 |
| AISDFDY | A | Humanised 2 Heavy Chain CDR3 | 246 |
| ARSDFDY | A | Humanised 3 Heavy Chain CDR3 | 125 |
| ATSDFDY | A | Humanised 4 Heavy Chain CDR3 | 247 |
| ARSDFDY | A | Humanised 5 Heavy Chain CDR3 | 125 |
| AXSDFDY (where X is R, I or T) | A | General Heavy Chain CDR3 | 248 |
| TSHRYNLFDS | F | Humanised 1 Heavy Chain CDR3 | 249 |
| AKHRYNLFDS | F | Humanised 2 Heavy Chain CDR3 | 250 |
| ARHRYNLFDS | F | Humanised 3 Heavy Chain CDR3 | 251 |
| ARHRYNLFDS | F | Humanised 4 Heavy Chain CDR3 | 251 |
| AKHRYNLFDS | F | Humanised 5 Heavy Chain CDR3 | 250 |
| XXHRYNLFDS (where $X_1$ is A or T and $X_2$ is S, K or R) | F | General Heavy Chain CDR3 | 252 |
| NISSE | | ROR1 epitope for clone A | 253 |
| FQDDL | | Substituted sequence for epitope mapping | 254 |

The CDR sequences and the framework regions in the table above have been determined based on information on framework regions and CDRs from the IMGT (the international ImMunoGeneTics information system) database (see www.imgt.org).

An alternative method for labelling CDRs is using the Kabat system and this can give slightly different results. However, this can easily be determined by someone skilled in the art. For the avoidance of doubt, the CDR sequences in the variable regions based on the Kabat system are as follows, where the Kabat CDRs are in bold:

```
Clone G3 light chain variable region
                                                        (SEQ ID NO: 75)
DVVMTQTPVSLPVSLGGQVSISCRSSQSLEHSNGDTFLHWYLQKPGQSPRLLIYRVSNRFSGVPDR

FSGSGSGTDFTLKISRIEPEDLGDYYCLQSTHFPNTFGAGTKLELK

Clone G5 light chain variable region
                                                        (SEQ ID NO: 76)
DIQLTQSPSTLSASLGERVTISCRASQSISNSLNWYQQKPDGTVKRLIYSTSTLESGVPSRFSGSGSG

TDFSLSISSLESEDFAMYYCLQFATYPQVTFGSGTKLEIK

Clone E7 light chain variable region
                                                        (SEQ ID NO: 77)
DIVLTQSPALAVSVGQRATISCRASQSVSISRYNFMHWYQQKPGQQPKLLIYRASNLASGIPARFSG

SGSGTDFTLTINPVQADDIATYYCQQNRESPRTFGGGTKLELK

Clone J light chain variable region
                                                        (SEQ ID NO: 78)
DIVLTQSPALAVSVGQRATISCRASQSVSISRYDFMHWYQQKPGQQPKLLIYRASNLASGIPARFSG

SGSGTDFTLTINPVQADDIATYYCQQNRESPRTFGGGTKLELK

Clone F light chain variable region
                                                        (SEQ ID NO: 79)
DIQMTQSPSFLSASVGDRVTINCKASQNIDRYLVNYQQKLGEAPKRLLYNTNKLQTGIPSRFSGSG

SATDFTLTISSLQPEDFATYFCLQYNSLPLTFGSGTKLEIK

Clone A light chain variable region
                                                        (SEQ ID NO: 80)
DIQMTQSPSSMSASLGDRVTFTCQASQDIGNNLIWFQQKPGKSPRPLMYFATSLANGVPSRFSGSR

SGSDYSLTISSLESEDLADYHCLQYREYPLTFGSGTKLDLK

Clone B light chain variable region
                                                        (SEQ ID NO: 81)
DIRMTQSPASLSASLGETVTIECLTSEDIYSDLAWFQQKPGKSPQLLIYDANSLQNGVPSRFGGCGS

GTQYSLQISSLQSEDVATYFCQQYKNYPPTFGGGTKLVLK

Clone I light chain variable region
                                                        (SEQ ID NO: 82)
DIQLTQSPSSMSASLGDRVSLTCQSSQGIGKYLSWYQHKPGKPPKAMIYYATKLADGVPSRFSGSR

SGSDFSLTISSLESEDIAIYYCLQFDDYPWTFGGGTKLELK

Clone O light chain variable region
                                                        (SEQ ID NO: 83)
DIVLTQSPALAVSLEQRVTIACKTSQNVDNHGISYMHWYQQKSGQEPKLLIYEGSNLAVGIPARFS

GSGSGTDFTLTIDPVEADDIETYYCQQSKDDPRTFGGGTKLELK

Clone R light chain variable region
                                                        (SEQ ID NO: 84)
QFTLTQPKSVSGSLRSTITIPCERSSGDIGDSYVSWYQQHLGRPPINVIYADDQRPSEVSDRFSGSIDS

SSNSASLTITNLQMDDEADYFCQSYDRNVDFNTVFGGGTKVTVL

Clone Pi light chain variable region
                                                        (SEQ ID NO: 85)
DIQLTQSPSSLSASLGDRVSLTCQSSQGIGKYLSWFQHKPGKPPKPVINYATNLADGVPSRFSGRRS

GSDFSLTISSLESEDTAIYYCLQFDDFRWTVGGGTKLELK

Clone Mu light chain variable region
                                                        (SEQ ID NO: 86)
QFTLTQPKSVSGSLRSTITIPCERSSGDIGDNYVSWYQQHLGRPPINVIYADDQRPSEVSDRFSGSID

SSSNSASLTITNLQMDDEADYFCQSFDSNFDIPVFGGGTKLTVL
```

```
Clone V light chain variable region
                                                  (SEQ ID NO: 87)
DIKMTQSPSFLSASVGDRVTINCKASQNITRFLNWYQQELGEAPTLLIYNTNNLQTGIPSRFSGSGS

GTDFTLTISSLQPEDVATYFCLQHGSRPRTFGGGTKLELK

Clone G3 heavy chain variable region
                                                  (SEQ ID NO: 168)
EVQLQESGPGLVKPAQSLSLTCSVTGYSITNMYRWNWIRKFPGNKLEWMGYINTAGSTDYSPSLRGRV

SITGDTSKNQFFLHLTSVTTEDTATYYCAGFITNPFDFWGQGVMVTVSS

Clone G5 heavy chain variable region
                                                  (SEQ ID NO: 169)
EVQVVESGGGLVQPGRSLKLSCVPSGFTFNNYWMTWIRQAPGKAPEWVASISNTGGSTFYPDSVRGRF

SISRDNTKGTLYLHMTSLRSEDTATYYCIRNMDAWGQGTSVTVSS

Clone E7 heavy chain variable region
                                                  (SEQ ID NO: 170)
GKLVESGGGLLKPGGSLKLSCVASGFTFDKYWMHWVRQAPGKGLEWIAEIEYDGTETNYAPSIKDRF

TISRDNAKNTLYLQMSNVRSEDAATYFCTTEEMYTTDYYYGFAYWGQGTLVTVSS

Clone J heavy chain variable region
                                                  (SEQ ID NO: 171)
DVKLVESGGGLLKPGGSLKLSCVASGFSFSKYWMHWVRQAPGQGLEWIAEIEYDGTETNYAPSIKDR

FTISRDNAKNTLYLQMSNVRFEDAATYFCTTEEMHTTDYYYGFAYWGQGTLVTVSS

Clone F heavy chain variable region
                                                  (SEQ ID NO: 172)
EVQLVESGGGLVQPGRSLKLSCAASGFIFSEHNMAWVRQAPKKGLEWVATISDDGRNTYYRDSMRGR

FTISRENARSTLYLQLDSLRSEDTATYYCASHRYNLFDSWGQGVMVTVSS

Clone A heavy chain variable region
                                                  (SEQ ID NO: 173)
QVQLQQSGTELVKPASSVRISCKASGYTLTTNYMHWIRQQPGNGLEWIG**WIYPGNGNTKFNHKF

DGRTTLTADKSSSIVYMQLSSLTSEDSAVYFCARSDFDY**WGQGVMVTVSS

Clone B heavy chain variable region
                                                  (SEQ ID NO: 174)
DVQLEESGGGLVRPGRSLKLSCADSGVNFSNRGMAWVRQAPTKGLEWVATISYDGRHYYRDSVKGR

FSISRENAKSTLYLQMDSLRSEDTATYYCARHPIAADWYFDFWGPGTMVTVSS

Clone I heavy chain variable region
                                                  (SEQ ID NO: 175)
EVQLVESGGGSVQPGRSLKLSCAASGFTFSDYNMAWVRQAPKKGPEWVATITYDVHNAYYRDSVKG

RFTISRDDAKSTLYLQMDSLRSEDTATYFCARPGAYWGQGTLVTVSS

Clone O heavy chain variable region
                                                  (SEQ ID NO: 176)
QVRLLQSGAALVKPGASVKMSCKASGYTFTDYWMSWVKQSHGKSLEWIGEIYPNSGATNFNEKFKD

KATLTVDRSTSTAYMELSRLTSEDSAIYYCARGFPNNYLSWFAYWGQGTLVTVSS

Clone R heavy chain variable region
                                                  (SEQ ID NO: 177)
QIQLVQSGPELKKPGESVKISCKASGYTFTNYGMYWVKQAPGQGLQYMGWINTETGKPTYADDFKG

RFVFFLETSASTAYLQINNLKNEDMATYFCAREVKHGLFHWFAYWGQGTLVTVSS

Clone Pi heavy chain variable region
                                                  (SEQ ID NO: 178)
EVQLVESGGGLVQPGRSLTLSCSASGFTFRDYNMAWVRQAPRKGLEWVATISFDDYNTYYRDSVKGR

FTISRDDAKSTLYLQMDSLRSEDTATYYCARPGTYWGQGTLVTVSS

Clone Mu heavy chain variable region
                                                  (SEQ ID NO: 179)
QVQLQQSGAELVKPGSSVRISCKASGYTITSYDMHWIKQQPGNGLEGIGWIHPGNGKIKYNQKFNGKA

TLTVDKSSSTAYMQLSSLTSEDSAVYFCARGTTRVFPWFAYWGQGTLVTVSS
```

-continued

```
Clone V heavy chain variable region
                                                    (SEQ ID NO: 180)
EVQLVESGGGLVQPGRSLKLSCAASGFSFSNYGMHWIRQAPTKGLEWVASISPTGGNTYYRDSVKGRF

TISRDNTKSTLYLQMDSLRSEDTATYYCATDDLYYSGPFAYWGQGTLVTVSS

Clone A Humanised 1 light chain variable region
                                                    (SEQ ID NO: 210)
DIQMTQSPSSLSASVGDRVTITCQASQDIGNNLIWFQQKPGKAPKSLIYFATSLANGVPSRFSGSGS

GTDFTLTISSLQPEDFATYYCLQYREYPLTFGPGTKVDIK

Clone A Humanised 2 light chain variable region
                                                    (SEQ ID NO: 211)
DIQMTQSPSAMSASVGDRVTITCQASQDIGNNLIWFQQKPGKVPKRLIYFATSLANGVPSRFSGSG

SGTEFTLTISSLQPEDFATYYCLQYREYPLTFGPGTKVDIK

Clone A Humanised 3 light chain variable region
                                                    (SEQ ID NO: 212)
DIQMTQSPSSLSASVGDRVTITCQASQDIGNNLIWYQQKPGKAPKRLIYFATSLANGVPSRFSGSGS

GTEFTLTISSLQPEDFATYYCLQYREYPLTFGQGTKLEIK

Clone A Humanised 4 light chain variable region
                                                    (SEQ ID NO: 213)
DIQMTQSPSSLSASVGDRVTITCQASQDIGNNLIWYQQKPGKAPKLLIYFATSLANGVPSRFSGSGS

GTDFTFTISSLQPEDIATYYCLQYREYPLTFGQGTKLEIK

Clone A Humanised 5 light chain variable region
                                                    (SEQ ID NO: 214)
DIQMTQSPSSVSASVGDRVTITCQASQDIGNNLIWYQQKPGKAPKLLIYFATSLANGVPSRFSGSGS

GTDFTLTISSLQPEDFATYYCLQYREYPLTFGQGTKVEIK

Clone A Humanised 1 heavy chain variable region
                                                    (SEQ ID NO: 192)
QVQLVQSGAEVKKPGASVKVSCKASGYTLTTNYMHWVRQAPGQRLEWMG**WIYPGNGNTKFNHKFD

GRVTITRDTSASTAYMELSSLRSEDTAVYYCARSDFDY**WGQGTLVTVSS

Clone A Humanised 2 heavy chain variable region
                                                    (SEQ ID NO: 193)
QVQLVQSGAEVKKPGASVKVSCKASGYTLTTNYMHWVRQAPGQGLEWMG**WIYPGNGNTKFNHKFD

GRVTMTRDTSTSTVYMELSSLRSEDTAVYYCAISDFDY**WGQGTMVTVSS

Clone A Humanised 3 heavy chain variable region
                                                    (SEQ ID NO: 194)
QVQLVQSGAEVKKPGASVKVSCKASGYTLTTNYMHWVRQAPGQGLEWMG**WIYPGNGNTKFNHKFD

GRVTMTRDTSISTAYMELSRLRSDDTAVYYCARSDFDY**WGQGTLVTVSS

Clone A Humanised 4 heavy chain variable region
                                                    (SEQ ID NO: 195)
QVQLVQSGAEVKKPGSSVKVSCKASGYTLTTNYMHWVRQAPGQGLEWMG**WIYPGNGNTKFNHKFD

GRVTITADKSTSTAYMELSSLRSEDTAVYYCATSDFDY**WGQGTLVTVSS

Clone A Humanised 5 heavy chain variable region
                                                    (SEQ ID NO: 196)
QVQLVQSGSELKKPGASVKVSCKASGYTLTTNYMHWVRQAPGQGLEWMG**WIYPGNGNTKFNHKFD

GRFVFSLDTSVSTAYLQISSLKAEDTAVYYCARSDFDY**WGQGTLVTVSS

Clone F Humanised 1 light chain variable region
                                                    (SEQ ID NO: 241)
DIQMTQSPSSLSASVGDRVTITCKASQNIDRYLNWYQQKPGKAPKRLIYNTNKLQTGVPSRFSGSG

SGTEFTLTISSLQPEDFATYYCLQYNSLPLTFGQGTKLEIK

Clone F Humanised 2 light chain variable region
                                                    (SEQ ID NO: 242)
DIQMTQSPSSLSASVGDRVTITCKASQNIDRYLNWFQQKPGKAPKSLIYNTNKLQTGVPSKFSGSG

SGTDFTLTISSLQPEDFATYYCLQYNSLPLTFGQGTRLEIK
```

Clone F Humanised 3 light chain variable region
(SEQ ID NO: 243)
DIQMTQSPSSLSASVGDRVTITCKASQNIDRYLNWYQQKPGKAPKLLIYNTNKLQTGVPSRFSGSG

SGTDFTLTISSLQPEDFATYYCLQYNSLPLTFGQGTKLEIK

Clone F Humanised 4 light chain variable region
(SEQ ID NO: 244)
DIQLTQSPSFLSASVGDRVTITCKASQNIDRYLNWYQQKPGKAPKLLIYNTNKLQTGVPSRFSGSG

SGTEFTLTISSLQPEDFATYYCLQYNSLPLTFGQGTKLEIK

Clone F Humanised 5 light chain variable region
(SEQ ID NO: 245)
DIQMTQSPSTLSASVGDRVTITCKASQNIDRYLNWYQQKPGKAPKLLIYNTNKLQTGVPSRFSGSG

SGTEFTLTISSLQPDDFATYYCLQYNSLPLTFGQGTKLEIK

Clone F Humanised 1 heavy chain variable region
(SEQ ID NO: 225)
QVQLVESGGGVVQPGRSLRLSCAASGFIFSEHNMAWVRQAPGKGLEWVATISDDGRNTYYRDSMRG

RFTISRDNSKNTLYLQMNSLRAEDTAVYYCTSHRYNLFDSWGQGTMVTVSS

Clone F Humanised 2 heavy chain variable region
(SEQ ID NO: 226)
EVQLVESGGGLVQPGGSLRLSCAASGFIFSEHNMAWVRQAPGKGLEWVSTISDDGRNTYYRDSMRGR

FTISRDNSKNTLYLQMNSLRAEDTAVYYCAKHRYNLFDSWGQGTLVTVSS

Clone F Humanised 3 heavy chain variable region
(SEQ ID NO: 227)
EVQLVESGGGLVQPGGSLRLSCAASGFIFSEHNMAWVRQAPGKGLEWVATISDDGRNTYYRDSMRGR

FTISRDNAKNSLYLQMNSLRAEDTAVYYCARHRYNLFDSWGQGTMVTVSS

Clone F Humanised 4 heavy chain variable region
(SEQ ID NO: 228)
EVQLVESGGGLVQPGGSLRLSCAASGFIFSEHNMAWVRQAPGKGLVWVSTISDDGRNTYYRDSMRGR

FTISRDNAKNTLYLQMNSLRAEDTAVYYCARHRYNLFDSWGQGTLVTVSS

Clone F Humanised 5 heavy chain variable region
(SEQ ID NO: 229)
EVQLVESGGGLVQPGRSLRLSCAASGFIFSEHNMAWVRQAPGKGLEWVSTISDDGRNTYYRDSMRGR

FTISRDNAKNSLYLQMNSLRAEDTALYYCAKHRYNLFDSWGQGTLVTVSS

Therefore, the CDRs when determined using the Kabat system are as follows:

| Sequence | Clone | Description | SEQ ID NO: |
| --- | --- | --- | --- |
| RSSQSLEHSNGDTFLH | G3 | Light Chain CDR1 | 255 |
| RVSNRFS | G3 | Light Chain CDR2 | 256 |
| LQSTHFPNT | G3 | Light Chain CDR3 | 6 |
| NMYRWN | G3 | Heavy Chain CDR1 | 257 |
| YINTAGSTDYSPSLRG | G3 | Heavy Chain CDR2 | 258 |
| FITNPFDF | G3 | Heavy Chain CDR3 | 259 |
| RASQSISNSLN | G5 | Light Chain CDR1 | 260 |
| STSTLES | G5 | Light Chain CDR2 | 261 |
| LQFATYPQVT | G5 | Light Chain CDR3 | 13 |
| NYWMT | G5 | Heavy Chain CDR1 | 262 |
| SISNTGGSTFYPDSVRG | G5 | Heavy Chain CDR2 | 263 |
| NMDA | G5 | Heavy Chain CDR3 | 264 |
| RASQSVSISRYNFMH | E7 | Light Chain CDR1 | 265 |
| RASNLAS | E7 | Light Chain CDR2 | 266 |
| QQNRESPRT | E7 | Light Chain CDR3 | 20 |
| KYWMH | E7 | Heavy Chain CDR1 | 267 |
| EIEYDGTETNYAPSIKD | E7 | Heavy Chain CDR2 | 268 |
| EEMYTTDYYYGFAY | E7 | Heavy Chain CDR3 | 269 |
| RASQSVSISRYDFMH | J | Light Chain CDR1 | 270 |
| RASNLAS | J | Light Chain CDR2 | 266 |
| QQNRESPRT | J | Light Chain CDR3 | 20 |
| KYWMH | J | Heavy Chain CDR1 | 267 |

| Sequence | Clone | Description | SEQ ID NO: |
|---|---|---|---|
| EIEYDGTETNYAPSIKD | J | Heavy Chain CDR2 | 268 |
| EEMHTTDYYYGFAY | J | Heavy Chain CDR3 | 271 |
| KASQNIDRYLN | F | Light Chain CDR1 | 272 |
| NTNKLQT | F | Light Chain CDR2 | 273 |
| LQYNSLPLT | F | Light Chain CDR3 | 28 |
| EHNMA | F | Heavy Chain CDR1 | 274 |
| TISDDGRNTYYRDSMRG | F | Heavy Chain CDR2 | 275 |
| HRYNLFDS | F | Heavy Chain CDR3 | 276 |
| QASQDIGNNLI | A | Light Chain CDR1 | 277 |
| FATSLAN | A | Light Chain CDR2 | 278 |
| LQYREYPLT | A | Light Chain CDR3 | 34 |
| TNYMH | A | Heavy Chain CDR1 | 279 |
| WIYPGNGNTKFNHKFDG | A | Heavy Chain CDR2 | 280 |
| SDFDY | A | Heavy Chain CDR3 | 281 |
| LTSEDIYSDLA | B | Light Chain CDR1 | 282 |
| DANSLQN | B | Light Chain CDR2 | 283 |
| QQYKNYPPT | B | Light Chain CDR3 | 41 |
| NRGMA | B | Heavy Chain CDR1 | 284 |
| TISYDGRIIYYRDSVKG | B | Heavy Chain CDR2 | 285 |
| HPIAADWYFDF | B | Heavy Chain CDR3 | 286 |
| QSSQGIGKYLS | I | Light Chain CDR1 | 287 |
| YATKLAD | I | Light Chain CDR2 | 288 |
| LQFDDYPWT | I | Light Chain CDR3 | 48 |
| DYNMA | I | Heavy Chain CDR1 | 289 |
| TITYDVHNAYYRDSVKG | I | Heavy Chain CDR2 | 290 |
| PGAY | I | Heavy Chain CDR3 | 291 |
| KTSQNVDNHGISYMH | O | Light Chain CDR1 | 292 |
| EGSNLAV | O | Light Chain CDR2 | 293 |
| QQSKDDPRT | O | Light Chain CDR3 | 54 |
| DYWMS | O | Heavy Chain CDR1 | 294 |
| EIYPNSGATNFNEKFKD | O | Heavy Chain CDR2 | 295 |
| GFPNNYLSWFAY | O | Heavy Chain CDR3 | 296 |
| ERSSGDIGDSYVS | R | Light Chain CDR1 | 297 |
| ADDQRPS | R | Light Chain CDR2 | 298 |
| QSYDRNVDFNTV | R | Light Chain CDR3 | 60 |
| NYGMY | R | Heavy Chain CDR1 | 299 |
| WINTETGKPTYADDFKG | R | Heavy Chain CDR2 | 300 |
| EVKHGLFHWFAY | R | Heavy Chain CDR3 | 301 |
| QSSQGIGKYLS | Pi | Light Chain CDR1 | 287 |
| YATNLAD | Pi | Light Chain CDR2 | 302 |
| LQFDDFRWT | Pi | Light Chain CDR3 | 65 |
| DYNMA | Pi | Heavy Chain CDR1 | 289 |
| TISFDDYNTYYRDSVKG | Pi | Heavy Chain CDR2 | 303 |
| PGTY | Pi | Heavy Chain CDR3 | 304 |
| ERSSGDIGDNYV | Mu | Light Chain CDR1 | 305 |
| ADDQRPS | Mu | Light Chain CDR2 | 298 |
| QSFDSNFDIPV | Mu | Light Chain CDR3 | 68 |
| SYDMH | Mu | Heavy Chain CDR1 | 306 |
| WIHPGNGKIKYNQKFNG | Mu | Heavy Chain CDR2 | 307 |
| GTTRVFPWFAY | Mu | Heavy Chain CDR3 | 308 |
| KASQNITRFLN | V | Light Chain CDR1 | 309 |
| NTNNLQT | V | Light Chain CDR2 | 310 |
| LQHGSRPRT | V | Light Chain CDR3 | 74 |
| NYGMH | V | Heavy Chain CDR1 | 311 |
| SISPTGGNTYYRDSVKG | V | Heavy Chain CDR2 | 312 |
| DDLYYSGPFAY | V | Heavy Chain CDR3 | 313 |
| QASQDIGNNLI | Humanised A | Light Chain CDR1 | 277 |
| FATSLAN | Humanised A | Light Chain CDR2 | 278 |
| LQYREYPLT | Humanised A | Light Chain CDR3 | 34 |
| TNYMH | Humanised A | Heavy Chain CDR1 | 279 |
| WIYPGNGNTKFNHKFDG | Humanised A | Heavy Chain CDR2 | 280 |
| SDFDY | Humanised A | Heavy Chain CDR3 | 281 |
| KASQNIDRYLN | Humanised F | Light Chain CDR1 | 272 |
| NTNKLQT | Humanised F | Light Chain CDR2 | 273 |
| LQYNSLPLT | Humanised F | Light Chain CDR3 | 28 |
| EHNMA | Humanised F | Heavy Chain CDR1 | 274 |
| TISDDGRNTYYRDSMRG | Humanised F | Heavy Chain CDR2 | 275 |
| HRYNLFDS | Humanised F | Heavy Chain CDR3 | 276 |

The invention claimed is:

1. An isolated monoclonal antibody comprising a light chain variable domain and a heavy chain variable domain wherein the light chain variable domain comprises a light chain complementarity determining region (LCDR)1, an LCDR2 and an LCDR3, and wherein the heavy chain variable domain comprises a heavy chain complementarity determining region (HCDR)1, an HCDR2 and an HCDR3,
  wherein LCDR1 comprises the amino acid sequence set forth in SEQ ID NO: 24; LCDR2 comprises the amino acid sequence set forth in SEQ ID NO: 26; and LCDR3 comprises the amino acid sequence set forth in SEQ ID NO: 28; wherein HCDR1 comprises the amino acid sequence set forth in SEQ ID NO: 115; HCDR2 comprises the amino acid sequence set forth in SEQ ID NO: 117; and HCDR3 comprises the amino acid sequence set forth in SEQ ID NO: 252 ($X_1X_2$HRYNLFDS, wherein $X_1$ is Ala or Thr and $X_2$ is Ser, Lys or Arg),
  or wherein the LCDR1 comprises the amino acid sequence set forth as SEQ ID NO: 272, the LCDR2 comprises the amino acid sequence set forth as SEQ ID NO: 273, the LCDR3 comprises the amino acid sequence set forth as SEQ ID NO: 28, the HCDR1 comprises the amino acid sequence set forth as SEQ ID NO: 274, the HCDR2 comprises the amino acid sequence set forth as SEQ ID NO: 275, and the HCDR3 comprises the amino acid sequence set forth as SEQ ID NO: 276;
  and wherein the monoclonal antibody specifically binds to a ROR1 polypeptide.

2. An isolated monoclonal antibody according to claim 1, wherein when HCDR3 comprises an amino acid sequence having the sequence set forth as SEQ ID NO: 252 ($X_1X_2$HRYNLFDS, wherein $X_1$ is Ala or Thr and X2 is Ser, Lys or Arg), HCDR3 comprises the amino acid sequence as set forth in SEQ ID NO: 119, 249, 250 or 251.

3. An isolated monoclonal antibody according to claim 1 wherein:
  (a) the light chain variable domain comprises a Light Chain Framework Region (LCFR)1 comprising the amino acid sequence as set forth as one of SEQ ID NO: 23, SEQ ID NO: 230, SEQ ID NO: 238 or SEQ ID NO: 239; an LCFR2 comprising the amino acid sequence as set forth as one of SEQ ID NO: 25, SEQ ID NO: 231, SEQ ID NO: 233 or SEQ ID NO: 236; an LCFR3 comprising the amino acid sequence as set forth as one of SEQ ID NO: 27, SEQ ID NO: 232, SEQ ID NO: 234, SEQ ID NO: 237 or SEQ ID NO: 240; and an LCFR4 comprising the amino acid sequence as set forth as one of SEQ ID NO: 14, SEQ ID NO: 205 or SEQ ID NO: 234, wherein the Light Chain Framework Regions may include up to 10 amino acid substitutions in the amino acid sequences as set forth above, or
  (b) the heavy chain variable domain comprises a Heavy Chain Framework Region (HCFR)1 comprising the amino acid sequence as set forth as one of SEQ ID NO: 114, SEQ ID NO: 215, SEQ ID NO: 218 or SEQ ID NO: 223; an HCFR2 comprising the amino acid sequence as set forth as one of SEQ ID NO: 116, SEQ ID NO: 216, SEQ ID NO: 219 or SEQ ID NO: 221; an HCFR3 comprising the amino acid sequence as set forth as one of SEQ ID NO: 118, SEQ ID NO: 217, SEQ ID NO: 220, SEQ ID NO: 222 or SEQ ID NO: 224; and an HCFR4 comprising the amino acid sequence as set forth as one of SEQ ID NO: 94, SEQ ID NO: 186 or SEQ ID NO: 108, wherein the Heavy Chain Framework Regions may include up to 10 amino acid substitutions in the amino acid sequences as set forth above.

4. An isolated monoclonal antibody according to claim 1 wherein:
  (a) the light chain variable domain comprises the amino acid sequence as set forth as one of SEQ ID NO: 79, SEQ ID NO: 241, SEQ ID NO: 242, SEQ ID NO: 243, SEQ ID NO: 244 or SEQ ID NO: 245, or an amino acid sequence having at least 90% identity to the specified amino acid sequences; or
  (b) the heavy chain variable domain comprises the amino acid sequence as set forth as one of SEQ ID NO: 172, SEQ ID NO: 225, SEQ ID NO: 226, SEQ ID NO: 227, SEQ ID NO: 228 or SEQ ID NO: 229, or an amino acid sequence having at least 90% identity to the specified amino acid sequences.

5. An isolated monoclonal antibody comprising a light chain variable domain and a heavy chain variable domain wherein:
  (a) the light chain variable domain comprises the amino acid sequence as set forth as SEQ ID NO: 79 and the heavy chain variable domain comprises the amino acid sequence as set forth as SEQ ID NO: 172;
  (b) the light chain variable domain comprises the amino acid sequence as set forth as SEQ ID NO: 241 and the heavy chain variable domain comprises the amino acid sequence as set forth as SEQ ID NO: 225;
  (c) the light chain variable domain comprises the amino acid sequence as set forth as SEQ ID NO: 242 and the heavy chain variable domain comprises the amino acid sequence as set forth as SEQ ID NO: 226;
(d) the light chain variable domain comprises the amino acid sequence as set forth as SEQ ID NO: 243 and the heavy chain variable domain comprises the amino acid sequence as set forth as SEQ ID NO: 227;
(e) the light chain variable domain comprises the amino acid sequence as set forth as SEQ ID NO: 244 and the heavy chain variable domain comprises the amino acid sequence as set forth as SEQ ID NO: 228; or
(f) the light chain variable domain comprises the amino acid sequence as set forth as SEQ ID NO: 245 and the heavy chain variable domain comprises the amino acid sequence as set forth as SEQ ID NO: 229.

6. The isolated monoclonal antibody of claim 1 or 5, wherein:
(a) the antibody is an IgG, IgM or IgA;
(b) the antibody is a humanised antibody;
(c) the antibody binds to an epitope of ROR1, wherein the epitope comprises amino acid Gln-261;
(d) the antibody is labeled; or
(e) the antibody is labeled, wherein the label is a fluorescent, an enzymatic, or a radioactive label.

7. An isolated antigen binding fragment of the isolated monoclonal antibody of claim 1 or 5.

8. The isolated antigen binding fragment of claim 7, wherein:
(a) the fragment is a Fab fragment, a Fab' fragment, a F(ab)'2 fragment, a single chain Fv protein (scFv), or a disulfide stabilized Fv protein (dsFv);
(b) the antigen binding fragment is a Fab or an scFv fragment;
(c) the antigen binding fragment is labeled;
(d) the antigen binding fragment is labeled, wherein the label is a fluorescent, an enzymatic, or a radioactive label; or
(e) the antigen binding fragment is included in a bispecific antibody.

9. A composition comprising the antibody of claim 1 or 5, or an antigen binding fragment thereof, and a pharmaceutically acceptable carrier.

10. An isolated nucleic acid encoding the monoclonal antibody of claim 1 or 5, or an antigen binding fragment thereof.

11. An isolated host cell transformed with a nucleic acid encoding the monoclonal antibody of claim 1 or 5, or an antigen binding fragment thereof.

12. A method of detecting cancer in a subject comprising:
contacting a biological sample from the subject with at least one isolated monoclonal antibody of claim 1 or 5, or an antigen binding fragment thereof; and
detecting antibody bound to the sample,
wherein the presence of antibody bound to the sample indicates that the subject has cancer.

13. The method of detecting of claim 12, wherein:
(a) the antibody specifically binds a ROR1 polypeptide, and wherein the presence of antibody bound to the sample indicates that the subject has leukemia, pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma or renal cancer;
(b) the isolated monoclonal antibody is directly labeled; or
(c) the method further comprises:
contacting the sample with a second antibody that specifically binds the isolated monoclonal antibody; and
detecting the binding of the second antibody,
wherein an increase in binding of the second antibody to the sample as compared to binding of the second antibody to a control sample detects the presence of cancer in the subject.

14. A method for treating cancer in a subject, comprising administering to the subject a therapeutically effective amount of at least one antibody of claim 1 or 5, or an antigen binding fragment thereof, thereby treating cancer.

15. The method of treating cancer of claim 14, wherein the cancer is leukemia, pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma or renal cancer.

16. A kit comprising an antibody according to claim 1 or 5, or an antigen binding fragment thereof.

17. A kit according to claim 16 wherein:
(a) the antibody or fragment is directly labelled; or
(b) the kit further comprises an immunoassay.

18. A method of detecting cancer of claim 13, wherein the leukemia is Chronic Lymphocytic Leukaemia (CLL), Acute Lymphoblastic Leukaemia (ALL), Mantle Cell Leukaemia or Hairy Cell Leukaemia.

19. A method of treating cancer of claim 15, wherein the leukemia is Chronic Lymphocytic Leukaemia (CLL), Acute Lymphoblastic Leukaemia (ALL), Mantle Cell Leukaemia or Hairy Cell Leukaemia.

* * * * *

SEQUENCE LISTING

<160> NUMBER OF SEQ ID NOS: 313

<210> SEQ ID NO 1
<211> LENGTH: 26
<212> TYPE: PRT
<213> ORGANISM: Rattus norvegicus

<400> SEQUENCE: 1

Asp Val Val Met Thr Gln Thr Pro Val Ser Leu Pro Val Ser Leu Gly
1               5                   10                  15

Gly Gln Val Ser Ile Ser Cys Arg Ser Ser
            20                  25

<210> SEQ ID NO 2
<211> LENGTH: 11
<212> TYPE: PRT
<213> ORGANISM: Rattus norvegicus

<400> SEQUENCE: 2

Gln Ser Leu Glu His Ser Asn Gly Asp Thr Phe
1               5                   10

<210> SEQ ID NO 3
<211> LENGTH: 17
<212> TYPE: PRT
<213> ORGANISM: Rattus norvegicus

<400> SEQUENCE: 3

Leu His Trp Tyr Leu Gln Lys Pro Gly Gln Ser Pro Arg Leu Leu Ile
1               5                   10                  15

Tyr

<210> SEQ ID NO 4
<211> LENGTH: 3
<212> TYPE: PRT
<213> ORGANISM: Rattus norvegicus

<400> SEQUENCE: 4

Arg Val Ser
1

<210> SEQ ID NO 5
<211> LENGTH: 36
<212> TYPE: PRT
<213> ORGANISM: Rattus norvegicus

<400> SEQUENCE: 5

Asn Arg Phe Ser Gly Val Pro Asp Arg Phe Ser Gly Ser Gly Ser Gly
1               5                   10                  15

Thr Asp Phe Thr Leu Lys Ile Ser Arg Ile Glu Pro Glu Asp Leu Gly
            20                  25                  30

Asp Tyr Tyr Cys
            35

<210> SEQ ID NO 6
<211> LENGTH: 9
<212> TYPE: PRT
<213> ORGANISM: Rattus norvegicus

<400> SEQUENCE: 6

Leu Gln Ser Thr His Phe Pro Asn Thr
1               5

```
<210> SEQ ID NO 7
<211> LENGTH: 10
<212> TYPE: PRT
<213> ORGANISM: Rattus norvegicus

<400> SEQUENCE: 7

Phe Gly Ala Gly Thr Lys Leu Glu Leu Lys
1               5                   10

<210> SEQ ID NO 8
<211> LENGTH: 26
<212> TYPE: PRT
<213> ORGANISM: Rattus norvegicus

<400> SEQUENCE: 8

Asp Ile Gln Leu Thr Gln Ser Pro Ser Thr Leu Ser Ala Ser Leu Gly
1               5                   10                  15

Glu Arg Val Thr Ile Ser Cys Arg Ala Ser
            20                  25

<210> SEQ ID NO 9
<211> LENGTH: 6
<212> TYPE: PRT
<213> ORGANISM: Rattus norvegicus

<400> SEQUENCE: 9

Gln Ser Ile Ser Asn Ser
1               5

<210> SEQ ID NO 10
<211> LENGTH: 17
<212> TYPE: PRT
<213> ORGANISM: Rattus norvegicus

<400> SEQUENCE: 10

Leu Asn Trp Tyr Gln Gln Lys Pro Asp Gly Thr Val Lys Arg Leu Ile
1               5                   10                  15

Tyr

<210> SEQ ID NO 11
<211> LENGTH: 3
<212> TYPE: PRT
<213> ORGANISM: Rattus norvegicus

<400> SEQUENCE: 11

Ser Thr Ser
1

<210> SEQ ID NO 12
<211> LENGTH: 36
<212> TYPE: PRT
<213> ORGANISM: Rattus norvegicus

<400> SEQUENCE: 12

Thr Leu Glu Ser Gly Val Pro Ser Arg Phe Ser Gly Ser Gly Ser Gly
1               5                   10                  15

Thr Asp Phe Ser Leu Ser Ile Ser Ser Leu Glu Ser Glu Asp Phe Ala
            20                  25                  30

Met Tyr Tyr Cys
        35

<210> SEQ ID NO 13
```

```
<211> LENGTH: 10
<212> TYPE: PRT
<213> ORGANISM: Rattus norvegicus

<400> SEQUENCE: 13

Leu Gln Phe Ala Thr Tyr Pro Gln Val Thr
1               5                   10

<210> SEQ ID NO 14
<211> LENGTH: 10
<212> TYPE: PRT
<213> ORGANISM: Rattus norvegicus

<400> SEQUENCE: 14

Phe Gly Ser Gly Thr Lys Leu Glu Ile Lys
1               5                   10

<210> SEQ ID NO 15
<211> LENGTH: 25
<212> TYPE: PRT
<213> ORGANISM: Rattus norvegicus

<400> SEQUENCE: 15

Asp Ile Val Leu Thr Gln Ser Pro Ala Leu Ala Val Ser Val Gly Gln
1               5                   10                  15

Arg Ala Thr Ile Ser Cys Arg Ala Ser
            20                  25

<210> SEQ ID NO 16
<211> LENGTH: 10
<212> TYPE: PRT
<213> ORGANISM: Rattus norvegicus

<400> SEQUENCE: 16

Gln Ser Val Ser Ile Ser Arg Tyr Asn Phe
1               5                   10

<210> SEQ ID NO 17
<211> LENGTH: 17
<212> TYPE: PRT
<213> ORGANISM: Rattus norvegicus

<400> SEQUENCE: 17

Met His Trp Tyr Gln Gln Lys Pro Gly Gln Gln Pro Lys Leu Leu Ile
1               5                   10                  15

Tyr

<210> SEQ ID NO 18
<211> LENGTH: 3
<212> TYPE: PRT
<213> ORGANISM: Rattus norvegicus

<400> SEQUENCE: 18

Arg Ala Ser
1

<210> SEQ ID NO 19
<211> LENGTH: 36
<212> TYPE: PRT
<213> ORGANISM: Rattus norvegicus

<400> SEQUENCE: 19

Asn Leu Ala Ser Gly Ile Pro Ala Arg Phe Ser Gly Ser Gly Ser Gly
1               5                   10                  15
```

Thr Asp Phe Thr Leu Thr Ile Asn Pro Val Gln Ala Asp Ile Ala
            20                  25                  30

Thr Tyr Tyr Cys
        35

<210> SEQ ID NO 20
<211> LENGTH: 9
<212> TYPE: PRT
<213> ORGANISM: Rattus norvegicus

<400> SEQUENCE: 20

Gln Gln Asn Arg Glu Ser Pro Arg Thr
1               5

<210> SEQ ID NO 21
<211> LENGTH: 10
<212> TYPE: PRT
<213> ORGANISM: Rattus norvegicus

<400> SEQUENCE: 21

Phe Gly Gly Gly Thr Lys Leu Glu Leu Lys
1               5                   10

<210> SEQ ID NO 22
<211> LENGTH: 10
<212> TYPE: PRT
<213> ORGANISM: Rattus norvegicus

<400> SEQUENCE: 22

Gln Ser Val Ser Ile Ser Arg Tyr Asp Phe
1               5                   10

<210> SEQ ID NO 23
<211> LENGTH: 26
<212> TYPE: PRT
<213> ORGANISM: Rattus norvegicus

<400> SEQUENCE: 23

Asp Ile Gln Met Thr Gln Ser Pro Ser Phe Leu Ser Ala Ser Val Gly
1               5                   10                  15

Asp Arg Val Thr Ile Asn Cys Lys Ala Ser
            20                  25

<210> SEQ ID NO 24
<211> LENGTH: 6
<212> TYPE: PRT
<213> ORGANISM: Rattus norvegicus

<400> SEQUENCE: 24

Gln Asn Ile Asp Arg Tyr
1               5

<210> SEQ ID NO 25
<211> LENGTH: 17
<212> TYPE: PRT
<213> ORGANISM: Rattus norvegicus

<400> SEQUENCE: 25

Leu Asn Trp Tyr Gln Gln Lys Leu Gly Glu Ala Pro Lys Arg Leu Leu
1               5                   10                  15

Tyr

```
<210> SEQ ID NO 26
<211> LENGTH: 3
<212> TYPE: PRT
<213> ORGANISM: Rattus norvegicus

<400> SEQUENCE: 26

Asn Thr Asn
1

<210> SEQ ID NO 27
<211> LENGTH: 36
<212> TYPE: PRT
<213> ORGANISM: Rattus norvegicus

<400> SEQUENCE: 27

Lys Leu Gln Thr Gly Ile Pro Ser Arg Phe Ser Gly Ser Gly Ser Ala
1               5                   10                  15

Thr Asp Phe Thr Leu Thr Ile Ser Ser Leu Gln Pro Glu Asp Phe Ala
            20                  25                  30

Thr Tyr Phe Cys
        35

<210> SEQ ID NO 28
<211> LENGTH: 9
<212> TYPE: PRT
<213> ORGANISM: Rattus norvegicus

<400> SEQUENCE: 28

Leu Gln Tyr Asn Ser Leu Pro Leu Thr
1               5

<210> SEQ ID NO 29
<211> LENGTH: 26
<212> TYPE: PRT
<213> ORGANISM: Rattus norvegicus

<400> SEQUENCE: 29

Asp Ile Gln Met Thr Gln Ser Pro Ser Ser Met Ser Ala Ser Leu Gly
1               5                   10                  15

Asp Arg Val Thr Phe Thr Cys Gln Ala Ser
            20                  25

<210> SEQ ID NO 30
<211> LENGTH: 6
<212> TYPE: PRT
<213> ORGANISM: Rattus norvegicus

<400> SEQUENCE: 30

Gln Asp Ile Gly Asn Asn
1               5

<210> SEQ ID NO 31
<211> LENGTH: 17
<212> TYPE: PRT
<213> ORGANISM: Rattus norvegicus

<400> SEQUENCE: 31

Leu Ile Trp Phe Gln Gln Lys Pro Gly Lys Ser Pro Arg Pro Leu Met
1               5                   10                  15

Tyr

<210> SEQ ID NO 32
<211> LENGTH: 3
```

<212> TYPE: PRT
<213> ORGANISM: Rattus norvegicus

<400> SEQUENCE: 32

Phe Ala Thr
1

<210> SEQ ID NO 33
<211> LENGTH: 36
<212> TYPE: PRT
<213> ORGANISM: Rattus norvegicus

<400> SEQUENCE: 33

Ser Leu Ala Asn Gly Val Pro Ser Arg Phe Ser Gly Ser Arg Ser Gly
1               5                   10                  15

Ser Asp Tyr Ser Leu Thr Ile Ser Ser Leu Glu Ser Glu Asp Leu Ala
            20                  25                  30

Asp Tyr His Cys
        35

<210> SEQ ID NO 34
<211> LENGTH: 9
<212> TYPE: PRT
<213> ORGANISM: Rattus norvegicus

<400> SEQUENCE: 34

Leu Gln Tyr Arg Glu Tyr Pro Leu Thr
1               5

<210> SEQ ID NO 35
<211> LENGTH: 10
<212> TYPE: PRT
<213> ORGANISM: Rattus norvegicus

<400> SEQUENCE: 35

Phe Gly Ser Gly Thr Lys Leu Asp Leu Lys
1               5                   10

<210> SEQ ID NO 36
<211> LENGTH: 26
<212> TYPE: PRT
<213> ORGANISM: Rattus norvegicus

<400> SEQUENCE: 36

Asp Ile Arg Met Thr Gln Ser Pro Ala Ser Leu Ser Ala Ser Leu Gly
1               5                   10                  15

Glu Thr Val Thr Ile Glu Cys Leu Thr Ser
            20                  25

<210> SEQ ID NO 37
<211> LENGTH: 6
<212> TYPE: PRT
<213> ORGANISM: Rattus norvegicus

<400> SEQUENCE: 37

Glu Asp Ile Tyr Ser Asp
1               5

<210> SEQ ID NO 38
<211> LENGTH: 17
<212> TYPE: PRT
<213> ORGANISM: Rattus norvegicus

<400> SEQUENCE: 38

Leu Ala Trp Phe Gln Gln Lys Pro Gly Lys Ser Pro Gln Leu Leu Ile
1               5                   10                  15
Tyr

<210> SEQ ID NO 39
<211> LENGTH: 3
<212> TYPE: PRT
<213> ORGANISM: Rattus norvegicus

<400> SEQUENCE: 39

Asp Ala Asn
1

<210> SEQ ID NO 40
<211> LENGTH: 36
<212> TYPE: PRT
<213> ORGANISM: Rattus norvegicus

<400> SEQUENCE: 40

Ser Leu Gln Asn Gly Val Pro Ser Arg Phe Gly Gly Cys Gly Ser Gly
1               5                   10                  15

Thr Gln Tyr Ser Leu Gln Ile Ser Ser Leu Gln Ser Glu Asp Val Ala
            20                  25                  30

Thr Tyr Phe Cys
        35

<210> SEQ ID NO 41
<211> LENGTH: 9
<212> TYPE: PRT
<213> ORGANISM: Rattus norvegicus

<400> SEQUENCE: 41

Gln Gln Tyr Lys Asn Tyr Pro Pro Thr
1               5

<210> SEQ ID NO 42
<211> LENGTH: 10
<212> TYPE: PRT
<213> ORGANISM: Rattus norvegicus

<400> SEQUENCE: 42

Phe Gly Gly Gly Thr Lys Leu Val Leu Lys
1               5                   10

<210> SEQ ID NO 43
<211> LENGTH: 26
<212> TYPE: PRT
<213> ORGANISM: Rattus norvegicus

<400> SEQUENCE: 43

Asp Ile Gln Leu Thr Gln Ser Pro Ser Ser Met Ser Ala Ser Leu Gly
1               5                   10                  15

Asp Arg Val Ser Leu Thr Cys Gln Ser Ser
            20                  25

<210> SEQ ID NO 44
<211> LENGTH: 6
<212> TYPE: PRT
<213> ORGANISM: Rattus norvegicus

<400> SEQUENCE: 44

Gln Gly Ile Gly Lys Tyr
1               5

<210> SEQ ID NO 45
<211> LENGTH: 17
<212> TYPE: PRT
<213> ORGANISM: Rattus norvegicus

<400> SEQUENCE: 45

Leu Ser Trp Tyr Gln His Lys Pro Gly Lys Pro Pro Lys Ala Met Ile
1               5                   10                  15

Tyr

<210> SEQ ID NO 46
<211> LENGTH: 3
<212> TYPE: PRT
<213> ORGANISM: Rattus norvegicus

<400> SEQUENCE: 46

Tyr Ala Thr
1

<210> SEQ ID NO 47
<211> LENGTH: 36
<212> TYPE: PRT
<213> ORGANISM: Rattus norvegicus

<400> SEQUENCE: 47

Lys Leu Ala Asp Gly Val Pro Ser Arg Phe Ser Gly Ser Arg Ser Gly
1               5                   10                  15

Ser Asp Phe Ser Leu Thr Ile Ser Ser Leu Glu Ser Glu Asp Ile Ala
            20                  25                  30

Ile Tyr Tyr Cys
        35

<210> SEQ ID NO 48
<211> LENGTH: 9
<212> TYPE: PRT
<213> ORGANISM: Rattus norvegicus

<400> SEQUENCE: 48

Leu Gln Phe Asp Asp Tyr Pro Trp Thr
1               5

<210> SEQ ID NO 49
<211> LENGTH: 25
<212> TYPE: PRT
<213> ORGANISM: Rattus norvegicus

<400> SEQUENCE: 49

Asp Ile Val Leu Thr Gln Ser Pro Ala Leu Ala Val Ser Leu Glu Gln
1               5                   10                  15

Arg Val Thr Ile Ala Cys Lys Thr Ser
            20                  25

<210> SEQ ID NO 50
<211> LENGTH: 10
<212> TYPE: PRT
<213> ORGANISM: Rattus norvegicus -continued

<400> SEQUENCE: 50

Gln Asn Val Asp Asn His Gly Ile Ser Tyr
1               5                   10

<210> SEQ ID NO 51
<211> LENGTH: 17
<212> TYPE: PRT
<213> ORGANISM: Rattus norvegicus

<400> SEQUENCE: 51

Met His Trp Tyr Gln Gln Lys Ser Gly Gln Glu Pro Lys Leu Leu Ile
1               5                   10                  15

Tyr

<210> SEQ ID NO 52
<211> LENGTH: 3
<212> TYPE: PRT
<213> ORGANISM: Rattus norvegicus

<400> SEQUENCE: 52

Glu Gly Ser
1

<210> SEQ ID NO 53
<211> LENGTH: 36
<212> TYPE: PRT
<213> ORGANISM: Rattus norvegicus

<400> SEQUENCE: 53

Asn Leu Ala Val Gly Ile Pro Ala Arg Phe Ser Gly Ser Gly Ser Gly
1               5                   10                  15

Thr Asp Phe Thr Leu Thr Ile Asp Pro Val Glu Ala Asp Asp Ile Glu
            20                  25                  30

Thr Tyr Tyr Cys
        35

<210> SEQ ID NO 54
<211> LENGTH: 9
<212> TYPE: PRT
<213> ORGANISM: Rattus norvegicus

<400> SEQUENCE: 54

Gln Gln Ser Lys Asp Asp Pro Arg Thr
1               5

<210> SEQ ID NO 55
<211> LENGTH: 25
<212> TYPE: PRT
<213> ORGANISM: Rattus norvegicus

<400> SEQUENCE: 55

Gln Phe Thr Leu Thr Gln Pro Lys Ser Val Ser Gly Ser Leu Arg Ser
1               5                   10                  15

Thr Ile Thr Ile Pro Cys Glu Arg Ser
            20                  25

<210> SEQ ID NO 56
<211> LENGTH: 8
<212> TYPE: PRT
<213> ORGANISM: Rattus norvegicus

```
<400> SEQUENCE: 56

Ser Gly Asp Ile Gly Asp Ser Tyr
1               5

<210> SEQ ID NO 57
<211> LENGTH: 17
<212> TYPE: PRT
<213> ORGANISM: Rattus norvegicus

<400> SEQUENCE: 57

Val Ser Trp Tyr Gln Gln His Leu Gly Arg Pro Pro Ile Asn Val Ile
1               5                   10                  15

Tyr

<210> SEQ ID NO 58
<211> LENGTH: 3
<212> TYPE: PRT
<213> ORGANISM: Rattus norvegicus

<400> SEQUENCE: 58

Ala Asp Asp
1

<210> SEQ ID NO 59
<211> LENGTH: 38
<212> TYPE: PRT
<213> ORGANISM: Rattus norvegicus

<400> SEQUENCE: 59

Gln Arg Pro Ser Glu Val Ser Asp Arg Phe Ser Gly Ser Ile Asp Ser
1               5                   10                  15

Ser Ser Asn Ser Ala Ser Leu Thr Ile Thr Asn Leu Gln Met Asp Asp
            20                  25                  30

Glu Ala Asp Tyr Phe Cys
        35

<210> SEQ ID NO 60
<211> LENGTH: 12
<212> TYPE: PRT
<213> ORGANISM: Rattus norvegicus

<400> SEQUENCE: 60

Gln Ser Tyr Asp Arg Asn Val Asp Phe Asn Thr Val
1               5                   10

<210> SEQ ID NO 61
<211> LENGTH: 10
<212> TYPE: PRT
<213> ORGANISM: Rattus norvegicus

<400> SEQUENCE: 61

Phe Gly Gly Gly Thr Lys Val Thr Val Leu
1               5                   10

<210> SEQ ID NO 62
<211> LENGTH: 26
<212> TYPE: PRT
<213> ORGANISM: Rattus norvegicus

<400> SEQUENCE: 62

Asp Ile Gln Leu Thr Gln Ser Pro Ser Ser Leu Ser Ala Ser Leu Gly
1               5                   10                  15
```

```
Asp Arg Val Ser Leu Thr Cys Gln Ser Ser
            20                  25
```

<210> SEQ ID NO 63
<211> LENGTH: 17
<212> TYPE: PRT
<213> ORGANISM: Rattus norvegicus

<400> SEQUENCE: 63

```
Leu Ser Trp Phe Gln His Lys Pro Gly Lys Pro Pro Lys Pro Val Ile
1               5                   10                  15

Asn
```

<210> SEQ ID NO 64
<211> LENGTH: 36
<212> TYPE: PRT
<213> ORGANISM: Rattus norvegicus

<400> SEQUENCE: 64

```
Asn Leu Ala Asp Gly Val Pro Ser Arg Phe Ser Gly Arg Arg Ser Gly
1               5                   10                  15

Ser Asp Phe Ser Leu Thr Ile Ser Ser Leu Glu Ser Glu Asp Thr Ala
            20                  25                  30

Ile Tyr Tyr Cys
        35
```

<210> SEQ ID NO 65
<211> LENGTH: 9
<212> TYPE: PRT
<213> ORGANISM: Rattus norvegicus

<400> SEQUENCE: 65

```
Leu Gln Phe Asp Asp Phe Arg Trp Thr
1               5
```

<210> SEQ ID NO 66
<211> LENGTH: 10
<212> TYPE: PRT
<213> ORGANISM: Rattus norvegicus

<400> SEQUENCE: 66

```
Val Gly Gly Gly Thr Lys Leu Glu Leu Lys
1               5                   10
```

<210> SEQ ID NO 67
<211> LENGTH: 8
<212> TYPE: PRT
<213> ORGANISM: Rattus norvegicus

<400> SEQUENCE: 67

```
Ser Gly Asp Ile Gly Asp Asn Tyr
1               5
```

<210> SEQ ID NO 68
<211> LENGTH: 11
<212> TYPE: PRT
<213> ORGANISM: Rattus norvegicus

<400> SEQUENCE: 68

```
Gln Ser Phe Asp Ser Asn Phe Asp Ile Pro Val
1               5                   10
```

```
<210> SEQ ID NO 69
<211> LENGTH: 10
<212> TYPE: PRT
<213> ORGANISM: Rattus norvegicus

<400> SEQUENCE: 69

Phe Gly Gly Gly Thr Lys Leu Thr Val Leu
1               5                   10

<210> SEQ ID NO 70
<211> LENGTH: 26
<212> TYPE: PRT
<213> ORGANISM: Rattus norvegicus

<400> SEQUENCE: 70

Asp Ile Lys Met Thr Gln Ser Pro Ser Phe Leu Ser Ala Ser Val Gly
1               5                   10                  15

Asp Arg Val Thr Ile Asn Cys Lys Ala Ser
            20                  25

<210> SEQ ID NO 71
<211> LENGTH: 6
<212> TYPE: PRT
<213> ORGANISM: Rattus norvegicus

<400> SEQUENCE: 71

Gln Asn Ile Thr Arg Phe
1               5

<210> SEQ ID NO 72
<211> LENGTH: 17
<212> TYPE: PRT
<213> ORGANISM: Rattus norvegicus

<400> SEQUENCE: 72

Leu Asn Trp Tyr Gln Gln Glu Leu Gly Glu Ala Pro Thr Leu Leu Ile
1               5                   10                  15

Tyr

<210> SEQ ID NO 73
<211> LENGTH: 36
<212> TYPE: PRT
<213> ORGANISM: Rattus norvegicus

<400> SEQUENCE: 73

Asn Leu Gln Thr Gly Ile Pro Ser Arg Phe Ser Gly Ser Gly Ser Gly
1               5                   10                  15

Thr Asp Phe Thr Leu Thr Ile Ser Ser Leu Gln Pro Glu Asp Val Ala
            20                  25                  30

Thr Tyr Phe Cys
        35

<210> SEQ ID NO 74
<211> LENGTH: 9
<212> TYPE: PRT
<213> ORGANISM: Rattus norvegicus

<400> SEQUENCE: 74

Leu Gln His Gly Ser Arg Pro Arg Thr
1               5

<210> SEQ ID NO 75
<211> LENGTH: 112
```

<212> TYPE: PRT
<213> ORGANISM: Rattus norvegicus

<400> SEQUENCE: 75

Asp Val Val Met Thr Gln Thr Pro Val Ser Leu Pro Val Ser Leu Gly
1               5                   10                  15

Gly Gln Val Ser Ile Ser Cys Arg Ser Ser Gln Ser Leu Glu His Ser
            20                  25                  30

Asn Gly Asp Thr Phe Leu His Trp Tyr Leu Gln Lys Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Ile Glu Pro Glu Asp Leu Gly Asp Tyr Tyr Cys Leu Gln Ser
                85                  90                  95

Thr His Phe Pro Asn Thr Phe Gly Ala Gly Thr Lys Leu Glu Leu Lys
            100                 105                 110

<210> SEQ ID NO 76
<211> LENGTH: 108
<212> TYPE: PRT
<213> ORGANISM: Rattus norvegicus

<400> SEQUENCE: 76

Asp Ile Gln Leu Thr Gln Ser Pro Ser Thr Leu Ser Ala Ser Leu Gly
1               5                   10                  15

Glu Arg Val Thr Ile Ser Cys Arg Ala Ser Gln Ser Ile Ser Asn Ser
            20                  25                  30

Leu Asn Trp Tyr Gln Gln Lys Pro Asp Gly Thr Val Lys Arg Leu Ile
        35                  40                  45

Tyr Ser Thr Ser Thr Leu Glu Ser Gly Val Pro Ser Arg Phe Ser Gly
    50                  55                  60

Ser Gly Ser Gly Thr Asp Phe Ser Leu Ser Ile Ser Ser Leu Glu Ser
65                  70                  75                  80

Glu Asp Phe Ala Met Tyr Tyr Cys Leu Gln Phe Ala Thr Tyr Pro Gln
                85                  90                  95

Val Thr Phe Gly Ser Gly Thr Lys Leu Glu Ile Lys
            100                 105

<210> SEQ ID NO 77
<211> LENGTH: 110
<212> TYPE: PRT
<213> ORGANISM: Rattus norvegicus

<400> SEQUENCE: 77

Asp Ile Val Leu Thr Gln Ser Pro Ala Leu Ala Val Ser Val Gly Gln
1               5                   10                  15

Arg Ala Thr Ile Ser Cys Arg Ala Ser Gln Ser Val Ser Ile Ser Arg
            20                  25                  30

Tyr Asn Phe Met His Trp Tyr Gln Gln Lys Pro Gly Gln Gln Pro Lys
        35                  40                  45

Leu Leu Ile Tyr Arg Ala Ser Asn Leu Ala Ser Gly Ile Pro Ala Arg
    50                  55                  60

Phe Ser Gly Ser Gly Ser Gly Thr Asp Phe Thr Leu Thr Ile Asn Pro
65                  70                  75                  80

```
Val Gln Ala Asp Asp Ile Ala Thr Tyr Tyr Cys Gln Gln Asn Arg Glu
                85                  90                  95

Ser Pro Arg Thr Phe Gly Gly Gly Thr Lys Leu Glu Leu Lys
            100                 105                 110

<210> SEQ ID NO 78
<211> LENGTH: 110
<212> TYPE: PRT
<213> ORGANISM: Rattus norvegicus

<400> SEQUENCE: 78

Asp Ile Val Leu Thr Gln Ser Pro Ala Leu Ala Val Ser Val Gly Gln
1               5                   10                  15

Arg Ala Thr Ile Ser Cys Arg Ala Ser Gln Ser Val Ser Ile Ser Arg
            20                  25                  30

Tyr Asp Phe Met His Trp Tyr Gln Gln Lys Pro Gly Gln Gln Pro Lys
        35                  40                  45

Leu Leu Ile Tyr Arg Ala Ser Asn Leu Ala Ser Gly Ile Pro Ala Arg
    50                  55                  60

Phe Ser Gly Ser Gly Ser Gly Thr Asp Phe Thr Leu Thr Ile Asn Pro
65                  70                  75                  80

Val Gln Ala Asp Asp Ile Ala Thr Tyr Tyr Cys Gln Gln Asn Arg Glu
                85                  90                  95

Ser Pro Arg Thr Phe Gly Gly Gly Thr Lys Leu Glu Leu Lys
            100                 105                 110

<210> SEQ ID NO 79
<211> LENGTH: 107
<212> TYPE: PRT
<213> ORGANISM: Rattus norvegicus

<400> SEQUENCE: 79

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asp Arg Tyr
            20                  25                  30

Leu Asn Trp Tyr Gln Gln Lys Leu Gly Glu Ala Pro Lys Arg Leu Leu
        35                  40                  45

Tyr Asn Thr Asn Lys Leu Gln Thr Gly Ile Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Phe Ala Thr Tyr Phe Cys Leu Gln Tyr Asn Ser Leu Pro Leu
                85                  90                  95

Thr Phe Gly Ser Gly Thr Lys Leu Glu Ile Lys
            100                 105

<210> SEQ ID NO 80
<211> LENGTH: 107
<212> TYPE: PRT
<213> ORGANISM: Rattus norvegicus

<400> SEQUENCE: 80

Asp Ile Gln Met Thr Gln Ser Pro Ser Met Ser Ala Ser Leu Gly
1               5                   10                  15

Asp Arg Val Thr Phe Thr Cys Gln Ala Ser Gln Asp Ile Gly Asn Asn
            20                  25                  30
```

```
Leu Ile Trp Phe Gln Gln Lys Pro Gly Lys Ser Pro Arg Pro Leu Met
            35                  40                  45

Tyr Phe Ala Thr Ser Leu Ala Asn Gly Val Pro Ser Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Leu Ala Asp Tyr His Cys Leu Gln Tyr Arg Glu Tyr Pro Leu
                 85                  90                  95

Thr Phe Gly Ser Gly Thr Lys Leu Asp Leu Lys
            100                 105
```

<210> SEQ ID NO 81
<211> LENGTH: 107
<212> TYPE: PRT
<213> ORGANISM: Rattus norvegicus

<400> SEQUENCE: 81

```
Asp Ile Arg Met Thr Gln Ser Pro Ala Ser Leu Ser Ala Ser Leu Gly
 1               5                  10                  15

Glu Thr Val Thr Ile Glu Cys Leu Thr Ser Glu Asp Ile Tyr Ser Asp
                20                  25                  30

Leu Ala Trp Phe Gln Gln Lys Pro Gly Lys Ser Pro Gln Leu Leu Ile
            35                  40                  45

Tyr Asp Ala Asn Ser Leu Gln Asn Gly Val Pro Ser Arg Phe Gly Gly
 50                  55                  60

Cys Gly Ser Gly Thr Gln Tyr Ser Leu Gln Ile Ser Ser Leu Gln Ser
 65                  70                  75                  80

Glu Asp Val Ala Thr Tyr Phe Cys Gln Gln Tyr Lys Asn Tyr Pro Pro
                 85                  90                  95

Thr Phe Gly Gly Gly Thr Lys Leu Val Leu Lys
            100                 105
```

<210> SEQ ID NO 82
<211> LENGTH: 107
<212> TYPE: PRT
<213> ORGANISM: Rattus norvegicus

<400> SEQUENCE: 82

```
Asp Ile Gln Leu Thr Gln Ser Pro Ser Ser Met Ser Ala Ser Leu Gly
 1               5                  10                  15

Asp Arg Val Ser Leu Thr Cys Gln Ser Ser Gln Gly Ile Gly Lys Tyr
                20                  25                  30

Leu Ser Trp Tyr Gln His Lys Pro Gly Lys Pro Pro Lys Ala Met Ile
            35                  40                  45

Tyr Tyr Ala Thr Lys Leu Ala Asp Gly Val Pro Ser Arg Phe Ser Gly
 50                  55                  60

Ser Arg Ser Gly Ser Asp Phe Ser Leu Thr Ile Ser Ser Leu Glu Ser
 65                  70                  75                  80

Glu Asp Ile Ala Ile Tyr Tyr Cys Leu Gln Phe Asp Asp Tyr Pro Trp
                 85                  90                  95

Thr Phe Gly Gly Gly Thr Lys Leu Glu Leu Lys
            100                 105
```

<210> SEQ ID NO 83
<211> LENGTH: 110
<212> TYPE: PRT
<213> ORGANISM: Rattus norvegicus

```
<400> SEQUENCE: 83

Asp Ile Val Leu Thr Gln Ser Pro Ala Leu Ala Val Ser Leu Glu Gln
1               5                   10                  15

Arg Val Thr Ile Ala Cys Lys Thr Ser Gln Asn Val Asp Asn His Gly
            20                  25                  30

Ile Ser Tyr Met His Trp Tyr Gln Gln Lys Ser Gly Gln Glu Pro Lys
        35                  40                  45

Leu Leu Ile Tyr Glu Gly Ser Asn Leu Ala Val Gly Ile Pro Ala Arg
    50                  55                  60

Phe Ser Gly Ser Gly Ser Gly Thr Asp Phe Thr Leu Thr Ile Asp Pro
65                  70                  75                  80

Val Glu Ala Asp Asp Ile Glu Thr Tyr Tyr Cys Gln Gln Ser Lys Asp
                85                  90                  95

Asp Pro Arg Thr Phe Gly Gly Gly Thr Lys Leu Glu Leu Lys
            100                 105                 110

<210> SEQ ID NO 84
<211> LENGTH: 113
<212> TYPE: PRT
<213> ORGANISM: Rattus norvegicus

<400> SEQUENCE: 84

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Ser
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Arg
                85                  90                  95

Asn Val Asp Phe Asn Thr Val Phe Gly Gly Gly Thr Lys Val Thr Val
            100                 105                 110

Leu

<210> SEQ ID NO 85
<211> LENGTH: 107
<212> TYPE: PRT
<213> ORGANISM: Rattus norvegicus

<400> SEQUENCE: 85

Asp Ile Gln Leu Thr Gln Ser Pro Ser Ser Leu Ser Ala Ser Leu Gly
1               5                   10                  15

Asp Arg Val Ser Leu Thr Cys Gln Ser Ser Gln Gly Ile Gly Lys Tyr
            20                  25                  30

Leu Ser Trp Phe Gln His Lys Pro Gly Lys Pro Pro Lys Pro Val Ile
        35                  40                  45

Asn Tyr Ala Thr Asn Leu Ala Asp Gly Val Pro Ser Arg Phe Ser Gly
    50                  55                  60

Arg Arg Ser Gly Ser Asp Phe Ser Leu Thr Ile Ser Ser Leu Glu Ser
65                  70                  75                  80

Glu Asp Thr Ala Ile Tyr Tyr Cys Leu Gln Phe Asp Asp Phe Arg Trp
                85                  90                  95
```

Thr Val Gly Gly Gly Thr Lys Leu Glu Leu Lys
            100                 105

<210> SEQ ID NO 86
<211> LENGTH: 112
<212> TYPE: PRT
<213> ORGANISM: Rattus norvegicus

<400> SEQUENCE: 86

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Asn
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Asp Arg Phe Ser
    50                  55                  60

Gly Ser Ile Asp Ser Ser Asn Ser Ala Ser Leu Thr Ile Thr Asn
65                  70                  75                  80

Leu Gln Met Asp Asp Glu Ala Asp Tyr Phe Cys Gln Ser Phe Asp Ser
                85                  90                  95

Asn Phe Asp Ile Pro Val Phe Gly Gly Gly Thr Lys Leu Thr Val Leu
            100                 105                 110

<210> SEQ ID NO 87
<211> LENGTH: 107
<212> TYPE: PRT
<213> ORGANISM: Rattus norvegicus

<400> SEQUENCE: 87

Asp Ile Lys Met Thr Gln Ser Pro Ser Phe Leu Ser Ala Ser Val Gly
1               5                   10                  15

Asp Arg Val Thr Ile Asn Cys Lys Ala Ser Gln Asn Ile Thr Arg Phe
            20                  25                  30

Leu Asn Trp Tyr Gln Gln Glu Leu Gly Glu Ala Pro Thr Leu Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Gly Ser Arg Pro Arg
                85                  90                  95

Thr Phe Gly Gly Gly Thr Lys Leu Glu Leu Lys
            100                 105

<210> SEQ ID NO 88
<211> LENGTH: 25
<212> TYPE: PRT
<213> ORGANISM: Rattus norvegicus

<400> SEQUENCE: 88

Glu Val Gln Leu Gln Glu Ser Gly Pro Gly Leu Val Lys Pro Ala Gln
1               5                   10                  15

Ser Leu Ser Leu Thr Cys Ser Val Thr
            20                  25

<210> SEQ ID NO 89
<211> LENGTH: 9

<210> SEQ ID NO 89
<211> LENGTH: (not shown)
<212> TYPE: PRT
<213> ORGANISM: Rattus norvegicus

<400> SEQUENCE: 89

Gly Tyr Ser Ile Thr Asn Met Tyr Arg
1               5

<210> SEQ ID NO 90
<211> LENGTH: 17
<212> TYPE: PRT
<213> ORGANISM: Rattus norvegicus

<400> SEQUENCE: 90

Trp Asn Trp Ile Arg Lys Phe Pro Gly Asn Lys Leu Glu Trp Met Gly
1               5                   10                  15

Tyr

<210> SEQ ID NO 91
<211> LENGTH: 7
<212> TYPE: PRT
<213> ORGANISM: Rattus norvegicus

<400> SEQUENCE: 91

Ile Asn Thr Ala Gly Ser Thr
1               5

<210> SEQ ID NO 92
<211> LENGTH: 38
<212> TYPE: PRT
<213> ORGANISM: Rattus norvegicus

<400> SEQUENCE: 92

Asp Tyr Ser Pro Ser Leu Arg Gly Arg Val Ser Ile Thr Gly Asp Thr
1               5                   10                  15

Ser Lys Asn Gln Phe Phe Leu His Leu Thr Ser Val Thr Thr Glu Asp
            20                  25                  30

Thr Ala Thr Tyr Tyr Cys
        35

<210> SEQ ID NO 93
<211> LENGTH: 10
<212> TYPE: PRT
<213> ORGANISM: Rattus norvegicus

<400> SEQUENCE: 93

Ala Gly Phe Ile Thr Asn Pro Phe Asp Phe
1               5                   10

<210> SEQ ID NO 94
<211> LENGTH: 11
<212> TYPE: PRT
<213> ORGANISM: Rattus norvegicus

<400> SEQUENCE: 94

Trp Gly Gln Gly Val Met Val Thr Val Ser Ser
1               5                   10

<210> SEQ ID NO 95
<211> LENGTH: 25
<212> TYPE: PRT
<213> ORGANISM: Rattus norvegicus

<400> SEQUENCE: 95

Glu Val Gln Val Val Glu Ser Gly Gly Gly Leu Val Gln Pro Gly Arg
1               5                   10                  15

Ser Leu Lys Leu Ser Cys Val Pro Ser
            20                  25

<210> SEQ ID NO 96
<211> LENGTH: 8
<212> TYPE: PRT
<213> ORGANISM: Rattus norvegicus

<400> SEQUENCE: 96

Gly Phe Thr Phe Asn Asn Tyr Trp
1               5

<210> SEQ ID NO 97
<211> LENGTH: 17
<212> TYPE: PRT
<213> ORGANISM: Rattus norvegicus

<400> SEQUENCE: 97

Met Thr Trp Ile Arg Gln Ala Pro Gly Lys Ala Pro Glu Trp Val Ala
1               5                   10                  15

Ser

<210> SEQ ID NO 98
<211> LENGTH: 8
<212> TYPE: PRT
<213> ORGANISM: Rattus norvegicus

<400> SEQUENCE: 98

Ile Ser Asn Thr Gly Gly Ser Thr
1               5

<210> SEQ ID NO 99
<211> LENGTH: 38
<212> TYPE: PRT
<213> ORGANISM: Rattus norvegicus

<400> SEQUENCE: 99

Phe Tyr Pro Asp Ser Val Arg Gly Arg Phe Ser Ile Ser Arg Asp Asn
1               5                   10                  15

Thr Lys Gly Thr Leu Tyr Leu His Met Thr Ser Leu Arg Ser Glu Asp
            20                  25                  30

Thr Ala Thr Tyr Tyr Cys
        35

<210> SEQ ID NO 100
<211> LENGTH: 6
<212> TYPE: PRT
<213> ORGANISM: Rattus norvegicus

<400> SEQUENCE: 100

Ile Arg Asn Met Asp Ala
1               5

<210> SEQ ID NO 101
<211> LENGTH: 11
<212> TYPE: PRT
<213> ORGANISM: Rattus norvegicus

<400> SEQUENCE: 101

Trp Gly Gln Gly Thr Ser Val Thr Val Ser Ser
1               5                   10

<210> SEQ ID NO 102
<211> LENGTH: 24
<212> TYPE: PRT
<213> ORGANISM: Rattus norvegicus

<400> SEQUENCE: 102

Gly Lys Leu Val Glu Ser Gly Gly Gly Leu Leu Lys Pro Gly Gly Ser
1               5                   10                  15

Leu Lys Leu Ser Cys Val Ala Ser
            20

<210> SEQ ID NO 103
<211> LENGTH: 8
<212> TYPE: PRT
<213> ORGANISM: Rattus norvegicus

<400> SEQUENCE: 103

Gly Phe Thr Phe Asp Lys Tyr Trp
1               5

<210> SEQ ID NO 104
<211> LENGTH: 17
<212> TYPE: PRT
<213> ORGANISM: Rattus norvegicus

<400> SEQUENCE: 104

Met His Trp Val Arg Gln Ala Pro Gly Lys Gly Leu Glu Trp Ile Ala
1               5                   10                  15

Glu

<210> SEQ ID NO 105
<211> LENGTH: 8
<212> TYPE: PRT
<213> ORGANISM: Rattus norvegicus

<400> SEQUENCE: 105

Ile Glu Tyr Asp Gly Thr Glu Thr
1               5

<210> SEQ ID NO 106
<211> LENGTH: 38
<212> TYPE: PRT
<213> ORGANISM: Rattus norvegicus

<400> SEQUENCE: 106

Asn Tyr Ala Pro Ser Ile Lys Asp Arg Phe Thr Ile Ser Arg Asp Asn
1               5                   10                  15

Ala Lys Asn Thr Leu Tyr Leu Gln Met Ser Asn Val Arg Ser Glu Asp
            20                  25                  30

Ala Ala Thr Tyr Phe Cys
        35

<210> SEQ ID NO 107
<211> LENGTH: 16
<212> TYPE: PRT
<213> ORGANISM: Rattus norvegicus

<400> SEQUENCE: 107

Thr Thr Glu Glu Met Tyr Thr Thr Asp Tyr Tyr Gly Phe Ala Tyr
1               5                   10                  15

<210> SEQ ID NO 108
<211> LENGTH: 11
<212> TYPE: PRT
<213> ORGANISM: Rattus norvegicus

<400> SEQUENCE: 108

Trp Gly Gln Gly Thr Leu Val Thr Val Ser Ser
1               5                   10

<210> SEQ ID NO 109
<211> LENGTH: 25
<212> TYPE: PRT
<213> ORGANISM: Rattus norvegicus

<400> SEQUENCE: 109

Asp Val Lys Leu Val Glu Ser Gly Gly Gly Leu Leu Lys Pro Gly Gly
1               5                   10                  15

Ser Leu Lys Leu Ser Cys Val Ala Ser
            20                  25

<210> SEQ ID NO 110
<211> LENGTH: 8
<212> TYPE: PRT
<213> ORGANISM: Rattus norvegicus

<400> SEQUENCE: 110

Gly Phe Ser Phe Ser Lys Tyr Trp
1               5

<210> SEQ ID NO 111
<211> LENGTH: 17
<212> TYPE: PRT
<213> ORGANISM: Rattus norvegicus

<400> SEQUENCE: 111

Met His Trp Val Arg Gln Ala Pro Gly Gln Gly Leu Glu Trp Ile Ala
1               5                   10                  15

Glu

<210> SEQ ID NO 112
<211> LENGTH: 38
<212> TYPE: PRT
<213> ORGANISM: Rattus norvegicus

<400> SEQUENCE: 112

Asn Tyr Ala Pro Ser Ile Lys Asp Arg Phe Thr Ile Ser Arg Asp Asn
1               5                   10                  15

Ala Lys Asn Thr Leu Tyr Leu Gln Met Ser Asn Val Arg Phe Glu Asp
            20                  25                  30

Ala Ala Thr Tyr Phe Cys
        35

<210> SEQ ID NO 113
<211> LENGTH: 16
<212> TYPE: PRT
<213> ORGANISM: Rattus norvegicus

<400> SEQUENCE: 113

Thr Thr Glu Glu Met His Thr Thr Asp Tyr Tyr Tyr Gly Phe Ala Tyr
1               5                   10                  15

<210> SEQ ID NO 114
<211> LENGTH: 25
<212> TYPE: PRT
<213> ORGANISM: Rattus norvegicus

<400> SEQUENCE: 114

Glu Val Gln Leu Val Glu Ser Gly Gly Gly Leu Val Gln Pro Gly Arg
1               5                   10                  15

Ser Leu Lys Leu Ser Cys Ala Ala Ser
            20                  25

<210> SEQ ID NO 115
<211> LENGTH: 8
<212> TYPE: PRT
<213> ORGANISM: Rattus norvegicus

<400> SEQUENCE: 115

Gly Phe Ile Phe Ser Glu His Asn
1               5

<210> SEQ ID NO 116
<211> LENGTH: 17
<212> TYPE: PRT
<213> ORGANISM: Rattus norvegicus

<400> SEQUENCE: 116

Met Ala Trp Val Arg Gln Ala Pro Lys Lys Gly Leu Glu Trp Val Ala
1               5                   10                  15

Thr

<210> SEQ ID NO 117
<211> LENGTH: 8
<212> TYPE: PRT
<213> ORGANISM: Rattus norvegicus

<400> SEQUENCE: 117

Ile Ser Asp Asp Gly Arg Asn Thr
1               5

<210> SEQ ID NO 118
<211> LENGTH: 38
<212> TYPE: PRT
<213> ORGANISM: Rattus norvegicus

<400> SEQUENCE: 118

Tyr Tyr Arg Asp Ser Met Arg Gly Arg Phe Thr Ile Ser Arg Glu Asn
1               5                   10                  15

Ala Arg Ser Thr Leu Tyr Leu Gln Leu Asp Ser Leu Arg Ser Glu Asp
            20                  25                  30

Thr Ala Thr Tyr Tyr Cys
            35

<210> SEQ ID NO 119
<211> LENGTH: 10
<212> TYPE: PRT
<213> ORGANISM: Rattus norvegicus

<400> SEQUENCE: 119

Ala Ser His Arg Tyr Asn Leu Phe Asp Ser
1               5                   10

<210> SEQ ID NO 120
<211> LENGTH: 25
<212> TYPE: PRT
<213> ORGANISM: Rattus norvegicus

<400> SEQUENCE: 120

Gln Val Gln Leu Gln Gln Ser Gly Thr Glu Leu Val Lys Pro Ala Ser
1               5                   10                  15

Ser Val Arg Ile Ser Cys Lys Ala Ser
            20                  25

<210> SEQ ID NO 121
<211> LENGTH: 8
<212> TYPE: PRT
<213> ORGANISM: Rattus norvegicus

<400> SEQUENCE: 121

Gly Tyr Thr Leu Thr Thr Asn Tyr
1               5

<210> SEQ ID NO 122
<211> LENGTH: 17
<212> TYPE: PRT
<213> ORGANISM: Rattus norvegicus

<400> SEQUENCE: 122

Met His Trp Ile Arg Gln Gln Pro Gly Asn Gly Leu Glu Trp Ile Gly
1               5                   10                  15

Trp

<210> SEQ ID NO 123
<211> LENGTH: 8
<212> TYPE: PRT
<213> ORGANISM: Rattus norvegicus

<400> SEQUENCE: 123

Ile Tyr Pro Gly Asn Gly Asn Thr
1               5

<210> SEQ ID NO 124
<211> LENGTH: 38
<212> TYPE: PRT
<213> ORGANISM: Rattus norvegicus

<400> SEQUENCE: 124

Lys Phe Asn His Lys Phe Asp Gly Arg Thr Thr Leu Thr Ala Asp Lys
1               5                   10                  15

Ser Ser Ser Ile Val Tyr Met Gln Leu Ser Ser Leu Thr Ser Glu Asp
            20                  25                  30

Ser Ala Val Tyr Phe Cys
        35

<210> SEQ ID NO 125
<211> LENGTH: 7
<212> TYPE: PRT
<213> ORGANISM: Rattus norvegicus

<400> SEQUENCE: 125

Ala Arg Ser Asp Phe Asp Tyr
1               5

<210> SEQ ID NO 126
<211> LENGTH: 25
<212> TYPE: PRT
<213> ORGANISM: Rattus norvegicus

<400> SEQUENCE: 126

Asp Val Gln Leu Glu Glu Ser Gly Gly Gly Leu Val Arg Pro Gly Arg
1               5                   10                  15

Ser Leu Lys Leu Ser Cys Ala Asp Ser
            20                  25

<210> SEQ ID NO 127
<211> LENGTH: 8
<212> TYPE: PRT
<213> ORGANISM: Rattus norvegicus

<400> SEQUENCE: 127

Gly Val Asn Phe Ser Asn Arg Gly
1               5

<210> SEQ ID NO 128
<211> LENGTH: 17
<212> TYPE: PRT
<213> ORGANISM: Rattus norvegicus

<400> SEQUENCE: 128

Met Ala Trp Val Arg Gln Ala Pro Thr Lys Gly Leu Glu Trp Val Ala
1               5                   10                  15

Thr

<210> SEQ ID NO 129
<211> LENGTH: 8
<212> TYPE: PRT
<213> ORGANISM: Rattus norvegicus

<400> SEQUENCE: 129

Ile Ser Tyr Asp Gly Arg Ile Ile
1               5

<210> SEQ ID NO 130
<211> LENGTH: 38
<212> TYPE: PRT
<213> ORGANISM: Rattus norvegicus

<400> SEQUENCE: 130

Tyr Tyr Arg Asp Ser Val Lys Gly Arg Phe Ser Ile Ser Arg Glu Asn
1               5                   10                  15

Ala Lys Ser Thr Leu Tyr Leu Gln Met Asp Ser Leu Arg Ser Glu Asp
            20                  25                  30

Thr Ala Thr Tyr Tyr Cys
        35

<210> SEQ ID NO 131
<211> LENGTH: 13
<212> TYPE: PRT
<213> ORGANISM: Rattus norvegicus

<400> SEQUENCE: 131

Ala Arg His Pro Ile Ala Ala Asp Trp Tyr Phe Asp Phe
1               5                   10

<210> SEQ ID NO 132
<211> LENGTH: 11
<212> TYPE: PRT
<213> ORGANISM: Rattus norvegicus

<400> SEQUENCE: 132

Trp Gly Pro Gly Thr Met Val Thr Val Ser Ser
1               5                   10

<210> SEQ ID NO 133
<211> LENGTH: 25
<212> TYPE: PRT
<213> ORGANISM: Rattus norvegicus

<400> SEQUENCE: 133

Glu Val Gln Leu Val Glu Ser Gly Gly Ser Val Gln Pro Gly Arg
1               5                   10                  15

Ser Leu Lys Leu Ser Cys Ala Ala Ser
            20                  25

<210> SEQ ID NO 134
<211> LENGTH: 8
<212> TYPE: PRT
<213> ORGANISM: Rattus norvegicus

<400> SEQUENCE: 134

Gly Phe Thr Phe Ser Asp Tyr Asn
1               5

<210> SEQ ID NO 135
<211> LENGTH: 17
<212> TYPE: PRT
<213> ORGANISM: Rattus norvegicus

<400> SEQUENCE: 135

Met Ala Trp Val Arg Gln Ala Pro Lys Lys Gly Pro Glu Trp Val Ala
1               5                   10                  15

Thr

<210> SEQ ID NO 136
<211> LENGTH: 8
<212> TYPE: PRT
<213> ORGANISM: Rattus norvegicus

<400> SEQUENCE: 136

Ile Thr Tyr Asp Val His Asn Ala
1               5

<210> SEQ ID NO 137
<211> LENGTH: 38
<212> TYPE: PRT
<213> ORGANISM: Rattus norvegicus

<400> SEQUENCE: 137

Tyr Tyr Arg Asp Ser Val Lys Gly Arg Phe Thr Ile Ser Arg Asp Asp
1               5                   10                  15

Ala Lys Ser Thr Leu Tyr Leu Gln Met Asp Ser Leu Arg Ser Glu Asp
            20                  25                  30

```
Thr Ala Thr Tyr Phe Cys
        35

<210> SEQ ID NO 138
<211> LENGTH: 6
<212> TYPE: PRT
<213> ORGANISM: Rattus norvegicus

<400> SEQUENCE: 138

Ala Arg Pro Gly Ala Tyr
1               5

<210> SEQ ID NO 139
<211> LENGTH: 25
<212> TYPE: PRT
<213> ORGANISM: Rattus norvegicus

<400> SEQUENCE: 139

Gln Val Arg Leu Leu Gln Ser Gly Ala Ala Leu Val Lys Pro Gly Ala
1               5                   10                  15

Ser Val Lys Met Ser Cys Lys Ala Ser
            20                  25

<210> SEQ ID NO 140
<211> LENGTH: 8
<212> TYPE: PRT
<213> ORGANISM: Rattus norvegicus

<400> SEQUENCE: 140

Gly Tyr Thr Phe Thr Asp Tyr Trp
1               5

<210> SEQ ID NO 141
<211> LENGTH: 17
<212> TYPE: PRT
<213> ORGANISM: Rattus norvegicus

<400> SEQUENCE: 141

Met Ser Trp Val Lys Gln Ser His Gly Lys Ser Leu Glu Trp Ile Gly
1               5                   10                  15

Glu

<210> SEQ ID NO 142
<211> LENGTH: 8
<212> TYPE: PRT
<213> ORGANISM: Rattus norvegicus

<400> SEQUENCE: 142

Ile Tyr Pro Asn Ser Gly Ala Thr
1               5

<210> SEQ ID NO 143
<211> LENGTH: 38
<212> TYPE: PRT
<213> ORGANISM: Rattus norvegicus

<400> SEQUENCE: 143

Asn Phe Asn Glu Lys Phe Lys Asp Lys Ala Thr Leu Thr Val Asp Arg
1               5                   10                  15

Ser Thr Ser Thr Ala Tyr Met Glu Leu Ser Arg Leu Thr Ser Glu Asp
            20                  25                  30
```

Ser Ala Ile Tyr Tyr Cys
        35

<210> SEQ ID NO 144
<211> LENGTH: 14
<212> TYPE: PRT
<213> ORGANISM: Rattus norvegicus

<400> SEQUENCE: 144

Ala Arg Gly Phe Pro Asn Asn Tyr Leu Ser Trp Phe Ala Tyr
1               5                   10

<210> SEQ ID NO 145
<211> LENGTH: 25
<212> TYPE: PRT
<213> ORGANISM: Rattus norvegicus

<400> SEQUENCE: 145

Gln Ile Gln Leu Val Gln Ser Gly Pro Glu Leu Lys Lys Pro Gly Glu
1               5                   10                  15

Ser Val Lys Ile Ser Cys Lys Ala Ser
            20                  25

<210> SEQ ID NO 146
<211> LENGTH: 8
<212> TYPE: PRT
<213> ORGANISM: Rattus norvegicus

<400> SEQUENCE: 146

Gly Tyr Thr Phe Thr Asn Tyr Gly
1               5

<210> SEQ ID NO 147
<211> LENGTH: 17
<212> TYPE: PRT
<213> ORGANISM: Rattus norvegicus

<400> SEQUENCE: 147

Met Tyr Trp Val Lys Gln Ala Pro Gly Gln Gly Leu Gln Tyr Met Gly
1               5                   10                  15

Trp

<210> SEQ ID NO 148
<211> LENGTH: 8
<212> TYPE: PRT
<213> ORGANISM: Rattus norvegicus

<400> SEQUENCE: 148

Ile Asn Thr Glu Thr Gly Lys Pro
1               5

<210> SEQ ID NO 149
<211> LENGTH: 38
<212> TYPE: PRT
<213> ORGANISM: Rattus norvegicus

<400> SEQUENCE: 149

Thr Tyr Ala Asp Asp Phe Lys Gly Arg Phe Val Phe Phe Leu Glu Thr
1               5                   10                  15

Ser Ala Ser Thr Ala Tyr Leu Gln Ile Asn Asn Leu Lys Asn Glu Asp
            20                  25                  30

Met Ala Thr Tyr Phe Cys
        35

<210> SEQ ID NO 150
<211> LENGTH: 14
<212> TYPE: PRT
<213> ORGANISM: Rattus norvegicus

<400> SEQUENCE: 150

Ala Arg Glu Val Lys His Gly Leu Phe His Trp Phe Ala Tyr
1               5                   10

<210> SEQ ID NO 151
<211> LENGTH: 25
<212> TYPE: PRT
<213> ORGANISM: Rattus norvegicus

<400> SEQUENCE: 151

Glu Val Gln Leu Val Glu Ser Gly Gly Gly Leu Val Gln Pro Gly Arg
1               5                   10                  15

Ser Leu Thr Leu Ser Cys Ser Ala Ser
            20                  25

<210> SEQ ID NO 152
<211> LENGTH: 8
<212> TYPE: PRT
<213> ORGANISM: Rattus norvegicus

<400> SEQUENCE: 152

Gly Phe Thr Phe Arg Asp Tyr Asn
1               5

<210> SEQ ID NO 153
<211> LENGTH: 17
<212> TYPE: PRT
<213> ORGANISM: Rattus norvegicus

<400> SEQUENCE: 153

Met Ala Trp Val Arg Gln Ala Pro Arg Lys Gly Leu Glu Trp Val Ala
1               5                   10                  15

Thr

<210> SEQ ID NO 154
<211> LENGTH: 8
<212> TYPE: PRT
<213> ORGANISM: Rattus norvegicus

<400> SEQUENCE: 154

Ile Ser Phe Asp Asp Tyr Asn Thr
1               5

<210> SEQ ID NO 155
<211> LENGTH: 38
<212> TYPE: PRT
<213> ORGANISM: Rattus norvegicus

<400> SEQUENCE: 155

Tyr Tyr Arg Asp Ser Val Lys Gly Arg Phe Thr Ile Ser Arg Asp Asp
1               5                   10                  15

Ala Lys Ser Thr Leu Tyr Leu Gln Met Asp Ser Leu Arg Ser Glu Asp
            20                  25                  30

```
Thr Ala Thr Tyr Tyr Cys
        35

<210> SEQ ID NO 156
<211> LENGTH: 6
<212> TYPE: PRT
<213> ORGANISM: Rattus norvegicus

<400> SEQUENCE: 156

Ala Arg Pro Gly Thr Tyr
1               5

<210> SEQ ID NO 157
<211> LENGTH: 25
<212> TYPE: PRT
<213> ORGANISM: Rattus norvegicus

<400> SEQUENCE: 157

Gln Val Gln Leu Gln Gln Ser Gly Ala Glu Leu Val Lys Pro Gly Ser
1               5                   10                  15

Ser Val Arg Ile Ser Cys Lys Ala Ser
            20                  25

<210> SEQ ID NO 158
<211> LENGTH: 8
<212> TYPE: PRT
<213> ORGANISM: Rattus norvegicus

<400> SEQUENCE: 158

Gly Tyr Thr Ile Thr Ser Tyr Asp
1               5

<210> SEQ ID NO 159
<211> LENGTH: 17
<212> TYPE: PRT
<213> ORGANISM: Rattus norvegicus

<400> SEQUENCE: 159

Met His Trp Ile Lys Gln Gln Pro Gly Asn Gly Leu Glu Gly Ile Gly
1               5                   10                  15

Trp

<210> SEQ ID NO 160
<211> LENGTH: 8
<212> TYPE: PRT
<213> ORGANISM: Rattus norvegicus

<400> SEQUENCE: 160

Ile His Pro Gly Asn Gly Lys Ile
1               5

<210> SEQ ID NO 161
<211> LENGTH: 38
<212> TYPE: PRT
<213> ORGANISM: Rattus norvegicus

<400> SEQUENCE: 161

Lys Tyr Asn Gln Lys Phe Asn Gly Lys Ala Thr Leu Thr Val Asp Lys
1               5                   10                  15

Ser Ser Ser Thr Ala Tyr Met Gln Leu Ser Ser Leu Thr Ser Glu Asp
            20                  25                  30
```

Ser Ala Val Tyr Phe Cys
        35

<210> SEQ ID NO 162
<211> LENGTH: 13
<212> TYPE: PRT
<213> ORGANISM: Rattus norvegicus

<400> SEQUENCE: 162

Ala Arg Gly Thr Thr Arg Val Phe Pro Trp Phe Ala Tyr
1               5                   10

<210> SEQ ID NO 163
<211> LENGTH: 8
<212> TYPE: PRT
<213> ORGANISM: Rattus norvegicus

<400> SEQUENCE: 163

Gly Phe Ser Phe Ser Asn Tyr Gly
1               5

<210> SEQ ID NO 164
<211> LENGTH: 17
<212> TYPE: PRT
<213> ORGANISM: Rattus norvegicus

<400> SEQUENCE: 164

Met His Trp Ile Arg Gln Ala Pro Thr Lys Gly Leu Glu Trp Val Ala
1               5                   10                  15

Ser

<210> SEQ ID NO 165
<211> LENGTH: 8
<212> TYPE: PRT
<213> ORGANISM: Rattus norvegicus

<400> SEQUENCE: 165

Ile Ser Pro Thr Gly Gly Asn Thr
1               5

<210> SEQ ID NO 166
<211> LENGTH: 38
<212> TYPE: PRT
<213> ORGANISM: Rattus norvegicus

<400> SEQUENCE: 166

Tyr Tyr Arg Asp Ser Val Lys Gly Arg Phe Thr Ile Ser Arg Asp Asn
1               5                   10                  15

Thr Lys Ser Thr Leu Tyr Leu Gln Met Asp Ser Leu Arg Ser Glu Asp
            20                  25                  30

Thr Ala Thr Tyr Tyr Cys
        35

<210> SEQ ID NO 167
<211> LENGTH: 13
<212> TYPE: PRT
<213> ORGANISM: Rattus norvegicus

<400> SEQUENCE: 167

Ala Thr Asp Asp Leu Tyr Tyr Ser Gly Pro Phe Ala Tyr
1               5                   10

```
<210> SEQ ID NO 168
<211> LENGTH: 117
<212> TYPE: PRT
<213> ORGANISM: Rattus norvegicus

<400> SEQUENCE: 168

Glu Val Gln Leu Gln Glu Ser Gly Pro Gly Leu Val Lys Pro Ala Gln
1               5                   10                  15

Ser Leu Ser Leu Thr Cys Ser Val Thr Gly Tyr Ser Ile Thr Asn Met
            20                  25                  30

Tyr Arg Trp Asn Trp Ile Arg Lys Phe Pro Gly Asn Lys Leu Glu Trp
        35                  40                  45

Met Gly Tyr Ile Asn Thr Ala Gly Ser Thr Asp Tyr Ser Pro Ser Leu
    50                  55                  60

Arg Gly Arg Val Ser Ile Thr Gly Asp Thr Ser Lys Asn Gln Phe Phe
65                  70                  75                  80

Leu His Leu Thr Ser Val Thr Thr Glu Asp Thr Ala Thr Tyr Tyr Cys
                85                  90                  95

Ala Gly Phe Ile Thr Asn Pro Phe Asp Phe Trp Gly Gln Gly Val Met
            100                 105                 110

Val Thr Val Ser Ser
        115

<210> SEQ ID NO 169
<211> LENGTH: 113
<212> TYPE: PRT
<213> ORGANISM: Rattus norvegicus

<400> SEQUENCE: 169

Glu Val Gln Val Val Glu Ser Gly Gly Gly Leu Val Gln Pro Gly Arg
1               5                   10                  15

Ser Leu Lys Leu Ser Cys Val Pro Ser Gly Phe Thr Phe Asn Asn Tyr
            20                  25                  30

Trp Met Thr Trp Ile Arg Gln Ala Pro Gly Lys Ala Pro Glu Trp Val
        35                  40                  45

Ala Ser Ile Ser Asn Thr Gly Gly Ser Thr Phe Tyr Pro Asp Ser Val
    50                  55                  60

Arg Gly Arg Phe Ser Ile Ser Arg Asp Asn Thr Lys Gly Thr Leu Tyr
65                  70                  75                  80

Leu His Met Thr Ser Leu Arg Ser Glu Asp Thr Ala Thr Tyr Tyr Cys
                85                  90                  95

Ile Arg Asn Met Asp Ala Trp Gly Gln Gly Thr Ser Val Thr Val Ser
            100                 105                 110

Ser

<210> SEQ ID NO 170
<211> LENGTH: 122
<212> TYPE: PRT
<213> ORGANISM: Rattus norvegicus

<400> SEQUENCE: 170

Gly Lys Leu Val Glu Ser Gly Gly Gly Leu Leu Lys Pro Gly Gly Ser
1               5                   10                  15

Leu Lys Leu Ser Cys Val Ala Ser Gly Phe Thr Phe Asp Lys Tyr Trp
            20                  25                  30

Met His Trp Val Arg Gln Ala Pro Gly Lys Gly Leu Glu Trp Ile Ala
        35                  40                  45
```

```
Glu Ile Glu Tyr Asp Gly Thr Glu Thr Asn Tyr Ala Pro Ser Ile Lys
         50                  55                  60

Asp Arg Phe Thr Ile Ser Arg Asp Asn Ala Lys Asn Thr Leu Tyr Leu
 65                  70                  75                  80

Gln Met Ser Asn Val Arg Ser Glu Asp Ala Ala Thr Tyr Phe Cys Thr
                 85                  90                  95

Thr Glu Glu Met Tyr Thr Thr Asp Tyr Tyr Gly Phe Ala Tyr Trp
                100                 105                 110

Gly Gln Gly Thr Leu Val Thr Val Ser Ser
            115                 120

<210> SEQ ID NO 171
<211> LENGTH: 123
<212> TYPE: PRT
<213> ORGANISM: Rattus norvegicus

<400> SEQUENCE: 171

Asp Val Lys Leu Val Glu Ser Gly Gly Gly Leu Leu Lys Pro Gly Gly
  1               5                  10                  15

Ser Leu Lys Leu Ser Cys Val Ala Ser Gly Phe Ser Phe Ser Lys Tyr
                 20                  25                  30

Trp Met His Trp Val Arg Gln Ala Pro Gly Gln Gly Leu Glu Trp Ile
             35                  40                  45

Ala Glu Ile Glu Tyr Asp Gly Thr Glu Thr Asn Tyr Ala Pro Ser Ile
         50                  55                  60

Lys Asp Arg Phe Thr Ile Ser Arg Asp Asn Ala Lys Asn Thr Leu Tyr
 65                  70                  75                  80

Leu Gln Met Ser Asn Val Arg Phe Glu Asp Ala Ala Thr Tyr Phe Cys
                 85                  90                  95

Thr Thr Glu Glu Met His Thr Thr Asp Tyr Tyr Gly Phe Ala Tyr
                100                 105                 110

Trp Gly Gln Gly Thr Leu Val Thr Val Ser Ser
            115                 120

<210> SEQ ID NO 172
<211> LENGTH: 117
<212> TYPE: PRT
<213> ORGANISM: Rattus norvegicus

<400> SEQUENCE: 172

Glu Val Gln Leu Val Glu Ser Gly Gly Gly Leu Val Gln Pro Gly Arg
  1               5                  10                  15

Ser Leu Lys Leu Ser Cys Ala Ala Ser Gly Phe Ile Phe Ser Glu His
                 20                  25                  30

Asn Met Ala Trp Val Arg Gln Ala Pro Lys Lys Gly Leu Glu Trp Val
             35                  40                  45

Ala Thr Ile Ser Asp Asp Gly Arg Asn Thr Tyr Tyr Arg Asp Ser Met
         50                  55                  60

Arg Gly Arg Phe Thr Ile Ser Arg Glu Asn Ala Arg Ser Thr Leu Tyr
 65                  70                  75                  80

Leu Gln Leu Asp Ser Leu Arg Ser Glu Asp Thr Ala Thr Tyr Tyr Cys
                 85                  90                  95

Ala Ser His Arg Tyr Asn Leu Phe Asp Ser Trp Gly Gln Gly Val Met
                100                 105                 110

Val Thr Val Ser Ser
            115
```

<210> SEQ ID NO 173
<211> LENGTH: 114
<212> TYPE: PRT
<213> ORGANISM: Rattus norvegicus

<400> SEQUENCE: 173

Gln Val Gln Leu Gln Gln Ser Gly Thr Glu Leu Val Lys Pro Ala Ser
1               5                   10                  15

Ser Val Arg Ile Ser Cys Lys Ala Ser Gly Tyr Thr Leu Thr Thr Asn
            20                  25                  30

Tyr Met His Trp Ile Arg Gln Gln Pro Gly Asn Gly Leu Glu Trp Ile
        35                  40                  45

Gly Trp Ile Tyr Pro Gly Asn Gly Asn Thr Lys Phe Asn His Lys Phe
    50                  55                  60

Asp Gly Arg Thr Thr Leu Thr Ala Asp Lys Ser Ser Ser Ile Val Tyr
65                  70                  75                  80

Met Gln Leu Ser Ser Leu Thr Ser Glu Asp Ser Ala Val Tyr Phe Cys
                85                  90                  95

Ala Arg Ser Asp Phe Asp Tyr Trp Gly Gln Gly Val Met Val Thr Val
            100                 105                 110

Ser Ser

<210> SEQ ID NO 174
<211> LENGTH: 120
<212> TYPE: PRT
<213> ORGANISM: Rattus norvegicus

<400> SEQUENCE: 174

Asp Val Gln Leu Glu Glu Ser Gly Gly Gly Leu Val Arg Pro Gly Arg
1               5                   10                  15

Ser Leu Lys Leu Ser Cys Ala Asp Ser Gly Val Asn Phe Ser Asn Arg
            20                  25                  30

Gly Met Ala Trp Val Arg Gln Ala Pro Thr Lys Gly Leu Glu Trp Val
        35                  40                  45

Ala Thr Ile Ser Tyr Asp Gly Arg Ile Ile Tyr Tyr Arg Asp Ser Val
    50                  55                  60

Lys Gly Arg Phe Ser Ile Ser Arg Glu Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Pro Ile Ala Ala Asp Trp Tyr Phe Asp Phe Trp Gly Pro
            100                 105                 110

Gly Thr Met Val Thr Val Ser Ser
        115                 120

<210> SEQ ID NO 175
<211> LENGTH: 113
<212> TYPE: PRT
<213> ORGANISM: Rattus norvegicus

<400> SEQUENCE: 175

Glu Val Gln Leu Val Glu Ser Gly Gly Gly Ser Val Gln Pro Gly Arg
1               5                   10                  15

Ser Leu Lys Leu Ser Cys Ala Ala Ser Gly Phe Thr Phe Ser Asp Tyr
            20                  25                  30

Asn Met Ala Trp Val Arg Gln Ala Pro Lys Lys Gly Pro Glu Trp Val
        35                  40                  45

```
Ala Thr Ile Thr Tyr Asp Val His Asn Ala Tyr Tyr Arg Asp Ser Val
        50                  55                  60

Lys Gly Arg Phe Thr Ile Ser Arg Asp Asp Ala Lys Ser Thr Leu Tyr
65                  70                  75                  80

Leu Gln Met Asp Ser Leu Arg Ser Glu Asp Thr Ala Thr Tyr Phe Cys
                85                  90                  95

Ala Arg Pro Gly Ala Tyr Trp Gly Gln Gly Thr Leu Val Thr Val Ser
                100                 105                 110

Ser

<210> SEQ ID NO 176
<211> LENGTH: 121
<212> TYPE: PRT
<213> ORGANISM: Rattus norvegicus

<400> SEQUENCE: 176

Gln Val Arg Leu Leu Gln Ser Gly Ala Ala Leu Val Lys Pro Gly Ala
1               5                   10                  15

Ser Val Lys Met Ser Cys Lys Ala Ser Gly Tyr Thr Phe Thr Asp Tyr
                20                  25                  30

Trp Met Ser Trp Val Lys Gln Ser His Gly Lys Ser Leu Glu Trp Ile
            35                  40                  45

Gly Glu Ile Tyr Pro Asn Ser Gly Ala Thr Asn Phe Asn Glu Lys Phe
        50                  55                  60

Lys Asp Lys Ala Thr Leu Thr Val Asp Arg Ser Thr Ser Thr Ala Tyr
65                  70                  75                  80

Met Glu Leu Ser Arg Leu Thr Ser Glu Asp Ser Ala Ile Tyr Tyr Cys
                85                  90                  95

Ala Arg Gly Phe Pro Asn Asn Tyr Leu Ser Trp Phe Ala Tyr Trp Gly
                100                 105                 110

Gln Gly Thr Leu Val Thr Val Ser Ser
            115                 120

<210> SEQ ID NO 177
<211> LENGTH: 121
<212> TYPE: PRT
<213> ORGANISM: Rattus norvegicus

<400> SEQUENCE: 177

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asn Tyr
                20                  25                  30

Gly Met Tyr Trp Val Lys Gln Ala Pro Gly Gln Gly Leu Gln Tyr Met
            35                  40                  45

Gly Trp Ile Asn Thr Glu Thr Gly Lys Pro Thr Tyr Ala Asp Asp Phe
        50                  55                  60

Lys Gly Arg Phe Val Phe Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Glu Val Lys His Gly Leu Phe His Trp Phe Ala Tyr Trp Gly
                100                 105                 110

Gln Gly Thr Leu Val Thr Val Ser Ser
            115                 120
```

<210> SEQ ID NO 178
<211> LENGTH: 113
<212> TYPE: PRT
<213> ORGANISM: Rattus norvegicus

<400> SEQUENCE: 178

Glu Val Gln Leu Val Glu Ser Gly Gly Gly Leu Val Gln Pro Gly Arg
1               5                   10                  15

Ser Leu Thr Leu Ser Cys Ser Ala Ser Gly Phe Thr Phe Arg Asp Tyr
            20                  25                  30

Asn Met Ala Trp Val Arg Gln Ala Pro Arg Lys Gly Leu Glu Trp Val
        35                  40                  45

Ala Thr Ile Ser Phe Asp Asp Tyr Asn Thr Tyr Tyr Arg Asp Ser Val
    50                  55                  60

Lys Gly Arg Phe Thr Ile Ser Arg Asp Asp Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Pro Gly Thr Tyr Trp Gly Gln Gly Thr Leu Val Thr Val Ser
            100                 105                 110

Ser

<210> SEQ ID NO 179
<211> LENGTH: 120
<212> TYPE: PRT
<213> ORGANISM: Rattus norvegicus

<400> SEQUENCE: 179

Gln Val Gln Leu Gln Gln Ser Gly Ala Glu Leu Val Lys Pro Gly Ser
1               5                   10                  15

Ser Val Arg Ile Ser Cys Lys Ala Ser Gly Tyr Thr Ile Thr Ser Tyr
            20                  25                  30

Asp Met His Trp Ile Lys Gln Gln Pro Gly Asn Gly Leu Glu Gly Ile
        35                  40                  45

Gly Trp Ile His Pro Gly Asn Gly Lys Ile Lys Tyr Asn Gln Lys Phe
    50                  55                  60

Asn Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Thr Thr Arg Val Phe Pro Trp Phe Ala Tyr Trp Gly Gln
            100                 105                 110

Gly Thr Leu Val Thr Val Ser Ser
        115                 120

<210> SEQ ID NO 180
<211> LENGTH: 120
<212> TYPE: PRT
<213> ORGANISM: Rattus norvegicus

<400> SEQUENCE: 180

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ser Phe Ser Asn Tyr
            20                  25                  30

Gly Met His Trp Ile Arg Gln Ala Pro Thr Lys Gly Leu Glu Trp Val
        35                  40                  45

```
Ala Ser Ile Ser Pro Thr Gly Asn Thr Tyr Tyr Arg Asp Ser Val
         50                  55                  60

Lys Gly Arg Phe Thr Ile Ser Arg Asp Asn Thr Lys Ser Thr Leu Tyr
 65                  70                  75                  80

Leu Gln Met Asp Ser Leu Arg Ser Glu Asp Thr Ala Thr Tyr Tyr Cys
                 85                  90                  95

Ala Thr Asp Asp Leu Tyr Tyr Ser Gly Pro Phe Ala Tyr Trp Gly Gln
            100                 105                 110

Gly Thr Leu Val Thr Val Ser Ser
            115                 120

<210> SEQ ID NO 181
<211> LENGTH: 25
<212> TYPE: PRT
<213> ORGANISM: Homo sapiens

<400> SEQUENCE: 181

Gln Val Gln Leu Val Gln Ser Gly Ala Glu Val Lys Lys Pro Gly Ala
 1               5                  10                  15

Ser Val Lys Val Ser Cys Lys Ala Ser
             20                  25

<210> SEQ ID NO 182
<211> LENGTH: 17
<212> TYPE: PRT
<213> ORGANISM: Homo sapiens

<400> SEQUENCE: 182

Met His Trp Val Arg Gln Ala Pro Gly Gln Arg Leu Glu Trp Met Gly
 1               5                  10                  15

Trp

<210> SEQ ID NO 183
<211> LENGTH: 38
<212> TYPE: PRT
<213> ORGANISM: Homo sapiens

<400> SEQUENCE: 183

Lys Phe Asn His Lys Phe Asp Gly Arg Val Thr Ile Thr Arg Asp Thr
 1               5                  10                  15

Ser Ala Ser Thr Ala Tyr Met Glu Leu Ser Ser Leu Arg Ser Glu Asp
             20                  25                  30

Thr Ala Val Tyr Tyr Cys
            35

<210> SEQ ID NO 184
<211> LENGTH: 17
<212> TYPE: PRT
<213> ORGANISM: Homo sapiens

<400> SEQUENCE: 184

Met His Trp Val Arg Gln Ala Pro Gly Gln Gly Leu Glu Trp Met Gly
 1               5                  10                  15

Trp

<210> SEQ ID NO 185
<211> LENGTH: 38
<212> TYPE: PRT
<213> ORGANISM: Homo sapiens
```

```
<400> SEQUENCE: 185

Lys Phe Asn His Lys Phe Asp Gly Arg Val Thr Met Thr Arg Asp Thr
1               5                   10                  15

Ser Thr Ser Thr Val Tyr Met Glu Leu Ser Ser Leu Arg Ser Glu Asp
            20                  25                  30

Thr Ala Val Tyr Tyr Cys
        35

<210> SEQ ID NO 186
<211> LENGTH: 11
<212> TYPE: PRT
<213> ORGANISM: Homo sapiens

<400> SEQUENCE: 186

Trp Gly Gln Gly Thr Met Val Thr Val Ser Ser
1               5                   10

<210> SEQ ID NO 187
<211> LENGTH: 38
<212> TYPE: PRT
<213> ORGANISM: Homo sapiens

<400> SEQUENCE: 187

Lys Phe Asn His Lys Phe Asp Gly Arg Val Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Val Tyr Tyr Cys
        35

<210> SEQ ID NO 188
<211> LENGTH: 25
<212> TYPE: PRT
<213> ORGANISM: Homo sapiens

<400> SEQUENCE: 188

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 189
<211> LENGTH: 38
<212> TYPE: PRT
<213> ORGANISM: Homo sapiens

<400> SEQUENCE: 189

Lys Phe Asn His Lys Phe Asp Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 190
<211> LENGTH: 25
<212> TYPE: PRT
<213> ORGANISM: Homo sapiens
```

<400> SEQUENCE: 190

Gln Val Gln Leu Val Gln Ser Gly Ser Glu Leu Lys Lys Pro Gly Ala
1               5                   10                  15

Ser Val Lys Val Ser Cys Lys Ala Ser
            20                  25

<210> SEQ ID NO 191
<211> LENGTH: 38
<212> TYPE: PRT
<213> ORGANISM: Homo sapiens

<400> SEQUENCE: 191

Lys Phe Asn His Lys Phe Asp Gly Arg Phe Val Phe Ser Leu Asp Thr
1               5                   10                  15

Ser Val Ser Thr Ala Tyr Leu Gln Ile Ser Ser Leu Lys Ala Glu Asp
            20                  25                  30

Thr Ala Val Tyr Tyr Cys
            35

<210> SEQ ID NO 192
<211> LENGTH: 114
<212> TYPE: PRT
<213> ORGANISM: Artificial sequence
<220> FEATURE:
<223> OTHER INFORMATION: Humanised heavy chain variable region

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Thr Asn
            20                  25                  30

Tyr Met His Trp Val Arg Gln Ala Pro Gly Gln Arg Leu Glu Trp Met
        35                  40                  45

Gly Trp Ile Tyr Pro Gly Asn Gly Asn Thr Lys Phe Asn His Lys Phe
    50                  55                  60

Asp Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Phe Asp Tyr Trp Gly Gln Gly Thr Leu Val Thr Val
            100                 105                 110

Ser Ser

<210> SEQ ID NO 193
<211> LENGTH: 114
<212> TYPE: PRT
<213> ORGANISM: Artificial sequence
<220> FEATURE:
<223> OTHER INFORMATION: Humanised heavy chain variable region

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Thr Asn
            20                  25                  30

Tyr Met His Trp Val Arg Gln Ala Pro Gly Gln Gly Leu Glu Trp Met
        35                  40                  45

Gly Trp Ile Tyr Pro Gly Asn Gly Asn Thr Lys Phe Asn His Lys Phe
            50                  55                  60

Asp Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ile Ser Asp Phe Asp Tyr Trp Gly Gln Gly Thr Met Val Thr Val
            100                 105                 110

Ser Ser

<210> SEQ ID NO 194
<211> LENGTH: 114
<212> TYPE: PRT
<213> ORGANISM: Artificial sequence
<220> FEATURE:
<223> OTHER INFORMATION: Humanised heavy chain variable region

<400> SEQUENCE: 194

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Thr Thr Asn
                20                  25                  30

Tyr Met His Trp Val Arg Gln Ala Pro Gly Gln Gly Leu Glu Trp Met
             35                  40                  45

Gly Trp Ile Tyr Pro Gly Asn Gly Asn Thr Lys Phe Asn His Lys Phe
            50                  55                  60

Asp Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Asp Phe Asp Tyr Trp Gly Gln Gly Thr Leu Val Thr Val
            100                 105                 110

Ser Ser

<210> SEQ ID NO 195
<211> LENGTH: 114
<212> TYPE: PRT
<213> ORGANISM: Artificial sequence
<220> FEATURE:
<223> OTHER INFORMATION: Humanised heavy chain variable region

<400> SEQUENCE: 195

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Leu Thr Thr Asn
                20                  25                  30

Tyr Met His Trp Val Arg Gln Ala Pro Gly Gln Gly Leu Glu Trp Met
             35                  40                  45

Gly Trp Ile Tyr Pro Gly Asn Gly Asn Thr Lys Phe Asn His Lys Phe
            50                  55                  60

Asp Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Ser Asp Phe Asp Tyr Trp Gly Gln Gly Thr Leu Val Thr Val
            100                 105                 110

Ser Ser

<210> SEQ ID NO 196
<211> LENGTH: 114
<212> TYPE: PRT
<213> ORGANISM: Artificial sequence
<220> FEATURE:
<223> OTHER INFORMATION: Humanised heavy chain variable region

<400> SEQUENCE: 196

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr Thr Asn
            20                  25                  30

Tyr Met His Trp Val Arg Gln Ala Pro Gly Gln Gly Leu Glu Trp Met
        35                  40                  45

Gly Trp Ile Tyr Pro Gly Asn Gly Asn Thr Lys Phe Asn His Lys Phe
    50                  55                  60

Asp Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Asp Phe Asp Tyr Trp Gly Gln Gly Thr Leu Val Thr Val
            100                 105                 110

Ser Ser

<210> SEQ ID NO 197
<211> LENGTH: 26
<212> TYPE: PRT
<213> ORGANISM: Homo sapiens

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Gln Ala Ser
            20                  25

<210> SEQ ID NO 198
<211> LENGTH: 17
<212> TYPE: PRT
<213> ORGANISM: Homo sapiens

<400> SEQUENCE: 198

Leu Ile Trp Phe Gln Gln Lys Pro Gly Lys Ala Pro Lys Ser Leu Ile
1               5                   10                  15

Tyr

<210> SEQ ID NO 199
<211> LENGTH: 36
<212> TYPE: PRT
<213> ORGANISM: Homo sapiens

<400> SEQUENCE: 199

Ser Leu Ala Asn Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 200
<211> LENGTH: 10
<212> TYPE: PRT
<213> ORGANISM: Homo sapiens

<400> SEQUENCE: 200

Phe Gly Pro Gly Thr Lys Val Asp Ile Lys
1               5                   10

<210> SEQ ID NO 201
<211> LENGTH: 26
<212> TYPE: PRT
<213> ORGANISM: Homo sapiens

<400> SEQUENCE: 201

Asp Ile Gln Met Thr Gln Ser Pro Ser Ala Met Ser Ala Ser Val Gly
1               5                   10                  15

Asp Arg Val Thr Ile Thr Cys Gln Ala Ser
            20                  25

<210> SEQ ID NO 202
<211> LENGTH: 17
<212> TYPE: PRT
<213> ORGANISM: Homo sapiens

<400> SEQUENCE: 202

Leu Ile Trp Phe Gln Gln Lys Pro Gly Lys Val Pro Lys Arg Leu Ile
1               5                   10                  15

Tyr

<210> SEQ ID NO 203
<211> LENGTH: 36
<212> TYPE: PRT
<213> ORGANISM: Homo sapiens

<400> SEQUENCE: 203

Ser Leu Ala Asn Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 204
<211> LENGTH: 17
<212> TYPE: PRT
<213> ORGANISM: Homo sapiens

<400> SEQUENCE: 204

Leu Ile Trp Tyr Gln Gln Lys Pro Gly Lys Ala Pro Lys Arg Leu Ile
1               5                   10                  15

Tyr

<210> SEQ ID NO 205
<211> LENGTH: 10
<212> TYPE: PRT
<213> ORGANISM: Homo sapiens

```
<400> SEQUENCE: 205

Phe Gly Gln Gly Thr Lys Leu Glu Ile Lys
1               5                   10

<210> SEQ ID NO 206
<211> LENGTH: 17
<212> TYPE: PRT
<213> ORGANISM: Homo sapiens

<400> SEQUENCE: 206

Leu Ile Trp Tyr Gln Gln Lys Pro Gly Lys Ala Pro Lys Leu Leu Ile
1               5                   10                  15

Tyr

<210> SEQ ID NO 207
<211> LENGTH: 36
<212> TYPE: PRT
<213> ORGANISM: Homo sapiens

<400> SEQUENCE: 207

Ser Leu Ala Asn Gly Val Pro Ser Arg Phe Ser Gly Ser Gly Ser Gly
1               5                   10                  15

Thr Asp Phe Thr Phe Thr Ile Ser Ser Leu Gln Pro Glu Asp Ile Ala
                20                  25                  30

Thr Tyr Tyr Cys
            35

<210> SEQ ID NO 208
<211> LENGTH: 26
<212> TYPE: PRT
<213> ORGANISM: Homo sapiens

<400> SEQUENCE: 208

Asp Ile Gln Met Thr Gln Ser Pro Ser Ser Val Ser Ala Ser Val Gly
1               5                   10                  15

Asp Arg Val Thr Ile Thr Cys Gln Ala Ser
                20                  25

<210> SEQ ID NO 209
<211> LENGTH: 10
<212> TYPE: PRT
<213> ORGANISM: Homo sapiens

<400> SEQUENCE: 209

Phe Gly Gln Gly Thr Lys Val Glu Ile Lys
1               5                   10

<210> SEQ ID NO 210
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Asn
                20                  25                  30

Leu Ile Trp Phe Gln Gln Lys Pro Gly Lys Ala Pro Lys Ser Leu Ile
            35                  40                  45
```

```
Tyr Phe Ala Thr Ser Leu Ala Asn Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Arg Glu Tyr Pro Leu
                 85                  90                  95

Thr Phe Gly Pro Gly Thr Lys Val Asp Ile Lys
                100                 105

<210> SEQ ID NO 211
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 211

Asp Ile Gln Met Thr Gln Ser Pro Ser Ala Met Ser Ala Ser Val Gly
 1               5                  10                  15

Asp Arg Val Thr Ile Thr Cys Gln Ala Ser Gln Asp Ile Gly Asn Asn
                20                  25                  30

Leu Ile Trp Phe Gln Gln Lys Pro Gly Lys Val Pro Lys Arg Leu Ile
            35                  40                  45

Tyr Phe Ala Thr Ser Leu Ala Asn Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Arg Glu Tyr Pro Leu
                 85                  90                  95

Thr Phe Gly Pro Gly Thr Lys Val Asp Ile Lys
                100                 105

<210> SEQ ID NO 212
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 212

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Gly Asn Asn
                20                  25                  30

Leu Ile Trp Tyr Gln Gln Lys Pro Gly Lys Ala Pro Lys Arg Leu Ile
            35                  40                  45

Tyr Phe Ala Thr Ser Leu Ala Asn Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Arg Glu Tyr Pro Leu
                 85                  90                  95

Thr Phe Gly Gln Gly Thr Lys Leu Glu Ile Lys
                100                 105

<210> SEQ ID NO 213
<211> LENGTH: 107
<212> TYPE: PRT
```

<213> ORGANISM: Artificial sequence
<220> FEATURE:
<223> OTHER INFORMATION: Humanised light chain variable region

<400> SEQUENCE: 213

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Asn
            20                  25                  30

Leu Ile Trp Tyr Gln Gln Lys Pro Gly Lys Ala Pro Lys Leu Leu Ile
        35                  40                  45

Tyr Phe Ala Thr Ser Leu Ala Asn Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Arg Glu Tyr Pro Leu
                85                  90                  95

Thr Phe Gly Gln Gly Thr Lys Leu Glu Ile Lys
            100                 105
```

<210> SEQ ID NO 214
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 214

```
Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asp Ile Gly Asn Asn
            20                  25                  30

Leu Ile Trp Tyr Gln Gln Lys Pro Gly Lys Ala Pro Lys Leu Leu Ile
        35                  40                  45

Tyr Phe Ala Thr Ser Leu Ala Asn Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Glu Tyr Pro Leu
                85                  90                  95

Thr Phe Gly Gln Gly Thr Lys Val Glu Ile Lys
            100                 105
```

<210> SEQ ID NO 215
<211> LENGTH: 25
<212> TYPE: PRT
<213> ORGANISM: Homo sapiens

<400> SEQUENCE: 215

```
Gln Val Gln Leu Val Glu Ser Gly Gly Val Val Gln Pro Gly Arg
1               5                   10                  15

Ser Leu Arg Leu Ser Cys Ala Ala Ser
            20                  25
```

<210> SEQ ID NO 216
<211> LENGTH: 17
<212> TYPE: PRT
<213> ORGANISM: Homo sapiens

<400> SEQUENCE: 216

Met Ala Trp Val Arg Gln Ala Pro Gly Lys Gly Leu Glu Trp Val Ala
1               5                   10                  15

Thr

<210> SEQ ID NO 217
<211> LENGTH: 38
<212> TYPE: PRT
<213> ORGANISM: Homo sapiens

<400> SEQUENCE: 217

Tyr Tyr Arg Asp Ser Met Arg Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 218
<211> LENGTH: 25
<212> TYPE: PRT
<213> ORGANISM: Homo sapiens

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 219
<211> LENGTH: 17
<212> TYPE: PRT
<213> ORGANISM: Homo sapiens

<400> SEQUENCE: 219

Met Ala Trp Val Arg Gln Ala Pro Gly Lys Gly Leu Glu Trp Val Ser
1               5                   10                  15

Thr

<210> SEQ ID NO 220
<211> LENGTH: 38
<212> TYPE: PRT
<213> ORGANISM: Homo sapiens

<400> SEQUENCE: 220

Tyr Tyr Arg Asp Ser Met Arg Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 221
<211> LENGTH: 17
<212> TYPE: PRT
<213> ORGANISM: Homo sapiens -continued

<400> SEQUENCE: 221

Met Ala Trp Val Arg Gln Ala Pro Gly Lys Gly Leu Val Trp Val Ser
1               5                   10                  15

Thr

<210> SEQ ID NO 222
<211> LENGTH: 38
<212> TYPE: PRT
<213> ORGANISM: Homo sapiens

<400> SEQUENCE: 222

Tyr Tyr Arg Asp Ser Met Arg Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 223
<211> LENGTH: 25
<212> TYPE: PRT
<213> ORGANISM: Homo sapiens

<400> SEQUENCE: 223

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 224
<211> LENGTH: 38
<212> TYPE: PRT
<213> ORGANISM: Homo sapiens

<400> SEQUENCE: 224

Tyr Tyr Arg Asp Ser Met Arg Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Leu Tyr Tyr Cys
        35

<210> SEQ ID NO 225
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 225

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ala Thr Ile Ser Asp Asp Gly Arg Asn Thr Tyr Tyr Arg Asp Ser Met
    50                  55                  60

```
Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ser His Arg Tyr Asn Leu Phe Asp Ser Trp Gly Gln Gly Thr Met
            100                 105                 110

Val Thr Val Ser Ser
        115

<210> SEQ ID NO 226
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 226

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ile Phe Ser Glu His
                 20                  25                  30

Asn Met Ala Trp Val Arg Gln Ala Pro Gly Lys Gly Leu Glu Trp Val
             35                  40                  45

Ser Thr Ile Ser Asp Asp Gly Arg Asn Thr Tyr Tyr Arg Asp Ser Met
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Arg Tyr Asn Leu Phe Asp Ser Trp Gly Gln Gly Thr Leu
            100                 105                 110

Val Thr Val Ser Ser
        115

<210> SEQ ID NO 227
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 227

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ile Phe Ser Glu His
                 20                  25                  30

Asn Met Ala Trp Val Arg Gln Ala Pro Gly Lys Gly Leu Glu Trp Val
             35                  40                  45

Ala Thr Ile Ser Asp Asp Gly Arg Asn Thr Tyr Tyr Arg Asp Ser Met
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ala Arg His Arg Tyr Asn Leu Phe Asp Ser Trp Gly Gln Gly Thr Met
            100                 105                 110

Val Thr Val Ser Ser
        115

<210> SEQ ID NO 228
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 228

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Val Trp Val
        35                  40                  45

Ser Thr Ile Ser Asp Asp Gly Arg Asn Thr Tyr Tyr Arg Asp Ser Met
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Tyr Asn Leu Phe Asp Ser Trp Gly Gln Gly Thr Leu
            100                 105                 110

Val Thr Val Ser Ser
        115

<210> SEQ ID NO 229
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 229

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ser Thr Ile Ser Asp Asp Gly Arg Asn Thr Tyr Tyr Arg Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys His Arg Tyr Asn Leu Phe Asp Ser Trp Gly Gln Gly Thr Leu
            100                 105                 110

Val Thr Val Ser Ser
        115

<210> SEQ ID NO 230
<211> LENGTH: 26
<212> TYPE: PRT

<213> ORGANISM: Homo sapiens

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Lys Ala Ser
            20                  25

<210> SEQ ID NO 231
<211> LENGTH: 17
<212> TYPE: PRT
<213> ORGANISM: Homo sapiens

<400> SEQUENCE: 231

Leu Asn Trp Tyr Gln Gln Lys Pro Gly Lys Ala Pro Lys Arg Leu Ile
1               5                   10                  15

Tyr

<210> SEQ ID NO 232
<211> LENGTH: 36
<212> TYPE: PRT
<213> ORGANISM: Homo sapiens

<400> SEQUENCE: 232

Lys Leu Gln Thr Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 233
<211> LENGTH: 17
<212> TYPE: PRT
<213> ORGANISM: Homo sapiens

<400> SEQUENCE: 233

Leu Asn Trp Phe Gln Gln Lys Pro Gly Lys Ala Pro Lys Ser Leu Ile
1               5                   10                  15

Tyr

<210> SEQ ID NO 234
<211> LENGTH: 36
<212> TYPE: PRT
<213> ORGANISM: Homo sapiens

<400> SEQUENCE: 234

Lys Leu Gln Thr Gly Val Pro Ser Lys Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 235
<211> LENGTH: 10
<212> TYPE: PRT
<213> ORGANISM: Homo sapiens

<400> SEQUENCE: 235

Phe Gly Gln Gly Thr Arg Leu Glu Ile Lys
1               5                   10

<210> SEQ ID NO 236
<211> LENGTH: 17
<212> TYPE: PRT
<213> ORGANISM: Homo sapiens

<400> SEQUENCE: 236

Leu Asn Trp Tyr Gln Gln Lys Pro Gly Lys Ala Pro Lys Leu Leu Ile
1               5                   10                  15

Tyr

<210> SEQ ID NO 237
<211> LENGTH: 36
<212> TYPE: PRT
<213> ORGANISM: Homo sapiens

<400> SEQUENCE: 237

Lys Leu Gln Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 238
<211> LENGTH: 26
<212> TYPE: PRT
<213> ORGANISM: Homo sapiens

<400> SEQUENCE: 238

Asp Ile Gln Leu Thr Gln Ser Pro Ser Phe Leu Ser Ala Ser Val Gly
1               5                   10                  15

Asp Arg Val Thr Ile Thr Cys Lys Ala Ser
            20                  25

<210> SEQ ID NO 239
<211> LENGTH: 26
<212> TYPE: PRT
<213> ORGANISM: Homo sapiens

<400> SEQUENCE: 239

Asp Ile Gln Met Thr Gln Ser Pro Ser Thr Leu Ser Ala Ser Val Gly
1               5                   10                  15

Asp Arg Val Thr Ile Thr Cys Lys Ala Ser
            20                  25

<210> SEQ ID NO 240
<211> LENGTH: 36
<212> TYPE: PRT
<213> ORGANISM: Homo sapiens

<400> SEQUENCE: 240

Lys Leu Gln Thr Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
             20                  25                  30

Thr Tyr Tyr Cys
        35

<210> SEQ ID NO 241
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 241

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Arg Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 242
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Phe Gln Gln Lys Pro Gly Lys Ala Pro Lys Ser Leu Ile
        35                  40                  45

Tyr Asn Thr Asn Lys Leu Gln Thr Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Arg Leu Glu Ile Lys
            100                 105

<210> SEQ ID NO 243
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 243

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 244
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 244

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 245
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 245

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gln Tyr Asn Ser Leu Pro Leu
            85                  90                  95

Thr Phe Gly Gln Gly Thr Lys Leu Glu Ile Lys
            100                 105

<210> SEQ ID NO 246
<211> LENGTH: 7
<212> TYPE: PRT
<213> ORGANISM: Artificial sequence
<220> FEATURE:
<223> OTHER INFORMATION: Humanised heavy chain CDR3

<400> SEQUENCE: 246

Ala Ile Ser Asp Phe Asp Tyr
1               5

<210> SEQ ID NO 247
<211> LENGTH: 7
<212> TYPE: PRT
<213> ORGANISM: Artificial sequence
<220> FEATURE:
<223> OTHER INFORMATION: Humanised heavy chain CDR3

<400> SEQUENCE: 247

Ala Thr Ser Asp Phe Asp Tyr
1               5

<210> SEQ ID NO 248
<211> LENGTH: 7
<212> TYPE: PRT
<213> ORGANISM: Artificial sequence
<220> FEATURE:
<223> OTHER INFORMATION: Humanised heavy chain CDR3
<220> FEATURE:
<221> NAME/KEY: misc_feature
<222> LOCATION: (2)..(2)
<223> OTHER INFORMATION: Xaa can be Arg, Ile or Thr

<400> SEQUENCE: 248

Ala Xaa Ser Asp Phe Asp Tyr
1               5

<210> SEQ ID NO 249
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 249

Thr Ser His Arg Tyr Asn Leu Phe Asp Ser
1               5                   10

<210> SEQ ID NO 250
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 250

Ala Lys His Arg Tyr Asn Leu Phe Asp Ser
1               5                   10

<210> SEQ ID NO 251
<211> LENGTH: 10

```
<212> TYPE: PRT
<213> ORGANISM: Artificial sequence
<220> FEATURE:
<223> OTHER INFORMATION: Humanised heavy chain CDR3

<400> SEQUENCE: 251

Ala Arg His Arg Tyr Asn Leu Phe Asp Ser
1               5                   10

<210> SEQ ID NO 252
<211> LENGTH: 10
<212> TYPE: PRT
<213> ORGANISM: Artificial sequence
<220> FEATURE:
<223> OTHER INFORMATION: Humanised heavy chain CDR3
<220> FEATURE:
<221> NAME/KEY: misc_feature
<222> LOCATION: (1)..(1)
<223> OTHER INFORMATION: Xaa can be Ala or Thr
<220> FEATURE:
<221> NAME/KEY: misc_feature
<222> LOCATION: (2)..(2)
<223> OTHER INFORMATION: Xaa can be Ser, Lys or Arg

<400> SEQUENCE: 252

Xaa Xaa His Arg Tyr Asn Leu Phe Asp Ser
1               5                   10

<210> SEQ ID NO 253
<211> LENGTH: 5
<212> TYPE: PRT
<213> ORGANISM: Homo sapiens

<400> SEQUENCE: 253

Asn Ile Ser Ser Glu
1               5

<210> SEQ ID NO 254
<211> LENGTH: 5
<212> TYPE: PRT
<213> ORGANISM: Artificial sequence
<220> FEATURE:
<223> OTHER INFORMATION: Substituted sequence for epitope mapping

<400> SEQUENCE: 254

Phe Gln Asp Asp Leu
1               5

<210> SEQ ID NO 255
<211> LENGTH: 16
<212> TYPE: PRT
<213> ORGANISM: Rattus norvegicus

<400> SEQUENCE: 255

Arg Ser Ser Gln Ser Leu Glu His Ser Asn Gly Asp Thr Phe Leu His
1               5                   10                  15

<210> SEQ ID NO 256
<211> LENGTH: 7
<212> TYPE: PRT
<213> ORGANISM: Rattus norvegicus

<400> SEQUENCE: 256

Arg Val Ser Asn Arg Phe Ser
1               5

<210> SEQ ID NO 257
```

```
<211> LENGTH: 6
<212> TYPE: PRT
<213> ORGANISM: Rattus norvegicus

<400> SEQUENCE: 257

Asn Met Tyr Arg Trp Asn
1               5

<210> SEQ ID NO 258
<211> LENGTH: 16
<212> TYPE: PRT
<213> ORGANISM: Rattus norvegicus

<400> SEQUENCE: 258

Tyr Ile Asn Thr Ala Gly Ser Thr Asp Tyr Ser Pro Ser Leu Arg Gly
1               5                   10                  15

<210> SEQ ID NO 259
<211> LENGTH: 8
<212> TYPE: PRT
<213> ORGANISM: Rattus norvegicus

<400> SEQUENCE: 259

Phe Ile Thr Asn Pro Phe Asp Phe
1               5

<210> SEQ ID NO 260
<211> LENGTH: 11
<212> TYPE: PRT
<213> ORGANISM: Rattus norvegicus

<400> SEQUENCE: 260

Arg Ala Ser Gln Ser Ile Ser Asn Ser Leu Asn
1               5                   10

<210> SEQ ID NO 261
<211> LENGTH: 7
<212> TYPE: PRT
<213> ORGANISM: Rattus norvegicus

<400> SEQUENCE: 261

Ser Thr Ser Thr Leu Glu Ser
1               5

<210> SEQ ID NO 262
<211> LENGTH: 5
<212> TYPE: PRT
<213> ORGANISM: Rattus norvegicus

<400> SEQUENCE: 262

Asn Tyr Trp Met Thr
1               5

<210> SEQ ID NO 263
<211> LENGTH: 17
<212> TYPE: PRT
<213> ORGANISM: Rattus norvegicus

<400> SEQUENCE: 263

Ser Ile Ser Asn Thr Gly Gly Ser Thr Phe Tyr Pro Asp Ser Val Arg
1               5                   10                  15

Gly

<210> SEQ ID NO 264
```

```
<211> LENGTH: 4
<212> TYPE: PRT
<213> ORGANISM: Rattus norvegicus

<400> SEQUENCE: 264

Asn Met Asp Ala
1

<210> SEQ ID NO 265
<211> LENGTH: 15
<212> TYPE: PRT
<213> ORGANISM: Rattus norvegicus

<400> SEQUENCE: 265

Arg Ala Ser Gln Ser Val Ser Ile Ser Arg Tyr Asn Phe Met His
1               5                   10                  15

<210> SEQ ID NO 266
<211> LENGTH: 7
<212> TYPE: PRT
<213> ORGANISM: Rattus norvegicus

<400> SEQUENCE: 266

Arg Ala Ser Asn Leu Ala Ser
1               5

<210> SEQ ID NO 267
<211> LENGTH: 5
<212> TYPE: PRT
<213> ORGANISM: Rattus norvegicus

<400> SEQUENCE: 267

Lys Tyr Trp Met His
1               5

<210> SEQ ID NO 268
<211> LENGTH: 17
<212> TYPE: PRT
<213> ORGANISM: Rattus norvegicus

<400> SEQUENCE: 268

Glu Ile Glu Tyr Asp Gly Thr Glu Thr Asn Tyr Ala Pro Ser Ile Lys
1               5                   10                  15

Asp

<210> SEQ ID NO 269
<211> LENGTH: 14
<212> TYPE: PRT
<213> ORGANISM: Rattus norvegicus

<400> SEQUENCE: 269

Glu Glu Met Tyr Thr Thr Asp Tyr Tyr Tyr Gly Phe Ala Tyr
1               5                   10

<210> SEQ ID NO 270
<211> LENGTH: 15
<212> TYPE: PRT
<213> ORGANISM: Rattus norvegicus

<400> SEQUENCE: 270

Arg Ala Ser Gln Ser Val Ser Ile Ser Arg Tyr Asp Phe Met His
1               5                   10                  15

<210> SEQ ID NO 271
```

```
<211> LENGTH: 14
<212> TYPE: PRT
<213> ORGANISM: Rattus norvegicus

<400> SEQUENCE: 271

Glu Glu Met His Thr Thr Asp Tyr Tyr Tyr Gly Phe Ala Tyr
1               5                   10

<210> SEQ ID NO 272
<211> LENGTH: 11
<212> TYPE: PRT
<213> ORGANISM: Rattus norvegicus

<400> SEQUENCE: 272

Lys Ala Ser Gln Asn Ile Asp Arg Tyr Leu Asn
1               5                   10

<210> SEQ ID NO 273
<211> LENGTH: 7
<212> TYPE: PRT
<213> ORGANISM: Rattus norvegicus

<400> SEQUENCE: 273

Asn Thr Asn Lys Leu Gln Thr
1               5

<210> SEQ ID NO 274
<211> LENGTH: 5
<212> TYPE: PRT
<213> ORGANISM: Rattus norvegicus

<400> SEQUENCE: 274

Glu His Asn Met Ala
1               5

<210> SEQ ID NO 275
<211> LENGTH: 17
<212> TYPE: PRT
<213> ORGANISM: Rattus norvegicus

<400> SEQUENCE: 275

Thr Ile Ser Asp Asp Gly Arg Asn Thr Tyr Tyr Arg Asp Ser Met Arg
1               5                   10                  15

Gly

<210> SEQ ID NO 276
<211> LENGTH: 8
<212> TYPE: PRT
<213> ORGANISM: Rattus norvegicus

<400> SEQUENCE: 276

His Arg Tyr Asn Leu Phe Asp Ser
1               5

<210> SEQ ID NO 277
<211> LENGTH: 11
<212> TYPE: PRT
<213> ORGANISM: Rattus norvegicus

<400> SEQUENCE: 277

Gln Ala Ser Gln Asp Ile Gly Asn Asn Leu Ile
1               5                   10

<210> SEQ ID NO 278
```

```
<211> LENGTH: 7
<212> TYPE: PRT
<213> ORGANISM: Rattus norvegicus

<400> SEQUENCE: 278

Phe Ala Thr Ser Leu Ala Asn
1               5

<210> SEQ ID NO 279
<211> LENGTH: 5
<212> TYPE: PRT
<213> ORGANISM: Rattus norvegicus

<400> SEQUENCE: 279

Thr Asn Tyr Met His
1               5

<210> SEQ ID NO 280
<211> LENGTH: 17
<212> TYPE: PRT
<213> ORGANISM: Rattus norvegicus

<400> SEQUENCE: 280

Trp Ile Tyr Pro Gly Asn Gly Asn Thr Lys Phe Asn His Lys Phe Asp
1               5                   10                  15

Gly

<210> SEQ ID NO 281
<211> LENGTH: 5
<212> TYPE: PRT
<213> ORGANISM: Rattus norvegicus

<400> SEQUENCE: 281

Ser Asp Phe Asp Tyr
1               5

<210> SEQ ID NO 282
<211> LENGTH: 11
<212> TYPE: PRT
<213> ORGANISM: Rattus norvegicus

<400> SEQUENCE: 282

Leu Thr Ser Glu Asp Ile Tyr Ser Asp Leu Ala
1               5                   10

<210> SEQ ID NO 283
<211> LENGTH: 7
<212> TYPE: PRT
<213> ORGANISM: Rattus norvegicus

<400> SEQUENCE: 283

Asp Ala Asn Ser Leu Gln Asn
1               5

<210> SEQ ID NO 284
<211> LENGTH: 5
<212> TYPE: PRT
<213> ORGANISM: Rattus norvegicus

<400> SEQUENCE: 284

Asn Arg Gly Met Ala
1               5

<210> SEQ ID NO 285
```

```
<211> LENGTH: 17
<212> TYPE: PRT
<213> ORGANISM: Rattus norvegicus

<400> SEQUENCE: 285

Thr Ile Ser Tyr Asp Gly Arg Ile Ile Tyr Tyr Arg Asp Ser Val Lys
1               5                   10                  15

Gly

<210> SEQ ID NO 286
<211> LENGTH: 11
<212> TYPE: PRT
<213> ORGANISM: Rattus norvegicus

<400> SEQUENCE: 286

His Pro Ile Ala Ala Asp Trp Tyr Phe Asp Phe
1               5                   10

<210> SEQ ID NO 287
<211> LENGTH: 11
<212> TYPE: PRT
<213> ORGANISM: Rattus norvegicus

<400> SEQUENCE: 287

Gln Ser Ser Gln Gly Ile Gly Lys Tyr Leu Ser
1               5                   10

<210> SEQ ID NO 288
<211> LENGTH: 7
<212> TYPE: PRT
<213> ORGANISM: Rattus norvegicus

<400> SEQUENCE: 288

Tyr Ala Thr Lys Leu Ala Asp
1               5

<210> SEQ ID NO 289
<211> LENGTH: 5
<212> TYPE: PRT
<213> ORGANISM: Rattus norvegicus

<400> SEQUENCE: 289

Asp Tyr Asn Met Ala
1               5

<210> SEQ ID NO 290
<211> LENGTH: 17
<212> TYPE: PRT
<213> ORGANISM: Rattus norvegicus

<400> SEQUENCE: 290

Thr Ile Thr Tyr Asp Val His Asn Ala Tyr Tyr Arg Asp Ser Val Lys
1               5                   10                  15

Gly

<210> SEQ ID NO 291
<211> LENGTH: 4
<212> TYPE: PRT
<213> ORGANISM: Rattus norvegicus

<400> SEQUENCE: 291

Pro Gly Ala Tyr
1
```

-continued

<210> SEQ ID NO 292
<211> LENGTH: 15
<212> TYPE: PRT
<213> ORGANISM: Rattus norvegicus

<400> SEQUENCE: 292

Lys Thr Ser Gln Asn Val Asp Asn His Gly Ile Ser Tyr Met His
1               5                   10                  15

<210> SEQ ID NO 293
<211> LENGTH: 7
<212> TYPE: PRT
<213> ORGANISM: Rattus norvegicus

<400> SEQUENCE: 293

Glu Gly Ser Asn Leu Ala Val
1               5

<210> SEQ ID NO 294
<211> LENGTH: 5
<212> TYPE: PRT
<213> ORGANISM: Rattus norvegicus

<400> SEQUENCE: 294

Asp Tyr Trp Met Ser
1               5

<210> SEQ ID NO 295
<211> LENGTH: 17
<212> TYPE: PRT
<213> ORGANISM: Rattus norvegicus

<400> SEQUENCE: 295

Glu Ile Tyr Pro Asn Ser Gly Ala Thr Asn Phe Asn Glu Lys Phe Lys
1               5                   10                  15

Asp

<210> SEQ ID NO 296
<211> LENGTH: 12
<212> TYPE: PRT
<213> ORGANISM: Rattus norvegicus

<400> SEQUENCE: 296

Gly Phe Pro Asn Asn Tyr Leu Ser Trp Phe Ala Tyr
1               5                   10

<210> SEQ ID NO 297
<211> LENGTH: 13
<212> TYPE: PRT
<213> ORGANISM: Rattus norvegicus

<400> SEQUENCE: 297

Glu Arg Ser Ser Gly Asp Ile Gly Asp Ser Tyr Val Ser
1               5                   10

<210> SEQ ID NO 298
<211> LENGTH: 7
<212> TYPE: PRT
<213> ORGANISM: Rattus norvegicus

<400> SEQUENCE: 298

Ala Asp Asp Gln Arg Pro Ser
1               5

<210> SEQ ID NO 299
<211> LENGTH: 5
<212> TYPE: PRT
<213> ORGANISM: Rattus norvegicus

<400> SEQUENCE: 299

Asn Tyr Gly Met Tyr
1               5

<210> SEQ ID NO 300
<211> LENGTH: 17
<212> TYPE: PRT
<213> ORGANISM: Rattus norvegicus

<400> SEQUENCE: 300

Trp Ile Asn Thr Glu Thr Gly Lys Pro Thr Tyr Ala Asp Asp Phe Lys
1               5                   10                  15

Gly

<210> SEQ ID NO 301
<211> LENGTH: 12
<212> TYPE: PRT
<213> ORGANISM: Rattus norvegicus

<400> SEQUENCE: 301

Glu Val Lys His Gly Leu Phe His Trp Phe Ala Tyr
1               5                   10

<210> SEQ ID NO 302
<211> LENGTH: 7
<212> TYPE: PRT
<213> ORGANISM: Rattus norvegicus

<400> SEQUENCE: 302

Tyr Ala Thr Asn Leu Ala Asp
1               5

<210> SEQ ID NO 303
<211> LENGTH: 17
<212> TYPE: PRT
<213> ORGANISM: Rattus norvegicus

<400> SEQUENCE: 303

Thr Ile Ser Phe Asp Asp Tyr Asn Thr Tyr Tyr Arg Asp Ser Val Lys
1               5                   10                  15

Gly

<210> SEQ ID NO 304
<211> LENGTH: 4
<212> TYPE: PRT
<213> ORGANISM: Rattus norvegicus

<400> SEQUENCE: 304

Pro Gly Thr Tyr
1

<210> SEQ ID NO 305
<211> LENGTH: 12
<212> TYPE: PRT
<213> ORGANISM: Rattus norvegicus

<400> SEQUENCE: 305

Glu Arg Ser Ser Gly Asp Ile Gly Asp Asn Tyr Val
1               5                   10

<210> SEQ ID NO 306
<211> LENGTH: 5
<212> TYPE: PRT
<213> ORGANISM: Rattus norvegicus

<400> SEQUENCE: 306

Ser Tyr Asp Met His
1               5

<210> SEQ ID NO 307
<211> LENGTH: 17
<212> TYPE: PRT
<213> ORGANISM: Rattus norvegicus

<400> SEQUENCE: 307

Trp Ile His Pro Gly Asn Gly Lys Ile Lys Tyr Asn Gln Lys Phe Asn
1               5                   10                  15

Gly

<210> SEQ ID NO 308
<211> LENGTH: 11
<212> TYPE: PRT
<213> ORGANISM: Rattus norvegicus

<400> SEQUENCE: 308

Gly Thr Thr Arg Val Phe Pro Trp Phe Ala Tyr
1               5                   10

<210> SEQ ID NO 309
<211> LENGTH: 11
<212> TYPE: PRT
<213> ORGANISM: Rattus norvegicus

<400> SEQUENCE: 309

Lys Ala Ser Gln Asn Ile Thr Arg Phe Leu Asn
1               5                   10

<210> SEQ ID NO 310
<211> LENGTH: 7
<212> TYPE: PRT
<213> ORGANISM: Rattus norvegicus

<400> SEQUENCE: 310

Asn Thr Asn Asn Leu Gln Thr
1               5

<210> SEQ ID NO 311
<211> LENGTH: 5
<212> TYPE: PRT
<213> ORGANISM: Rattus norvegicus

<400> SEQUENCE: 311

Asn Tyr Gly Met His
1               5

<210> SEQ ID NO 312
<211> LENGTH: 17
<212> TYPE: PRT
<213> ORGANISM: Rattus norvegicus

```
<400> SEQUENCE: 312

Ser Ile Ser Pro Thr Gly Gly Asn Thr Tyr Tyr Arg Asp Ser Val Lys
1               5                   10                  15

Gly

<210> SEQ ID NO 313
<211> LENGTH: 11
<212> TYPE: PRT
<213> ORGANISM: Rattus norvegicus

<400> SEQUENCE: 313

Asp Asp Leu Tyr Tyr Ser Gly Pro Phe Ala Tyr
1               5                   10
```